(12) United States Patent
Adams et al.

(10) Patent No.: US 9,249,440 B2
(45) Date of Patent: Feb. 2, 2016

(54) HYDROGENASE POLYPEPTIDE AND METHODS OF USE

(71) Applicant: UNIVERSITY OF GEORGIA RESEARCH FOUNDATION, INC., Athens, GA (US)

(72) Inventors: Michael W. W. Adams, Athens, GA (US); Robert C. Hopkins, Athens, GA (US); Francis E. Jenney, Jr., Athens, GA (US); Junsong Sun, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/204,802

(22) Filed: Mar. 11, 2014

(65) Prior Publication Data
US 2014/0308700 A1    Oct. 16, 2014

Related U.S. Application Data

(63) Continuation of application No. 12/746,154, filed as application No. PCT/US2008/013449 on Dec. 5, 2008, now abandoned.

(60) Provisional application No. 61/005,383, filed on Dec. 5, 2007.

(51) Int. Cl.
| | |
|---|---|
| *C12N 9/04* | (2006.01) |
| *C12N 15/00* | (2006.01) |
| *C12N 1/20* | (2006.01) |

(Continued)

(52) U.S. Cl.
CPC ............... *C12P 21/00* (2013.01); *C12N 9/0004* (2013.01); *C12N 9/0006* (2013.01); *C12N 15/62* (2013.01); *C12N 15/74* (2013.01)

(58) Field of Classification Search
CPC .... C12N 9/0067; C12N 15/74; C12N 9/0006; C07K 2319/21
See application file for complete search history.

(56) References Cited

U.S. PATENT DOCUMENTS

| | | | |
|---|---|---|---|
| 4,703,004 A | 10/1987 | Hopp et al. | |
| 4,782,137 A | 11/1988 | Hopp et al. | |

(Continued)

FOREIGN PATENT DOCUMENTS

| | | |
|---|---|---|
| WO | WO 2009/055699 | 4/2009 |
| WO | WO 2009/075798 A2 | 6/2009 |

OTHER PUBLICATIONS

Dabrowski et al. Cloning and expression in *Escherichia coli* of the recombinant his-tagged DNA polymerases from *Pyrococcus furiosus* and *Pyrococcus woesei*. Protein Expr Purif. Oct. 1998;14(1):131-8.*

(Continued)

*Primary Examiner* — Yong Pak
(74) *Attorney, Agent, or Firm* — Mueting, Raasch & Gebhardt, P.A.

(57) ABSTRACT

Provided herein are polypeptides having hydrogenase activity. The polypeptide may be multimeric, and may have hydrogenase activity of at least 0.05 micromoles $H_2$ produced $min^{-1}$ mg protein$^{-1}$. Also provided herein are polynucleotides encoding the polypeptides, genetically modified microbes that include polynucleotides encoding one or more subunits of the multimeric polypeptide, and methods for making and using the polypeptides.

16 Claims, 48 Drawing Sheets

(51) Int. Cl.
| | |
|---|---|
| C12P 21/06 | (2006.01) |
| C07H 21/04 | (2006.01) |
| C12P 21/00 | (2006.01) |
| C12N 15/74 | (2006.01) |
| C12N 9/02 | (2006.01) |
| C12N 15/62 | (2006.01) |

(56) References Cited

U.S. PATENT DOCUMENTS

| | | | |
|---|---|---|---|
| 5,594,115 | A | 1/1997 | Sharma |
| 5,935,824 | A | 8/1999 | Sgarlato |
| 2004/0214053 | A1 | 10/2004 | Armstrong |
| 2006/0183193 | A1 | 8/2006 | Horanyi et al. |
| 2007/0264534 | A1 | 11/2007 | Zhang et al. |
| 2011/0020875 | A1 | 1/2011 | Adams et al. |

OTHER PUBLICATIONS

Aagaard et al. General vectors for archaeal hyperthermophiles: strategies based on a mobile intron and a plasmid. FEMS Microbiol Rev. May 1996;18(2-3):93-104. Review.*
U.S. Appl. No. 61/000,338, filed Oct. 25, 2007, Westpheling et al.
International Search Report (PCT/ISA/210) and Written Opinion (PCT/ISA/237) from PCT/US2008/013449, Jul. 16, 2009, 12 pgs.
Adams et al., "Hydrogenase," *Biochim Biophys Acta*, 1980;594:105-176.
Adams, "The structure and mechanism of iron-hydrogenases," *Biochimica Et Biophysica Acta*, 1990;1020:115-145.
Albracht, "Nickel hydrogenases: in search of the active site," *Biochimica Et Biophysica Acta-Bioenergetics*, 1994:1188;167-204.
Arnau et al. "Current strategies for the use of affinity tags and tag removal for the purification of recombinant proteins". 2006. *Protein Expr. Purif.* 48(1):1-13.
Bagley et al., "Infrared-Detectable Groups Sense Changes in Charge Density on the Nickel Center in Hydrogenase from *Chromatium vinosum*," *Biochemistry*, 1995;34(16):5527-5535.
Bascones et al., "Generation of New Hydrogen-Recycling *Rhizobiaceae* Strains by Introduction of a Novel *hup* Minitransposon," *Appl Environ Microbiol*, Oct. 2000;66(10):4292-4299.
Blokesch et al., "Maturation of [NiFe]-hydrogenases in *Escherichia coli*: The HypC Cycle," *J of Molecular Biol.*, 2002;324:287-296.
Bharadwaj et al., "Catalytic partial oxidation of natural gas to syngas," *Fuel Processing Technology*, 1995;42:109-127.
Böck et al., "Maturation of Hydrogenases," *Adv Microb Physiol*, 2006;51:1-71.
Bowie et al., "Deciphering the Message in Protein Sequences: Tolerance to Amino Acid Substitutions," *Science*, 1990;247:1306-1310.
Boyke et al., "[Fe$_2$(Sr)$_2$(μ-CO)(CNMe)$_6$]$^{2+}$ and Analogues: A New Class of Diiron Dithiolates as Structural Models for the H$_{ox}^{Air}$ State of the Fe-Only Hydrogenase," *J. American Chemical Society*, 2004;126:15151-15160.
Branden et al. "Introduction to Protein Structure". 1991. Garland Publishing Inc., New York. 247.
Bryant et al., "Characterization of Hydrogenase from the Hyperthermophilic Archaebacterium, *Pyrococcus furiosus*," *J Biol Chem*, 1989;264(9):5070-5079.
Cammack et al., *Hydrogen as a fuel: learning from nature*, Taylor & Francis, London, New York, 2001; cover page, title page and table of contents only, 14 pgs.
Chen et al., "Infrared Studies of the CO-Inhibited Form of the Fe-Only Hydrogenase from *Clostridium pasteurianum* I: Examination of Its Light Sensitivity at Cryogenic Temperatures," *Biochemistry*, 2002;41(6):2036-2043.
Eberly and Ely, "Thermotolerant Hydrogenases: Biological Diversity, Properties, and Biotechnological Applications," *Crit Rev Microbiol*, 2008;34:117-130.
Fiala and Setter, "*Pyrococcus furiosus* sp. nov. represents a novel genus of marine heterotrophic archaebacteria growing optimally at 100° C.," *Archives of Microbiology*, 1986;145:56-61.

Friedrich and Schwartz, "Molecular Biology of Hydrogen Utilization in Aerobic Chemolithotrophs," *Annual Review of Microbiology*, 1993;47:351-383.
Garcin et al., "Structural bases for the catalytic mechanism of [NiFe] hydrogenases," *Biochemical Society Transactions*, 1998;26:396-401.
Ghenciu, "Review of fuel processing catalysts for hydrogen production in PEM fuel cell systems," *Current Opinion in Solid State & Materials Science*, 2002;6:389-399.
Happe et al., "Biological activation of hydrogen," *Nature*, Jan. 9, 1997;385:126.
Harker et al., "Further evidence that Two Unique Subunits are Essential for Expression of Hydrogenase Activity in *Rhizobium japonicum*," *J. of Bacteriology*, Oct. 1985, 164(1):187-191.
Higuchi, "Removal of the bridging ligand atom at the Ni—Fe active site of [NiFe] hydrogenase upon reduction with H$_2$, as revealed by X-ray structure analysis at 1.4 Å resolution," *Structure*, 1999;7:549-556.
Hummel, "Large-scale applications of NAD(P)-dependent oxidoreductases: recent developments," *Trends Biotechnol*, 1999;17:487-492.
Kim et al., "Stability and Sulfur-Reduction Activity in Non-Aqueous Phase Liquids of the Hydrogenase from the Hyperthermophile *Pyrococcus furiosus*," *Biotechnol., Bioeng.*, 1999;65:108-113.
King et al., "Functional Studies of [FeFe] Hydrogenase Maturation in an *Escherichia coli* Biosynthetic System," *J. Bacteriol*, 2006;188(6):2163-2172.
Lenz et al., "Requirements for Heterologous Production of a Complex Metalloenzyme: the Membrane-Bound [NiFe] Hydrogenase,"*J Bacteriol*, 2005;187(18):6590-6595.
Lyon et al., "Carbon Monoxide as an Intrinsic Ligand to Iron in the Active Site of the Iron—Sulfur-Cluster-Free Hydrogenase H$_2$-Forming Methylenetetrahydromethanopterin Dehydrogenase as Revealed by Infrared Spectroscopy," *J of American Chemical Society*, 2004;126:14239-14248.
Ma and Adams, "Hydrogenase I and II from *Pyrococcus furiosus*," *Methods Enzymol*, 2001;331:208-216.
Ma et al., "Characterization of Hydrogenase II from the Hyperthermophilic Archaeon *Pyrococcus furiosus* and Assessment of Its Role in Sulfur Reduction," *J Bacteriol*, 2000;182(7):1864-1871.
Ma et al., "Hydrogen production from pyruvate by enzymes purified from the hyperthermophilic archaeon, *Pyrococcus furiosus*: A key role for NADPH," *FEMS Microbiology Letters*, 1994;122:245-250.
Ma et al., "Hydrogenase of the hyperthermophile *Pyrococcus furiosus* is an elemental sulfur reductase or sulfhydrogenase: Evidence for a sulfur-reducing hydrogenase ancestor," *PNAS USA*, Jun. 1, 1993;90(11):5341-5344.
Maeda et al., "Enhanced hydrogen production from glucose by metabolically engineered *Eschericha coli*," *App Microbiol Biotechnol.*, Oct. 16, 2007;77:879-890.
Maeda et al., "Inhibition of hydrogen uptake in *Escherichia coli* by expressing the hydrogenase from the cyanobacterium *Synechocystis* sp. PCC 6803," *BMC Biotechnol*, 2007;7:25.
Maeda et al., "*Escherichia coli* hydrogenase 3 is a reversible enzyme possessing hydrogen uptake and synthesis activities," *Appl Microbiol Biotechnol*, 2007;76:1035-1042.
Mertens et al., "Practical applications of hydrogenase I from *Pyrococcus furiosus* for NADPH generation and regeneration," *J Mol CataB: Enzym*, 2003;24-25:39-52.
Meyer, J., "[FeFe] hydrogenases and their evolution: a genomic perspective," *Cellular and Molecular Life Sciences*, 2007;64:1063-1084.
Mishra et al., "Molecular cloning, characterization, and overexpression of a novel [Fe]-hydrogenase isolated from a high rate of hydrogen producing *Enterobacter cloacae* IIT-BT 08," *Biochemical and Biophysical Research Communications*, 2004;324:679-685.
Morimoto et al., "Overexpression of a hydrogenase gene in *Clostridium paraputrificum* to enhance hydrogen gas production," *FEMS Microbiology Letters*, 2005;246:229-234.
Nicolet et al., "Fe-only hydrogenases: structure, function and evolution," *J Inorg Biochem*, 2002;91:1-8.

(56) References Cited

OTHER PUBLICATIONS

Nicolet et al., "Crystallographic and FTIR Spectroscopic Evidence of Changes in Fe Coordination Upon Reduction of the Active Site of the Fe-Only Hydrogenase from *Desulfovibrio desulfuricans*," *J. American Chemical Society*, 2001; 123:1596-1601.

Nicolet et al., "A novel FeS cluster in Fe-only hydrogenases," *Trends in Biochemical Sciences*, 2000;25:138-143.

Nicolet et al., "*Desulfovibrio desulfuricans* iron hydrogenase: the structure shows unusual coordination to an active site Fe binuclear center," *Structure with Folding and Design*, 1999;7:13-23.

Paschos et al., "Carbamoylphosphate requirement for synthesis of the active center of [NiFe]-hydrogenases," *FEBS Lett*, 2001;488:9-12.

Pedroni et al. "Characterization of the lucus encoding the [Ni—Fe] sulfhydrogenase from the archaeon *Pyrococcus furiosus*: evidence for a relationship to bacterial sulfite reductases". 1995. *Microbiology*. 141(2):449-458).

Peters et al., "X-ray Crystal Structure of the Fe-Only Hydrogenase (CpI) from *Clostridium pasteurianum* to 1.8 Angstrom Resolution," *Science*, 1998;282:1853-1858.

Pierik et al., "Carbon Monoxide and Cyanide as Intrinsic Ligands to Iron in the Active Site of [NiFe]-Hydrogenases: $NiFe(CN)_2CO$, Biology's Way to Activate $H_2$," *J of Biological Chemistry*, 1999;274(6):3331-3337.

Porthun et al., "Expression of a functional NAD-reducing [NiFe] hydrogenase from the gram-positive *Rhodococcus opacus* in the gram-negative *Ralstonia eutropha*," *Arch Microbiol*, 2002;177:159-166.

Posewitz et al., "Discovery of Two Novel Radical *S*-Adenosylmethionine Proteins Required for the Assembly of an Active [Fe] Hydrogenase," *J of Biological Chemistry*, 2004;279(24):25711-25720.

Przybyla et al., "Structure-function relationships among the nickel-containing hydrogenases," *FEMS Microbiology Reviews*, 1992;88:109-135.

Qazi et al., "Development of *gfp* Vectors for Expression in *Listeria monocytogenes* and Other Low G+C Gram Positive Bacteria," *Microb Ecol*, 2001;41:301-309.

Rousset et al., "Heterologous Expression of the *Desulfovibrio gigas* [NiFe] Hydrogenase in *Desulfovibrio fructosovorans* MR400," *J of Bacteriology*, 1998;180(18):4982-4986.

Rygus et al., "Molecular cloning, structure, promoters and regulatory elements for transcription of the *Bacillus megaterium* encoded regulon for xylose utilization," *Arch Microbiol.*, 1991;155:535-542.

Sambrook et al., *Molecular Cloning: A Laboratory Manual, Books 1-3*, $2^{nd}$ ed. Cold Spring Harbor Laboratory Press, Cold Spring Harbor, NY, 1989; title page, publisher's page and table of contents only: 30 pgs.

Sapra et al., "A simple energy-conserving system: Proton reduction coupled to proton translocation," *PNAS USA*, 2003;100(13):7545-50.

Skerra and Schmidt, "Applications of a peptide ligand for streptavidin: the *Strep*-tag," *Biomol Eng.*, 1999;16:79-86.

Studier, F.W., "Protein production by auto-induction in hih-density shaking cultures," *Protein Expr Purif*, 2005;41:207-234.

Tatusova et al., "BLAST 2 Sequences, a new tool for comparing protein and nucleotide sequences," *FEMS Microbiol Lett.*, May 15, 1999; 174(2):247-50.

Terpe, "Overview of bacterial expression systems for heterologous protein production: from molecular and biochemical fundamentals to commercial systems," *Appl Microbiol Biotechnol*, 2006;72:211-222.

Tye et al., "De Novo Design of Synthetic Di-Iron(I) Complexes as Structural Models of the Reduced Form of Iron—Iron Hydrogenase," *Inorg Chem.*, 2006;45:1552-1559.

Verhagen et al., "*Pyrococcus furiosis*: Large-scale Cultivation and Enzyme Purification," *Hyperthermophilic Enzymes*, 2001;PT A 330:25-30.

Vignais et al., "Classificatioin and phylogeny of hydrogenases," *FEMS Microbiology Reviews*, 2001;25:455-501.

Vignais and Billoud, "Occurrence, Classification, and Biological Function of Hydrogenases: An Overview," *Chem Rev*, 2007;108:4206-4272.

Volbeda et al., "Structure of the [NiFe] Hydrogenase Active Site: Evidence for Biologically Uncommon Fe Ligands," *J of the American Chemical Society*, 1996;118:12989-12996.

Volbeda and Fontecilla-Camps, "The active site and catalytic mechanism of NiFe hydrogenases," *Dalton Transactions*, 2003;4030-4038.

Woodward et al., "In vitro hydrogen production by glucose dehydrogenase and hydrogenase," *Nature Biotechnology*, 1996;14:872-874.

Zhang et al., "High-Yield Hydrogen Production from Starch and Water by a Synthetic Enzymatic Pathway," *PloS One* 2, 2007;e456.

Zilberman et al., "Theoretical Studies of [FeFe]-Hydrogenase: Infrared Fingerprints of the Dithiol-Bridging Ligand in the Active Site," *Inorg Chem.*, 2007;46(4):1153-1161.

International Patent Application No. PCT/US2008/013449, filed Dec. 5, 2008; International Preliminary Report on Patentability issued Jun. 8, 2010; 8 pages.

Massanz et al., "Subforms and In Vitro Reconstitution of the NAD-Reducing Hydrogenase of *Alcaligenes eutrophus*" *J of Bacteriology*, Mar. 1998; 180(5):1023-9.

Schneider et al., "Effect of nickel on activity and subunit composition of purified hydrogenase from *Nocardia opaca* 1b" *J. Biochem.*, 1984; 138:533-41.

Umeda et al., "Conjugal Transfer of Hydrogen-Oxidizing Ability of *Alcaligenes* Hydrogenophilus to *Pseudomonas oxalaticus*" *Biochem and Biophys Research Communications*, 1986; 137(1):108-13.

Yagi et al., "Isolation of Hydrogen-Oxidation Gene from *Alcaligenes* Hydrogenophilus and its Expression in *Pseudomonas oxalaticus*" *Biochem and Biophys Research Communications*, 1986; 137(1):114-9.

Zaborosch et al., "EPR and Mössbauer Spectroscopic Studies on the Tetrameric, NAD-Linked Hydrogenase of *Nocardia* Opaca 1b and its Two Dimers: 1. The Beta-Delta-Dimer—A Prototype of a Simple Hydrogenase" *Biometals*, 1995; 8(2):149-62.

\* cited by examiner

Hours denote time after anaerobic switch

FIG 7A

Coding regions and deduced polypeptide sequences of *Pyrococcus furiosus* DSM3638 used herein. All *Pyrococcus furiosus* DNA and predicted protein sequences were derived from the deposited Genbank sequence NC_003413. Accession numbers below refer to specific sections of this DNA sequence or the translated open reading frames encoded therein.

AE010204 – The following genbank sequence under this accession number encompasses the entire soluble Hydrogenase I operon (PF0891-PF0894). Below are the extracted individual gene sequences

```
   1 aggggttttt aaccttggt tttcaatttt cgggtttaaa aaggcttttt tatctccctc
  61 accaacttta gactgggaaa caaaaatgtt cactaacgaa aatttgagga gtattggtca
 121 attatgctca ttgggaggtg gtttgtgtga ggtatgttaa gttacccaag gaaaacactt
 181 acgagttttt ggaaagactt aaagactggg ggaagcttta cgctccagta aaaatttcgg
 241 acaagttcta tgacttcagg gagattgatg atgttagaaa gatagaattc cactacaaca
 301 ggacaataat gccacctaag aagttcttct tcaagccgag ggaaaagctc tttgagttcg
 361 acatttcaaa accagaatac agggaggtaa tagaggaagt tgaaccattt attatatttg
 421 gagtccacgc gtgtgacata tatggcctaa agatcctaga cacggtatac cttgatgagt
 481 tccccgacaa gtactacaag gtgaggagag agaagggat aatcattgga ataagctgta
 541 tgccagatga atattgcttc tgtaacttaa gagaaacaga cttcgctgat gatggttttg
 601 acttgttctt ccatgaactg cccgatggat ggttggtaag ggttggcact ccaactgggc
 661 acaggcttgt tgacaagaac ataaagctct ttgaagaggt aacggacaag gatatctgtg
 721 catttagaga ttttgaaaag aggagacagc aagcattcaa ataccacgaa gactggggca
 781 acttgaggta tcttctcgag ttggaaatgg aacatccaat gtgggatgag gaggcagata
 841 agtgcttggc ttgtggaata tgtaacacca catgcccaac gtgtagatgc tatgaagttc
 901 aggatattgt aaacctagat ggagttactg gatacaggga aagaagatgg gattcttgtc
 961 agttcagaag tcatggctta gttgctgggg gccaacactt caggcccaca aagaaggatc
1021 gctttaggaa cagataccta tgtaagaacg catataacga aaagcttgga ttaagctact
1081 gtgtcggttg tggaaggtgt actgcattct gtccagccaa tataagtttt gtaggcaatc
1141 ttagaaggat tttaggactt gaggagaaca aatgtccccc aacggttagt gaggagattc
1201 caaagagagg atttgcatat tcctctaaca ttagaggtga tggagtatga tgttgccaaa
1261 agagattatg atgccaaatg ataatccgta tgcccttcat agagtcaaag ttctaaaggt
1321 ttactccttg acggaaacgg aaaagctttt cctctttaga tttgaggatc ccgagttggc
1381 agagaagtgg acgttcaaac ctggacagtt tgtccagctg acgatacctg gagttggaga
1441 ggttcccata agtatatgct cttctccaat gaggaaagga ttctttgagc tctgtataag
1501 aaaggcagga agggtcacaa ctgttgtcca tagactaaag cctgcgata ctgttcttgt
1561 gagagggcct tacggtaatg gattcccagt ggatgagtgg gaaggaatgg atctactatt
1621 aatagctgct ggccttggaa ctgcacctct taggagcgtc tttctctatg caatggacaa
1681 caggtggaag tatggaaaca ttaccttcat aaacaccgca cgttatggga aggatctcct
1741 cttctacaag gagctggagg caatgaaaga cctagctgag gctgaaaacg tgaaaatcat
1801 ccagagcgtc actagggatc caaactggcc gggcctaaag ggtaggccac agcagttcat
1861 cgttgaggcc aacacaaatc caagaaacac tgcagttgca atctgtgggc ctcctagaat
1921 gtataagtca gtgtttgagg ccctcatcaa ctacggttat cgcccagaga acatcttcgt
1981 gacattggag agaagaatga aatgtggaat cgggaagtgc ggccactgca acgtcggaac
2041 gagcacgagc tggaagtaca tctgtaaaga tggaccagtc ttcacgtact tcgacatagt
2101 ttcaaccccca ggactgctgg actgaggtga ggaaaatggg aaaagttagg attggatttt
2161 acgcattaac ctcgtgctac ggctgtcaat tgcagctagc tatgatggac gagttattac
2221 aacttatccc aaatgctgaa atagtttgct ggttcatgat tgatagagat agcattgagg
2281 atgaaaaggt cgacatagct tttatagaag gaagcgtttc aactgaggaa gaagttgaac
2341 tcgtgaaaaa aattagggag aatgcaaaga tcgtcgttgc ggttggagct tgtgctgttc
```

FIG 7B

```
2401 aaggaggagt tcagagctgg agtgaaaagc cattagaaga gctctggaag aaggtttatg
2461 gagacgcaaa agtcaagttc caaccgaaga aggctgaacc agtttcaaaa tacataaaag
2521 ttgactacaa catctacggt tgcccaccag agaagaagga cttcctctac gccctgggaa
2581 cattcttgat tggttcatgg ccagaggata tagattatcc agtttgtcta gaatgtaggc
2641 tcaatggaca tccatgtatc cttcttgaga aaggagaacc ctgtctaggt ccagtaacaa
2701 gggcaggatg taacgcgaga tgtccaggat ttggagttgc gtgtatagga tgcagagggg
2761 caatagggta cgatgtagct tggttcgact ctctagctaa ggtgttcaag gagaagggga
2821 tgacaaaaga ggagataatt gagagaatga aaatgttcaa tggacatgat gagagggttg
2881 agaaaatggt tgaaaaaata ttctcaggtg gtgaacaatg aagaacctct atcttccaat
2941 caccattgat catatagcaa gagttgaggg gaagggtggt gtggagataa taattgggga
3001 tgatggagtc aaggaggtca agctaaacat aattgaaggg cccagattct ttgaggccat
3061 aactattggg aagaagcttg aggaagctct ggccatttac ccgagaatat gctcattctg
3121 ttcagccgcc cacaagttaa ccgcattaga ggctgcagaa aaggccgtcg gttttgtccc
3181 aagggaagag atacaggccc ttagagaagt actatacatc ggagacatga tagagagtca
3241 tgcccttcac ctatatcttc tagttcttcc cgactacagg ggctactcga gcccacttaa
3301 gatggtgaat gaatacaaga gggagataga gatagcccct aagctgaaga accttggcac
3361 ctggatgatg gacattctag ggtcaagagc catacaccaa gaaaatgcgg ttttgggcgg
3421 attcggaaag ctccctgaga agagtgtcct tgagaaaatg aaagccgagc ttagggaagc
3481 cctaccactt gccgagtata cttttgagtt atttgcaaag cttgagcagt acagcgaagt
3541 tgaaggcgca ataacacact tggccgtgaa gccgagggga gatgcttatg gaatttatgg
3601 agattacata aaggcaagtg atggggagga gttcccaagt gaaaagtaca gagattatat
3661 aaaggagttc gtcgttgaac acagttttgc aaagcacagt cactacaagg gcagaccgtt
3721 catggttggg gctatatcta gagttattaa caatgctgac ctcctatacg gcaaggccaa
3781 ggagctgtat gaggcaaaca aagaccatt aaagggaaca aatccgtttg caaataactt
3841 agcccaggcc ctcgaaatag tttacttat agagagggca atagatctgc tcgacgaggc
3901 tctcgccaag tggccaatta agcccaggga tgaagttgag ataaaggacg gctttggtgt
3961 ctcaacgact gaggctccaa ggggaatctt agtctatgcc ctcaaagttg agaatggaag
4021 ggtttcttat gccgacataa taacacctac agcattcaac ttgcaatga tggaagaaca
4081 tgtaagaatg atggcagaaa agcactacaa tgacgatcca gaaaggttaa agatactggc
4141 tgagatggtt gttagggctt atgatccatg catatcttgc tcagtccacg tggttagact
4201 ttaatccttt ttatctattt ttgttgagta cttgtggaga ttctcattca catcacaata
4261 ggagagctct tctcttgagg agatgataac aatgccttc tctttgagaa tttcgaggat
4321 agactttagg actttatgtt ttgagtcctc atcaatggca acaactggat cgtcaagaac
4381 ataaatctcg gcattcacta gcaaggtgga tgccaattga actcttcaa ttgttccctg
4441 ggaaagctct cccagcttct tctttaaatc caagacctcc acggattcaa gtgcatccat
4501 aatttcattt ttattaactt taactccata aagactggcc actgctttta aataatcctc
4561 aacacttatt ttcctggca cgattatttc ttcaggaagg aaaaatattt tgcccttaac
4621 ttttgttata gggactccat tataaattat ttctcccttg aggggtttca aatatgttga
4681 tattgttttt aaaagtgtgg ttttttcctat cccatttgga ccgtggaagt tcacgacatt
4741 acctttctct atggtcattg ttattctttc gagaactggt ttatcataac caacactaag
4801 atctctaatc tcaagtttca ttcccatccc tcccaaattc ctattattcc agaaatagat
4861 actaaaagga gggggattgc agcaatacca tttcctttgc taaccaatat tattcctata
4921 atgaagggag ctatgaatcc aagaatccag ccacacaact ttctaattga actaacttcc
4981 actgtcggtt cccacacaaa cattaatttc ttgaaatcta tagttacttt tacaggtgtc
5041 attagggaga gatattgaag aacttcatga acatataccg ctccaactag tggcaacact
5101 acatttttca ctatagattt catatagcaa ttagtgaatt ccctgttat tttacctata
5161 agaaaactaa tccaaagtac tagagctaca agaaatccta catatatgct taccattttt
5221 atgaaattta aaaattgcct agacatttct tatcaccctt tctagcttta tcctcacaaa
5281 atatgcaagt ggagagataa gaattaacaa gggaattacc cacataggaa taatttttcct
5341 tataataaat ggagcaccca ggataattag atacagaaat aggaagctgt ttctttcaaa
5401 acttggcaat gttattgata atacaactct acttatcgct aacatgaaaa ataagatata
5461 tagtgtccct aaatactccc tttcaagaat tgccaaggaa taaaatgtca acggaacaat
5521 tagcgaaatc aagaagagta gaatttcctt tattagtctt cttaaatagt tctctggttt
5581 tagatagtgg agataggcta tataagaatc aacataacta tcaccaacca ggaataaagg
5641 ccaaatcata gggcagtta tgcatatagt aactagcgta cttgcaatcc tctctataat
5701 atagaatttt tgcttatcta caatgatatg taatggtaac aaggctttaa atgctccaac
```

FIG 7C

```
5761 tccacaccca aatttcactc cttgcattct caggtgctgg gccataagtg tgaaaactat
5821 agagagaata atagcgattc ccctaatttc aaaggaaagg gtagaaatat agatgtttct
5881 aactagataa actcttatca gcctatcttt tagaacagag gctaccaagt atgcaattac
5941 gaggatgata taacctatca gagtcatctt tctaccacta attgctagga gaccaagaat
6001 tgtggctatg cacttaattt taaatgaaac agacagtgga agtatagata aagcggcaaa
6061 tacaataata ttggagggca aaaaacctgg gtaaagatag gagcaactaa ggatggaggg
6121 gagatttata actactgaga caaatagcac aatgagatca gtgtcgggtc tatatttgag
6181 gatcactcca gttttcttag gatcaaagga atttgaaaag agaagtggaa ttgcacctaa
6241 caaggcaaaa actattatgt cttcgataat cttaccttt aagaagattg ttaatggtat
6301 aagagagatc atcccagcga gataattata gttttttata gataccaaaa tatggtatct
6361 taatatttcc actattctca ctttcattac ctcctaaatc ttctaaggat ttttattgag
6421 ctcacaaccc ccaaaagata acataggatt cttgttattg gagttacctt tactgagaca
6481 taatatggct catttattgc attaaataga atgccctgcc cgggtggtat tttatttgta
6541 gtcaaaatga agattgccaa caaataacta actaaaatag aaaatgaaag agctaagggt
6601 attgccgaaa ccaaggctag ggcaaaaaat agtttttag atcttaccac acgaaatcac
6661 ctcctatcgc agttggaagc gctggatctg taggattatc tggcatacat tcacagaggc
6721 atttgatctc aactcctgaa atagttgctt ttgtctgtgg cccacagtcg gacattatac
6781 ctccacctgt actacacaag attgggcact ccctacaata gccatagcac atctttgtgt
6841 agtatgtcgc tgtagcagct attattacaa ataaaactat tacccacaat cctacaccat
6901 aatactttg ttttctttaa tacatatata atcaccattt aaattatgct actataaatt
6961 ttataaaatt ttcgagaata tcactataac agaagctatt aaaatataat aattattcct
7021 aatttgatcg acgatactgt caggataact ggggtatcac ctcttgaagc cattcagtca
7081 catcaccagg cggtccacca aaccgagaat gaattctaac aaaattatac cagaatgaaa
7141 acagaaaaac aaacctgtga accctcctcc agtctctagc cctgaagtta ttccagaaac
7201 gctttgttct ctctttaaca gtcctaaacc agcgctcaac acagttcctc ggcccgaaag
7261 tcacatgcag ataatccagc ccgagagatt taaacgctga tttataccac ggccctttgt
7321 caaccaggaa aattggctgt ccctcgcagg atttcaaaac aactagaatg aagtccctgg
7381 caatccacca gttcctaacg cttgtaatcc atactgctag gatttctttg ctctcaacgt
7441 cgattgcagc ccagagaaat ctcttctggc cgttgatctt tatcactgtc tcgtcaattg
7501 cgatgaagtt tctctgtttt ttgactgcga ggattttcgg ctggtaaact gctttcgcga
7561 attttggac tgtttcccag actgttgtgt ggctgattc gaggattgtt cctacctgtc
7621 tgtaacttag tccgtgcagg tacaggttta ttgccctggt tttcttttt gctgggattt
7681 tgttccggcg aaaggttttt aagactgaaa ccagtaagta gataatggtt tcagtcctca
7741 tttctctccc cttttctgaa gaggtatcag aaacttaaac ctaacgtccc actgcttatc
7801 ctgacagtgt cttgatcgac tttagaaaca tttttattct tgtttatgtt cccttagact
7861 atgagcacca ggggagactt gatcagaatt ttaggtgaga tagaggaaaa gatgaacgaa
7921 ctgaaaatgg atggctttaa ccctgacata atccttttg gcagagaggc ttataacttt
7981 ctttcaaatc tcttaaaaaa ggaaatgaa gaggaagggc cttttacgca tgtctctaat
8041 atcaagatag aaattcttga ggaattagga ggagacgcag ttgttataga ttcaaaagtc
8101 ctaggcctag ttcctggggc cgcaaagaga atcaaaatta ttaagtagcg ctttccaaag
8161 tacaggagat gctcacttcc tccttagcta ggattagacc aaaatataac ataaaggagt
8221 tgagtgttgc ccaggagggg actagcctcc ttgatattaa taaagggtct ctgcgaagag
8281 ttttgtcctg tatcatatta aagagttcgt taattcttgc atctgcaagt tgaaggccta
8341 accttgtccg agatttggct gtaatgactt taacagagta atgtttaacc aaaaaaagaa
8401 gactttaaaa ccttccactc acaataagta gacgagtcaa caacaatttg agggaaaaga
8461 catgggaaat gaaggtgtcc accccacct gcggaaaagg ttttggagag agatgggtat
8521 aaatgcagaa tttgtgatca cagctatctc gatattcatt acaaggacgg gaatgtagag
8581 aacaagaatt tagaaaattt gatagtttg tgcaaacaat gtcattatcg acttcaccaa
8641 aaggaaagga tggaaagcat taaacaagct ttcgaggatt tcctcgatga actttctaaa
8701 aatcctattg aagttgttat agatttcagt ttcaaaaaaa ttgtagagag taatgaagaa
8761 aaaatccgaa gagagattat acagggattt actcgtcctt ttggtgttat atcaaggatc
8821 caagagaaag ttagggatgc aataatgaag gaaatcgagg aggaaataga aaaagagcaa
8881 gcaagtactc ctgaacatct ccgaaaggtt gttcttgaaa gaaataatta tagatgttca
8941 gtgtgcggat acggatattt agaggttcac catgtggatg gaaatattct aaataacacc
9001 ttggataatt tagtaaccct ctgtagaagg tgtcatcgta aagtccatta tcatccaagt
9061 tttcatacaa caccggagga tatggacaaa tgtattagaa gttttcatca tgagtttat
```

FIG 7D

```
 9121 agtacgatct atgaaataat gaagaacaaa aagggaaaca ttagaataag cattaaattc
 9181 gatcaactag gtgttaaagg tgtaaaaatt agtagagctc aatttaaaag aattaatggg
 9241 ctctttaatc atgaagtcat aaatgatggt attttttaagc agtgggaaag agaaattaag
 9301 aattatttaa gccgacttga atgggaacag caaaaagaaa tatatagaaa tgtatacttc
 9361 ttgctagaat gtattttgcc taaagattca tttgaagcgt ttgttaacct tgcaaggaaa
 9421 ggaaaatttg atagaagaac attaagggaa gcaaagaaag tactaaagaa ctcaattaaa
 9481 taattttttgt aattttttccc tggaaataca gctcctattc tactattttt aaagtgctgt
 9541 cttcttcttt tataaaccca tattttttgt tactcttttag gaagttcttt attatttcac
 9601 aaagctcagg gttgagagat cttttcagtt acacacttct tattattcct aaagtacgaa
 9661 tagaacttag gacttccact ggagtggtat actccaagta tcttcttgtt tctcagcttt
 9721 tcagctatgt cgggaaaaat cttcttgtat atttttttct tttagccaa ctttttcata
 9781 atttcgtagg actctcgccc caaacataaa attaagtccc ccgctatgaa atcaagtacg
 9841 cgacctaaaa acttccctat gcagttttgt agggtttctg caggtagtgg gactctaaca
 9901 ttttcactct cacagtatac taattctcca aacagaattg tacttcctcc ggtaaattaa
 9961 aacagtcttt gctttctttta agaattctag tgtgtttgca aagtatttat agtggaaagg
10021 atagttacgg tagttcttga taaattctga gacccatgtg tcatggattt ctttaaaagc
10081 tttgatggcg ttactttttgc tatattctga agtaaataat ccatgctttt tcaggatgtc
10141 tgtgtagtaa agtctttcaa atggtaagtg ggggcctgga tttattccaa aaataccaat
10201 ttttgctttt tctctggaag gctcgccttg aagtgtagaa aggattagaa cccttggaat
10261 aatgccctca tccttggaat tctttatacc ttcacacttc tccttctctg agcataagat
10321 catctcactg cctaactcca agaatgcctc aggcatcatg gtaatgattt tacacagaga
10381 atttaataat aatttcggat ttctcaatgc ttcttaattg agaagctaca ttttgaaaat
10441 tgagaaaaat caaaggtacc agtgtgtctc agaaaagtga atat
```

PF0891     AE010204.1 gtgagggtatgttaagttacccaaggaaaacacttacgagttttttggaaagacttaaagactgggggaagctttacgctccagtaaa
aatttcggacaagttctatgacttcaggggagattgatgatgttagaaagatagaattccactacaacaggacaataatgccacctaa
gaagttcttcttcaagccgagggaaaagctctttgagttcgacatttcaaaaccagaatacagggaggtaatagaggaagttgaa
ccatttattatatttggagtccacgcgtgtgacatatatggcctaaagatcctagacacggtataccttgatgagttccccgacaagt
actacaaggtgaggagagagaagggggataatcattggaataagctgtatgccagatgaatattgcttctgtaacttaagagaaac
agacttcgctgatgatggttttgacttgttcttccatgaactgcccgatggatggttggtaaggggttggcactccaactgggcacag
gcttgttgacaagaacataaagctctttgaagaggtaacggacaaggatatctgtgcatttagagattttgaaaagaggagacagc
aagcattcaaataccacgaagactggggcaacttgaggtatcttctcgagttggaaatggaacatccaatgtgggatgaggagg
cagataagtgcttggccttgtggaatatgtaacaccacatgcccaacgtgtagatgctatgaagttcaggatattgtaaacctagatg
gagttactggatacagggaaagaagatgggatttcttgtcagttcagaagtcatggcttagttgctgggggccacaacttcaggcc
cacaaagaaggatcgcttlaggaacagatacctctgtaagaacgcatataacgaaaagcttggattaagctactgtgtcggttgtg
gaaggtgtactgcattctgtccagccaatataagttttgtaggcaatcttagaaggatttlaggacttgaggagaacaaatgtcccc
caacggttagtgaggagattccaaagagaggatttgcatattcctctaacattagaggtgatggagtatga

PF0891     AAL81015

MRYVKLPKENTYEFLERLKDWGKLYAPVKISDKFYDFREIDDVRKIEFHYNRTIMPPKKFFFKPREKLFEF
DISKPEYREVIEEVEPFIIFGVHACDIYGLKILDTVYLDEFPDKYYKVRREKGIIIGISCMPDEYCFCNLR
ETDFADDGFDLFFHELPDGWLVRVGTPTGHRLVDKNIKLFEEVTDKDICAFRDFEKRRQQAFKYHEDWGNL
RYLLELEMEHPMWDEEADKCLACGICNTTCPTCRCYEVQDIVNLDGVTGYRERRWDSCQFRSHGLVAGGHN
FRPTKKDRFRNRYLCKNAYNEKLGLSYCVGCGRCTAFCPANISFVGNLRRILGLEENKCPPTVSEEIPKRG
FAYSSNIRGDGV

FIG 7E

PF0892   AE010204.1 atgatgttgccaaaagagattatgatgccaaatgataatccgtatgcccttcatagagtcaaagttctaaaggtttactccttgacgg
aaacggaaaagctttcctctttagatttgaggatcccgagttggcagagaagtggacgttcaaacctggacagtttgtccagctg
acgatacctggagttggagaggttcccataagtatatgctcttctccaatgaggaaaggattctttgagctctgtataagaaaggca
ggaagggtcacaactgttgtccatagactaaagcctggcgatactgttcttgtgagagggccttacggtaatggattcccagtgga
tgagtgggaaggaatggatctactattaatagctgctggccttggaactgcacctcttaggagcgtcttctctatgcaatggacaa
caggtggaagtatggaaacattaccttcataaacaccgcacgttatgggaaggatctcctcttctacaaggagctggaggcaatg
aaagacctagctgaggctgaaaacgtgaaaatcatccagagcgtcactagggatccaaactggccgggcctaaagggtaggc
cacagcagttcatcgttgaggccaacacaaatccaaagaacactgcagttgcaatctgtgggcctcctagaatgtataagtcagt
gtttgaggccctcatcaactacggttatcgcccagagaacatcttcgtgacattggagagaagaatgaaatgtggaatcggggaag
tgcggccactgcaacgtcggaacgagcacgagctggaagtacatctgtaaagatggaccagtcttcacgtacttcgacatagttt
caaccccaggactgctggactga

PF0892   AAL81016

MMLPKEIMMPNDNPYALHRVKVLKVYSLTETEKLFLFRFEDPELAEKWTFKPGQFVQLTIPGVGEVPISIC
SSPMRKGFFELCIRKAGRVTTVVHRLKPGDTVLVRGPYGNGFPVDEWEGMDLLLIAAGLGTAPLRSVFLYA
MDNRWKYGNITFINTARYGKDLLFYKELEAMKDLAEAENVKIIQSVTRDPNWPGLKGRPQQFIVEANTNPK
NTAVAICGPPRMYKSVFEALINYGYRPENIFVTLERRMKCGIGKCGHCNVGTSTSWKYICKDGPVFTYFDI
VSTPGLLD

PF0893   AE010204.1 atgggaaaagttaggattggattttacgcattaacctcgtgctacggctgtcaattgcagctagctatgatggacgagttattacaac
ttatcccaaatgctgaaatagtttgctggttcatgattgatagagatagcattgaggatgaaaaggtcgacatagctttatagaagg
aagcgtttcaactgaggaagaagttgaactcgtgaaaaaaattaggagaatgcaaagatcgtcgttgcggttggagcttgtgct
gttcaaggaggagttcagagctggagtgaaaagccattagaagagctctggaagaaggtttatggagacgcaaaagtcaagttc
caaccgaagaaggctgaaccagtttcaaaatacataaaagttgactacaacatctacggttgcccaccagagaagaaggacttc
ctctacgccctggggaacattcttgattggtcatggccagaggatatagattatccagtttgtctagaatgtaggctcaatggacatc
catgtatccttcttgagaaaggagaaccctgtctaggtccagtaacaagggcaggatgtaacgcgagatgtccaggattggagt
tgcgtgtataggatgcagaggggcaatagggtacgatgtagcttggttcgactctctagctaaggtgttcaaggagaagggat
gacaaaagaggagataattgagagaatgaaaatgttcaatggacatgatgagagggttgagaaatggttgaaaaaatattctca
ggtggtgaacaatga

PF0893   AAL81017

MGKVRIGFYALTSCYGCQLQLAMMDELLQLIPNAEIVCWFMIDRDSIEDEKVDIAFIEGSVSTEEEVELVK
KIRENAKIVVAVGACAVQGGVQSWSEKPLEELWKKVYGDAKVKFQPKKAEPVSKYIKVDYNIYGCPPEKKD
FLYALGTFLIGSWPEDIDYPVCLECRLNGHPCILLEKGEPCLGPVTRAGCNARCPGFGVACIGCRGAIGYD
VAWFDSLAKVFKEKGMTKEEIIERMKMFNGHDERVEKMVEKIFSGGEQ

FIG 7F

PF0894    AE010204.1 atgaagaacctctatcttccaatcaccattgatcatatagcaagagttgaggggaaggggtggtgtggagataataattggggatga
tggagtcaaggaggtcaagctaaacataattgaagggcccagattctttgaggccataactattgggaagaagcttgaggaagct
ctggccatttacccgagaatatgctcattctgttcagccgcccacaagttaaccgcattagaggctgcagaaaaggccgtcggttt
tgtcccaagggaagagatacaggcccttagagaagtactatacatcggagacatgatagagagtcatgcccttcacctatatcttc
tagttcttcccgactacagggggctactcgagcccacttaagatggtgaatgaatacaagagggagatagagatagcccttaagct
gaagaaccttggcacctggatgatggacattctagggtcaagagccatacaccaagaaaatgcggttttgggcggattcggaaa
gctccctgagaagagtgtccttgagaaaatgaaagccgagcttagggaagcectaccacttgccgagtatactttgagttatttg
caaagcttgagcagtacagcgaagttgaagggccaataacacacttggccgtgaagccgaggggagatgcttatggaattatg
gagattacataaaggcaagtgatggggaggagttcccaagtgaaaagtacagagattatataaaggagttcgtcgttgaacaca
gttttgcaaagcacagtcactacaagggcagaccccttcatggttggggctatatctagagttattaacaatgctgacctcctatacg
gcaaggccaaggagctgtatgaggcaaacaaagacctattaaagggaacaaatccgtttgcaaataacttagcccaggccctc
gaaatagtttactttatagagagggcaatagatctgctcgacgaggctctcgccaagtggccaattaagcccaggggatgaagttg
agataaaggacggctttggtgtctcaacgactgaggctccaaggggaatcttagtctatgccctcaaagttgagaatggaagggt
ttcttatgccgacataataacacctacagcattcaacttggcaatgatggaagaacatgtaagaatgatggcagaaaagcactaca
atgacgatccagaaaggttaaagatactggctgagatggttgttagggcttatgatccatgcatatcttgctcagtccacgtggtta
gactttaa

PF0894    AAL81018

MKNLYLPITIDHIARVEGKGGVEIIIGDDGVKEVKLNIIEGPRFFEAITIGKKLEEALAIYPRICSFCSAA
HKLTALEAAEKAVGFVPREEIQALREVLYIGDMIESHALHLYLLVLPDYRGYSSPLKMVNEYKREIEIALK
LKNLGTWMMDILGSRAIHQENAVLGGFGKLPEKSVLEKMKAELREALPLAEYTFELFAKLEQYSEVEGPIT
HLAVKPRGDAYGIYGDYIKASDGEEFPSEKYRDYIKEFVVEHSFAKHSHYKGRPFMVGAISRVINNADLLY
GKAKELYEANKDLLKGTNPFANNLAQALEIVYFIERAIDLLDEALAKWPIKPRDEVEIKDGFGVSTTEAPR
GILVYALKVENGRVSYADIITPTAFNLAMMEEHVRMMAEKHYNDDPERLKILAEMVVRAYDPCISCSVHVV
RL

AE010177.1 – The following Genbank sequence under this accession number contains both PF0548 and PF0549. Below are the extracted individual gene sequences.

```
  1 agtaataaaa ctacataaaa cttttaccct agttcccatc aggtcgttag aattattaag
 61 tacttaaatt ttttgattgg ttggtggttg ttatgaactt tcagcaggaa atcctgatca
121 taaaatccga aatctatccg atagtcagca aacactaccc gaaaacact cgcagggaag
181 taatcagcct ctacgacctg ataaccttcg caatactagc ccacctgcac ttcggaggag
241 tttacaaaca cgcttacgga gccctaatcg aggaaatgaa actgttcccc aaaatcaggt
301 acaacaaact aacagaacgc ttgaacaggc acgaaaaact tctgctccta gcgcaggaag
361 aattattcaa aaaacacgcc agagaatacg ttagaatact ggactcaaaa cccattcaga
421 ccaaggagtt ggccagaaaa aacaggaagg ataaggaggg ttcttcagaa atcatctctg
481 aaaagcccgc agttgggttt gttccctcta aaaaagttt tactatgggt acaagctgac
541 ctgttactct gatgggaacc tgttggcttt gctgtccgtt gatccggcaa acaagcatga
```

FIG 7G

```
 601 tgtgagtgtt gtcagggaaa agttctgggt gattgttgag gagttttccg gctgttttct
 661 gtttttggat aagggttacg ttagtagaga acttcaggag gaattcctga agtttggcgt
 721 tgtttacacg ccggtgaagc gggagaatca ggttagtaat ctggaggaga agaagtttta
 781 caagtacttg tctgactttc gcagaaggat tgagactttg ttttcgaagt tttctgagtt
 841 tcttctgagg ccgagcagga gtgttagttt gaggggtta gctgtcagga ttttaggggc
 901 gattctggcc gtgaatctgg acagattata caacttcaca gatggtggga actagggtta
 961 aaactttttg atcgtcaatt aatcataata atggcaaaag tttacttagt ggattattat
1021 gccacttatg atcttttcat aggggttagt atggaaaacc atatcaagat attgaaggac
1081 atgaagtggg gggtaagaaa tggttcgtgt tacgctcgtt aactatacaa agaggcccct
1141 agaaacaata acttgggctg cccttataag ctattggggg gaatggagca cggaatcatt
1201 tgaaggata agtgagaatg atgtagaaaa gcatctccct cggatattgg gttatggtca
1261 tgagagcatt ttggagcatg caacgtttac ttttctcaatc gaaggttgta gtagggtttg
1321 tactcatcaa cttgtgaggc atagaatagc cagctacacc cagcaaagcc agcgttacat
1381 tgttcttgac gaggagaacg ttgaggaaac gtttgtaatt cctgaatcga taaagaaaga
1441 tagagagctt tatgaaaaat ggaagaaggt catggctgag acaataagcc tttacaagga
1501 gagcataaat agggagttc accaggaaga tgctcgattc attcttcctc aagctgtgaa
1561 aacgaagata attgtgacga tgaacttgag agaattgaag cacttctttg gccttagact
1621 atgtgaaagg gctcaatggg agattaggga agttgcatgg aagatgttag aggagatggc
1681 gaagagggat gatataaggc cgataataaa gtgggctaaa cttgggccta ggtgcattca
1741 gtttggctat tgtcccgaga gagatctaat gcctcctggg tgcttaaaga aaactagaaa
1801 aaagtgggaa aaagttgcgg aaagtaagag ctaaattgtt atattgagta aaagcttct
1861 ttctttattt gtctttatgg caaaatccca gaagttcagc tattgaatta gagaactgtt
1921 cgtcactgaa agtaaacttc tatgggattc ttctgaatta tatggtaagg tttggaaaat
1981 tggacataa aagtcttaaa gtttcctttt tcaactctaa actagggtga gctaatggat
2041 actgaaaaac ttatgaaagc cggagaaata gcaaaaaag taagagagaa agctattaaa
2101 cttgctagac ctgggatgtt gttgttagaa cttgcagagt ctatagaaaa gatgataatg
2161 gaacttgggg gtaaacctgc tttcccagta aatttatcaa ttaatgaaat tgcagctcac
2221 tatactcctt acaagggaga tactactgtt ctgaaaggag gggattatct aaagatcgac
2281 gtgggggttc acatagatgg atttatagca gatactgcag ttacagttag agtagggatg
2341 gaagaagatg agcttatgga ggctgccaag gaagcgttaa acgccgcaat ttctgtagct
2401 agggcgggag tggagataaa ggaactagga aaggcaatag aaaatgaaat taggaagaga
2461 ggattcaaac caatagttaa tctaagtggg cacaagatag aaagatacaa gcttcatgca
2521 gggattagca ttccgaacat ttatagaccg catgataact atgttttaaa ggaaggagat
2581 gttttcgcaa ttgagccttt cgctactata ggtgctggtc aagtaattga ggttccccca
2641 accttaatct acatgtacgt tagagatgtt ccagttagag tggcccaagc taggttcctt
2701 ttggctaaga taaaaggga atatggaacc ctacccttg cctataggtg gcttcagaat
2761 gacatgccag aaggacagct taagttggcc ctaaaaaccc tcgaaaaggc tggagctata
2821 tatggctatc cagtgcttaa agaaattaga aatggcattg tggcacaatt tgagcacaca
2881 atcattgttg aaaaggattc tgtgatagtg acgacagaat gagttaaact ttataagttc
2941 tcatgtatca agaaattggg agcgccgggg tagcctagtc agggaaggcg cgggactcga
3001 gatcccgtgg gcgttcgccc gccggggttc aaatcccgc cccggcgcca tttgttaagc
3061 acttggaggt ttgataatat ggcatttcta aaggtagtgt cattggaaga agcaatttca
3121 ataattaata gctttagact tgaaatagga tttgaggaag ttacttagag taaagctctg
3181 gggaggatag ttgcagagga tatttattcc cccttggata ttcctccctt tgatagatcg
3241 accgttgatg ggtatgctgt tagggcggag gatactttta tggccagtga agctaatcca
3301 gtggaactca aagtaattgg agaagttcat gccggagaac aaccttcagt aaagttaagc
3361 aagggagagg cggtctacat tacaacgggg tcaatgatgc cagagaacgc aaatgctgtg
3421 attcctttt aggatgttga gagagaagga gatattataa gaatttataa gcctgcatac
3481 ccaggtttag gagtcatgaa gaaaggaact gacataaaaa agggccaact cttaattaga
3541 agaggaacta agctaacgtt taaagaaact gccctgcttt ctgctgcggg atttttaaaa
3601 gtaaaggtct ttaaaaagcc taaagttgcg gtcataagta cgggaatga aattgttctc
3661 ccaggtgaag agcttaggcc tggccaaata tatgacatca atggtagagc aatagttgat
3721 gccgttaatg aattgggtgg agagggaata ttcgttggga ttgccaggga tgacagagaa
3781 agtctcaaaa aattaatact tcaagcctta gaagttggag atattatcgt tattagtggg
3841 gggcaagtg ggggaataaa agacttaaca gcctcggtaa tagaggaact tggagaggtt
3901 aaagttcatg gaattgcaat tcagccaggt aaacccacaa taatagggt tataaacggt
3961 aagcctgtct ttggcctacc tgggtatccg acaagttgcc taacaaactt caccctctta
```

FIG 7H

```
4021 gttgctcccc tgcttttgag gctacttgga agggaaggaa aaattaagaa ggttaaggcg
4081 aaaattaagc ataaagtatt ttcggtaaag ggaagaagac aattcctccc agttaaactt
4141 gagggagatg tagcggttcc tatcttgaag ggaagcggag cagtcacaag ctttgtggag
4201 gcagatggtt ttgtggaaat tcccgagaat gtagaaagcc ttgatgaggg agaagaagta
4261 acggtaacgt tgttctcgtt ttaggaggtg atagtatggt caaggttaag gttaagtact
4321 ttgctagatt taggcaactt gcaggagttg atgaagagga gatttgagctt ccagagggag
4381 ctagagttag ggacttgata gaagaaataa agaaaagaca tgaaaaattt aaggaggagg
4441 tcttttggaga aggatacgat gaggatgccg atgttaacat tgccgtaaat ggaaggtatg
4501 taagctggga tgaagagtta aaggatgggg atgttgttgg agtatttcct cccgtaagcg
4561 gaggttaaca tttacatact tttacataaa cttctcttct cctgggtcca tctaactcta
4621 caaagagaat gctctgccaa gttcctaaca taagttggcc atttactatt ggaatagtca
4681 cgcttgggcc aagtattata gctctgaggt gagagtgggc gttgttatct atagaatcgt
4741 gtctgtatcc tgcacctttg ggaattaatt ttgagagaat atttttctatg tcgttaagga
4801 gccttggctc gttctcattt actattattc ctgtggtggt atgcctagta tagacaacgg
4861 caattccatt atcgatgcca cttttttctaa cgatttcctg gacttttttcc gttatatcta
4921 ttatttcaac ttctttggaa gtccttatag tgatggtttc aatcatattt cttccctct
4981 agatacctt ttatcatctc cctagcgttt tctatatgct tatttgcctc ttcttcatta
5041 atgtttttta acgtggccct aacagtaaca atgctctcaa aggcctccaa taacctttga
5101 tctgttgtct cttttagaat tcttttttagc attaagtatg cttcgtctat gctctcctct
5161 cttagggttt tcttagatag tccttcgagg attcgatcta gaatgaatat tctatcttgc
5221 aatagcttcc ttcttagtat taatcttctc attgactttc ccctctacca cttttactaa
5281 aagttcggaa gcaagttttg aagcaatacc tctatcttta atattcaaaa caacgtcaat
5341 agcatctcca acacgccaa ttctaatgag ataatgggct aggaatccta aggcaactga
5401 cctgtgccgt tgctattaa ttctttttat tactctaact gcctgttgaa ggttgttgag
5461 ctctaaataa tactttgtta ttcctactag tatgtcttcg cttattccct ctttctcgag
5521 gaggacttga atcattggct ccatcttggg agaaccctc tctagaatcc taaatatgat
5581 atccttaacc attaggacca tatcaggggg aaggcttttcc attaaaattt tcagcttatc
5641 taagtcttct ttagaaagta gagaagttag aattttccccta actattattc tttgcgtggt
5701 gggcggtatt gtcttttaata cttcaatcga ttgttggata aatccgtgaa ttgcaaatat
5761 gtaggcaata tcttcccctta tatcttctcc cacttttta gccagctcct cactctcttc
5821 tatcaaaatt tttactattt ctgagttttc ctcattattc ttcaaaaatt ctagaacctc
5881 atttaatgcc tgtgctatcc agagttttgct ccctatagag tttattaact caagaacaag
5941 cttgtattct cctagtgaaa gtagtggttt aattgacttg actattgcct cctctctata
6001 gggctcctca atagtttcga gaattaggag tacttttcctt ctttttatata tttttgtttag
6061 tttttccccct tccaaatttt ctaaaacttt ttcgagtatt tcaagaagtt tttttgttttct
6121 aagcttcttg ttcttaatct ccacggcata aaataccgct tcgtcagtgt cttttaatga
6181 aagcaaataa tcgattgctt cggcttttac aatgtcctga atttcctctg gaagaagttg
6241 tgccgatgat atggcctctc taaatgcttt ctttgctgat ttaagccctg ctaaacttgt
6301 tgaatatcca atggcgagaa gagctcttac taaaatataa ggatcttcta tttttgataa
6361 ttcttcgaaa gctttctga atgcttttcc tgccctggga tctttttattt tagacaaata
6421 tactcctatt ctcccatatg ttaatacccct aacgaatggg tctggtatcg agggtactaa
6481 ctctaatatt tcatctatta ccataatacc tcaccataag attatacatg gcaaaacgca
6541 cttactaagg taaatttatg gacatagata ttttaatctt ttcgttttttg aagcaaatct
6601 ttttgtagga agatgatgaa ctaatggttt caaaatggtt aaataaaagc ttaaggtgta
6661 gtcaaaatgt tgtctcaaat ttaaagaaaa gaggcgaaac aaagaaaata gagggaagat
6721 actttacttc ttgagcttttt cacacttctt tacccactcc tcaagaacgt ctctgagctt
6781 tggcttgcct atttcctcaa gctcatactt gactcttact gcaggcttgt tgaggttcat
6841 gaatcttctt aggtctactg gagttcccat aacgacaacg tctgcatctg ctctgttaat
6901 tgtttcctct agctctttga tctgcttctt gccgtatccc attgctggga gtatgttgct
6961 taggtgtggg tacttcttgt atgtttcaat tattgaccca acagcgtatg gccttggatc
7021 tactatctcc ttagctccga acttcttggc tgctatgtaa cctgcaccga agctcattcc
7081 accatgggtg agggtcggac catcctcaac tacgagaacg cgcttaccct tgattagctc
7141 tggcttgtcc acgaagattg gtgatgctgc ttcaatgact atagcatttg gatttatctt
7201 ttcaatgttc tctctaatct tctgtatgtt ctctggtggg gctgtgtcta ttttattgat
7261 tataataaca tcagcacttc tgaagtttgt ttaccctggg tggtgtgtca actcatgacc
7321 aggtctgtgt gggtcagtga caactatcca taagtcgggc tcgaagaatg ggaagtcgtt
```

FIG 7I

```
7381 gttcccaccg tcccagagga ttatgtcggc ctctttctct gcctccctca gtatcttctc
7441 gtagtcaact ccagcgtata ctaccattcc tctctctagg tatggctcat actcttctct
7501 ctcctcaatt gtacactcat atctgtcgag gtcctcaaag gtcgcaaagc gctgaacaac
7561 ttgctttctt agatcaccgt agggcattgg gtgtctgact gcaactacct tgaatcccat
7621 ctcttggagg atttgggcca cttttcttga ggtctggctc tttccacatc ctgttctgac
7681 tgcagttacg gctacaacgg gcttgcttga ctttagcatt gtgctctttg gtccaagtag
7741 ccagaagtca gccccagcac tgtgggctct acttgctaag tgcatgacgt gttcgtgaga
7801 aacgtcagag tacgcgaaaa ccactatgtc aacatcatgc tcttgatta tcttttccaa
7861 atcatcttct ggtagaattg gaattccatt tggatacagt tcaccagcta gctctggggg
7921 atatattctc ccctctatat ctggaatttg ggtggcagtg aaggcaacaa cctcgtaatc
7981 tgggttatct ctgaaaaaga cgttgaagtt gtggaagtct ctacccgcag cacccagaat
8041 tacaacccctt ctccttttt tctcggccat tttgatcacc tcagaatgtt ttatttcgag
8101 ataatactca atctagacat ttataacgat tttcatttaa attggaaata atttttcgaa
8161 tgattttaag taaaagttgt gtaaagtcga aaatatttcg aataaatgtg tgtattatta
8221 aagggattaa gaaaagggaa aaggttgaaa acttcaagtt tcaaaaccc ctaaaaagtc
8281 taaatcaaac cctctaatgg tgggagtaaa atgtgccttg caatcccagg gaaagtggtg
8341 gagattaaag gtaacgttgg aatagtggat tttggaggaa tacggagaa ggtaaggtta
8401 gatcttttga gtgatgttaa agttggcgat tacgttatag ttcacactgg ctttgctata
8461 gaaaagttag atgagaggag agctagagaa attcttgaag cctgggaaga agtttttctca
8521 gtaattgggg gtgagtaaat gcttgaaaaa tttggagaca aagctgtagc tcaaaagatt
8581 ttagaaaaaa ttaaagagga agctaaaggg atagaagagc tacgatttat gcacgttgt
8641 gggactcatg aggacacagt aactaggagt ggaatcagat cacttcttcc agaaaatgta
8701 aaaatcatga gtggcccagg atgtcccgtc tgtataaccc ccgttgagga catagtgaag
8761 atgatggaaa ttatgaaagt tgcgagagag gagagggaag aaattattct cactactttt
8821 ggtgacatgt atagaattcc aactccaata ggaagctttg cagacttaaa gagtcagggt
8881 tacgatgtga ggatagttta ctctatatac gactcctata aaatagccaa ggaaaatcca
8941 gataagcttg tagtgcactt ttctcctggg tttgagacta ccgccgctcc aacagctgaa
9001 atgcttgaga gcattgtgga agagggcta gagaacttta agatttattc cgttcatagg
9061 ttaacccctc ctgcagttga agctctccta aatgcgggga ctgttttca cggtttaata
9121 gatcctggtc atgtctctac aataattggg gtgaaaggat gggcgtatct cacagaaaag
9181 tttggaattc ctcaagttgt ggctggcttt gagccagttg atgttttact cggaatactt
9241 attctcatta ggcttgtgaa gaggggcgaa gcgaaaataa tcaacgagta taatagagtt
9301 gtaaagtggg aaggaaatgt caaggcccaa gaactgattt ggaagtactt tgaagttaaa
9361 gatgcaaagt ggagggccct aggagtaatt ccaaggagcg gattggaact taagaaagag
9421 tggaaggagc tagaaattag aacttattac aatcccgagg ttccaaagct cccagatctt
9481 gaaaaaggat gtctctgtgg ggcagtcctt agaggattag ccttaccgac ccagtgccaa
9541 cactttggaa agacatgtac accaagacat ccggtaggtc cttgtatggt ttcgtacgaa
9601 ggaacttgtc acatatttta caaatatggc gccctgatgt agttttatt acgcaaaagt
9661 aatataccac tacagcataa accccaaata tggattatcg aaaaattctc gatattcatc
9721 atagtttttgg ttgttttttc atcagttgct cttctgtcaa agccttatct tccaagagaa
9781 cagaaaagaa taacgtactc aggagaaaag ataatcttgc ctgcccaag aactgaagga
9841 gaaatgagtg ttgaagaagc tattgcaaaa agaaggagca ttaggacata caaaaatgag
9901 cctctaaaga tagaggagct tggtcaacta ttatgggctg cacaaggtat aactcatgaa
9961 tataagaggg cagccccaag tgcaggagca acatatccct ttgaaatctt cgttgtcgtt
10021 ggtaatgtc
```

PF0548    AE010177.1 atgtgccttgcaatcccagggaaagtggtggagattaaaggtaacgttggaatagtggattttggaggaatacggagagaggta
aggttagatcttttgagtgatgttaaagttggcgattacgttatagttcacactggctttgctatagaaaagttagatgagaggagag
ctagagaaattcttgaagcctgggaagaagtttctcagtaattgggggtgagtaa

FIG 7J

PF0548   AAL80672

MCLAIPGKVVEIKGNVGIVDFGGIRREVRLDLLSDVKVGDYVIVHTGFAIEKLDERRAREILEAWEEVFSV
IGGE

PF0549   AE010177.1

Atgcttgaaaaatttggagacaaagctgtagctcaaaagattttagaaaaaattaaagaggaagctaaagggatagaagagcta
cgatttatgcacgtttgtgggactcatgaggacacagtaactaggagtggaatcagatcacttcttccagaaaatgtaaaaatcatg
agtggcccaggatgtcccgtctgtataaccccgttgaggacatagtgaagatgatggaaattatgaaagttgcgagagaggag
agggaagaaattattctcactacttttggtgacatgtatagaattccaactccaataggaagctttgcagacttaaagagtcagggtt
acgatgtgaggatagtttactctatatacgactcctataaaatagccaaggaaaatccagataagcttgagtgcactttctcctgg
gtttgagactaccgccgctccaacagctggaatgcttgagagcattgtggaagaggggctagag
aactttaagattattccgttcataggttaacccctcctgcagttgaagctctcctaaatgcggggactgttttcacggtttaatagat
cctggtcatgtctctacaataattggggtgaaaggatgggcgtatctcacagaaaagtttggaattcctcaagttgtggctggctttg
agccagttgatgttttactcggaatacttatlctcattaggcttgtgaagaggggcgaagcgaaaataatcaacgagtataatagag
ttgtaaagtgggaaggaaatgtcaaggcccaagaactgatttggaagtactttgaagttaaagatgcaaagtggagggccctag
gagtaattccaaggagcggattggaacttaagaaagagtggaaggagctagaaattagaacttattacaatcccgaggttccaaa
gctcccagatcttgaaaaaggatgtctctgtggggcagtccttagaggattagcctaccgacccagtgccaacacttggaaag
acatgtacaccaagacatccggtaggtccttgtatggttcgtacgaaggaacttgtcacatattttacaaatatggcgccctgatgt
ag

PF0549   AAL80673

MLEKFGDKAVAQKILEKIKEEAKGIEELRFMHVCGTHEDTVTRSGIRSLLPENVKIMSGPGCPVCITPVED
IVKMMEIMKVAREEREEIILTTFGDMYRIPTPIGSFADLKSQGYDVRIVYSIYDSYKIAKENPDKLVVHFS
PGFETTAAPTAGMLESIVEEGLENFKIYSVHRLTPPAVEALLNAGTVFHGLIDPGHVSTIIGVKGWAYLTE
KFGIPQVVAGFEPVDVLLGILILIRLVKRGEAKIINEYNRVVKWEGNVKAQELIWKYFEVKDAKWRALGVI
PRSGLELKKEWKELEIRTYYNPEVPKLPDLEKGCLCGAVLRGLALPTQCQHFGKTCTPRHPVGPCMVSYEG
TCHIFYKYGALM

PF0559   AE010178.1

Atgtatctgggggagagaatgaaagcttatagaattcacgttcagggaatagttcaggccgtgggatttaggcccttcgtttatag
aatagctcatgctcacaacttgaggggatacgttaggaacttaggcgatgctggagttgaaattgttgtcgagggaagggagga
agacatagaggcattcatcaaggatttatacaagaagaaaccccacttgcaaggattgataaggttgagagggaggaaattcct
cttcagggctttgacagatttacatagagagaaaagctcgacggaaaagaaggggggagggagattcaataatccctccggacata
gctatttgtgaggactgtcttagggagtlatttaatccaactgacaagcgctacatgtatcctttcatagtatgtacaaactgtgggcc
gaggttcacgataattgaagatcttccctacgataggagagaacacagcgatgagagaattcccgatgtgcgagtctgtaggagt
gaatacgaggatccccctgaataggaggtatcatgcagagccggttgcatgtccaacttgtgggccgagctataggctttacacga
gcgatggaaatgagataattggagaccccctgagaaaggcggcaaaactaatcgataagggatacatagttgcgataaagggt
ataggtggaattcatttggcctgcgatgctacaagagaggatgtggtggccgagcttaggaagaggattttaggcctcagaagc
cttcgccattatggccaaagatttagaaactgtaaggacttttgcctatatttctcccgaagaggaggaagaattaacaagctatag
aaggccaatagtggctttgaagaagaaggagcccttcccacttcccgaaaacctcgctcctgggcttcacacaattggggtaatg

FIG 7K cttccctatgctggaacccactacatattattccactggagcaagactccagtttacgttatgacttccgcaaacttcccagggatgc
cgatgataaaggacaatgaagaggcatttgaaaagcttagggacgttgctgactacctcttgctccacaataggagaattccaaat
agagctgacgatagcgttgttcgctttgtagatggtagaagagctgttattaggaggagcagaggatttgttccacttggaataga
gattccatttgagtacaaaggattggcagttggtgctgagttaatgaatgctttcggagttgttaagaatggaaaagtttatccaagt
cagtacataggggatacatcaaagattgaagttttagagtttatgagggaagccgtgaggcacttcttcaagatattgagagttgat
aacttagatctagttgttgcagatttgcatccaagctacaacacaactaagctggggaatggagatcgctgaggaatttggggcaga
attccttcaagttcaacatcactacgctcacgtggcctctgtaatggctgagcacaacttggaggaagttgttggaattgctctagat
ggtgttgggtatggaaccgacggaaaaacttggggtgggggaagtaatatatctaagctatgaagatgtggagaggttggcccac
atagagtattatccactcccaggaggggattggccagctactatcccttgagggccttaattggaatactcagcttaaaccacga
cttagaggaagttgagaaaatcataagggagttctgtccaaatgcaataaagagcttaaagtatggggaaacagagtttagggta
attatgaggcaactcagcagcgggataaacgttgcctatgcctcttcaacgggaagggtgcttgatgcctctcggtactttgaac
gtttcctacaggaggcactatgagggagagcctgcgatgaagctggagagctttgcataccaaggaaagaacgatctaaagct
cacg gctccaattgaaggtgaggaaataaaggtttcagagttgtttgaggaagttcttgagctgatgggcaaggccaatcctaaagacat
agcttactccgttcacttagccttagctagggcatttgctgaagttagcgtggagaaagctaaggagtttggagctaaaactgtcgt
tttgggtgggggagtagggtacaatgagctaatagttaagacgataagaaagatagtagaggggagagggctaaggttcttaac
aacttacgaagttcccaggggagataatggaattaatgtaggccaggccttcctgggaggattgtacttggaaggatacttaaata
gggaagatttgagcatttag

PF0559    AAL80683

MYLGERMKAYRIHVQGIVQAVGFRPFVYRIAHAHNLRGYVRNLGDAGVEIVVEGREEDIEAFIKDLYKKKP
PLARIDKVEREEIPLQGFDRFYIEKSSTEKKGEGDSIIPPDIAICEDCLRELFNPTDKRYMYPFIVCTNCG
PRFTIIEDLPYDRENTAMREFPMCEFCRSEYEDPLNRRYHAEPVACPTCGPSYRLYTSDGNEIIGDPLRKA
AKLIDKGYIVAIKGIGGIHLACDATREDVVAELRKRIFRPQKPFAIMAKDLETVRTFAYISPEEEEELTSY
RRPIVALKKKEPFPLPENLAPGLHTIGVMLPYAGTHYILFHWSKTPVYVMTSANFPGMPMIKDNEEAFEKL
RDVADYLLLHNRRIPNRADDSVVRFVDGRRAVIRRSRGFVPLGIEIPFEYKGLAVGAELMNAFGVVKNGKV
YPSQYIGDTSKIEVLEFMREAVRHFFKILRVDNLDLVVADLHPSYNTTKLGMEIAEEFGAEFLQVQHHYAH
VASVMAEHNLEEVVGIALDGVGYGTDGKTWGGEVIYLSYEDVERLAHIEYYPLPGGDLASYYPLRALIGIL
SLNHDLEEVEKIIREFCPNAIKSLKYGETEFRVIMRQLSSGINVAYASSTGRVLDAFSVLLNVSYRRHYEG
EPAMKLESFAYQGKNDLKLTAPIEGEEIKVSELFEEVLELMGKANPKDIAYSVHLALARAFAEVSVEKAKE
FGAKTVVLGGGVGYNELIVKTIRKIVEGRGLRFLTTYEVPRGDNGINVGQAFLGGLYLEGYLNREDLSI

PF0604    AE010182.1

Atggaagaactaattagggaggtaatcctcaagaatttaacccttaattctgctggaggaataggattagaggagcttgatgacg
gagctacaatcccccttggagataagcatttagtgtttacaatagatgggcatacagtaaagccgatattcttccaggggggagac
atcggaaggttggccgttagcggaactgtaaacgatttggctgtcatgggagctcaacccttggcaattgcaagctcgttgataat
cgaggaagggtttgaagttagtgagctggaaaagattctgaagtcgatggacgaaacagctaaagaggttccagttccaattgtt
actggagacacaaaagtcgttgaagacaggataggaatcttcgttataacagctggagtgggggtagctgagaggccgataag
cgatgccggcgcaaaagttggggatgtcgttttagtgagtggaacaattggagaccacggaatagcactaatgagccatagaga
ggggatctcctttgagacagagcttaagagcgatgtagctccaatttggggatgtcgtaaaggccgttgcagatgccattggttggg
agaacatccacgcaatgaaagatcccacaagaggaggattgagcaacgcactaaacgagatggcaagaaaggcaaacgttg
gaattttggtaagagaggaggcaataccaattaggccagaagtaaaagctgccagcgaaatgcttgaataagtccctatgaag
ttgcaaacgaaggaaaagttgtaatgatagtggcgaaggagtatgcggaggaggcacttgaggccatgaagaagacagaaaa

FIG 7L gggtagggatgccgcaataataggagaagttattggtgaatacagaggaaaagttattctggagacgggaattggtggaagaa
gattttagagccgcctctcggtgatcccgttcctagagtttgttag

PF0604     AAL80728

MEELIREVILKNLTLNSAGGIGLEELDDGATIPLGDKHLVFTIDGHTVKPIFFPGGDIGRLAVSGTVNDLA
VMGAQPLAIASSLIIEEGFEVSELEKILKSMDETAKEVPVPIVTGDTKVVEDRIGIFVITAGVGVAERPIS
DAGAKVGDVVLVSGTIGDHGIALMSHREGISFETELKSDVAPIWDVVKAVADAIGWENIHAMKDPTRGGLS
NALNEMARKANVGILVREEAIPIRPEVKAASEMLGISPYEVANEGKVVMIVAKEYAEEALEAMKKTEKGRD
AAIIGEVIGEYRGKVILETGIGGRRFLEPPLGDPVPRVC

PF0615     AE010183.1 atgcacgaatgggcgttggcagatgcaatagtaaggactgttttagattacgctcaaaaggagggtgcaagtagggtaaaggcc
gtcaaggtagtcctcggagaactccaagatgttggggaggatatagtaaagtttgccatggaagagctcttcaggggaacaata
gcggaaggggcagagataatattcgaagaggaagaggccgtctttaagtgccgcaactgcgggcatgtatggaagcttaagg
aagtcaaagataagttggatgagaggataagagaggacatccactttattccagaggtcgttcatgcatttctatcctgtccaaaat
gtggaagccatgattttgaagtggtgaagggaaggggagtttacatttctggaataatgatcgagaaggagggagaagaatga

PF0615     AAL80739

MHEWALADAIVRTVLDYAQKEGASRVKAVKVVLGELQDVGEDIVKFAMEELFRGTIAEGAEIIFEEEEAVF
KCRNCGHVWKLKEVKDKLDERIREDIHFIPEVVHAFLSCPKCGSHDFEVVKGRGVYISGIMIEKEGEE

PF0616     AE010183.1 atgatagatcccagagaactcgcaatttcagcgaagcttgagggagtaaaaagaataatcccagttgtaagtgggaagggagg
agtaggaaaatccctaatctccacaactcttgccctagttctatcagaacaaaaatacaaagttggacttctcgacttggatttccat
ggagcaagtgaccacgtcatcctggatttgaacccaaagaacttcccgaggaagacaaaggagttattcccccaacggttcac
ggaataaagttcatgacaatagcgtattacaccgaggacaggccaactcctttaagaggaaaggagattagcgacgccctaata
gagctactaacaataaccaggtgggatgagctcgacttttagttgttgacatgccccctgggatgggagatcagttcttagacgtt
ttaaagtacttcaagaggggagaattcttgatagtcgcaactccgtcaaagctctctcttaatgttgttaggaagcttatagagttgct
aaaagaagagaagcatcagatacttggaatagttgagaatatgaagctggatgaagaggaagatgttatgagaattgcccagga
atatgggattaggtatcttggaggaataccctgtacagggatctagagagtaaagttggaaatgttaatgaactttagccacaga
gtttgccgagaaaattagaggaatagctaaaaagatttga

PF0616     AAL80740

MIDPRELAISAKLEGVKRIIPVVSGKGGVGKSLISTTLALVLSEQKYKVGLLDLDFHGASDHVILGFEPKE
LPEEDKGVIPPTVHGIKFMTIAYYTEDRPTPLRGKEISDALIELLTITRWDELDFLVVDMPPGMGDQFLDV
LKYFKRGEFLIVATPSKLSLNVVRKLIELLKEEKHQILGIVENMKLDEEEDVMRIAQEYGIRYLGGIPLYR
DLESKVGNVNELLATEFAEKIRGIAKKI

FIG 7M

PF0617    AE010183.1 atggaagagctgagagaagctctaaaaaatgctaagagaattgtaatatgtggaatagggaatgacatcaggggagacgacag
cttcggggtttatattgcagaaaaattaaagagagttataaagaaggcaaacattctagtcctcaactgtggagaggttccagaga
actacacagggaagatactaaactttcaccctgatttaatcattttatagacgcagtaaacttcggaggaaagcctggagaaataa
taattacagatccagaaaatactgaaggggccggagtttccacccacagtcttcccctcaagttttggccacttatctcaaagcta
atacaaatgccaagacaatcttaataggatgccagccaaagaacattgggcttttgaagatatgagcgaagaagtaaaagccgt
tgcggaagtcttattaaaaattcctttatgaaagtcttgagctttcttag

PF0617    AAL80741

MEELREALKNAKRIVICGIGNDIRGDDSFGVYIAEKLKRVIKKANILVLNCGEVPENYTGKILNFHPDLII
FIDAVNFGGKPGEIIITDPENTEGAGVSTHSLPLKFLATYLKANTNAKTILIGCQPKNIGLFEDMSEEVKA
VAEVLLKFLYESLELS

PF1401    AE010243.1 atgaaagtagagaaaggagatgtcataagacttcattacactggaaaggttaaagaaactggagaaatcttcgacacaacttatg
aggatgttgcaaaagaagctagaatatacaatccaaacggaatctatgggccagtccctatagcggttggagcgggacacgtat
tgcccggactagacaagagacttataggggcttgaagttaagaaaaaatacgtcattgaagttccacccgaagaaggctttggatt
gagagatccaggaaaaattaagattatcccacttggaaagttcagaaaatctggaataatcccgtaccctgggctagaaattgaa
gttgaaacagaaaatgggagaaaaatgagaggtaggttcttacagttagcggaggaagagttagagtagacttcaatcatccat
tagcaggaaagactctcgtatatgaagttgaagttgttgagaaaattgaagatccaatagaaaagattaaggcactaatagaacta
agactgccaatgattgacaaagataaggttattattgagattagtgaaaaagatgtaaagctaaacttcaaagacgttgatattgatc
caaagacactaattttgggcgaaattcttctcgaaagtgacttgaaatttataggatatgagaaagttgaatttgagccaaccattga
agagttattaaagcccaagtctgccgaggagcaagagtctcctaacgaagaacagcaagaggagagtgagtctaaagcggaa
gaatcttaa

PF1401    AAL81525

MKVEKGDVIRLHYTGKVKETGEIFDTTYEDVAKEARIYNPNGIYGPVPIAVGAGHVLPGLDKRLIGLEVKK
KYVIEVPPEEGFGLRDPGKIKIIPLGKFRKSGIIPYPGLEIEVETENGRKMRGRVLTVSGGRVRVDFNHPL
AGKTLVYEVEVVEKIEDPIEKIKALIELRLPMIDKDKVIIEISEKDVKLNFKDVDIDPKTLILGEILLESD
LKFIGYEKVEFEPTIEELLKPKSAEEQESPNEEQQEESESKAEES

FIG 8B pEA-SH1 Sequence:
ttgtacaaacttgtgatcgagccgtggtgatgatggtgatgacccatatcgcacgtctctcctccttgcgacaccggcaggacaccgggcgc
ttatggtcggcaagcgacgtccctgtagcaaggcaaaccatcgcttcacgtgagatgctgaaaacgaaagctcatccttctgcactggcgca
cgtcgccagaaagtattgttaataaagcgtagtgaaactttgcacaaaacaatacaaactgtgtggatttatctttagcgataaaaatggacct
attttctttggccgggcggtggggatgtttagccggttgctaaacgagtaaaagagaaggaattcgagctcgaattcggatcctagaggga
aaccgttgtggtctccctatagtgagtcgtattaattcgcgggatcgagatctcgggcagcgttgggtcctggccacgggtgcgcatgatcg
tgctcctgtcgttgaggacccggctaggctggcggggttgccttactggttagcagaatgaatcaccgatacgcgagcgaacgtgaagcga
ctgctgctgcaaaacgtctgcgaccctgagcaacaacatgaatggtcttcggtttccgtgtttcgtaaagtctggaaacgcggaagtcagcgc
cctgcaccattatgttccggatctgcatcgcaggatgctgctggctaccctgtggaacacctacatctgtattaacgaagcgctggcattgacc
ctgagtgattttctctggtcccgccgcatccataccgccagttgtttaccctcacaacgttccagtaaccgggcatgttcatcatcagtaaccc
gtatcgtgagcatcctctctcgtttcatcggtatcattaccccatgaacagaaatcccctacacggaggcatcagtgaccaaacaggaaa
aaaccgcccttaacatggcccgctttatcagaagccagacattaacgcttctggagaaactcaacgagctggacgcggatgaacaggcag
acatctgtgaatcgcttcacgaccacgctgatgagctttaccgcagctgcctcgcgcgtttcggtgatgacggtgaaaacctctgacacatgc
agctcccggagacggtcacagcttgtctgtaagcggatgccggagcagacaagcccgtcagggcgcgtcagcgggtgttggcgggtg
tcggggcgcagccatgacccagtcacgtagcgatagcggagtgtatactggcttaactatgcggcatcagagcagattgtactgagagtgc
accatatatgcggtgtgaaataccgcacagatgcgtaaggagaaaataccgcatcaggcgctcttccgcttcctcgctcactgactcgctgc
gctcggtcgttcggctgcggcgagcggtatcagctcactcaaaggcggtaatacggttatccacagaatcaggggataacgcagganaga
acatgtgagcaaaaggccagcaaaaggccaggaaccgtaaaaaggccgcgttgctggcgtttttccataggctccgcccccctgacgag
catcacaaaaatcgacgctcaagtcagaggtggcgaaacccgacaggactataaagataccaggcgtttccccctggaagctccctcgtg
cgctctcctgttccgaccctgccgcttaccggatacctgtccgcctttctccttcgggaagcgtggcgctttctcatagctcacgctgtaggta
tctcagttcggtgtaggtcgttcgctccaagctgggctgtgtgcacgaaccccccgttcagcccgaccgctgcgccttatccggtaactatcg
tcttgagtccaacccggtaagacacgacttatcgccactggcagcagccactggtaacaggattagcagagcgaggtatgtaggcggtgct
acagagttcttgaagtggtggcctaactacggctacactagaaggacagtatttggtatctgcgctctgctgaagccagttaccttcggaaaa
agagttggtagctcttgatccggcaaacaaaccaccgctggtagcggtggtttttttgttgcaagcagcagattacgcgcagaaaaaaaggg
atctcaagaagatcctttgatctttctacggggtctgacgctcagtggaacgaaaactcacgttaagggattttggtcatgagattatcaaaaa
ggatcttcacctagatccttttaaattaaaaatgaagtttttaaatcaatctaaagtatatatgagtaaacttggtctgacagttaccaatgcttaatc
agtgaggcacctatctcagcgatctgtctatttcgttcatccatagttgcctgactccccgtcgtgtagataactacgatacgggagggcttacc
atctggccccagtgctgcaatgataccgcgagacccacgctcaccggctccagatttatcagcaataaaccagccagccggaagggccg
agcgcagaagtggtcctgcaactttatccgcctccatccagtctattaattgttgccgggaagctagagtaagtagttcgccagttaatagtttg
cgcaacgttgttgccattgctgcaggcatcgtggtgtcacgctcgtcgtttggtatggcttcattcagctccggttcccaacgatcaaggcgag
ttacatgatccccccatgttgtgcaaaaaagcggttagctccttcggtcctccgatcgttgtcagaagtaagttggccgcagtgttatcactcatg
gttatggcagcactgcataatcctcttactgtcatgccatccgtaagatgcttttctgtgactggtgagtactcaaccaagtcattctgagaatagt
gtatgcggcgaccgagttgctcttgcccggcgtcaatacgggataataccgcgccacatagcagaactttaaaagtgctcatcattggaaaa
cgttcttcggggcgaaaactctcaaggatcttaccgctgttgagatccagttcgatgtaacccactcgtgcacccaactgatcttcagcatcttt
tactttcaccagcgtttctgggtgagcaaaaacaggaaggcaaaatgccgcaaaaaagggaataagggcgacacggaaatgttgaatact
catactcttcctttttcaatattattgaagcatttatcagggttattgtctcatgagcggatacatatttgaatgtatttagaaaaataaacaaatagg
ggttccgcgcacatttccccgaaaagtgccacctgaaattgtaaacgttaatattttgttaaaattcgcgttaaattttttaaatcagctcatttttt
aaccaataggccgaaatcggcaaaatcccttataaatcaaaagaatagaccgagatagggttgagtgttgttccagtttggaacaagagtcc
actattaaagaacgtggactccaacgtcaaaggcgcgaaaaaccgtctatcugggcgatgcccactacgtgaaccatcacccctaatcaagt
tttttggggtcgaggtgccgtaaagcactaaatcggaaccctaaagggagcccccgatttagagcttgacggggaaagccggcgaacgtg
gcgagaaaggaagggaagaaagcgaaaggagcgggcgctaggcgctggcaagtgtagcggtcacgctgcgcgtaaccaccacacc
cgccgcgcttaatgcgccgctacagggcgcgtcccattcgccaatccggatatagttcctcctttcagcaaaaaaccccctcaagacccgttta
gaggccccaaggggttatgctagttattgctcagcggtggcagcagccaactcagcttcctttcgggctttgttagcagccggatctcagtgg
tggtggtggtggtgctcgagtgcggccgcaagcttgtcgacggagcgcaagcttagcagccggatctgatcttaattaattatcaccacttig
tacaagaaagctgggtctcctccctgaaaatacaggtttcctaaagtctaaccacgtggactgagcaagatatgcatggatcataagcccta
acaaccatctcagccagtatctttaaccttctggatcgtcattgtagtgcttttctgccatcattcttacatgttcttccatcattgccaagttgaatg

FIG 8C ctgtaggtgttattatgtcggcataagaaacccttccattctcaactttgagggcatagactaagattcccttggagcctcagtcgttgagaca
ccaaagccgtcctttatctcaacttcatccctgggcttaattggccacttggcgagagcctcgtcgagcagatctattgccctctctataaagta
aactattcgagggcctgggctaagttatttgcaaacggatttgttcccttaataggtctttgtttgcctcatacagctccttggccttgccgtata
ggaggtcagcattgttaataactctagatatagccccaaccatgaagggtctgcccttgtagtgactgtgcttgcaaaactgtgttcaacgac
gaactcctttatataatctctgtactttcacttgggaactcctccccatcacttgcctttatgtaatctccataaattccataagcatctccctcgg
cttcacggccaagtgtgttattggcccttcaacttcgctgtactgctcaagctttgcaaataactcaaaagtatactcggcaagtggtagggctt
ccctaagctcggcttcattttctcaaggacactcttctcagggagctttccgaatccgcccaaaaccgcattttcttggtgtatggctcttgacc
ctagaatgtccatcatccaggtgccaaggttcttcagcttaagggctatctctatctccctcttgtattcattcaccatcttaagtgggctcgagta
gcccctgtagtcgggaagaactagaagatataggtgaagggcatgactctctatcatgtctccgatgtatagtacttctctaagggcctgtatc
tcttcccttgggacaaaaccgacggcctttctgcagcctctaatgcggttaacttgtgggcggctgaacagaatgagcatattctcgggtaaa
tggccagagcttcctcaagcttcttcccaatagttatggcctcaaagaatctgggcccttcaattatgtttagcttgacctccttgactccatcatc
cccaattattatctccacaccacccttcccctcaactcttgctatatgatcaatggtgattggaagatagaggttcttcattgttcaccacctgaga
atatttttttcaaccatttttctcaaccctctcatcatgtccattgaacattttcattctctcaattatctccttcttttgtcatcccttctccttgaacacctta
gctagagagtcgaaccaagctacatcgtacccctattgcccctctgcatcctatacacgcaactccaatcctggacatctcgcgttacatcctg
cccttgttactggacctagacagggttctcctttctcaagaaggatacatggatgtccattgagcctacatctagacaaactggataatctatat
cctctggccatgaaccaatcaagaatgttcccagggcgtagaggaagtccttcttctctggtgggcaaccgtagatgttgtagtcaactttat
gtattttgaaactggttcagccttcttcggttggaacttgactttttgcgtctccataaaaccttcttccagagctcttctaatggcttttcactccagct
ctgaactcctccttgaacagcacaagctccaaccgcaacgacgatctttgcattctccctaatttttttcacgagttcaacttcttccctcagttgaa
acgcttccttctataaaagctatgtcgacctttttcatcctcaatgctatctctatcaatcatgaaccagcaaactatttcagcatttgggataagttg
taataactcgtccatcatagctagctgcaattgacagccgtagcacgaggttaatgcgtaaaatccaatcctaactttcccatttttcctcacctc
agtccagcagtcctggggttgaaactatgtcgaagtacgtgaagactggtccatcttacagatgtactccagctcgtgctcgttccgacgtt
gcagtggccgcactcccgattccacatttcattcttctctccaatgtcacgaagatgttctctgggcgataaccgtagttgatgagggcctcaa
acactgacttatacattctaggaggcccacagattgcaactgcagtgttctttggatttgtgttggcctcaacgatgaactgctgtggcctaccc
tttaggcccggccagtttggatccctagtgacgctctggatgattttcacgttttcagcctcagctaggtctttcattgcctccagctccttgtaga
agaggagatccttcccataacgtgcggtgtttatgaaggtaatgtttccatacttccacctgttgtccattgcatagagaaagacgctcctaaga
ggtgcagttccaaggccagcagctattaatagtagatccattcctcccactcatccactgggaatccattaccgtaaggccctctcacaaga
acagtatcgccaggctttagtctatggacaacagttgtgaccctcctgcctttcttatacagagctcaaagaatcctttcctcattggagaaga
gcatatacttatgggaacctctccaactccaggtatcgtcagctggacaaactgtccaggtttgaacgtccacttctctgccaactcgggatcc
tcaaatctaaugaggaaaagcttttccgtttccgtcaaggagtaaaccttlagaacttgactctatgaagggcatacggattatcatttggcatc
ataatctctttggcaacatcatactccatcacctctaatgttagaggaatatgcaaatcctctcttggaatctcctcactaaccgttgggggaca
tttgttctcctcaagtcctaaaatcctcttaagattgcctacaaaacttatattggctggacagaatgcagtacaccttccacaaccgacacagta
gcttaatccaagcttttcgttatatgcgttcttacagagggtatctgttcctaaagcgatcctcttttgtgggcctgaagttgtggccccccagcaact
aagccatgacttctgaactgacaagaatcccatcttctttccctgtatccagtaactccatctaggtttacaatatcctgaacttcatagcatctac
acgttgggcatgtggtgttacatattccacaagccaagcacttatctgcctcctcatcccacattggatgttccattccaactcgagaagatac
ctcaagttgccccagtcttcgtggtatttgaatgcttgctgtctcctcttttcaaaatctctaaatgcacagatatcctlgtccgttacctcttcaaag
agctttatgttcttgtcaacaagcctgtgcccagttggagtgccaaccccttaccaaccatccatcgggcagttcatggaagaacaagtcaaaa
ccatcatcagcgaagtctgtttctcttaagttacagaagcaatattcatctggcatacagcttattccaatgattatcccctctctctcctcaccttg
tagtacttgtcggggaactcatcaaggtataccgtgtctaggatctttaggccatatatgtcacacgcgtggactccaaatataataaatggttc
aacttcctctattacctccctgtattctggttttgaaatgtcgaactcaaagagctttccctcggcttgaagaagaacttcttaggtggcattattgt
cctgttgtagtggaattctatcttttctaacatcatcaatctccctgaagtcatagaacttgtccgaaattttttactggagcgtaaagcttcccccagt
ctttaagtctttccaaaaactcgtaagtgttttccttgggtaacttaacataccttcctccctgaaaatacaggtttctgagcctgctttt

FIG 8D pC11A-CDAB1

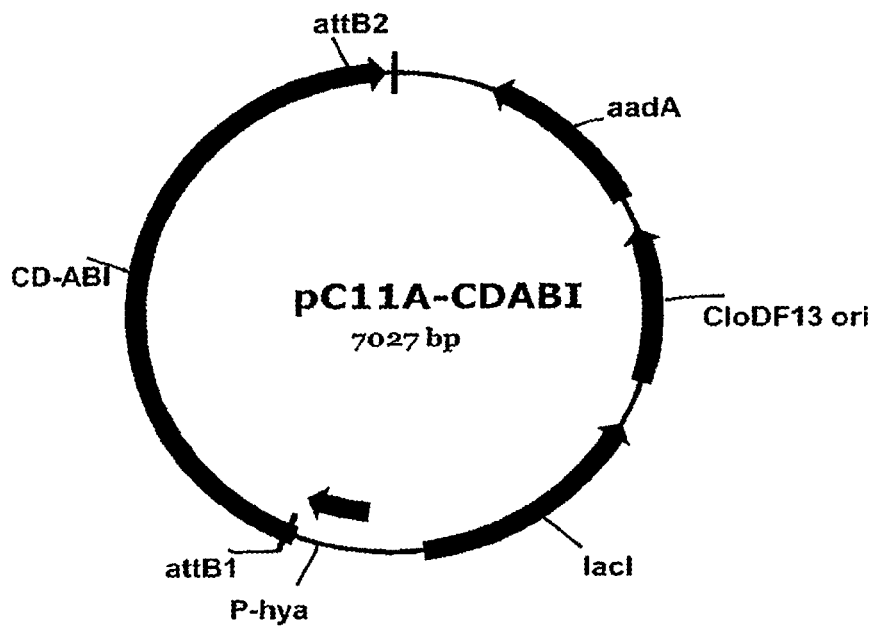

pC11A-CDAB1 Sequence ttgtacaaagtggttgatgagtccggatcccaattgggagctcgtgtacacggcgcgcctgcaggtcgacaagcttgcggccgcactcgag
tctggtaaagaaaccgctgctgcgaaatttgaacgccagcacatggactcgtctactagcgcagcttaattaacctaggctgctgccaccgct
gagcaataactagcataaccccttggggcctctaaacgggtcttgaggggtttttgctgaaacctcaggcatttgagaagcacacggtcaca
ctgcttccggtagtcaataaaccggtaaaccagcaatagacataagcggctatttaacgaccctgccctgaaccgacgaccgggtcatcgt
ggccggatcttgcggcccctcggcttgaacgaattgttagacattatttgccgactaccttggtgatctcgcctttcacgtagtggacaaattctt
ccaactgatctgcgcgcgaggccaagcgatcttcttcttgtccaagataagcctgtctagcttcaagtatgacgggctgatactgggccggc
aggcgctccattgcccagtcggcagcgacatccttcggcgcgattttgccggttactgcgctgtaccaaatgcgggacaacgtaagcacta
catttcgctcatcgccagcccagtcgggcggcgagttccatagcgttaaggtttcatttagcgcctcaaatagatcctgttcaggaaccggat
caaagagttcctccgccgctggacctaccaaggcaacgctatgttctcttgctttgtcagcaagatagccagatcaatgtcgatcgtggctg
gctcgaagatacctgcaagaatgtcattgcgctgccattctccaaattgcagttcgcgcttagctggataacgccacggaatgatgtcgtcgt
gcacaacaatggtgacttctacagcgcgcgagaatctcgctctctccaggggaagccgaagtttccaaaaggtcgttgatcaaagctcgccg
cgttgtttcatcaagccttacggtcaccgtaaccagcaaatcaatatcactgtgtggcttcaggccgccatccactgcggagccgtacaaatg
tacggccagcaacgtcggttcgagatggcgctcgatgacgccaactacctctgatagttgagtcgatacttcggcgatcaccgcttccctcat
actcttcctttttcaatattattgaagcatttatcagggttattgtctcatgagcggatacatatttgaatgtatttagaaaaataaacaaatagctag
ctcactcggtcgctacgctccgggcgtgagactgcggcgggcgctgcggcacatacaaagttaccacagattccgtggataagcagg
ggactaacatgtgaggcaaaacagcagggccgcgccggtggcgttttccataggctccgccctcctgccagagttcacataaacagacg
ctttccggtgcatctgtgggagccgtgaggctcaaccatgaatctgacagtacgggcgaaacccgacaggacttaaagatccccaccgttt

FIG 8E ccggcgggtcgctccctcttgcgctctcctgttccgaccctgccgtttaccggatacctgttccgcctttctcccttacgggaagtgtggcgctt
tctcatagctcacacactggtatctcggctcggtgtaggtcgttcgctccaagctgggctgaagcaagaactccccgttcagcccgactgct
gcgccttatccggtaactgttcacttgagtccaacccggaaaagcacggtaaaacgccactggcagcagccattggtaactgggagttcgc
agaggatttgtttagctaaacacgcggttgctcttgaagtgtgcgccaaagtccggctacactggaaggacagattggttgctgtgctctgc
gaaagccagttaccacggttaagcagttccccaactgacttaaccttcgatcaaaccacctccccaggtggttttttcgtttacagggcaaaag
attacgcgcagaaaaaaaggatctcaagaagatcctttgatctttctactgaaccgctctagattcagtgcaatttatctcttcaaatgtagcac
ctgaagtcagccccatacgatataagttgtaattctcatgttagtcatgccccgcgcccaccggaaggagctgactgggttgaaggctctcaa
gggcatcggtcgagatccggtgcctaatgagtgagctaacttacattaattgcgttgcgctcactgcccgcttccagtcgggaaacctgtc
gtgccagctgcattaatgaatcggccaacgcgcggggagaggcggtttgcgtattgggcgccagggtggtttttctttcaccagtgagacg
ggcaacagctgattgcccttcaccgcctggccctgagagagttgcagcaagcggtccacgctggtttgccccagcaggcgaaaatcctgtt
tgatggtggttaacggcgggatataacatgagctgtcttcggtatcgtcgtatcccactaccgagatgtccgcaccaacgcgcagcccggac
tcggtaatggcgcgcattgcgcccagcgccatctgatcgttggcaaccagcatcgcagtgggaacgatgccctcattcagcatttgcatggt
ttgttgaaaaccggacatggcactccagtcgcctcccgttccgctatcggctgaatttgattgcgagtgagatatttatgccagccagccaga
cgcagacgcgccgagacagaacttaatgggcccgctaacagcgcgatttgctggtgacccaatgcgaccagatgctccacgcccagtcg
cgtaccgtcttcatgggagaaaataatactgttgatgggtgtctggtcagagacatcaagaaataacgccggaacattagtgcaggcagctt
ccacagcaatggcatcctggtcatccagcggatagttaatgatcagcccactgacgcgttgcgcgagaagattgtgcaccgccgctttaca
ggcttcgacgccgcttcgttctaccatcgacaccaccacgctggcacccagttgatcggcgcgagatttaatcgccgcgacaatttgcgacg
gcgcgtgcagggccagactggaggtggcaacgccaatcagcaacgactgtttgcccgccagttgttgtgccacgcggttgggaatgtaatt
cagctccgccatcgccgcttccactttttcccgcgttttcgcagaaacgtggctggccttggttcaccacgcgggaaacggtctgataagaga
caccggcatactctgcgacatcgtataacgttactggtttcacattcaccaccctgaattgactctcttccgggcgctatcatgccataccgcga
aaggttttgcgccattcgatggtgtccgggatctcgacgctctccccttatgcgactcctgcattaggaaattaatacgactcactataggggaat
tgtgagcggataacaatcccctgtagaaataattttgtttaactttaataaggagatataccatggcacatcaccaccaccatcacgtgggtac
cggttcgaatgatctcgaattcctttctctttttactcgttagcaaccggctaaacatccccaccgcccggccaaaagaaaaataggtccatttta
tcgctaaaagataaatccacacagttgtattgtttgtgcaaaagtttcactacgcttattaacaatactttctggcgacgtgcgccagtgcaga
aggatgagctttcgtttcagcatctcacgtgaagcgatggtttgccttgctacagggacgtcgcttgccgaccataagcgcccggtgtcctg
ccggtgtcgcaaggaggagagacgtgcgatatgggtcatcaccatcatcaccacatcgacgacaaatcaacaagtttgtacaaaaaagca
ggctcagaaaacctgtatttcaggggaggatgcctgcaatcccagggaaagtggtggagattaaaggtaacgttggaatagtggatttgga
ggaatacggagagagaggtaaggttagatcttttgagtgatgttaaagttggcgattacgttatagttcacactggctttgctatagaaaagttagat
gagaggagagctagagaaattcttgaagcctgggaagaagttttctcagtaattgggggtgagtaaatgcttgaaaaattggagacaaagc
tgtagctcaaaagattttagaaaaaattaaagaggaagctaaagggatagaagagctacgatttatgcacgtttgtgggactcatgaggacac
agtaactaggagtggaatcagatcacttcttccagaaaatgtaaaaatcatgagtggcccaggatgtcccgtctgtataaccccccgttgagga
catagtgaagatgatggaaattatgaaagttgcgagagaggagagggaagaaattattctcactactttggtgacatgtatagaattccaact
ccaataggaagcttttgcagacttaaagagtcagggttacgatgtgaggatagtttactctatatacgactcctataaaatagccaaggaaaatc
cagatgaagcttgtagtgcactttctcctgggttttgagactaccgccgctccaacagctggaatgcttgagagcattgtggaagaggggctag
agaactttaagatttattccgttcataggttaaccccctcctgcagttgaagctctcctaaatgcggggactgttttcacggttaatagatcctggt
catgtctctacaataattggggtgaaaggatgggcgtatctcacagaaaagtttggaattcctcaagttgtggctggcttgagccagttgatgt
tttactcggaatacttattctcattaggcttgtgaagaggggcgaagcgaaaataatcaacgagtataatagagttgtaaagtgggaaggaaat
gtcaaggcccaagaactgatttggaatgtactttgaagttaaagatgcaaagtggagggcccctaggagtaattccaaggagcggattggaac
ttaagaaagagtggaaggagctagaaattagaacttattacaatcccgaggttccaaagctcccagatcttgaaaaaggatgtctctgtgggg
cagtcctttagaggattagccttaccgacccagtgccaacactttggaaagacatgtacaccaagcacatccggtaggtccttgtatggtttcgta
cgaaggaacttgtcacatatttttacaaatatggcgccctgatgtaggaggtgaaaatgcacgaatgggcgttggcagatgcaatagtaagg
actgttttagattacgctcaaaaggagggtgcaagtagggtaaaggccgtcaaggtagtcctcggagaactccaagatgttgggagggata
tagtaaagttgccatggangagctcttcaggggaacaaaagcggaaggggcagagataatattcgaagaggaagaggccgtctttaagtg
ccgcaactgcgggcatgtatggaagcttaaggaagtcaaagataagttggatgagaggataagagaggacatccacttattccagaggtc
gttcatgcatttctatcctgtccaaaatgtggaagccatgattttgaagtggtgaagggaaggggagtttacattctggaataatgatcgagaa
ggagggagaagaatgatagatcccagagaactcgcaatttcagcgaagcttgagggagtaaaaagaataatcccagttgtaagtgggaag

FIG 8F ggaggagtaggaaaatccctaatctccacaactcttgccctagttctatcagaacaaaaatacaaagttggacttctcgacttggatttccatg
gagcaagtgaccacgtcatcctgggatttgaacccaaagaacttcccgaggaagacaaaggagttattccccaacggttcacggaataaa
gtlcatgacaatagcgtattacaccgaggacaggccaactcctlaagaggaaaggagattagcgacgccctaatagagctactaacaatna
ccaggtgggatgagctcgacttttagttgttgacatgcccctgggatgggagatcagttcttagacgtttaaagtacttcaagagggaga
attcttgatagtcgcaactccgtcaaagctctctcttaatgttgttaggaagcttatagagttgctaaaagaagagaagcatcagatacttggaat
agttgagaatatgaagctggatgaagaggaagatgttatgagaattgcccaggaatatgggattaggtatcttggaggaatacctctgtacag
ggatctagagagtaaagttggaaatgttaatgaactttagccacagagtttgccgagaaaattagaggaatagctaaaaagatttgactggtg
caagctatggaagagctgagagaagctctaaaaaatgctaagagaattgtaatatgtggaatagggaatgacatcaggggagacgacagc
ttcggggtttatattgcagaaaaattaaagagagttataaagaaggcaaacattctagtcctcaactgtggagaggttccagagaactacaca
gggaagatactaaactttcaccctgatttaatcattttatagacgcagtaaacttcggaggaaagcctggagaaataataattacagatccag
aaaatactgaaggggccggagtttccacccacagtcttcccctcaagttttggccacttatctcaaagctaatacaaatgccaagacaatctt
aataggatgccagccaaagaacattgggcttttgaagatatgagcgaagangtaaaagccgttgcggaagtcttattaaaattcctttatgaa
agtcttgagcttcttaggaaaacctgtattlcagggaggagacccagctttc

FIG 8G

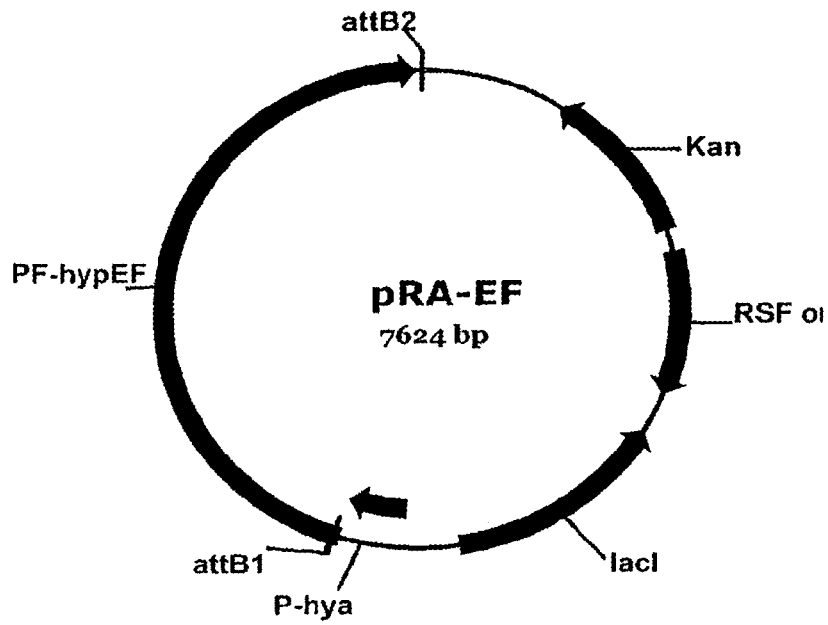

pRA-EF pRA-EF Sequence ttgtacaaagtggtgataattaattaagatcagatccggctgctaagcttgcgctcggcgcgcctgcaggtcgacaagcttgcggccgcata
atgcttaagtcgaacagaaagtaatcgtattgtacacggccgcataatcgaaattaatacgactcactataggggaattgtgagcggataaca
attcccatcttagtatattagttaagtataagaaggagatatacatatggcagatctcaattggatatcggccggccacgcgatcgctgacgt
cggtaccctcgagtctggtaaagaaaccgctgctgcgaaatttgaacgccagcacatggactcgtctactagcgcagcttaattaacctagg
ctgctgccaccgctgagcaataactagcataaccccttgggggcctctaaacgggtcttgaggggttttttgctgaaacctcaggcatttgaga
agcacacggtcacactgcttccggtagtcaatanaaccggtaaaccagcaatagacataagcggctatttaacgaccctgccctgaaccgac
gacaagctgacgaccgggtctccgcaagtggcactttccggggaaatgtgcgcggaacccctatttgtttatttttctaaatacattcaaatatg
tatccgctcatgaattaattcttagaaaaactcatcgagcatcaaatgaaactgcaatttattcatatcaggattatcaataccatattttgaaaaa
gccgtttctgtaatgaaggagaaaactcaccgaggcagttccataggatggcaagatcctggtatcggtctgcgattccgactcgtccaacat
caatacaacctattaatttcccctcgtcaaaaataaggttatcaagtgagaaatcaccatgagtgacgactgaatccggtgagaatggcaaaa
gtttatgcatttctttccagacttgttcaacaggccagccattacgctcgtcatcaaaatcactcgcatcaaccaaaccgttattcattcgtgattg
cgcctgagcgagacgaaatacgcggtcgctgttaaaaggacaattacaaacaggaatcgaatgcaaccggcgcaggaacactgccagc
gcatcaacaatatttcacctgaatcaggatatcttctaatacctggaatgctgttttcccggggatcgcagtggtgagtaaccatgcatcatca
ggagtacggataaaatgcttgatggtcggaagaggcataaattccgtcagccagtttagtctgaccatctcatctgtaacatcattggcaacg
ctacctttgccatgtttcagaaacaactctggcgcatcgggcttcccatacaatcgatagattgtcgcacctgattgcccgacattatcgcgag
cccatttataccatataaatcagcatccatgttggaatttaatcgcggcctagagcaagacgtttcccgttgaatatggctcatactcttccttttt

FIG 8H caatattattgaagcatttatcagggttattgtctcatgagcggatacatatttgaatgtatttagaaaaataaacaaataggcatgcagcgctctt
ccgcttcctcgctcactgactcgctacgctcggtcgttcgactgcggcgagcggtgtcagctcactcaaaagcggtaatacggttatccaca
gaatcaggggataaagccggaaagaacatgtgagcaaaaagcaaagcaccggaagaagccaacgccgcaggcgtttttccataggctc
cgccccctgacgagcatcacaaaatcgacgctcaagccagaggtggcgaaacccgacaggactataaagataccaggcgtttccccc
tggaagctccctcgtgcgctctcctgttccgaccctgccgcttaccggatacctgtccgcctttctcccttcgggaagcgtggcgctttctcata
gctcacgctgttggtatctcagttcggtgtaggtcgttcgctccaagctgggctgtgtgcacgaaccccccgttcagcccgaccgctgcgcct
tatccggtaactatcgtcttgagtccaacccggtaagacacgacttatcgccactggcagcagccattggtaactgatttagaggactttgtctt
gaagttatgcacctgttaaggctaaactgaaagaacagatttggtgagtgcggtcctccaacccacttaccttggtcaaagagttggtagct
cagcgaaccttgagaaaaccaccgttggtagcggtggttttctttatttatgagatgatgaatcaatcggtctatcaagtcaacgaacagctatt
ccgttactctagatttcagtgcaatttatctcttcaaatgtagcacctgaagtcagccccatacgatataagttgtaattctcatgttagtcatgccc
cgcgcccaccggaaggagctgactgggttgaaggctctcaagggcatcggtcgagatcccggtgcctaatgagtgagctaacttacattaa
ttgcgttgcgctcactgcccgctttccagtcgggaaacctgtcgtgccagctgcattaatgaatcggccaacgcgcggggagaggcggttt
gcgtattgggcgccagggtggttttcttttcaccagtgagacgggcaacagctgattgcccttcaccgcctggccctgagagagttgcagc
aagcggtccacgctggtttgccccagcaggcgaaaatcctgtttgatggtggttaacggcgggatataacatgagctgtcttcggtatcgtcg
tatcccactaccgagatgtccgcaccaacgcgcagcccggactcggtaatggcgcgcattgcgcccagcgccatctgatcgttggcaacc
agcatcgcagtgggaacgatgccctcattcagcatttgcatggtttgttgaaaaccggacatggcactccagtcgccttcccgttccgctatc
ggctgaatttgattgcgagtgagatatttatgccagccagccagacgcagacgcgccgagacagaacttaatgggcccgctaacagcgcg
atttgctggtgacccaatgcgaccagatgctccacgcccagtcgcgtaccgtcttcatgggagaaaataatacgtgtgatgggtgtctggtca
gagacatcaagaataacgccggaacattagtgcaggcagcttccacagcaatggcatcctggtcatccagcggatagttaatgatcagcc
cactgacgcgttgcgcgagaagattgtgcaccgccgcttacaggcttcgacgccgcttcgtctaccatcgacaccaccacgctggcacc
cagttgatcggcgcgagatttaatcgccgcgacaatttgcgacgcgcgtgcagggccagactggaggtggcaacgccaatcagcaacg
actgtttgcccgccagtgtttgtgccacgcggttgggaatgtaattcagctccgccatcgccgcttccacttttccccgcgtttccgcagaaacg
tggctggcctggttcaccacgcgggaaacggtctgataagagacaccggcatactctgcgacatcgtataacgttactggtttcacattcacc
accctgaattgactctcttccgggcgctatcatgccataccgcgaaaggttttgcgccattcgatggtgtccgggatctcgacgctctcccttat
gcgactcctgcattaggaaattaatacgactcactataggggaattgtgagcggataacaattcccctgtagaaataattttgttaactttaata
aggagatataccatgggcagcagccatcaccatcatcaccacagccaggatccgaattcgagctcgaattccttctctttactcgtttagcaa
ccggctaaacatccccaccgcccggccaaaagaaaaataggtccattttatcgctaaaagataaatccacacagtttgtattgtttgtgcaa
aagtttcactacgctttattaacaatactttctggcgacgtgcgccagtgcagaaggatgagctttcgtttcagcatctcacgtgaagcgatgg
tttgccttgctacagggacgtcgcttgccgaccataagcgcccggtgtcctgccggtgtcgcaaggaggagagacgtgcgatatgggtcat
caccatcatcaccacggctcgatcacaagtttgtacaaaaaagcaggctcagaaaacctgtattttcagggaggagaagaactaattaggga
ggtaatcctcaagaatttaaccccttaattctgctggaggaataggattagaggagcttgatgacggagctacaatcccccttggagataagca
tttagtgtttacaatagatgggcatacagtaaagccgatattcttcccaggggggagacatcggaaggttggccgttagcggaactgtaaacga
tttggctgtcatgggagctcaaccccttggcaattgcaagctcgttgataatcgaggaagggtttgaagttagtgagctgaaaagattctgaa
gtcgatggacgaaacagctaaagaggttccagttccaattgttactggagacacaaaagtcgttgaagacaggataggaatcttcgttataac
agctggagtgggggtagctgagaggccgataagcgatgccggcgcaaaagttggggatgtcgttttagtgagtggaacaattggagacca
cggaatagcactaatgagccatagagaggggatctccttgagacagagcttaagagcgatgtagctccaattgggatgtcgtaaaggcc
gttgcagatgccattggttgggagaacatccacgcaatgaaagatcccacaagaggaggattgagcaacgcactaaacgagatggcaag
aaaggcaaacgttggaattttggtaagagaggaggcaataccaattaggccagaagtaaaagctgccagcgaaatgcttggaataagtccc
tatgaagttgcaaacgaaggaaaagttgtaatgatagtggcgaaggagtatgcggaggaggcacttgaggccatgaagaagacagaaaa
gggtagggatgccgcaataataggagaagttattggtgaatacagaggaaaagttattctggagacgggaattggtggaagaagattttag
agccgcctctcggtgatcccgttcctagagttgttaggaggtggaaaatgtatctgggggagagaatgaaagcttatagaattcacgttcag
ggaatagttcaggccgtgggatttaggcccttcgtttatagaatagctcatgctcacaacttgaggggatacgttaggaacttaggcgatgctg
gagttgaaattgttgtcgagggaagggaggangacatagaggcattcatcaaggatttatacaagaagaaaccccacttgcaaggattgat
aaggttgagagggaggaaattcctcttcagggctttgacagattttacatagagaaaagctcgacggaaaagaaggggagggagattca
ataatccctccggacatagctatttgtgaggactgtcttagggagttatttaatccaactgacaagcgctacatgtatcctttcatagtatgtacaa
actgtgggccgaggttcacgataattgaagatcttccctacgatagggagaacacagcgatgagagaattcccgatgtgcgagttctgtagg

FIG 8I agtgaatacgaggatcccctgaataggaggtatcatgcagagccggttgcatgtccaacttgtgggccgagctataggctttacacgagcg
atggaaatgagataattggagacccctgagaaaggcggcaaaactaatcgataagggatacatagttgcgataaagggtataggtggaat
tcatttggcctgcgatgctacaagagaggatgtggtggccgagcttaggaagaggattttaggcctcagaagcctttcgccattatggccaa
agatttagaaactgtaaggactttgcctatatttctcccgaagaggaggaagaattaacaagctatagaaggccaatagtggctttgaagaa
gaaggagcccttcccacttcccgaaaacctcgctcctgggcttcacacaattggggtaatgcttccctatgctggaacccactacatattattc
cactggagcaagactccagtttacgttatgacttccgcaaacttcccagggatgccgatgataaaggacaatgaagaggcatttgaaaagct
tagggacgttgctgactacctcttgctccacaataggagaattccaaatagagctgacgatagcgttgttcgctttgtagatggtagaagagct
gttattaggaggagcagaggatttgttccacttggaatagagattccatttgagtacaaaggattggcagttggtgctgagttaatgaatgcttt
cggagttgttaagaatggaaaagtttatccaagtcagtacataggggatacatcaaagattgaagttttagagtttatgagggaagccgtgag
gcacttcttcaagatattgagagttgataacttagatctagttgttgcagatttgcatccaagctacaacacaactaagctgggaatggagatcg
ctgaggaatttggggcagaattccttcaagttcaacatcactacgctcacgtggcctctgtaatggctgagcacaacttggaggaagttgttg
gaattgctctagatggtgttgggtatggaaccgacggaaaaacttggggtggggaagtaatatatctaagctatgaagatgtggagaggttg
gcccacatagagtattatccactcccaggaggggatttggccagctactatcccttgagggccttaattggaatactcagcttaaaccacgac
ttagaggaagttgagaaaatcataagggagttctgtccaaatgcaataaagagcttaaagtatggggaaacagagttlagggtaattatgagg
caactcagcagcgggataaacgttgcctatgcctcttcaacgggaaggglgcttgatgccttctcggtacttttgaacgtttcctacaggaggc
actatgagggagagcctgcgatgaagctggagagctttgcataccaaggaaagaacgatctaaagctcacggctccaattgaaggtgagg
aaataaaggtttcagagttgtttgaggaagttcttgagctgatgggcaaggccaatcctaaagacatagcttactccgttcacttagccttagct
agggcatttgctgaagttagcgtggagaaagctaaggagtttggagctaaaactgtcgtttgggtgggggagtagggtacaatgagctaat
agttaagacgataagaaagatagtagaggggagagggctaaggttcttaacaactlacgaagttcccaggggagataatggaattaatgta
ggccaggccttcctgggaggattgtactlggaaggatacttaaatagggaagatttgagcatttaggaaaacctgtattttcagggaggagac
ccagctttc

FIG 8J pC3AR-slyD

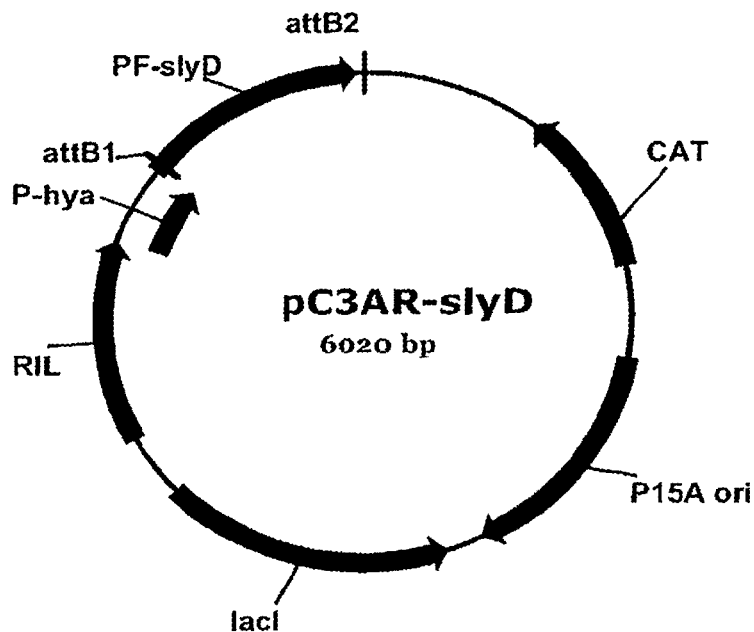

pC3AR-slyD Sequence ttgtacaaagtggtgataattaattaagatcagatccggctgctaagcttgcggccgcataatgcttaagtcgaacagaaagtaatcgtattgta
cacggccgcataatcgaaattaatacgactcactataggggaattgtgagcggataacaattcccatcttagtatattagttaagtataagaa
ggagatatacatatggcagatctcaattggatatcggccggccacgcgatcgctgacgtcggtaccctcgagtctggtaaaganaaccgctg
ctgcgaaatttgaacgccagcacatggactcgtctactagcgcagcttaattaacctaggctgctgccaccgctgagcaataactagcataa
ccccttggggcctctaaacgggtcttgaggggttttttgctgaaacctcaggcatttgagaagcacacggtcacactgcttccggtagtcaata
aaccggtaaaccagcaatagacataagcggctatttaacgaccctgccctgaaccgacgaccgggtcgaatttgcttttcgaatttctgccatt
catccgcttattatcacttattcaggcgtagcaccaggcgtttaagggcaccaataactgccttaaaaaaattacgccccgccctgccactcat
cgcagtactgttgtaattcattaagcattctgccgacatggaagccatcacagacggcatgatgaacctgaatcgccagcggcatcagcacc
ttgtcgccttgcgtataatatttgcccatagtgaaaacgggggcgaagaagttgtccatattggccacgtttaaatcaaaactggtgaaactca
cccagggattggctgagacgaaaaacatattctcaataaacccttaggaaataggccaggttttcaccgtaacacgccacatcttgcgaat
atatgtgtagaaactgccggaaatcgtcgtggtattcactccagagcgatgaaaacgttcagtttgctcatggaaaacggtgtaacaagggt
gaacactatcccatatcaccagctcaccgtctttcattgccatacggactccggatgagcattcatcaggcgggcaagaatgtgaataaag
gccggataaaacttgtgcttatttttctttacggtctttaaaaaggccgtaatatccagctgaacggtctggttataggtacattgagcaactgact
gaaatgcctcaaaatgttctttacgatgccattgggatatatcaacggtggtatatccagtgatttttctccatttagcttccttagctccctgaaa
atctcgataactcaaaaaatacgcccggtagtgatcttatttcattatggtgaaagttggaacctcttacgtgccgatcaacgtctcattttcgcc
aaaagttggcccagggcttcccggtatcaacagggacaccaggatttatttattctgcgaagtgatcttccgtcacaggtatttattcggcgca
aagtgcgtcgggtgatgctgccaacttactgatttagtgtatgatggtgttttgaggtgctccagtggcttctgttctatcagctgtcccctcctgt
tcagctactgacggggtggtgcgtaacggcaaaagcaccgccggacatcagcgctagcggagtgtataclggcttactatgttggcactga
tgagggtgtcagtgaagtgcttcatgtggcaggagaaaaaaggctgcaccggtgcgtcagcagaatatgtgatacaggatatattccgcttc
ctcgctcactgactcgctacgctcggtcgttcgactgcggcgagcggaaatggcttacgaacggggcggagatttcctggaagatgccag

FIG 8K gaagatacttaacagggaagtgagagggccgcggcaaagccgttttccataggctccgcccccctgacaagcatcacgaaatctgacgc
tcaaatcagtggtggcgaaacccgacaggactataaagataccaggcgtttcccctggcggctccctcgtgcgctctcctgttcctgccttc
ggtttaccggtgtcattccgctgttatggccgcgtttgtctcattccacgcctgacactcagttccgggtaggcagttcgctccaagctggactg
tatgcacgaaccccccgttcagtccgaccgctgcgccttatccggtaactatcgtcttgagtccaacccggaaagacatgcaaaagcacca
ctggcagcagccactggtaattgattagaggagttagtcttgaagtcatgcgccggttaaggctaaactgaaaggacaagttttggtgactg
cgctcctccaagccagttacctcggttcaaagagttggtagctcagagaaccttcgaaaaaccgccctgcaaggcggttttttcgttttcagag
caagagattacgcgcagaccaaaacgatctcaagaagatcatcttattaatcagataaaatattctagatttcagtgcaatttatctcttcaaatg
tagcacctgaagtcagccccatacgatataagttgtaattctcatgttagtcatgccccgcgcccaccggaaggagctgactgggttgaagg
ctctcaagggcatcggtcgagatcccggtgcctaatgagtgagctaacttacattaattgcgttgcgctcactgcccgctccagtcgggaa
acctgtcgtgccagctgcattaatgaatcggccaacgcgcggggagaggcggttgcgtattgggcgccagggtggttttcttttcaccagt
gagacgggcaacagctgattgcccttcaccgcctggccctgagagagttgcagcaagcggtccacgctggtttgcccagcaggcgaaa
atcctgtttgatggtggttaacggcgggatataaacatgagctgtcttcggtatcgtcgtatcccactaccgagatgtccgcaccaacgcgcag
cccggactcggtaatggcgcgcattgcgcccagcgccatctgatcgttggcaaccagcatcgcagtgggaacgatgccctcattcagcatt
tgcatggtttgttgaaaaccggacatggcactccagtcgccttcccgttccgctatcggctgaatttgattgcgagtgagatatttatgccagcc
agccagacgcagacgcgccgagacagaacttaatggcccgctaacagcgcgatttgctggtgacccaatgcgaccagatgctccacgc
ccagtcgcgtaccgtcttcatgggagaaaataatactgttgatggggtgtctggtcagagacatcaagaaataacgccggaacattagtgcag
gcagcttccacagcaatggcatcctggtcatccagcggatagttaatgatcagcccactgacgcgttgcgcgagaagattgtgcaccgccg
cttacaggcttcgacgccgcttcgttctaccatcgacaccaccacgctggcacccagttgatcggcgcgagatttaatcgccgcgacaattt
gcgacggcgcgtgcagggccagactggaggtggcaacgccaatcagcaacgactgtttgcccgccagttgttgtgccacgcggttggga
atgtaattcagctccgccatcgccgcttccactttttcccgcgttttcgcagaaacgtggctggcctggttcaccacgcggaaacggtctgat
aagagacaccggcatactctgcgacatcgtataacgttactggtttcacattcaccaccctgaattgactcttccgggcgctatcatgccata
ccgcgaaaggttttgcgccattcgatggtgtccgggatctcgacgctctcccttatgcgactcctgcattaggaaattaatacgactcactata
ggggaattgtgagcggataacaattcccctgtagaaatantttgtttaactttaataaggagatataccatgggcagcagccatcaccatcatc
accacagccaggatccgtcacccctgatgctgtacaattgacgacgacaagggcccgggcaaactagtaatcagacgcggtcgttcactt
gttcagcaaccagatcaaaagccattgactcagcaaggggttgaccgtataattcacgcgattacaccgcattgcggtatcaacgcgcccta
gctcagttggatagagcaacgaccttctaagtcgtgggccgcaggttcgaatcctgcagggcgcgccattacaattcaatcagttacgccttc
ttatatcctccagccatggccttgaaatggcgttagtcatgaaatatagaccgccatcgagtacccctgtacccttaactcttcctgatacgta
aataatgatttggtggcccttgctggacttgaaccagcgaccaagcgattatgagtcgcctgctctaaccactgagctaaagggccttgagtg
tgcaataacaatacttataaaccacgcaataaacatgatgatctagagaatcccgtcgtagccaccatctttttttgcgggagtggcgaaattg
gtagacgcaccagatttaggttctggcgccgctaggtgtgcgagttcaagtctcgcctcccgccaccattcaccagaaagcgttgatcggatg
ccctcgagtcgggcagcgttgggtcctggccacgggtgcgcatgatcgtgctcctgtcgttgaggaccccggctaggctggcggggttgcc
ttactggttagcagaatgaatcaccgatacgcgagcgaacgtgaagcgactgctgctgcaaaacgtctgcgacctgagctcgaattcctct
cttttactcgtttagcaaccggctaaacatccccaccgcccggccaaaagaaaaataggtccattttatcgctaaaagataaatccacacagt
ttgtattgttttgtgcaaaagtttcactacgctttattaacaatacttctggcgacgtgcgccagtgcagaaggatgagctttcgttttcagcatct
cacgtgaagcgatggtttgccttgctacagggacgtcgcttgccgaccataagcgcccggtgtcctgccggtgtcgcaaggaggagagac
gtgcgatatgggtcatcaccatcatcaccacggctcgatcacaagtttgtacaaaaaagcaggctcagaaacctgtattttcagggaggaa
aagtagagaaaggagatgtcataagacttcattacactggaaaggttaaagaaactggagaaatcttcgacacaacttatgaggatgttgca
aaagaagctagaatatacaatccaaacggaatctatgggccagtccctatagcggttggagcgggacacgtattgcccggactagacaag
agacttataggggcttgaagttaagaaaaaatacgtcattgaagttccacccgaagaaggctttggattgagagatccaggaaaaattaagatt
atcccacttggaaagttcagaaaatctggaataatcccgtaccctgggctagaaattgaagttgaaacagaaaatgggagaaaaatgagag
gtagggtcttacagttagcggaggaagagttagagtagacttcaatcatccattagcaggaaagactctcgtatatgaagttgaagttgttga
gaaaattgaagatccaatagaaaagattaaggcactaatagaactaagactgccaatgattgacaaagataaggttattattgagattagtaa
aaagatgtaaagctaaacttcaaagacgttgatattgatccaaagacactaattttgggcgaaattcttctcgaaagtgacttgaaatttatagga
tatgagaaagttgaatttgagccaaccattgaagagttattaaagcccaagtctgccgaggagcaagagtctcctaacgaagaacagcaag
aggagagtgagtctaaagcggaagaatcttaggaaaacctgtattttcagggaggagacccagcttc The tetrameric enzyme (αβγδ) should use NADPH and MV as electron donors The dimeric enzyme (αδ) should use MV but not NADPH as an electron donor

FIG 20B

Plasmid pEA-0893/0894 sequence:

ttgtacaaacttgtgatcgagccacccatatcgcacgtctctcctccttgcgacaccggcaggacaccgggcgcttatggtcggcaagcgac
gtccctgtagcaaggcaaaccatcgcttcacgtgagatgctgaaaacgaaagctcatccttctgcactggcgcacgtcgccagaaagtattg
ttaataaagcgtagtgaaactttgcacaaaacaatacaaactgtgtggatttatctttagcgataaaaatggacctattttcttttggccgggc
ggtggggatgtttagccggttgctaaacgagtaaaagagaaggaattcgagctcgaattcggatcctagagggaaaccgttgtggtctccct
atagtgagtcgtattaattcgcgggatcgagatctcgggcagcgttgggtcctggccacgggtgcgcatgatcgtgctcctgtcgttgagga
cccggctaggctggcggggttgccttactggttagcagaatgaatcaccgatacgcgagcgaacgtgaagcgacgctgctgcaaaacgt
ctgcgacctgagcaacaacatgaatggtcttcggtttccgtgttcgtaaagtctggaaacgcggaagtcagcgccctgcaccattatgttcc
ggatctgcatcgcaggatgctgctggctaccctgtggaacacctacatctgtattaacgaagcgctggcattgaccctgagtgattttctctg
gtcccgccgcatccataccgccagttgtttaccctcacaacgttccagtaaccgggcatgttcatcatcagtaacccgtatcgtgagcatcctc
tctcgtttcatcggtatcattaccccatgaacagaaatcccccttacacggaggcatcagtgaccaaacaggaaaaaaccgcccttaacatg
gcccgctttatcagaagccagacattaacgcttctggagaaactcaacgagctggacgcggatgaacaggcagacatctgtgaatcgcttc
acgaccacgctgatgagctttaccgcagctgcctcgcgcgtttcggtgatgacggtgaaaacctctgacacatgcagctcccggagacggt
cacagcttgtctgtaagcggatgccggggagcagacaagcccgtcagggcgcgtcagcgggtgttggcgggtgtcggggcgcagccatg
acccagtcacgtagcgatagcggugtgtatactggcttaactatgcggcatcagagcagattgtactgagagtgcaccatatatgcggtgtg
aaataccgcacagatgcgtaaggagaaaataccgcatcaggcgctcttccgcttcctcgctcactgactcgctgcgctcggtcgttcggctg
cggcgagcggtatcagctcactcaaaggcggtaatacggttatccacagaatcaggggataacgcaggaaagaacatgtgagcaaaagg
ccagcaaaaggccaggaaccgtaaaaaggccgcgttgctggcgtttttccataggctccgcccccctgacgagcatcacaaaaatcgacg
ctcaagtcagaggtggcgaaacccgacaggactataaagataccaggcgtttccccctggaagctccctcgtgcgctctcctgttccgacc
ctgccgcttaccggatacctgtccgcctttctcccttcgggaagcgtggcgctttctcatagctcacgctgtaggtatctcagttcggtgtaggt
cgttcgctccaagctgggctgtgtgcacgaaccccccgttcagcccgaccgctgcgccttatccggtaactatcgtcttgagtccaacccgg
taagacacgacttatcgccactggcagcagccactggtaacaggattagcagagcgaggtatgtaggcggtgctacagagttcttgaagtg
gtggcctaactacggctacactagaaggacagtatttggtatctgcgctctgctgaagccagttaccttcggaaaaagagttggtagctcttga
tccggcaaacaaaccaccgctggtagcggtggtttttttgtttgcaagcagcagattacgcgcagaaaaaaaggatctcaagaagatcctttg
atcttttctacggggtctgacgctcagtggaacgaaaactcacgttaagggattttggtcatgagattatcaaaaaggatcttcacctagatcctt
ttaaattaaaaatgaagttttaaatcaatctaaagtatatatgagtaaacttggtctgacagttaccaatgcttaatcagtgaggcacctatctcag
cgatctgtctatttcgttcatccatagttgcctgactccccgtcgtgtagataactacgatacgggagggcttaccatctggccccagtgctgca
atgataccgcgagacccacgctcaccggctccagatttatcagcaataaaccagccagccggaagggccgagcgcagaagtggtcctgc
aactttatccgcctccatccagtctattaattgttgccgggaagctagagtaagtagttcgccagttaatagtttgcgcaacgttgttgccattgct
gcaggcatcgtggtgtcacgctcgtcgtttggtatggcttcattcagctccggttcccaacgatcaaggcgagttacatgatccccatgttgt
gcaaaaaagcggttagctccttcggtcctccgatcgttgtcagaagtaagttggccgcagtgttatcactcatggttatggcagcactgcataa
ttctcttactgtcatgccatccgtaagatgcttttctgtgactggtgagtactcaaccaagtcattctgagaatagtgtatgcggcgaccgagttg
ctcttgcccggcgtcaatacgggataataccgcgccacatagcagaactttaaaagtgctcatcattggaaaacgttcttcggggcgaaaact
ctcaaggatcttaccgctgttgagatccagttcgatgtaacccactcgtgcacccaactgatcttcagcatcttttactttcaccagcgtttctgg
gtgagcaaaaacaggaaggcaaaatgccgcaaaaaagggaataagggcgacacggaaatgttgaatactcatactcttcctttttcaatatt
attgaagcatttatcagggttattgtctcatgagcggatacatatttgaatgtatttagaaaaataaacaaataggggttccgcgcacatttcccc
gaaaagtgccacctgaaattgtaaacgttaatattttgttaaaattcgcgttaaattttgttaaatcagctcattttttaaccaataggccgaaatcg
gcaaaatcccttataaatcaaaagaatagaccgagatagggttgagtgttgttccagtttggaacaagagtccactattaaagaacgtggact

FIG 20C ccaacgtcaaagggcgaaaaaccgtctatcagggcgatggcccactacgtgaaccatcaccctaatcaagtttttgggggtcgaggtgccg
taaagcactaaatcggaaccctaaagggagcccccgatttagagcttgacggggaaagccggcgaacgtggcgagaaaggaagggaa
gaaagcgaaaggagcgggcgctagggcgctggcaagtgtagcggtcacgctgcgcgtaaccaccacacccgccgcgcttaatgcgcc
gctacagggcgcgtcccattcgccaatccggatatagttcctccttttcagcaaaaaaccccctcaagacccgtttagaggccccaagggglta
tgctagttattgctcagcggtggcagcagccaactcagcttcctttcgggctttgttagcagccggatctcagtggtggtggtggtggtgctcg
agtgcggccgcaagcttagcagccggatctgatcttaattaattatcaccacttigtacaagaaagctgggtctccctattaaagtctaaccac
gtggactgagcaagatatgcatggatcataagccctaacaaccatctcagccagtatcttaacctttctggatcgtcattgtagtgcttttctgc
catcattcttacatgttcttccatcattgccaagttgaatgctgtaggtgttattatgtcggcataagaaaccctccattctcaactttgagggcat
agactaagattcccettggagcctcagtcgttgagacaccaaagccgtcctttatctcaacttcatccctgggcttaattggccactiggcgag
agcctcgtcgagcagatctattgccctctctataaagtaaactatttcgagggcctgggctaagttatttgcaaacggatttgttccctttaatag
gtctttgtttgcctcatacagctccttggccttgccgtataggaggtcagcattgttaataactctagatatagccccaaccatgaagggtctgcc
cttgtagtgactgtgcttgcaaaactgtgttcaacgacgaactcctttatataatctctgtacttttcacttgggaactcctccccatcacttgcctt
tatgtaatctccataaattccataagcatctcccctcggcttcacggccaagtgtgttattggcccttcaacttcgctgtactgctcaagctttgca
aataactcaaaagtatactcggcaagtggtagggcttccctaagctcggcttttcatttctcaaggacactcttctcagggagctttccgaatcc
gcccaaaaccgcattttcttggtgtatggctcttgaccctagaatgtccatcatccaggtgccaaggttcttcagcttaagggctatctctatctc
cctcttgtattcattcaccatcttaagtgggctcgagtagccccttgtagtcgggaagaactagaagatataggtgaagggcatgactctctatc
atgtctccgatgtatagtacttctctaagggcctgtatctcttcccttgggacaaaaccgacggccttttctgcagcctctaatgcggttaacttgt
gggcggctgaacagaatgagcatattctcgggtaaatggccagagcttcctcaagcttcttcccaatagttatggcctcaaagaatctgggcc
cttcaattatgtttagcttgaccctcctigactccatcatcccaattattatctccacaccacccticcctcaactcttgctatatgatcaatggtga
ttggaagatagaggttcttcattgttcaccacctgagaatatttittcaaccatttictcaaccctctcatcatgtccattgaacatttticattctctcaa
ttatctcctctittgtcatccccttctccttgaacaccttagctagagagtcgaaccaagctacatcgtaccctattgcccctctgcatcctatacac
gcaactccaaatcctggacatctcgcgttacatcctgcccttgttactggacctagacagggttctccttictcaagaaggatacatggatgtcc
attgagcctacattctagacaaactggataatctatatcctctggccatgaaccaatcaagaatgttcccagggcgtagaggaagtccttcttct
ctggtgggcaaccgtagatgttgtagtcaacttttatgtatttitgaaactggttcagccttcttcggttggaacttgacttttgcgtctccataaacc
ttcttccagagctcttctaatggcttttcactccagctctgaactcctccttgaacagcacaagctccaaccgcaacgacgatcttigcattctcc
ctaattttittcacgagttcaacttcttcctcagttgaaacgcttccttctataaaagctatgtcgacctttcatcctcaatgctatctctatcaatcat
gaaccagcaaactatttcagcatttgggataagttgtaataactcgtccatcatagctagctgcaattgacagccgtagcacgaggttaatgcg
taaaatccaatcctaactttcctcctgagcctgctttt

Figure 21A

```
                      1                                                  50
PF0891  Beta    (1)   ░░░░MRYVKLPKENTYEFLERLKDWGKLYAPVKISDKFYDFREIDDVRK
PAB1784 Beta    (1)   ░░░░MRYVKLPKENVYTFLERLKDWGKLYAPVKISEKFYDFREIDDVRK
TK2072  Beta    (1)   ░░░░MRYVKLPKENTYTFLERLKEWGKLYAPVKISEKFYDFREIDDVRK
PH1290  Beta    (1)   MEVTLLRYVKLPKENTYEFLERLKEWGKLYAPVKISEKFYDFREIDDVRK
                      51                                                100
PF0891  Beta    (46)  IEFHYNRTIMPPKKFFFKPREKLFEFDISKPEYREVIEEVEPEIIFGVHA
PAB1784 Beta    (46)  VEFHYTRTIMPPKKFFFKPREKLFEFDISKPEYREVIEDVEPFVLFGVHA
TK2072  Beta    (46)  VEFNYNRTIMPPKKFFFPREKLFEFDLSRPEYRETIEDVEPFVIFGLHA
PH1290  Beta    (51)  VEFHYTRTIMPPKKFFFKPREKMFEFDLSKPEYKEVIEDVEPFVLFGVHA
                      101                                               150
PF0891  Beta    (96)  CDIYGLKILDTVYLDEFPDKYYKVRREKGIIIGISCMPDEYCFCNLRETD
PAB1784 Beta    (96)  CDIYGLKLLDTVYLDEFPDKYYKVRREKGIIIGISCMPDEYCFCNLRETD
TK2072  Beta    (96)  CDIHGLKILDTVYLDELPDKYYKARREKGIIIGISCMPDEYCFCNLRETD
PH1290  Beta    (101) CDIYGLKILDTIYLDELPDKYYKIRREKGIIIGISCMPDEYCFCNLRKTD
                      151                                               200
PF0891  Beta    (146) FADDGFDLFEHELPDGWLVRVGTPTGHRLVDKNIKLFEEVTDKDICAFRD
PAB1784 Beta    (146) FADDGFDLFLHELPDGWLVRVGTPTGHRIVDKNIKLFEEVTNEDICAFRE
TK2072  Beta    (146) FADDGFDLFLHELPDGWLVRVGSPTGHRIVDKNMELFEEVTEDICNFRE
PH1290  Beta    (151) FADDGFDLFLHELPDGWLVRVGSPTGHRIVDKNIKLFEEVTDEDICAFRE
                      201                                               250
PF0891  Beta    (196) FEKRROQAFKYHEDWGNLRYLLELEMEHPMWDEEADKCLACGICNTTCPT
PAB1784 Beta    (196) FEKKRHEAFKYHEDWGNLRYLLELEMEHPMWDEEAEKCLACGICNTTCPT
TK2072  Beta    (196) FENKRSQAFKYHEDWSNLRYLLELEMEHPMWEEQADECLACGICNTTCPT
PH1290  Beta    (201) FEKKROEAFKYHEDWDNLRYLLELEMEHPMWEEEANKCLACGICTETCPT
                      251                                               300
PF0891  Beta    (246) CRCYEVQDIVNLDGVTGYRERRWDSCQFRSHGLVAGGHNFRPTKKDRFRN
PAB1784 Beta    (246) CRCYEVQDIVNLDGVTGYRERRWDSCQFRSHGLVAGGHNFRPTKKSRFEN
TK2072  Beta    (246) CRCYEVQDIVNLDGETGYRERRWDSCQFRSHGLVAGGHNFRPTKKDRFRN
PH1290  Beta    (251) CRCYEVQDIVNLDGITGYRERRWDSCQFRSHGLVAGGHNFRPTKKDRFRN
                      301                                               350
PF0891  Beta    (296) RYLCKNAYNEKLGLSYCVGCGRCTAFCPANISFVGNLRRILGLEENKCPP
PAB1784 Beta    (296) RYLCKNSYNEKLGISFCVGCGRCTAFCPAGISFVRNLRRILGLEEQKCPP
TK2072  Beta    (296) RYLCKNSYNEKLGLSYCVGCGRCTMFCPAGISFVRNLREILGLEEKSCPS
PH1290  Beta    (301) RYLCKNAYNEKLGLSYCVGCGRCTAFCPAGISFVRNLRVILGEEQRCPP
                      351              372
PF0891  Beta    (346) TVSEEIPKRGFAYSSNIRGDGW
PAB1784 Beta    (346) SVSEEIPKRGFAYSPGVGGEEE
TK2072  Beta    (346) EITEEIPKRGFAYASHIRGDGE
PH1290  Beta    (351) NVSEEIPKKGFAYSPGVGGDEE
```

Figure 21 B

```
1                                                        50
  PF0892  Gamma     (1)  MMLPKEIMMPNDNPYALHRVKVLKVYSLTETEKLFLFRFEDPELAEKW
  PAB1785 Gamma     (1)  MTLPKEVMMPNDNPYALHRVKVLKVYDLTEREKLFLFRFEDPKLAETW
  TK2071  Gamma     (1)  MSMVLPKEIMMPNDNPYALHRAKVLRVYBLTEKEKLFLFRFEDABLAEKW
  PH1291  Gamma     (1)  MNLPKDVMMPNDNPYALHRVKVLKVYDLTEKEKLFLFRFEDPKLAETW
                        51                                                       100
  PF0892  Gamma    (49)  TFKPGQFVQLTIPGVGEVPISICSSPMRKGFFELCIRKAGRVTTVVHRLK
  PAB1785 Gamma    (49)  TFKPGQFVQLTIPGVGEVPISICSSPMRKGFFELCIRRAGRVTTVVHRLK
  TK2071  Gamma    (51)  TFRPGQFVQLTIPGVGEVPISICSSAMRRGFFELCIRKAGRVTTVVHRLK
  PH1291  Gamma    (49)  TFKPGQFVQLTIPGVGEVPISICSSPMRRGFFELCIRRAGRVTTVVHRLK
                       101                                                       150
  PF0892  Gamma    (99)  PGDTVLVRGPYGNGFPVDEWEGMDLLLIAAGLGTAPLRSVFLYAMDNRWK
  PAB1785 Gamma    (99)  PGDTVLVRGPYGNGFPVDEWEGMDLLLIAAGLGTAPLRSVFLYAMDNRWK
  TK2071  Gamma   (101)  PGDTVLVRGPYGNGFPVDEWEGMDLLLIAAGLGTAPLRSVFLYAMDNRWK
  PH1291  Gamma    (99)  PGDIVLVRGPYGNGFPVDEWEGMDLLLIAAGLGAAPLRSVFLYAMDNRWK
                       151                                                       200
  PF0892  Gamma   (149)  YGNITFINTARYGKDLLFYKELEAMKDLAEAENVKIIQSVTRDPNWPGLK
  PAB1785 Gamma   (149)  YGNITFINTARYGKDLLFYKELEAMKDLAEAENVKIIQSVTRDPDWPGLH
  TK2071  Gamma   (151)  YGNITFINTARYGKDLLFYKELEAMKDLAEAENVKIIQSVTRDPDWPGLH
  PH1291  Gamma   (149)  YGNITFINTARYGKDLLFYKELEAIKDLAEAENVKIIQSVTRDPNWPGLH
                       201                                                       250
  PF0892  Gamma   (199)  GRPQQFIVEANTNPKNTAVAICGPPRMYKSVFEALINYGRPENIFVTLE
  PAB1785 Gamma   (199)  GRPQQFIVEANTNPKNTAVAICGPPRMYKAVFESLINYGRPENIYVTLE
  TK2071  Gamma   (201)  GRPQNFIBEANTNPKKTAVAICGPPRMYKAVFEALINYGRPENIYVTLE
  PH1291  Gamma   (199)  GRPQQFIVEANTNPKNTAVAICGPPRMYKSVFEALINYGRPENIYVTLE
                       251                                          294
  PF0892  Gamma   (249)  RRMKCGIGKCGHCNVGTSTSWKYICKDGPVFTYFDIVSTPGLLD
  PAB1785 Gamma   (249)  RRMKCGIGKCGHCVAGTSTSWKYVCKDGPVFGYFDIISTPGLLD
  TK2071  Gamma   (251)  RKMKCGIGKCGHCNVGTSTSWKYVCKDGPVFGYFDIISTPGLLD
  PH1291  Gamma   (249)  RKMKCGIGKCGHCVVGTSTSBKYICKDGPVFTYFDIVSTPGLLD
```

Figure 21 C

```
1                              50
  PF0893 Delta    (1)  ▓▓MG▓▓KVRIGFYALTSCYGCQLQLAMMDELLQLIPNAEIVCWEMIDRD
 PAB1786 Delta    (1)  ▓▓MG▓▓KLRIGFYALTSCYGCQLQLAMMDELLKLIPNAEIVCWYMLDRD
  TK2070 Delta    (1)  ▓▓MS▓KKIRIGFYALTSCYGCQLQFAMMDEILQLIPNVEIACWFMLERD
  PH1292 Delta    (1)  MG▓MGKKKIRIGFYALTSCYGCQLQLAMMDELLILLPHIELVCWYMVDRD
                        51                                              100
  PF0893 Delta   (46)  SIEDEKVDIAFIEGSVSTEEEVELVKKIRENAKIVVAVGACAVQGGVQSW
 PAB1786 Delta   (46)  SVEDKPVDIAFIEGSVSTEEEVELVKKIRENAKIVVAVGACAVQGGVQSW
  TK2070 Delta   (48)  SYEDEPVDIAFIEGSVSTEEEAELVKKIRENAKIVVAVGSCAVQGGVQSW
  PH1292 Delta   (51)  SIDDEPVDIAFIEGSVSTEEEVELVKKIRENSKIVVAVGACAVQGGVQSW
                        101                                             150
  PF0893 Delta   (96)  SREKPLEELWKKVYGDAKVKFQPKKAEPVSKYIKVDYNIYGCPPEKKDFL
 PAB1786 Delta   (96)  TEDKSLEELWKTVYGDAKVKFQPKKAEPVSKYIKVDYNIYGCPPEKRDFL
  TK2070 Delta   (98)  RKDKPLEELWKTVYGDAKVKFQPKMAEPISNYIKVDYNIYGCPPEKRDFL
  PH1292 Delta  (101)  TEDKSLEELWRTVYGDAKVKFKPKKAEPVSKYIKVDYNIYGCPPEKRDFL
                        151                                             200
  PF0893 Delta  (145)  YALGTFLIGSWPEDIDYPVCLECRLNGHPCILLEKGEPCLGPVTRAGCNA
 PAB1786 Delta  (145)  YALGTFLIGSWPEDIDYPVCLECRLNGYPCVLLEKGEPCLGPITRAGCNA
  TK2070 Delta  (148)  YTLGTILIGSWPEDIDYPVCLECRLRGNTCVLLERGEPCLGPVTRAGCDA
  PH1292 Delta  (150)  YALGTFLIGSWPEDIDYPVCLECRLNGYPCVLLEKGEPCLGPVTRAGCNA
                        201                                             250
  PF0893 Delta  (195)  RCPGFGVACIGCRGAIGYDVAWFDSLAKVFKEKGMTKEEIIERMKMFNGH
 PAB1786 Delta  (195)  RCPGFGIACIGCRGAIGYDVAWFDSLARVFKEKGLTKEEILERMKIFNGH
  TK2070 Delta  (198)  RCPAYGIACIGCRGAIGYDVAWFDSLARVFREKGLTKEEILERMRMFNAH
  PH1292 Delta  (200)  RCPGFGIACIGCRGAIGYDVAWFDSLARVFKEKGLTKEEIIERMKIFNGH
                        251           267
  PF0893 Delta  (245)  DERVEKMVEKIFSGGEQ
 PAB1786 Delta  (245)  DERIEKMVEKVFQDVKE
  TK2070 Delta  (248)  NEKLEMVNKIFQDVKE
  PH1292 Delta  (250)  DDRIEKMVEKIFQGVKE
```

Figure 21 D

```
PF0894  Alpha    (1) MKNLYLPITIDHIARVEGKGGVEIIIGDDGVKEVKLNIIEGPRFFEAITI
PAB1787 Alpha    (1) MRNLYIPITVDHIARVEGKGGVEIIVGDEGVKEVKLNIIEGPRFFEAITI
TK2069  Alpha    (1) MKNVYLPITVDHIARVEGKGGVEIVVGDDGVKEVKLNIIEGPRFFEAITL
PH1294  Alpha    (1) MKEIYIPITVDHIARIEGKAGVEILVGEDGVKEVKLNIIEGPRFFEAITL
                     51                                              100
PF0894  Alpha   (51) GKKLEEALAIYPRICSFCSAAHKLTALEAAEKAVGFVPREEIQALREVLY
PAB1787 Alpha   (51) GKKLEEALAIYPRICSFCSAAHKLTALEAAEKAIGFTPREEIQALREVLY
TK2069  Alpha   (51) GKKLDEALAIYPRICSFCSAAHKLTAVEAAEKAIGFTPREEIQALREVLY
PH1294  Alpha   (51) GKKLEEALAIYPRICSFCSAAHKLTALEAAEKAIGFTPREEIQALREILY
                     101                                             150
PF0894  Alpha  (101) IGDMIESHALHLYLLVLPDYRGYSSPLKMVNEYKREIEIALKLKNLGTWM
PAB1787 Alpha  (101) IGDMIESHALHLYLLVLPDYLGYSSPLKMVNEYKKELEIALKLKNLGSWM
TK2069  Alpha  (101) IGDMIESHALHLYLLVLPDYLGYSGPLHMIDEYKKEMSIALDLKNLGSWM
PH1294  Alpha  (101) IGDIIESHALHLYLLVLPDYLGYSSPLKMVDEYKKELEAIKLKNLGSWI
                     151                                             200
PF0894  Alpha  (151) MDILGSRAIHQENAVLGGFGKLPEKSVLEKMKAELREALPLAEYTFELFA
PAB1787 Alpha  (151) MDVLGSRAIHQENAILGGFGKLPSKETLEEMKAKLRESLSLAEYTFELFA
TK2069  Alpha  (151) MDVLGSRAIHQENAVLGGFGKLPDKSVLENMKRRLKEALPKAEYTFELFT
PH1294  Alpha  (151) MDVLGARAIHQENAILGGFGKLPSKETLEKIKDELKSALPLAEYTFELFS
                     201                                             250
PF0894  Alpha  (201) KLEQYSEVEGPITHLAVKPRGDAYGIYGDYIKASDGEEFPSEKYRDYIKE
PAB1787 Alpha  (201) KLEQYREVEGHITHLAVKPRGDVYGIYGDYIKASDGEEFPSEDYKEHINE
TK2069  Alpha  (201) KLEQYEEVEGPITHIAVKPRNGVYGIYGDYLKASDGNEFPSEEYREHIKE
PH1294  Alpha  (201) KLEQYKEVEGHITHLAVKPRKDAYGIYGDRIKASDGEEFPSEEYKNYIKE
                     251                                             300
PF0894  Alpha  (251) FVVEHSFAKHSHYKGRPFMVGAISRVINNADLLYGKAKELYEANKDLLKG
PAB1787 Alpha  (251) FVVEHSFAKHSHYKGKPFMVGAISRVVNNKDLLYGRAKDLYESHKELLKG
TK2069  Alpha  (251) FVVEHSFAKHSHYHGKPFMVGAISRLVNNADILYGRAKELYESKKDLLRS
PH1294  Alpha  (251) FVVEHSFAKHSHYKGRPFMVGAISRLVNNKKLLYGKAKELYENNKDLLRK
                     301                                             350
PF0894  Alpha  (301) TNPFANNLAQALEIVYFIERAIDLLDEALAKWPIKPRDEVEIKDGFGVST
PAB1787 Alpha  (301) TNPFANNLAQALELVYFIERAIDLIDEVLKKWPVKKRDKVEVRDGFGVST
TK2069  Alpha  (301) TNPFANNLAQALELVYFIERAIDLIDEALAKWPIRPRDEVALKDGFGVST
PH1294  Alpha  (301) TNPFANNLAQALEIVYFMERAIDLIDEVLAKWPIKPRDEVKVRDGFGVST
                     351                                  400
PF0894  Alpha  (351) TEAPRGILVYALKVENGRVSYADIITPTAFNLAMMEEHVRMMAEKHYNDD
PAB1787 Alpha  (351) TEAPRGILVYALKVENGRVAYADIITPTAFNLAMMEEHVRMMAEKHYNDD
TK2069  Alpha  (351) TEAPRGVLVYALKVENGRVSYADIITPTAFNLAMMEQHVRMMAEKHYNDD
PH1294  Alpha  (351) TEAPRGILVYALKVENGRVSYADIITPTAFNLAMMERHVRMMAEEHYKDD
                     401                      429
PF0894  Alpha  (401) PERLKILAEMVVRAYDPCISCSVHVVRL
PAB1787 Alpha  (401) PERLKLLAEMVVRAYDPCISCSVHVVKL
TK2069  Alpha  (401) PEKLKLLAEMVVRAYDPCISCSVHVARL
PH1294  Alpha  (401) PEKLKLLAEMVVRAYDPCISCSVHVVKL
```

HYDROGENASE POLYPEPTIDE AND METHODS OF USE

CONTINUING APPLICATION DATA

This application is a continuation patent application of U.S. patent application Ser. No. 12/746,154 filed on Aug. 27, 2010, which is the §371 U.S. National Stage of International Application No. PCT/US2008/013449, filed Dec. 5, 2008, which claims the benefit of U.S. Provisional Application Ser. No. 61/005,383, filed Dec. 5, 2007, each of which are incorporated by reference herein in their entireties.

SEQUENCE LISTING

This application contains a Sequence Listing electronically submitted via EFS-Web to the United States Patent and Trademark Office as an ASCII text file entitled "235-01020102_SequenceListing_ST25.txt" having a size of 162 kilobytes and created on May 2, 2014. The information contained in the Sequence Listing is incorporated by reference herein.

GOVERNMENT FUNDING

The invention was made with government support under Grant No. DE-FG02-05ER 15710, awarded by the Department of Energy. The government has certain rights in this invention.

BACKGROUND

Molecular hydrogen ($H_2$) is typically produced by steam reforming of methane, and platinum is the most commonly used catalyst for hydrogen production. Due to utilization of fossil fuels as a source of methane, as well as the expense, limited availability, sensitivity to poisoning, and bioincompatibility of the catalyst, it is not likely to be utilized in economical energy conversion systems (Bharadwaj and Schmidt. 1995. Fuel Processing Technology 42:109-127; Ghenciu. 2002. Current Opinion in Solid State & Materials Science 6:389-399). However, in 2003 President Bush in the State of the Union Address proposed the Hydrogen Fuel Initiative, the goal of which was to develop new technologies for production and utilization of $H_2$ as a potential source of energy to replace fossil fuels. In microorganisms, the molecular machine responsible for the biological uptake and evolution of hydrogen is an enzyme known as hydrogenase. Hydrogenase catalyzes the simplest of chemical reactions, the interconversion of the neutral molecule $H_2$ and its elementary constituents, two protons and two electrons (Eqn. 1).

$$2H^+ + 2e^- \leftarrow\rightarrow H_2 \qquad (1)$$

Ironically, however, while the reaction that they catalyze is simple, hydrogenase enzymes are multimeric proteins and typically are sensitive to air (oxygen). This has to-date precluded the facile production of a recombinant form of the major class of hydrogenase, the so-called 'nickel-iron' (NiFe) type.

Hydrogenases are found in representatives of most microbial genera, as well as some unicellular eukaryotes (Adams et al. 1980. Biochim Biophys Acta 594:105-76; Cammack et al. 2001. Hydrogen as a fuel: learning from nature. Taylor & Francis, London, New York; Friedrich and Schwartz. 1993. Annual Review of Microbiology 47:351-383; Przybyla et al. 1992. FEMS Microbiology Reviews 88:109-135, Vignais et al. 2001. FEMS Microbiology Reviews 25:455-501). The enzyme allows many microorganisms to use $H_2$ gas as a source of low potential reductant ($H_2/H^+$, $E°'=-420$ mV), either for carbon fixation or as a source of energy. In aerobic environments, $H_2$ oxidation can be coupled via membrane electron transport to the reduction of oxygen ($O_2/H_2O$, $E°'=+820$ my). There are a variety of electron acceptors that can be coupled to anaerobic $H_2$ oxidation, including carbon dioxide, which can be reduced to either methane (by methanogens) or acetate (by acetogens), and sulfate and ferric-iron, which are reduced to sulfide and ferrous iron, respectively. On the other hand, microorganisms that produce $H_2$ during growth are widespread in anaerobic environments. The production of $H_2$ is used as a mechanism to dispose of the excess reductant that is generated during the oxidation of organic material. These fermentative organisms conserve energy by chemical synthesis (substrate level phosphorylation) independent of the means by which they dispose of reductant (be it as $H_2$ or as a reduced organic compound such as ethanol). However, it was recently discovered that some organisms are able to conserve energy directly from the production of $H_2$ by a novel respiratory mechanism (Sapra et al. 2003. Proc Natl Acad Sci USA 100:7545-50).

Two major types of hydrogenase are known: the nickel-iron (NiFe) and the iron-only (Fe) enzymes (Adams. 1990. Biochimica Et Biophysica Acta 1020:115-145; Albracht. 1994. Biochimica Et Biophysica Acta-Bioenergetics 1188:167-204), which are unrelated phylogenetically (Meyer, J. 2007. Cellular and Molecular Life Sciences 64:1063-1084; Vignais et al. 2001. FEMS Microbiology Reviews 25:455-501). The iron-only type is found in only a few types of anaerobic bacteria and some photosynthetic algae, but they have been extensively studied. This includes structural characterization (Chen et al. 2002. Biochemistry 41:2036-2043; Nicolet et al. 2001. Journal of the American Chemical Society 123:1596-1601; Nicolet et al. 2000. Trends in Biochemical Sciences 25:138-143; Nicolet et al. 1999. Structure with Folding & Design 7:13-23; Peters et al. 1998. Science 282:1853-1858) including potential active site models (Boyke et al. 2004. Journal of the American Chemical Society 126:15151-15160; Tye et al. 2006. Inorg Chem 45:1552-9; Zilberman et al. 2007. Inorg Chem 46:1153-61), and recently insights have been provided into their biosynthesis (Mishra et al. 2004. Biochemical and Biophysical Research Communications 324:679-685; Posewitz et al. 2004. Journal of Biological Chemistry 279:25711-25720), as well there are some recent successful attempts to make recombinant forms of these enzymes (King et al. 2006. J Bacteriol 188:2163-72).

The majority of microorganisms that metabolize $H_2$, however, contain NiFe-hydrogenases, an example of which is the cytoplasmic NiFe hydrogenase I of the hyperthermophilic archaeon, *Pyrococcus furiosus*, which grows optimally at 100° C. (Fiala and Stetter. 1986. Archives of Microbiology 145:56-61, Verhagen et al. 2001. Hyperthermophilic Enzymes, Pt A 330:25-30). The NiFe-hydrogenases have also been extensively characterized over the last 40 years, and several crystal structures are available (Garcin et al. 1998. Biochemical Society Transactions 26:396-401, Higuchi. 1999. Structure 7:549-56, Volbeda and Fontecilla-Camps. 2003. Dalton Transactions: 4030-4038, Volbeda et al. 1996. Journal of the American Chemical Society 118:12989-12996). They all are made up of at least two subunits, one of which contains the NiFe-catalytic site, while the other contains three iron-sulfur (FeS) clusters. These clusters serve to shuttle electrons from the electron donor to the enzyme to and from the NiFe site in the catalytic subunit. The Ni atom is bound to four cysteinyl residues of this subunit, two of which are near the N-terminus and two near the C-terminus. Two of the four Cys bind a single Fe atom, which is also coordinated, remarkably, by one carbon monoxide (CO) and two cyanide (CN) ligands (Bagley et al. 1995. Biochemistry 34:5527-5535, Happe et al. 1997. Nature 385:126-126, Pierik et al. 1999. Journal of Biological Chemistry 274:3331-3337). These diatomic ligands serve to activate the iron atom (maintaining it in the low spin state) thereby facilitating catalysis. Interestingly, such ligands are also found at the active site of the iron-only hydrogenases (Nicolet et al. 2002. J Inorg Biochem 91:1-8), as well as the mononuclear iron site of a third type of hydrogenase found in a very limited number of archaea (Lyon et al. 2004. Journal of the American Chemical Society 126:14239-14248), an example of convergent evolution toward a similar function.

The hydrogenase of *P. furiosus* is of particular interest for additional reasons. First, it is obtained from an organism that grows optimally at 100° C. and has been shown to be an exceedingly robust and thermostable enzyme (Bryant and Adams. 1989. J Biol Chem 264:5070-9; Ma and Adams. 2001. Methods Enzymol 331:208-16). Second, in in vitro assays, the enzyme has been shown to be able to generate hydrogen gas by oxidizing NADPH in a reversible reaction (Ma and Adams. 2001. Methods Enzymol 331:208-16; Ma et al. 2000. J Bacteriol 182:1864-71; Ma et al. 1994. FEMS Microbiology Letters 122:245-250), which is a very rare property among the hydrogenases that have been characterized to date. Consequently, the reversible *P. furiosus* enzyme has utility in generating reductants such as NADPH. Likewise, the *P. furiosus* enzyme has utility in hydrogen production systems in which carbohydrates are oxidized to generate NADPH, which in turn can be converted to hydrogen gas by the hydrogenase. The production of hydrogen from glucose in an in vitro cell-free system using purified enzymes was first demonstrated over a decade ago (Woodward et al. 1996. Nat Biotechnol 14:872-4). This work was very recently extended in which the conversion of starch to hydrogen was described using an in vitro cell-free system made up of thirteen different enzymes (Zhang et al. 2007. PLoS ONE 2:e456). Twelve of the enzymes are used to oxidize starch and generate carbon dioxide and NADPH, and the thirteenth, *P. furiosus* hydrogenase, oxidizes NADPH and produces hydrogen gas. In this system, the hydrogenase was purified from *P. furiosus* biomass (Ma and Adams. 2001. Methods Enzymol 331:208-16) since a recombinant form of this enzyme was not available.

SUMMARY OF THE INVENTION

Provided herein are polypeptides having hydrogenase activity. In one aspect, the polypeptide is dimeric polypeptide. The amino acid sequence of the first subunit and the amino acid sequence of SEQ ID NO:6 have at least 80% identity, and the amino acid sequence of the second subunit and the amino acid sequence of SEQ ID NO:8 have at least 80% identity. At least one subunit may be a fusion that includes a heterologous amino acid sequence. The dimeric polypeptide may further include two more subunits to result in a tetrameric polypeptide. The amino acid sequence of the third subunit and the amino acid sequence of SEQ ID NO:2 have at least 80% identity, and the amino acid sequence of the fourth subunit and the amino acid sequence of SEQ ID NO:4 have at least 80% identity. The multimeric polypeptide may be isolated, or purified. The tetrameric polypeptide may be present in a genetically modified microbial cell. In some aspects, the genetically modified microbial cell is not *Pyrococcus furiosus, P. abyssi, P. horikoshii, Thermococcus kodakaraensis*, or *T. onnurineus*. It may be present in a microbial cell, such as, but not limited to *Escherichia coli*.

The multimeric polypeptide may have hydrogenase activity of at least 0.05 micromoles $H_2$ produced $min^{-1}$ mg $protein^{-1}$ when isolated by centrifugation of a whole cell extract at 100,000×g, heat-treatment at 80° C. for 30 minutes, and re-centrifugation at 100,000×g. The heterologous amino acid sequence may be present at, for instance, the amino terminal end of a subunit, or the carboxy terminal end of a subunit. The multimeric polypeptide may include one or more chemically modified subunits. Also provided herein is a polypeptide consisting of two subunits or four subunits.

Also provided herein are genetically modified microbes. A genetically modified microbe may include an exogenous polypeptide, wherein the exogenous polypeptide includes two subunits. The first subunit includes an amino acid sequence, and the amino acid sequence of the first subunit and the amino acid sequence of SEQ ID NO:6 have at least 80% identity. The second subunit includes an amino acid sequence, and the amino acid sequence of the second subunit and the amino acid sequence of SEQ ID NO:8 have at least 80% identity. The two subunits form a dimeric polypeptide having hydrogenase activity. The dimeric polypeptide may further include two more subunits to form a tetrameric polypeptide having hydrogenase activity, wherein the third subunit includes an amino acid sequence, and the amino acid sequence of the third subunit and the amino acid sequence of SEQ ID NO:2 have at least 80% identity. The fourth subunit includes an amino acid sequence, and the amino acid sequence of the fourth subunit and the amino acid sequence of SEQ ID NO:4 have at least 80% identity. At least one subunit can be a fusion that includes a heterologous amino acid sequence. A genetically modified microbe may include one or more of the accessory polynucleotides described herein.

A genetically modified microbe may include two exogenous polynucleotides, wherein the exogenous polynucleotides each encode a subunit. The first subunit can include an amino acid sequence, and the amino acid sequence of the first subunit and the amino acid sequence of SEQ ID NO:6 have at least 80% identity. The second subunit can include an amino acid sequence, and the amino acid sequence of the second subunit and the amino acid sequence of SEQ ID NO:8 have at least 80% identity. The two subunits form a dimeric polypeptide having hydrogenase activity. The genetically modified microbe can further include two more exogenous polynucleotides, wherein the two more exogenous polynucleotides each encode a subunit. The third subunit can include an amino acid sequence, and the amino acid sequence of the third subunit and the amino acid sequence of SEQ ID NO:2 have at least 80% identity. The fourth subunit can include an amino acid sequence, and the amino acid sequence of the fourth subunit and the amino acid sequence of SEQ ID NO:4 have at least 80% identity. The four subunits form a tetrameric polypeptide having hydrogenase activity. At least one subunit can be a fusion that includes a heterologous amino acid sequence, such as a histidine tag.

Further provided herein are methods for making a polypeptide having hydrogenase activity. The methods may include providing a genetically modified microbe including exogenous polynucleotides as described herein, and incubating the microbe under conditions suitable for expression of the exogenous polynucleotides to produce a multimeric polypeptide having hydrogenase activity. The method may further include isolating, or optionally purifying, the polypeptide after the incubating.

Provided herein are methods for using a polypeptide having hydrogenase activity. The methods may include providing a polypeptide described herein, and incubating the polypeptide under conditions suitable for producing $H_2$. The produced $H_2$ may be collected.

In one aspect, the polypeptide is an isolated or purified polypeptide. The polypeptide may be present on a surface, such as one that conducts electricity, e.g., an anode. The polypeptide may be chemically modified. The incubating may include conditions that include a polysaccharide, such as a starch or a cellulose. The conditions can include a temperature of at least 37° C. or at least 70° C. 70° C.

In another aspect, the polypeptide is present in a genetically modified microbe. The incubating may include incubating the microbial cell under conditions suitable for the expression of the polypeptide. The incubating may include conditions that include a polysaccharide, such as a starch or a cellulose. The conditions can include a temperature of at least 37° C. or at least 70° C.

Provided herein are methods for using a polypeptide having hydrogenase activity. The methods for using a polypeptide having hydrogenase activity may include providing a polypeptide described herein, and incubating the polypeptide under conditions suitable for producing NADPH. The produced NADPH may be collected.

In one aspect, the polypeptide is an isolated or purified polypeptide. The conditions may include molecular hydrogen, and a temperature of at least 37° C. In another aspect, the polypeptide is present in a genetically modified microbe. The incubating may include incubating the microbial cell under conditions suitable for the expression of the polypeptide. The conditions may include a temperature of at least 37° C.

Also provided herein is an expression system for assembling a polypeptide having hydrogenase activity. The expression system includes the plasmids described herein. The plasmids may be present in a microbe, such as an *E. coli*.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, trimers, tetramers). A polypeptide also may possess non-protein (non-amino acid) ligands including, but not limited to, inorganic iron (Fe), nickel (Ni), inorganic iron-sulfur centers such as [4Fe-4S] clusters, and other organic ligands such as carbon monoxide (CO), cyanide (CN) and flavin. Thus, the terms peptide, oligopeptide, enzyme, subunit, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring. As used herein, "heterologous amino acid sequence" refers to amino acid sequences that are not normally present as part of a polypeptide present in a wilt-type cell. For instance, "heterologous amino acid sequence" includes extra amino acids at the amino terminal end or carboxy terminal of a polypeptide that are not normally part of a polypeptide that is present in a wild-type cell.

As used herein, "hydrogenase activity" refers to the ability of a polypeptide to catalyze the formation of molecular hydrogen ($H_2$).

As used herein, "identity" refers to structural similarity between two polypeptides or two polynucleotides. The structural similarity between two polypeptides is determined by aligning the residues of the two polypeptides (e.g., a candidate amino acid sequence and a reference amino acid sequence, such as SEQ ID NO:2, 4, 6, or 8) to optimize the number of identical amino acids along the lengths of their sequences; gaps in either or both sequences are permitted in making the alignment in order to optimize the number of shared amino acids, although the amino acids in each sequence must nonetheless remain in their proper order. The structural similarity is typically at least 80% identity, at least 81% identity, at least 82% identity, at least 83% identity, at least 84% identity, at least 85% identity, at least 86% identity; at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. A candidate amino acid sequence can be isolated from a microbe, preferably a *Pyrococcus* spp., more preferably a *P. furiosus*, or can be produced using recombinant techniques, or chemically or enzymatically synthesized. Structural similarity may be determined, for example, using sequence techniques such as the BESTFIT algorithm in the GCG package (Madison Wis.), or the Blastp program of the BLAST 2 search algorithm, as described by Tatusova, et al. (*FEMS Microbiol Lett* 1999, 174:247-250), and available through the World Wide Web, for instance at the internet site maintained by the National Center for Biotechnology Information, National Institutes of Health. Preferably, structural similarity between two amino acid sequences is determined using the Blastp program of the BLAST 2 search algorithm. Preferably, the default values for all BLAST 2 search parameters are used, including matrix=BLOSUM62; open gap penalty=11, extension gap penalty=1, gap x_dropoff=50, expect=10, wordsize=3, and optionally, filter on. In the comparison of two amino acid sequences using the BLAST search algorithm, structural similarity is referred to as "identities."

The structural similarity between two polynucleotides is determined by aligning the residues of the two polynucleotides (e.g., a candidate nucleotide sequence and a reference nucleotide sequence, such as SEQ ID NO:1, 3, 5, or 7) to optimize the number of identical nucleotides along the lengths of their sequences; gaps in either or both sequences are permitted in making the alignment in order to optimize the number of shared nucleotides, although the nucleotides in each sequence must nonetheless remain in their proper order. The structural similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. A candidate nucleotide sequence can be isolated from a microbe, preferably a *Pyrococcus* spp., more preferably a *P. furiosus*, or can be produced using recombinant techniques, or chemically or enzymatically synthesized. Structural similarity may be determined, for example, using sequence techniques such as GCG FastA (Genetics Computer Group, Madison, Wis.), MacVector 4.5 (Kodak/IBI software package) or other suitable sequencing programs or methods known in the art. Preferably, structural similarity between two nucleotide sequences is determined using the Blastn program of the BLAST 2 search algorithm, as described by Tatusova, et al. (1999. FEMS Microbiol Lett. 174:247-250), and available through the World Wide Web, for instance at the internet site maintained by the National Center for Biotechnology Information, National Institutes of Health. Preferably, the default values for all BLAST 2 search parameters are used, including reward for match=1, penalty for mismatch=−2, open gap penalty=5, extension gap penalty=2, gap x_dropoff=50, expect=10, wordsize=11, and optionally, filter on. In the comparison of two nucleotide sequences using the BLAST search algorithm, structural similarity is referred to as "identities."

As used herein, an "isolated" substance is one that has been removed from its natural environment, produced using recombinant techniques, or chemically or enzymatically synthesized. For instance, a polypeptide, a polynucleotide, $H_2$, or NADPH can be isolated. Preferably, a substance is purified, i.e., is at least 60% free, preferably at least 75% free, and most preferably at least 90% free from other components with which it is naturally associated.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, the terms "coding region," "coding sequence," and "open reading frame" are used interchangeably and refer to a nucleotide sequence that encodes a polypeptide and, when placed under the control of appropriate regulatory sequences expresses the encoded polypeptide. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

A polynucleotide that includes a coding region may include heterologous nucleotides that flank one or both sides of the coding region. As used herein, "heterologous nucleotides" refer to nucleotides that are not normally present flanking a coding region that is present in a wild-type cell. For instance, a coding region present in a wild-type microbe and encoding a polypeptide described herein is flanked by homologous sequences, and any other nucleotide sequence flanking the coding region is considered to be heterologous. Examples of heterologous nucleotides include, but are not limited to regulatory sequences. Typically, heterologous nucleotides are present in a polynucleotide described herein through the use of standard genetic and/or recombinant methodologies well known to one skilled in the art. A polynucleotide described herein may be included in a suitable vector.

As used herein, an "exogenous polynucleotide" refers to a polynucleotide that is not normally or naturally found in a microbe. As used herein, the term "endogenous polynucleotide" refers to a polynucleotide that is normally or naturally found in a cell microbe. An "endogenous polynucleotide" is also referred to as a "native polynucleotide."

The term is "complement" and "complementary" as used herein, refer to the ability of two single stranded polynucleotides to base pair with each other, where an adenine on one strand of a polynucleotide will base pair to a thymine or uracil on a strand of a second polynucleotide and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary. The term "substantial complement" and cognates thereof as used herein, refer to a polynucleotide that is capable of selectively hybridizing to a specified polynucleotide under stringent hybridization conditions. Stringent hybridization can take place under a number of pH, salt and temperature conditions. The pH can vary from 6 to 9, preferably 6.8 to 8.5. The salt concentration can vary from 0.15 M sodium to 0.9 M sodium, and other cations can be used as long as the ionic strength is equivalent to that specified for sodium. The temperature of the hybridization reaction can vary from 30° C. to 80° C., preferably from 45° C. to 70° C. Additionally, other compounds can be added to a hybridization reaction to promote specific hybridization at lower temperatures, such as at or approaching room temperature. Among the compounds contemplated for lowering the temperature requirements is formamide. Thus, a polynucleotide is typically substantially complementary to a second polynucleotide if hybridization occurs between the polynucleotide and the second polynucleotide. As used herein, "specific hybridization" refers to hybridization between two polynucleotides under stringent hybridization conditions.

As used herein, "genetically modified microbe" refers to a microbe which has been altered "by the hand of man." A genetically modified microbe includes a microbe into which has been introduced an exogenous polynucleotide, e.g., an expression vector. Genetically modified microbe also refers to a microbe that has been genetically manipulated such that endogenous nucleotides have been altered to include a mutation, such as a deletion, an insertion, a transition, a transversion, or a combination thereof. For instance, an endogenous coding region could be deleted. Such mutations may result in a polypeptide having a different amino acid sequence than was encoded by the endogenous polynucleotide. Another example of a genetically modified microbe is one having an altered regulatory sequence, such as a promoter, to result in increased or decreased expression of an operably linked endogenous coding region.

Conditions that are "suitable" for an event to occur, such as expression of an exogenous polynucleotide in a cell to produce a polypeptide, or production of molecular hydrogen or NADPH, or "suitable" conditions are conditions that do not prevent such events from occurring. Thus, these conditions permit, enhance, facilitate, and/or are conducive to the event.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

BRIEF DESCRIPTION OF THE FIGURES

FIG. 7. Amino acid sequence and nucleotide sequence of the polypeptides and polynucleotides referenced in Table 1. Sequences shown include the PF0891 nucleotide sequence (SEQ ID NO:1), PF0891 amino acid sequence (SEQ ID NO:2), PF0892 nucleotide sequence (SEQ ID NO:3), PF0892 amino acid sequence (SEQ ID NO:4), PF0893 nucleotide sequence (SEQ ID NO:5), PF0893 amino acid sequence (SEQ ID NO:6), PF0894 nucleotide sequence (SEQ ID NO:7), PF0894 amino acid sequence (SEQ ID NO:8), PF0548 nucleotide sequence (SEQ ID NO:9), PF0548 amino acid sequence (SEQ ID NO:10), PF0549 nucleotide sequence (SEQ ID NO:11), PF0549 amino acid sequence (SEQ ID NO:12), PF0559 nucleotide sequence (SEQ ID NO:13), PF0559 amino acid sequence (SEQ ID NO:14), PF0604 nucleotide sequence (SEQ ID NO:15), PF0604 amino acid sequence (SEQ ID NO:16), PF0615 nucleotide sequence (SEQ ID NO:17), PF0615 amino acid sequence (SEQ ID NO:18), PF0616 nucleotide sequence (SEQ ID NO:19), PF0616 amino acid sequence (SEQ ID NO:20), PF0617 nucleotide sequence (SEQ ID NO:21), PF0617 amino acid sequence (SEQ ID NO:22), PF1401 nucleotide sequence (SEQ ID NO:23), and PF1401 amino acid sequence (SEQ ID NO:24). Nucleotide sequences and deduced amino acid sequence sequences of *Pyrococcus furiosus* DSM3638 (GenBank Accession No. AE010204 (SEQ ID NO:56) and GenBank Accession No. AE010177.1 (SEQ ID NO:57)) are used herein. All *P. furiosus* DNA and predicted protein sequences were derived from the deposited Genbank sequence NC 003413. Accession numbers refer to specific sections of this DNA sequence or the translated open reading frames encoded therein.

FIG. 21. Alignments of each of the four subunits of *P. furiosus* hydogenase I and other related hydrogenases from *P. abyssi, P. horikoshii*, and *Thermococcus kodakaraensis*. In each alignment identical residues are not shaded, similar residues are boxed, and non-similar residues are shaded dark gray. In each alignment, PF, *P. furiosus*; PAB, *P. abyssi*; TK, *Thermococcus kodakaraensis*; and PH, *P. horikoshii*. The gene identifiers refer to the coding regions encoding each polypeptide. PF0891-PF0894 (SEQ ID NOs:2, 4, 6, and 8, respectively) refers to the coding regions present at Genbank Accession No. NC 003413; PAB1784-PAB1787 (SEQ ID NOs:34, 35, 36, and 37, respectively) refers to the coding regions present at Genbank Accession No. AL096836; TK2069-TK2072 (SEQ ID NOs:38, 39, 40, and 41, respectively) refers to the coding regions present at Genbank Accession No. NC 006624; and PH1290 PH1291, PH1292, PH1294 (SEQ ID NOs:42, 43, 44, and 45, respectively) refers to the coding regions present at Genbank Accession No. NC_000961. A. Alignment of the beta subunits. B. Alignment of the gamma subunits. C. Alignment of the delta subunits. D. Alignment of the alpha subunits.

DETAILED DESCRIPTION OF ILLUSTRATIVE EMBODIMENTS

Figure 1:
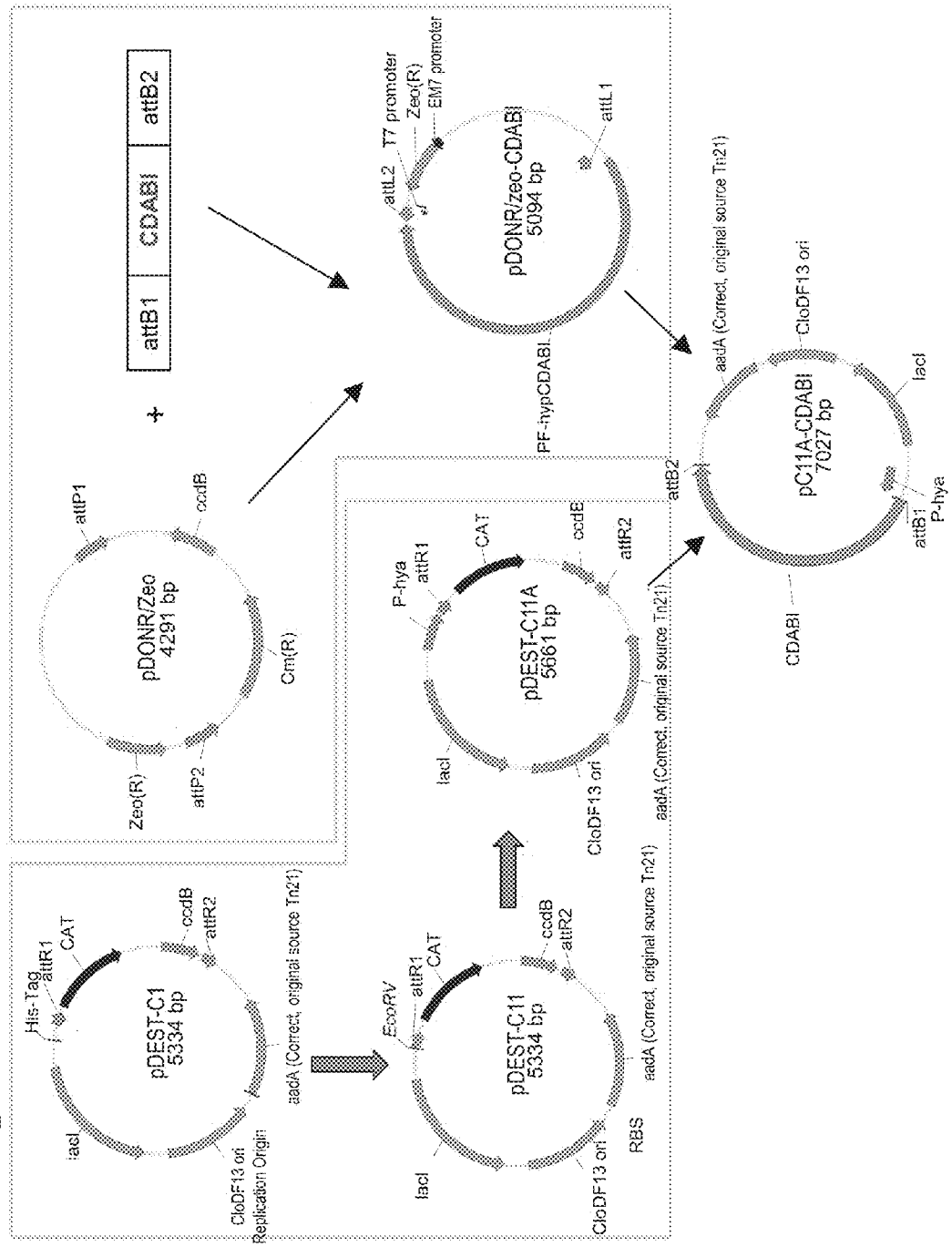
FIG. 1. Construction of anaerobic expression vector pC11A-CDABI.
Figure 2:
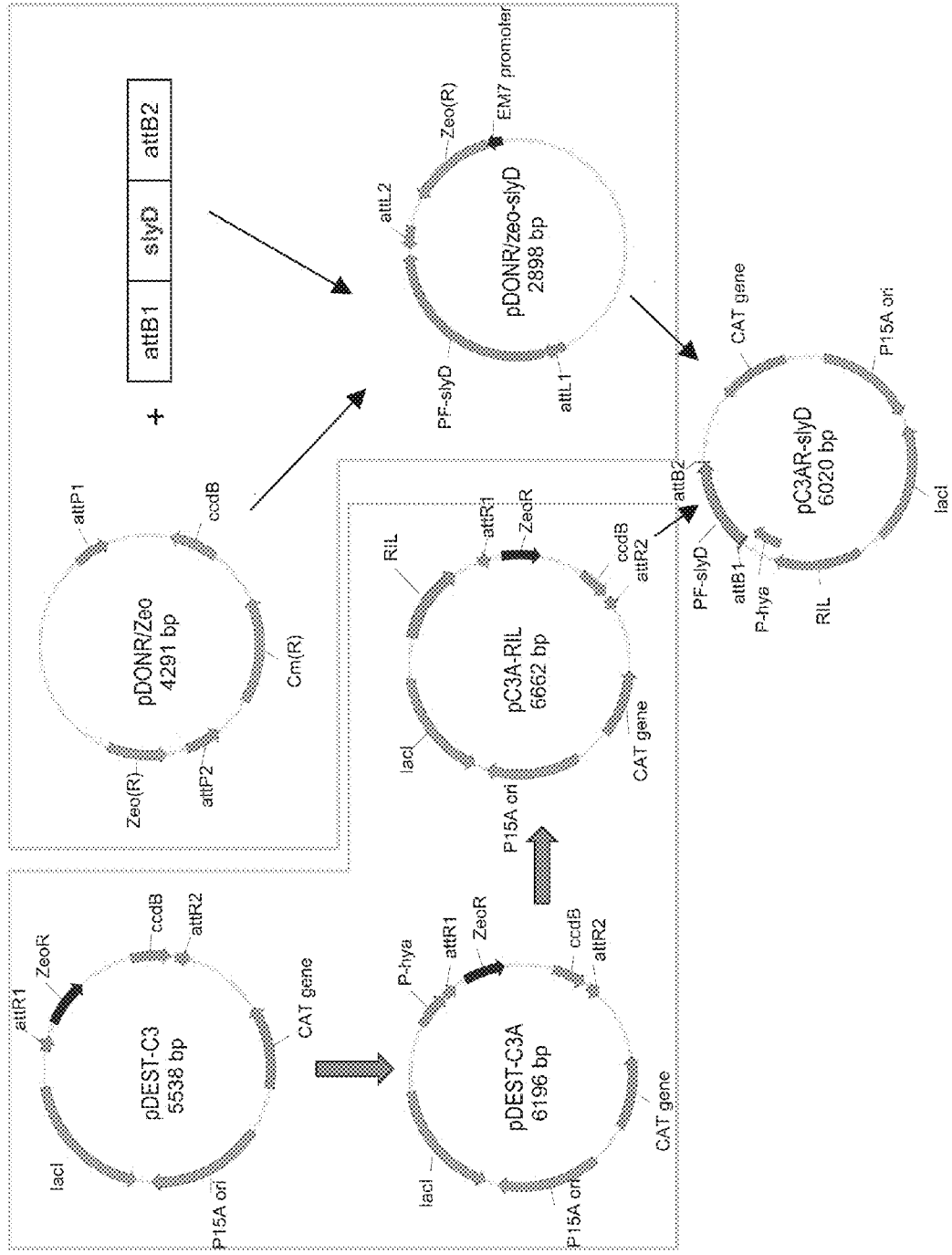
FIG. 2. Construction of anaerobic expression vector pC3AR-slyD.
Figure 3:
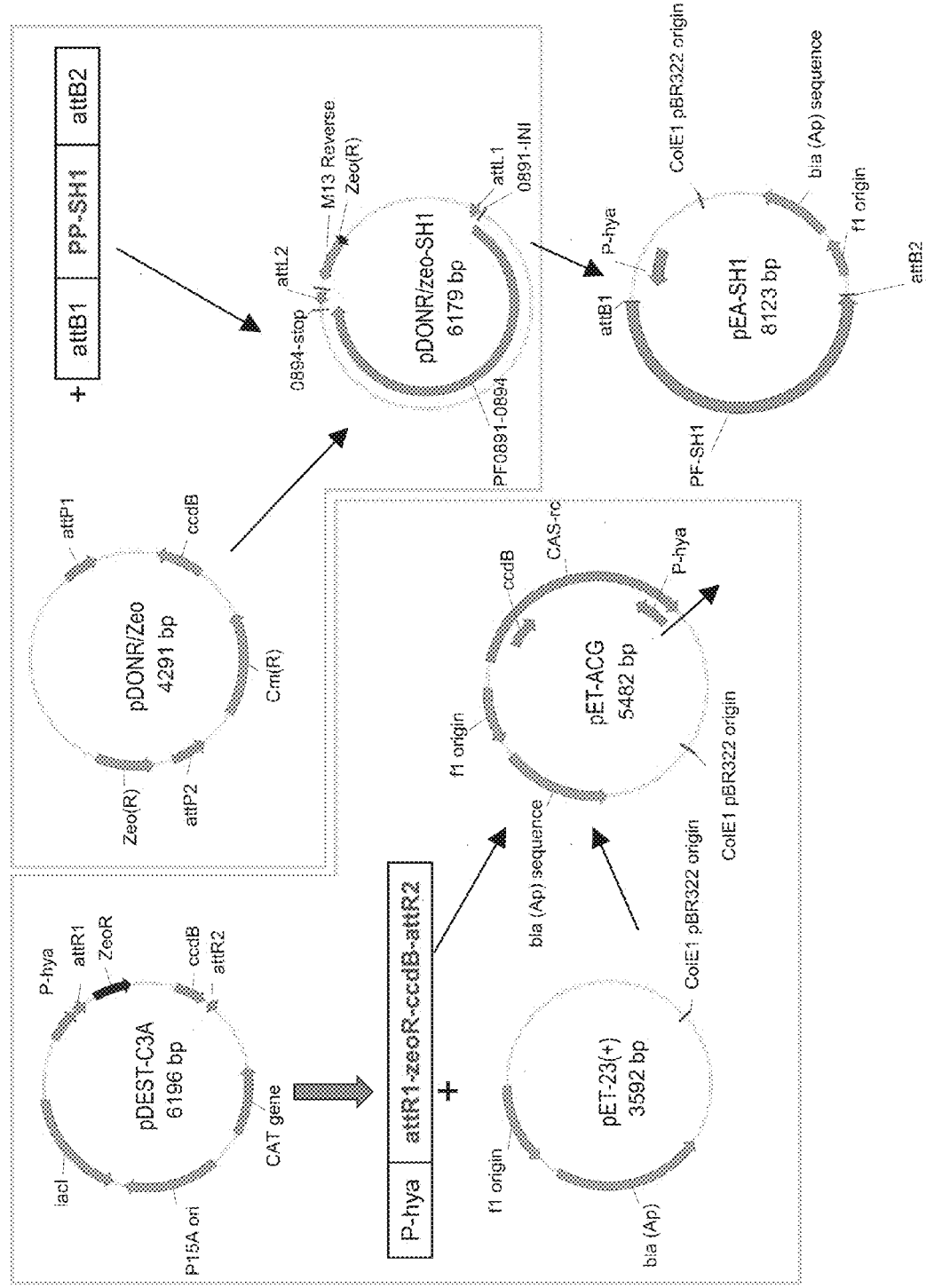
FIG. 3. Construction of anaerobic expression vector pEA-SHI.
Figure 4:
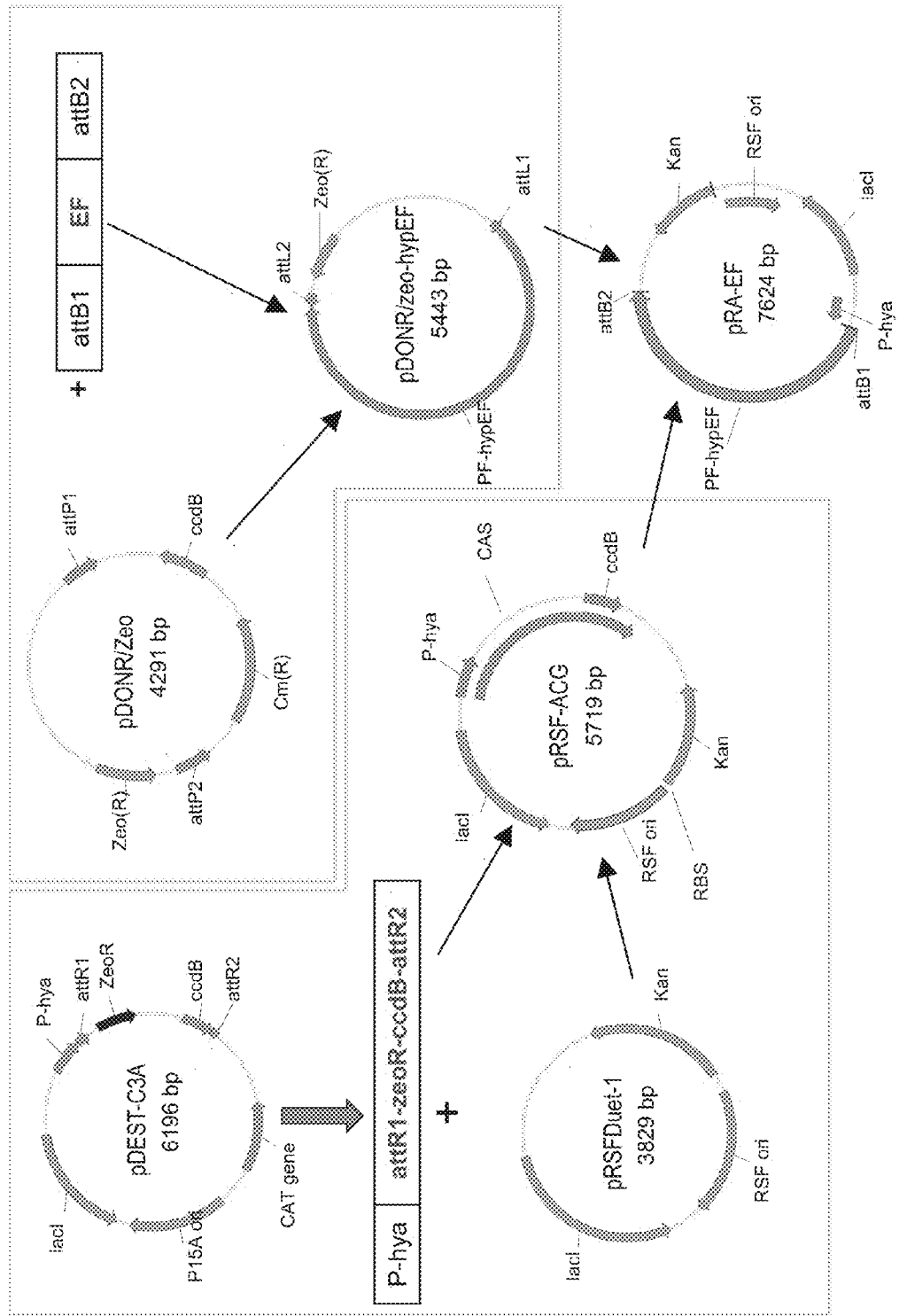
FIG. 4. Construction of anaerobic expression vector pRA-EF.

The expression of a NiFe-hydrogenase from an extremophile is expected to be inactive and unfolded and consequently not stable when expressed in *Escherichia coli*. We expressed the catalytic subunit (SEQ ID NO:8) in *E. coli* and to our surprise found that the monomeric subunit was stable. However, the stable expression of one subunit did not indicate that the other structural and accessory proteins would also be stable, and it was expected that chaperones (to stabilize unfolded protein) would be required for the proper assembly of the NiFe site. Furthermore, successful heterologous expression, meaning expression (transcription and translation) of genes not normally found in a given cell, of genes that encode such a molecular machine as a NiFe-hydrogenase has not been possible, in part because there are a large number of accessory proteins involved in its assembly. Despite the fact that the host bacterium used here, *E. coli* synthesizes its own native hydrogenases (all integral membrane proteins) under anaerobic conditions, attempts to express the genes encoding hydrogenases from other organisms have typically not been done in *E. coli*, but rather in very closely related organisms (Bascones et al. 2000. Appl Environ Microbiol 66:4292-9; King et al. 2006. J Bacteriol 188:2163-72; Lenz et al. 2005. J Bacteriol 187:6590-5; Morimoto et al. 2005. FEMS Microbiology Letters 246:229-34; Porthun et al. 2002. Arch Microbiol 177:159-66; Rousset et al. 1998. Journal of Bacteriology 180:4982-4986). Only recently have attempts been made to express hydrogenases (from *Synechocystis* sp.) in *E. coli* (Maeda et al. 2007. BMC Biotechnol 7:25) and this apparently only has the effect of limiting $H_2$ uptake in the recombinant strains. Proteins playing a role in the assembly of NiFe hydrogenases in *E. coli* have been extensively characterized (Bock et al. 2006. Adv Microb Physiol 51:1-71), and homologs of the genes encoding eight of these proteins exist in *P. furiosus*. Described herein is a system for successful heterologous overexpression of a functional and tagged hyperthermophilic NiFe hydrogenase under anaerobic conditions in the common laboratory protein expression host bacterium *E. coli*, using the heterologously-expressed accessory proteins from *P. furiosus* while simultaneously expressing those encoding the protein components of *P. furiosus* hydrogenase.

Provided herein are polypeptides having hydrogenase activity. Such polypeptides may be referred to herein as hydrogenase polypeptides. A polypeptide having hydrogenase activity may include four subunits. The first subunit includes the amino acid sequence SEQ ID NO:2, or an amino acid sequence having structural similarity thereto, the second subunit includes the amino acid sequence SEQ ID NO:4 or an amino acid sequence having structural similarity thereto, the third subunit includes the amino acid sequence SEQ ID NO:6 or an amino acid sequence having structural similarity thereto, and the fourth subunit includes the amino acid sequence SEQ ID NO:8 or an amino acid sequence having structural similarity thereto. Such a polypeptide may be isolated from a microbe, such as thermophiles (prokaryotic microbes that grow in environments at temperatures of between 60° C. and 79° C.), and hyperthermophiles (prokaryotic microbes that grow in environments at temperatures above 80° C.). Examples include archaea such as, but not limited to, a member of the genera *Pyrococcus*, for instance *P. furiosus, P. abyssi*, or *P. horikoshii*, or a member of the genera *Thermococcus*, for instance, *T. kodakaraensis* or *T. onnurineus*, or may be produced using recombinant techniques, or chemically or enzymatically synthesized.

A polypeptide provided herein also includes various subcomplexes. A subcomplex is defined as an engineered version of the hydrogenase polypeptide containing less than the natively purified four subunits. For example, a subcomplex may be the alpha subunit alone (SEQ ID NO: 8), the alpha subunit with one other subunit, (SEQ ID NO: 6, 4 or 2), or the alpha subunit with some combination of the two other subunits. Accordingly, a hydrogenase polypeptide may be monomeric, dimeric, trimeric, or tetrameric. One example of a hydrogenase polypeptide has 2 subunits, a first subunit that includes the amino acid sequence SEQ ID NO:8, or an amino acid sequence having structural similarity thereto, and a second subunit that includes the amino acid sequence SEQ ID NO:6 or an amino acid sequence having structural similarity thereto.

The hydrogenase activity of a hydrogenase polypeptide of the present invention may be determined by routine methods known in the art. Preferably, a hydrogen evolution assay is used as described herein. For instance, a cell extract may be tested for hydrogen evolution after preparation of a whole cell extract, centrifugation at 100,000×g, heat-treatment at 80° C. for 30 minutes, and re-centrifugation at 100,000×g (referred to as an S100 fraction). The standard assay conditions may include using 5 mL stoppered vials containing 2 mL of anaerobic 100 mM EPPS buffer pH 8.4, 10 mM sodium dithionite, and 1 mM Methyl Viologen under an atmosphere of argon. Typically, 0.5 milligrams of protein is added when measuring the activity of protein from an 80° C.-treated S100 fraction, and no greater than 0.005 milligrams of protein is added when measuring the activity of protein from a column, such as a DEAE Sepharose and/or Phenyl Sepharose column. The vials are preheated at 80° C. for 1 minute, and 200 µL of sample is injected into the vial. After a period of time, for instance, 6 minutes, samples (100 µL) of the headspace of the sealed vial can be removed with a gas-tight syringe, and then injected into a gas chromatograph. The resulting hydrogen peak can be compared to a known standard curve to calculate micromoles of hydrogen produced per mL of assay solution. The specific activity is at least 0.05, at least 0.1, or at least 0.125 micromoles $H_2$ produced $min^{-1}$ mg $protein^{-1}$. If the hydrogenase polypeptide is further purified, for instance using column chromatography with DEAE Sepharose or a similar matrix, and Phenyl Sepharose or a similar matrix, as described herein, the specific activity is at least 0.5, at least 1, least 5, or at least 7.5 micromoles $H_2$ produced $min^{-1}$ mg $protein^{-1}$. A hydrogenase polypeptide described herein that is to be tested may be expressed in a microbe, preferably an *E. coli* described herein, or produced using recombinant techniques, chemical or enzymatic synthesis. If the hydrogenase polypeptide is expressed in a microbe, preferably the microbe has undetectable levels of endogenous hydrogenase activity. Since most microbes do naturally express hydrogenase activity, microbes useful for expression of the hydrogenase polypeptides described herein may be engineered to not express endogenous hydrogenase activity. An example of such a microbe is MW1001 (Maeda et al. 2007. BMC Biotechnol 7:25). Other microbes can be engineered using methods known in the art to not express endogenous hydrogenase activity.

A hydrogenase polypeptide described herein typically has additional characteristics, including heat activation. A hydrogenase polypeptide described herein is typically activated by incubation at an elevated temperature. For instance, if a hydrogenase polypeptide is produced at temperatures prevalent when using *E. coli* to produce the polypeptide, e.g., 37° C., the specific activity can be increased by incubation at a temperature of at least 70° C., or at least 80° C. A hydrogenase polypeptide described herein also has the characteristic of being stable to incubation at high temperature. For instance, a hydrogenase polypeptide described herein does not lose any of its activity after incubation 90° C. for 10 hours. A hydrogenase polypeptide described herein also has the characteristic of being as sensitive to oxygen as the native form of the enzyme purified from *P. furiosus*. A hydrogenase polypeptide described herein that has hydrogenase activity catalyzes the proton reduction ($H_2$ production) coupled to the oxidation of an electron donor, such as NADPH, and also catalyzes the reverse, i.e., the oxidation of $H_2$ coupled to the reduction of an electron acceptor, such as NADP. Another reaction that may be catalyzed by hydrogenase polypeptides described herein is the reduction of elemental sulfur to hydrogen sulfide with the use of molecular hydrogen (Kim et al. 1999. Biotechnol. Bioeng. 65:108-113; Ma et al., Proc. Nat. Acad. Sci. USA. 90:5341-5344).

A candidate polypeptide having structural similarity to a reference polypeptide may include conservative substitutions of amino acids present in the reference polypeptide. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) can generally be substituted for another amino acid without substantially altering the secondary and/or tertiary structure of a polypeptide. For the purposes of this invention, conservative amino acid substitutions are defined to result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group containing side chains); Class VI: His, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains).

There are eight major groups of hydrogenase based on sequence similarities of their catalytic subunits (Vignais and Billoud. 2007. Chem Rev 107:4206-72). Hydrogenase polypeptides described herein are members of group 3b, the bidirectional NAD(P)-linked hydrogenases, and include, for instance, those found in other *Pyrococcus* and closely related species, e.g., *Thermococcus*, and also in photosynthetic bacteria (*Thiocapsa*) and aerobic hydrogen bacteria (*Ralstonia*). All [NiFe] hydrogenases (from all groups) are characterized by two CxxC domains, termed L1 and L2, that coordinate the Ni and Fe atom at the catalytic site of the catalytic subunit, alpha, an example of which is shown at SEQ ID NO:8. Each of the groups has conserved sequences surrounding these sites. The consensus L1 site is R[IV]C[AGS][FIL]Cxxx[HY]xx[AST][ANS]xx[AS][AILV] (SEQ ID NO:46), where x is any amino acid, and where one amino acid is chosen from each set enclosed by brackets (e.g., the second amino acid of the consensus is I or V). Examples of L1 sites include, but are not limited to, RICSFCSAAHKLTALEAA (SEQ ID NO:47), and RVCGICSAAHKLTALEAA (SEQ ID NO:48). The consensus L2 site is R[ANS][FHY]DPCISC[AS][ATV]H (SEQ ID NO:49), where one amino acid is chosen from each set enclosed by brackets (e.g., the second amino acid of the consensus is A or N or S). In both L1 and L2 sites, the change of any of the four cysteines is expected to result in a decrease or complete loss of hydrogenase activity. Further, regions of conservation can be determined by comparison of the amino acid sequences of each subunit (SEQ ID NO:2, 4, 6, or 8) with other hydrogenase subunits from other organisms (see FIG. 21). Thus, the skilled person can easily determine which amino acid residues can be altered without any effect on hydrogenase activity, and which cannot be changed or can be altered only through use of conservative substitutions.

Guidance concerning how to make phenotypically silent amino acid substitutions is provided in Bowie et al. (1990. Science, 247:1306-1310), wherein the authors indicate proteins are surprisingly tolerant of amino acid substitutions. For example, Bowie et al. disclose that there are two main approaches for studying the tolerance of a polypeptide sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

A candidate polypeptide having structural similarity to one of the polypeptides SEQ ID NO:2, 4, 6, or 8 has hydrogenase activity when expressed in a microbe with the other 3 reference structural polypeptides and the other 8 reference accessory polypeptides (SEQ ID NOs:10, 12, 14, 16, 18, 20, 22, and 24, described in detail below). For instance, when determining if a candidate polypeptide having some level of identity to SEQ ID NO:2 has hydrogenase activity, the candidate polypeptide is expressed in a microbe with reference polypeptides SEQ ID NO: 4, 6, 8, 10, 12, 14, 16, 18, 20, 22, and 24. Likewise, when determining if a candidate polypeptide having some level of identity to SEQ ID NO:4 has hydrogenase activity, the candidate polypeptide is expressed in a microbe with reference polypeptides SEQ ID NO: 2, 6, 8, 10, 12, 14, 16, 18, 20, 22, and 24, and so on for determining hydrogenase activity of candidate polypeptides having identity to each of the other structural or accessory polypeptides.

*P. furiosus* contains a second hydrogenase (SH-II) that is highly similar to the hydrogenase polypeptides described herein. SH-II was purified from native biomass of *P. furiosus* (Ma et al., 2000. J Bacteriol. 182(7):1864-71). It has very similar catalytic properties, and virtually identical physical properties to those of the hydrogenase polypeptides described herein. It contains four subunits of very similar size to those of the hydrogenase polypeptides described herein and these are predicted to coordinate exactly the same cofactors as the subunits of the hydrogenase polypeptides described herein. However, the sequences show only 55-63% sequence similarity. Nevertheless, *P. furiosus* has only one set of accessory genes to process and mature a hydrogenase, and so it is predicted that the set of accessory coding regions described herein that are used by *P. furiosus* to process the hydrogenase polypeptides described herein must also be used by the organism to process SH-II. Despite the apparent lack of sequence similarity the SH-I alpha and SH-II alpha subunits share a high degree of identity in the conserved L2 region and the C-terminal sequence that is cleaved for hydrogenase activity. Therefore, it is expected that the *E. coli* expression system described herein, which includes the accessory genes of *P. furiosus*, would also process and produce an active form of SH-II. In this case the plasmid containing the four SH-I genes would be replaced in *E. coli* by one containing the four SH-II genes.

Also provided are isolated polynucleotides encoding the polypeptides described herein. For instance, a polynucleotide may have a nucleotide sequence encoding a polypeptide having the amino acid sequence shown in SEQ ID NOs:2, 4, 6, or 8, and an example of the class of nucleotide sequences encoding each polypeptide is SEQ ID NOs:1, 3, 5, 7, respectively. It should be understood that a polynucleotide encoding a polypeptides represented by one of the sequences disclosed herein, e.g., SEQ ID NOs:2, 4, 6, or 8, is not limited to the nucleotide sequence disclosed at the polynucleotide sequences disclosed herein, e.g., SEQ ID NOs:1, 3, 5, or 7, respectively, but also includes the class of polynucleotides encoding such polypeptides as a result of the degeneracy of the genetic code. For example, the naturally occurring nucleotide sequence SEQ ID NO:1 is but one member of the class of nucleotide sequences encoding a polypeptide having the amino acid sequence SEQ ID NO:2. Likewise, the naturally occurring nucleotide sequences SEQ ID NO:3, 5, or 7, are but single members of the class of nucleotide sequences encoding a polypeptide having the amino acid sequence SEQ ID NO:4, 6, or 8, respectively. The class of nucleotide sequences encoding a selected polypeptide sequence is large but finite, and the nucleotide sequence of each member of the class may be readily determined by one skilled in the art by reference to the standard genetic code, wherein different nucleotide triplets (codons) are known to encode the same amino acid.

A polynucleotide disclosed herein may have structural similarity with the nucleotide sequence of SEQ ID NO:1, 3, 5, or 7. Such a polynucleotide may be isolated from a microbe, such as thermophiles (prokaryotic microbes that grow in environments at temperatures of between 60° C. and 79° C.), and hyperthermophiles (prokaryotic microbes that grow in environments at temperatures above 80° C.). Examples include archaea such as, but not limited to, a member of the genera *Pyrococcus*, for instance *P. furiosus, P. abyssi*, or *P. horikoshii*, or a member of the genera *Thermococcus*, for instance, *T. kodakaraensis* or *T. onnurineus*, or may be produced using recombinant techniques, or chemically or enzymatically synthesized. A polynucleotide disclosed herein may further include heterologous nucleotides flanking the open reading frame. Typically, heterologous nucleotides may be at the 5' end of the coding region, at the 3' end of the coding region, or the combination thereof. The number of heterologous nucleotides may be, for instance, at least 10, at least 100, or at least 1000.

An aspect of the present invention also includes fragments of the polypeptides described herein, and the polynucleotides encoding such fragments, such as SEQ ID NOs:2, 4, 6, and 8, as well as those polypeptides having structural similarity to SEQ ID NOs: 2, 4, 6, and 8. A polypeptide fragment may include a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 amino acid residues.

A polypeptide described herein or a fragment thereof may be expressed as a fusion polypeptide that includes a polypeptide of the present invention or a fragment thereof and a heterologous amino acid sequence. The heterologous amino acid sequence may be present at the amino terminal end or the carboxy terminal end of a polypeptide, or it may be present within the amino acid sequence of the polypeptide. For instance, the heterologous amino acid sequence may be useful for purification of the fusion polypeptide by affinity chromatography. Various methods are available for the addition of such affinity purification tags to proteins. Examples of tags include a polyhistidine-tag, maltose-binding protein, and Strep-tag®. Representative examples may be found in Hopp et al. (U.S. Pat. No. 4,703,004), Hopp et al. (U.S. Pat. No. 4,782,137), Sgarlato (U.S. Pat. No. 5,935,824), Sharma (U.S. Pat. No. 5,594,115, and Skerra and Schmidt, 1999, Biomol Eng. 16:79-86). In another example, the heterologous amino acid sequence may be a carrier polypeptide. The carrier polypeptide may be used to increase the immunogenicity of the fusion polypeptide to increase production of antibodies that specifically bind to a polypeptide of the invention. The invention is not limited by the types of carrier polypeptides that may be used to create fusion polypeptides. Examples of carrier polypeptides include, but are not limited to, keyhole limpet hemacyanin, bovine serum albumin, ovalbumin, mouse serum albumin, rabbit serum albumin, and the like. The heterologous amino acid sequence, for instance, a tag or a carrier, may also include a cleavable site that permits removal of most or all of the additional amino acid sequence. Examples of cleavable sites are known to the skilled person and routinely used, and include, but are not limited to, a TEV protease recognition site. The number of heterologous amino acids may be, for instance, at least 5, at least 10, at least 15, at least 20, at least 25, at least 30, at least 35, or at least 40.

A polypeptide described herein may be modified. An example of a modification is a chemical modification with a hydrophobic group. Examples of suitable hydrophobic groups include, but are not limited to, polyethylene glycol derivatives, such as polyoxyethylene glycol p-nitrophenyl carbonate (PEG-pNPC), methoxypolyethylene glycol p-nitrophenyl carbonate (MPEG-pNPC), and methoxypolyethylene glycol cyanuric chloride (MPEG-CC). Preferably, the molecular weight of a polyethylene glycol derivative is less than 5 KDa. Methods for chemically modifying polypeptides are routine and known in the art. Such modified polypeptides can have altered characteristics such as increased solubility in organic solvents while retaining enzymatic activity. An example is modification of a polypeptide described herein is taught by Kim et al. (1999. Biotechnol. Bioeng. 65:108-113), where an SH-I hydrogenase polypeptide obtained from *P. furiosus* was modified with MPEG-CC. The resulting polypeptide retained the ability to reduce elemental sulfur to hydrogen sulfide (Ma et al., Proc. Nat. Acad. Sci. USA. 90:5341-5344).

A polynucleotide disclosed herein can be present in a vector. A vector is a replicating polynucleotide, such as a plasmid, phage, or cosmid, to which another polynucleotide may be attached so as to bring about the replication of the attached polynucleotide. Construction of vectors containing a polynucleotide of the invention may employ standard ligation techniques known in the art. See, e.g., (Sambrook et al., 1989. Molecular cloning: a laboratory manual, 2nd ed. Cold Spring Harbor Laboratory Press, Cold Spring Harbor, N.Y.). A vector can provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, and artificial chromosome vectors. Preferably the vector is a plasmid.

Selection of a vector depends upon a variety of desired characteristics in the resulting construct, such as a selection marker, vector replication rate, and the like. Vectors can be introduced into a host cell using methods that are known and used routinely by the skilled person. The vector may replicate separately from the chromosome present in the microbe, or the polynucleotide may be integrated into a chromosome of the microbe.

An expression vector may optionally include a promoter that results in expression of an operably linked coding regino during growth in anaerobic conditions. Promoters act as regulatory signals that bind RNA polymerase in a cell to initiate transcription of a downstream (3' direction) coding region. The promoter used may be a constitutive or an inducible promoter. It may be, but need not be, heterologous with respect to a host cell. Examples of suitable promoters include, but are not limited to, P-hya (SEQ ID NO:25), P-hyc (SEQ ID NO:26), and P-xyl (SEQ ID NO:27). The hydrogenase promoters P-hya and P-hyc can be obtained from *E. coli*, and are expressed (and at different strengths) under anaerobic growth conditions and at undetectable levels under aerobic growth conditions. The xylose responsive promoter P-xyl is a slightly modified version of the *B. megaterium* xylose promoter (Qazi et al. 2001. Microb Ecol 41:301-309) denoted PxylA (Rygus et al. 1991. Arch Microbiol 155:535-42) (P-xyl, SEQ ID NO:27). This xylose promoter was discovered to be useful for expressing genes in *E. coli* under either aerobic or anaerobic conditions. This is a promoter sequence derived from an aerobic, gram positive organism (rather than from *E. coli*, which is a facultatively anaerobic gram negative organism), and it was not expected that this would function in *E. coli*. Fortuitously, we discovered that in *E. coli* it expresses at very high levels under both aerobic and anaerobic conditions.

It should be understood that a promoter that drives expression of an operably linked coding region during growth in anaerobic conditions is not limited to the nucleotide sequences disclosed at SEQ ID NOs:25, 26, or 27. A person of ordinary skill will understand that the promoters disclosed herein may be modified by substitution (such as transition or transversion), deletion, and/or insertion of one or more nucleotides, where the altered promoter maintains its ability to drive expression of an operably linked coding region during growth in anaerobic conditions. Such modified promoters can be easily constructed using routine methods known in the art such as classical mutagenesis, site-directed mutagenesis, and DNA shuffling. Other useful promoters can be obtained from the genomes of microbes by reference to the regions upstream of coding sequences that are expressed under anaerobic conditions, such as coding regions encoding hydrogenase enzymes or involved in anaerobic respiration.

A vector introduced into a host cell optionally includes one or more marker sequences, which typically encode a molecule that inactivates or otherwise detects or is detected by a compound in the growth medium. For example, the inclusion of a marker sequence may render the transformed cell resistant to an antibiotic, or it may confer compound-specific metabolism on the transformed cell. Examples of a marker sequence include, but are not limited to, sequences that confer resistance to kanamycin, ampicillin, chloramphenicol, tetracycline, streptomycin, and neomycin.

Provided herein is a series of expression vectors which express recombinant proteins under strictly anaerobic growth conditions in a microbe, preferably *E. coli*. No *E. coli* protein expression vectors currently used are capable of this. In fact, most *E. coli* expression systems use a modified bacteriophage T7 promoter, regulated by a modification of the *E. coli* lactose operon repressor, so that expression of target genes can be induced by addition of lactose or the lactose homolog isopropyl-β-D-thiogalactopyranoside (IPTG) (Studier, F. W. 2005. Protein Expr Purif 41:207-34; Terpe, 2006. Appl Microbiol Biotechnol 72:211-22). However, this system does not operate under strictly anaerobic conditions and herein we utilized promoters that *E. coli* uses when grown in the absence of air. The expression vectors include a P-hly, P-hlc, or P-xyl promoter. An expression vector may include other polynucleotides that aid in, for instance, the cloning, manipulation, or expression of an operably linked coding region, or the purification of a polypeptide encoded by the coding region.

Polypeptides and fragments thereof described herein may be produced using recombinant DNA techniques, such as an expression vector present in a cell. Such methods are routine and known in the art. The polypeptides and fragments thereof may also be synthesized in vitro, e.g., by solid phase peptide synthetic methods. Solid phase peptide synthetic methods are routine and known in the art. A polypeptide produced using recombinant techniques or by solid phase peptide synthetic methods may be further purified by routine methods, such as fractionation on immunoaffinity or ion-exchange columns, ethanol precipitation, reverse phase HPLC, chromatography on silica or on an anion-exchange resin such as DEAE, chromatofocusing, SDS-PAGE, ammonium sulfate precipitation, gel filtration using, for example, Sephadex G-75, or ligand affinity. A preferred method for isolating and optionally purifying a hydrogenase polypeptide described herein includes column chromatography using, for instance, ion exchange chromatography, such as DEAE sepharose, hydrophobic interaction chromatography, such as phenyl sepharose, or the combination thereof.

Polynucleotides of the present invention may be obtained from microbes, or produced in vitro or in vivo. For instance, methods for in vitro synthesis include, but are not limited to, chemical synthesis with a conventional DNA/RNA synthesizer. Commercial suppliers of synthetic polynucleotides and reagents for such synthesis are well known.

Also disclosed herein are genetically modified microbes that have exogenous polynucleotides encoding one or more of the polypeptides disclosed herein. Compared to a control microbe that is not genetically modified, a genetically modified microbe may exhibit production of a hydrogenase polypeptide, such as a tetrameric or a dimeric hydrogenase polypeptide. Accordingly, in one aspect of the invention a genetically modified microbe may include one or more exogenous polynucleotides that encode the subunits of a hydrogenase polypeptide. Exogenous polynucleotides encoding a hydrogenase polypeptide may be present in the microbe as a vector or integrated into a chromosome.

Examples of useful bacterial host cells include, but are not limited to, *Escherichia* (such as *Escherichia coli*), *Salmonella* (such as *Salmonella enterica*, *Salmonella typhi*, *Salmonella typhimurium*), a *Thermotoga* spp. (such as *T. maritime*), an *Aquifex* spp (such as *A. aeolicus*), photosynthetic organisms including cyanobacteria (such as a *Synechococcus* spp. such as *Synechococcus* sp. WH8102 or *Synechocystis* spp. such as *Synechocystis* PCC 6803) and photosynthetic bacteria (such as a *Rhodobacter* spp. such as *Rhodobacter sphaeroides*) and the like. Examples of useful archaeal host cells include, but are not limited to a *Pyrococcus* spp., such as *P. furiosus*, *P. abyssi*, and *P. horikoshii*, a *Sulfolobus* spp, such as *S. sollataricus*, a *Thermococcus* spp., such as *T. kodakaraensis*, and the like.

A genetically modified microbe having exogenous polynucleotides encoding one or more of the polypeptides disclosed herein may optionally include accessory polypeptides. These accessory polypeptides act to assemble the hydrogenase polypeptides described herein. Without intending to be limiting, it is believed the accessory polypeptides play a role in constructing the non-protein ligands present in the hydrogenase polypeptides. The accessory polypeptides include a first accessory polypeptide having the amino acid sequence SEQ ID NO:10 or an amino acid sequence having structural similarity thereto, a second accessory polypeptide having the amino acid sequence SEQ ID NO:12 or an amino acid sequence having structural similarity thereto, a third accessory polypeptide having the amino acid sequence SEQ ID NO:14 or an amino acid sequence having structural similarity thereto, a fourth accessory polypeptide having the amino acid sequence SEQ ID NO:16 or an amino acid sequence having structural similarity thereto, a fifth accessory polypeptide having the amino acid sequence SEQ ID NO:18 or an amino acid sequence having structural similarity thereto, a sixth accessory polypeptide having the amino acid sequence SEQ ID NO:20 or an amino acid sequence having structural similarity thereto, a seventh accessory polypeptide having the amino acid sequence SEQ ID NO:22 or an amino acid sequence having structural similarity thereto, and an eighth accessory polypeptide having the amino acid sequence SEQ ID NO:24 or an amino acid sequence having structural similarity thereto. Preferably, an exogenous polynucleotide encoding an accessory polypeptide is operably linked to a promoter that drives expression of the polynucleotide during growth in anaerobic conditions.

Also provided herein are isolated polypeptides having the amino acid sequence SEQ ID NOs:10, 12, 14, 16, 18, 20, 22, and 24, and amino acid sequences having structural similarity thereto, and isolated polynucleotides encoding the polypeptides.

A candidate polypeptide having structural similarity to one of the accessory polypeptides (SEQ ID NOs: 10, 12, 14, 16, 18, 20, 22, or 24) has activity when expressed in a microbe with the 4 reference polypeptides encoding a tetrameric hydrogenase polypeptide and the other 7 reference accessory polypeptides. For instance, when determining if a candidate polypeptide having some level of identity to SEQ ID NO:10 has the activity of catalyzing the biosynthesis of an active hydrogenase polypeptide, the candidate polypeptide is expressed in a microbe with reference polypeptides SEQ ID NO: 2, 4, 6, 8, 12, 14, 16, 18, 20, 22, and 24. Likewise, when determining if a candidate polypeptide having some level of identity to SEQ ID NO:12 has the activity of catalyzing the biosynthesis of an active hydrogenase polypeptide, the candidate polypeptide is expressed in a microbe with reference polypeptides SEQ ID NO: 2, 4, 6, 8, 10, 14, 16, 18, 20, 22, and 24, and so on.

In another aspect a genetically modified microbe may express an endogenous hydrogenase polypeptide at an increased level or having altered activity. For instance, a genetically modified microbe may include an altered regulatory sequence, where the altered regulatory sequence is operably linked to one or more coding regions encoding subunits of a hydrogenase polypeptide. In another example, an endogenous polynucleotide encoding a subunit of a hydrogenase polypeptide may include a mutation, such as a deletion, an insertion, a transition, a transversion, or a combination thereof, that alters a characteristic of the hydrogenase polypeptides, such as the activity. In those aspects where a genetically modified microbe expresses an endogenous hydrogenase polypeptide at an increased level or having altered activity, the microbe is typically an archaea, such as *Pyrococcus* spp., such as *P. furiosus, P. abyssi*, and *P. horikoshii*, a *Thermococcus* spp., such as *T. kodakaraensis* and *T. onnurineus*, and the like. Methods for modifying genomic DNA sequences of thermophiles and hyperthermophiles are known (Yang et al., PCT Application No. PCT/US2008/081157, filed Oct. 24, 2008, and Westpheling et al., U.S. Provisional Patent Application 61/000,338, filed Oct. 25, 2007).

A genetically modified microbe may include other modifications in addition to exogenous polynucleotides encoding one or more of the polypeptides disclosed herein, or expressing an endogenous hydrogenase polypeptide at an increased level or having altered activity. Such modifications may provide for increased production of electron donors used by a hydrogenase polypeptide described herein, such as NADPH. For instance, modifications may provide for increased levels in a cell of the enzymes used in the oxidative phase of the pentose phosphate pathway, such as glucose 6-phosphate dehydrogenase, 6-phosphogluconolactonase, and 6-phosphogluconate dehydrogenase. Modifications may provide for increased levels of substrates used in the oxidative phase of the pentose phosphate pathway by, for instance, increasing production of enzymes in biosynthetic pathways, reducing feedback inhibition at different locations in biosynthetic pathways, increasing importation of substrates and/or compounds used in biosynthetic pathways to make substrates, decreasing catabolism of substrates and/or compounds used in biosynthetic pathways to make substrates. Methods for modifying microbes to increase these and other compounds are routine and known in the art.

A genetically modified microbe of the present invention may include other modifications that provide for increased ability to use renewable resources, such as, but not limited to, biomass containing polysaccharides that can be broken down to yield glucose 6-phosphate, the first reactant of the pentose phosphate pathway and the substrate of the enzyme glucose 6-phosphate dehydrogenase. An example of such a polysaccharide is starch. Such modifications may provide for increased production of enzymes useful in the breakdown of biomass.

The hydrogenase polypeptides described herein can be used to produce molecular hydrogen. Molecular hydrogen is used in the petroleum and chemical industries. For instance, in a petrochemical plant, hydrogen is used for hydrodealkylation, hydrodesulfurization, and hydrocracking, all methods of refining crude oil for wider use. Molecular hydrogen is used for the production of ammonia, methanol, hydrochloric acid, and as a reducing agent for metal ores. In the food industry molecular hydrogen is used for hydrogenation of vegetable oils and fats, for instance, in producing margarine from liquid vegetable oil. Hydrogen is also useful as a fuel, both in traditional combustion engines as well as in fuel cells, and produces only water vapor when oxidized with oxygen.

In addition to hydrogen production systems, the applications for hydrogenase polypeptides described herein include cofactor [beta-1,4-nicotinamide adenindinucleotide, reduced form (NADH) or beta-1,4-nicotinamide adenindinucleotide phosphate, reduced form (NADPH)] regeneration (from NAD or NADP, respectively) using hydrogen as the source of energy (Hummel, 1999. Trends Biotechnol. 17:487-492; Mertens et al., 2003. J. Mol. Catal. B: Enzym. 24-25:39-52). The hydrogenase polypeptides described herein have significant advantages over other enzymatic methods to regenerate these reduced cofactors as there is no oxidation product to remove or dispose of other than protons (from hydrogen oxidation). This is in contrast to, for example, lactate dehydrogenase, where lactate is the source of energy and the product is the C3 compound pyruvate (Eberly and Ely, 2008. Crit. Rev. Microbiol. 34:117-130). Cofactor regeneration using hydrogen with no waste products would be of tremendous benefit for the pharmaceutical industry.

Hydrogenase polypeptides obtained from *P. furiosus* have also been chemically modified such that the enzyme is soluble and active in water-immicible organic solvents such as toluene (Kim et al. 1999. Biotechnol. Bioeng. 65:108-113). Hydrogenase polypeptides described herein can also be chemically modified. Thus, the polypeptides described herein can reduce water-insoluble compounds with hydrogen. For example, elemental sulfur can be reduced to $H_2S$, which is useful in removal of sulfur from some compositions used in the petroleum and coal industries.

Accordingly, provided herein are methods for making and using the hydrogenase polypeptides of the present invention. Methods for making a polypeptide having hydrogenase activity can include providing a genetically modified microbe that includes exogenous polynucleotides encoding 1, 2, 3, or 4 subunits of a hydrogenase polypeptide described herein, preferably 2 or 4 subunits, and incubating the microbe under conditions suitable for expression of the exogenous polynucleotides to produce a polypeptide, wherein the polypeptide has hydrogenase activity. The genetically modified microbe can be a bacterial cell, such as a gram negative, for instance, *E. coli*, or it can be an archaeal cell, for instance, a member of the genera *Pyrococcus*, for instance *P. furiosus, P. abyssi*, or *P. horikoshii*, or a member of the genera *Thermococcus*, for instance, *T. kodakaraensis* or *T. onnurineus*, or a photosynthetic bacterium; for instance, *Rhodobacter sphaeroides*. The genetically modified microbe may include exogenous polynucleotides encoding the accessory polypeptides described herein. In those aspects where the genetically modified microbe is a bacterial cell, such as *E. coli*, the genetically modified microbe typically does include exogenous polynucleotides encoding the accessory polypeptides. The incubation conditions are typically anaerobic, and the temperature may be at least 37° C., at least 60° C., at least 70° C., at least 80° C., or at least 90° C. The methods can be performed using any convenient manner. For instance, methods for growing microbial cells to high densities are routine and known in the art, and include batch and continuous fermentation processes. The method may further include isolating, and optionally purifying the hydrogenase polypeptide. Methods for isolating and optionally purifying hydrogenase polypeptides described herein are routine and known in the art.

Also provided herein are methods for using a hydrogenase polypeptide described herein. The methods can include providing a hydrogenase polypeptide, and incubating the hydrogenase polypeptide under conditions suitable for producing desirable products such as $H_2$ or NADPH. Optionally, the product is collected using methods routine and known in the art.

In one aspect, the hydrogenase polypeptide used in the methods is cell-free, for instance, it is isolated, or optionally purified. Conditions suitable for incubating an isolated hydrogenase polypeptide may generally include aqueous conditions containing a suitable buffer, such as, but not limited to, EPPS (4-(2-hydroxyethyl)piperazine-1-propanesulfonic acid) at a concentration of 50 mM and buffered near neutral pH (typically 7.5-8.5). The hydrogenase polypeptide may be incubated in an organic solvent, such as, but not limited to, toluene, xylene, benzene, methylene chloride, chloroform, or tetrahydrofuran. A hydrogenase polypeptide that is incubated in an organic solvent is typically chemically modified, preferably with a hydrophobic group, as described herein. The incubation conditions are typically anaerobic, and the temperature may be at least 60° C., at least 70° C., at least 80° C., or at least 90° C. The methods can be performed in any convenient manner. Thus, the reaction steps may be performed in a single reaction vessel. The process may be performed as a batch process or as a continuous process, with desired product and waste products being removed continuously and new raw materials being introduced.

Methods for using an isolated hydrogenase polypeptide include the use of such a polypeptide bound to a surface. In some aspects the surface can be one that conducts electricity, such as an anode. Hydrogenase polypeptides bound to surfaces are useful for applications such as, but not limited to, fuel cells (Armstrong, U.S. Published Patent Application 20040214053).

Methods for using an isolated hydrogenase polypeptide include production of desirable products, such as molecular hydrogen, using renewable resources. For instance, biomass derived polysaccharides can be used as a substrate for the production of monomeric carbohydrates that could then be used as a source of NADPH, which in turn can be used by a hydrogenase polypeptide disclosed herein to produce hydrogen. Examples of such methods include in vitro hydrogen production as taught by Woodward et al. (1996. Nat Biotechnol 14:872-4), and Zhang et al. (2007. PLoS ONE 2:e456, and U.S. Published Patent Application 20070264534). Examples of useful polysaccharides include, but are not limited to, starch and cellulose. Renewable sources of these polysaccharides are known in the art.

In another aspect, a hydrogenase polypeptide used in the methods is present in a microbial cell. The methods can include incubating the microbial cell under conditions suitable for the expression of the polypeptide. The microbial cell is typically a genetically modified microbe, and may be a bacterial cell, such as a gram negative, for instance, *E. coli*, a photosynthetic organism, for instance, *R. sphaeroides*, or it can be an archaeal cell, for instance, a member of the genera *Pyrococcus*, for instance *P. furiosus, P. abyssi*, or *P. horikoshii*, or a member of the genera *Thermococcus*, for instance, *T. kodakaraensis* or *T. onnurineus*. The microbe may include exogenous polynucleotides encoding the accessory polypeptides described herein. In those aspects where the microbe is a bacterial cell, such as *E. coli*, the microbe typically includes exogenous polynucleotides encoding the accessory polypeptides. The incubation conditions are typically anaerobic, and the temperature may be at least 37° C., at least 60° C., at least 70° C., at least 80° C., or at least 90° C. The conditions used to incubate the microbial cell typically include substrates that can be used by a cell to produce a reactant, such as NADPH, or the reductant such as NADPH can be photoproduced by a photosynthetic cell, and the NADPH can be used by the hydrogenase polypeptide to produce molecular hydrogen. Examples of useful substrates include renewable resources containing polysaccharides such as starch, cellulose, or the combination. Alternatively, the conditions used to incubate the microbial cell can include $H_2$, which can be used by the hydrogenase polypeptide to convert NADP to NADPH. The methods can be performed using any convenient manner. For instance, methods for growing microbial cells to high densities are routine and known in the art, and include batch and continuous fermentation processes.

The present invention is illustrated by the following examples. It is to be understood that the particular examples, materials, amounts, and procedures are to be interpreted broadly in accordance with the scope and spirit of the invention as set forth herein.

Example 1

Anaerobic Expression Vectors

Figure 8A:
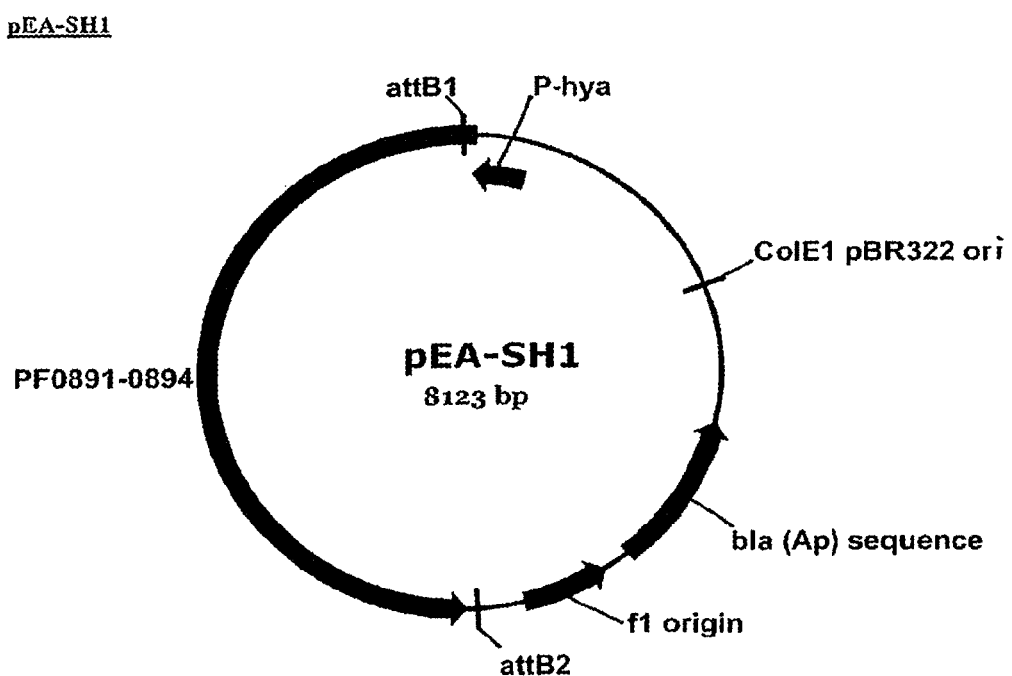
FIG. 8. Maps and complete nucleotide sequences of four expression vectors. pEA-SH1, SEQ ID NO:29; pC11A-CDABI, SEQ ID NO:30; pRA-EF, SEQ ID NO:31; and pC3AR-slyD, SEQ ID NO:32.

A series of compatible vectors has been constructed with the various promoters described above. The expression vectors described here are derivatives of those described in Horanyi et al., (U.S. Published Patent Application 20060183193). These are a series of four vectors with compatible origins of replication and different antibiotic resistance markers which allow coexpression of multiple genes in *E. coli* using the lac operon regulation. These vectors have been modified to include the "anaerobic" promoters described above (Table 2) and up to 12 genes derived from *P. furiosus*. These are a) the structural genes for the four subunits of *P. furiosus* hydrogenase (Table 1) and b) the eight genes that encode the hydrogenase processing genes in *P. furiosus* (Table 1). The complete list of vectors created is found in Table 3, and four particular examples are shown in FIGS. 1-4. The complete map and sequences of these four vectors are shown in FIG. 8.

TABLE 1

*Pyrococcus furiosus* genes encoding structural and accessory proteins for cytoplasmic hydrogenase I and Genbank accession numbers.

| SEQ ID NO | PF gene identifier | Gene | Genbank Accession# | Coding region or deduced polypeptide sequence encoded by coding region |
|---|---|---|---|---|
| 1 | PF0891 | Structural gene, hydrogenase I beta subunit | AE010204.1 | coding region |
| 2 | PF0891 | Structural gene, hydrogenase I beta subunit | AAL81015 | Polypeptide encoded by coding region |
| 3 | PF0892 | Structural gene, hydrogenase I gamma subunit | AE010204.1 | coding region |
| 4 | PF0892 | Structural gene, hydrogenase I gamma subunit | AAL81016 | Polypeptide encoded by coding region |
| 5 | PF0893 | Structural gene, hydrogenase I delta subunit | AE010204.1 | coding region |
| 6 | PF0893 | Structural gene, hydrogenase I delta subunit | AAL81017 | Polypeptide encoded by coding region |
| 7 | PF0894 | Structural gene, hydrogenase I alpha subunit | AE010204.1 | coding region |
| 8 | PF0894 | Structural gene, hydrogenase I alpha subunit | AAL81018 | Polypeptide encoded by coding region |
| 9 | PF0548 | HypC | AE010177.1 | coding region |
| 10 | PF0548 | HypC | AAL80672 | Polypeptide encoded by coding region |
| 11 | PF0549 | HypD | AE010177.1 | coding region |
| 12 | PF0549 | HypD | AAL80673 | Polypeptide encoded by coding region |
| 13 | PF0559 | HypF | AE010178.1 | coding region |
| 14 | PF0559 | HypF | AAL80683 | Polypeptide encoded by coding region |
| 15 | PF0604 | HypE | AE010182.1 | coding region |
| 16 | PF0604 | HypE | AAL80728 | Polypeptide encoded by coding region |
| 17 | PF0615 | HypA | AE010183.1 | coding region |
| 18 | PF0615 | HypA | AAL80739 | Polypeptide encoded by coding region |
| 19 | PF0616 | HypB | AE010183.1 | coding region |
| 20 | PF0616 | HypB | AAL80740 | Polypeptide encoded by coding region |
| 21 | PF0617 | HycI | AE010183.1 | coding region |
| 22 | PF0617 | HycI | AAL80741 | Polypeptide encoded by coding region |
| 23 | PF1401 | SlyD | AE010243.1 | coding region |
| 24 | PF1401 | SlyD | AAL81525 | Polypeptide encoded by coding region |

TABLE 2

*Escherichia coli* hydrogenase promoter DNA sequences derived from the K12 strain genome (accession number NC_000913), and *Bacillus megaterium* xylose promoter DNA sequences (derived from accession number X57598) (Qazi et al. 2001. Microb Ecol 41:301-309).

| SEQ ID NO | Gene identifier | Genbank Accession# | Genome nucleotide start and stop | DNA Sequence |
|---|---|---|---|---|
| 25 | *E. coli* K12 hya promoter | NC_000913.2 | 1031062-1031364 | CTCGAATTCCTTCTCTTTTACTCGTTTAGCAAC CGGCTAAACATCCCCACCGCCCGGCCAAAAGAA AAATAGGTCCATTTTTATCGCTAAAAGATAAAT CCACACAGTTTGTATTGTTTTGTGCAAAAGTTT CACTACGCTTTATTAACAATACTTTCTGGCGAC GTGCGCCAGTGCAGAAGGATGAGCTTTCGTTTT CAGCATCTCACGTGAAGCGATGGTTTGCCTTGC TACAGGGACGTCGCTTGCCGACCATAAGCGCCC GGTGTCCTGCCGGTGTCGCAAGGAGGAGAGACG TGCGATATGGGTCATCACCATCATCACCACGGC TCGATCACAAGTTTGTACAAAAAAGCAGGCTCA GAAACCTGTATTTTCAGGGAGGA(PFU GENE)* |

TABLE 2-continued

Escherichia coli hydrogenase promoter DNA sequences derived from the K12 strain genome (accession number NC_000913), and Bacillus megaterium xylose promoter DNA sequences (derived from accession number X57598) (Qazi et al. 2001. Microb Ecol 41:301-309).

| SEQ ID NO | Gene identifier | Genbank Accession# | Genome nucleotide start and stop | DNA Sequence |
|---|---|---|---|---|
| 26 | E. coli K12 hyc promoter | NC_000913.2 | 2848966-2848355 | CTCGAATTCTGCAGCATGTCACCATGACACTGTGG ACAGCGGCGGACGCGCTGGGTCAGTAGCGTCACAT ACTGTTGGCATGTTTCACACCAGCATTCGGCCTCT TGTTCTTCGAGGTGCAGTTTACAACCTTCCGCCAC GCTGCCGCGGCAAACCAGATCAAACAAAAGGCAA GAGAGCTGGTTTCGACACAAGAAAATGCGCCAATT TTGAGCCAGACCCCAGTTACGCGTTTTGCGCCGTG TTTTGCGGCCTGCTGTTCGATCAATTCCAGTGCCC GTTGGCAGAGGGTTATTTCGTGCATATCGCCTCCC ATTAACTATTGCCAGCTACAAGCAATAATTGTGCC AGTGTTGATTATCCCTGCGGTGAATAATGTCGATG ATGTCGAAATGACACGTCGACACGGCGACGAAATT CATCTTTAGCTTAAAAATCTCTTTAATAACAATAA ATTAAAAGTTGGCACAAAAAATGCTTAAAGCTGGC ATCTCTGTTAAACGGGTAACCTGACAATGACTATT TGGGAAATAAGCGAGAAAGCCGATTACATCGCACA GCGGCATCGTCGCCTACAGGACCAGTGGCACATCT ACTGCAATTCGCTGGTTCAGGGGAGAGGAGGAATA AAAAATG |
| 27 | B. megaterium xylA promoter | X57598 | | GAATTCTAGAATCTAATATTATAACTAAATTTTCT AAAAAAAACATTGGAATAGACATTTATTTTGTATA TGATGAAATAAAGTTAGTTTATTGGATAAACAAAC TAACTTTATTAAGGTAGTTGATGGATAAACTTGTT CACTTAAATCAACCCGGGAACAAGGAGGAATAAAA AATG |
| 28 | E. coli pRIL section | | | GGATCCCCGTCACCCTGGATGCTGTACAATTGACG ACGCAAGGGCCCGGGCAAACTAGTAATCAGACGC GGTCGTTCACTTGTTCAGCAACCAGATCAAAAGCC ATTGACTCAGCAAGGGTTGACCGTATAATTCACGC GATTACACCGCATTGCGGTATCAACGCGCCCTTAG CTCAGTTGGATAGAGCAACGACCTTCTAAGTCGTG GGCCGCAGGTTCGAATCCTGCAGGGCGCGCCATTA CAATTCAATCAGTTACGCCTTCTTTATATCCTCCA GCCATGGCCTTGAAATGGCGTTAGTCATGAAATAT AGACCGCCATCGAGTACCCCTTGTACCCTTAACTC TTCCTGATACGTAAATAATGATTTGGTGGCCCTTG CTGGACTTGAACCAGCGACCAAGCGATTATGAGTC GCCTGCTCTAACCACTGAGCTAAAGGGCCTTGAGT GTGCAATAACAATACTTATAAACCACGCAATAAAC ATGATGATCTAGAGAATCCCGTCGTAGCCACCATC TTTTTTTGCGGAGTGGCGAAATTGGTAGACGCAC CAGATTTAGGTTCTGGCGCCGCTAGGTGTGCGAGT TCAAGTCTCGCCTCCCGCACCATTCACCAGAAAGC GTTGATCGGATGCCCTCGAGTCGGGCAGCGTTGGG TCCTGGCCACGGGTGCGCATGATCGTGCTCCTGTC GTTGAGGACCCGGCTAGGCTGGCGGGGTTGCCTTA CTGGTTAGCAGAATGAATCACCGATACGCGAGCGA ACGTGAAGCGACTGCTGCTGCAAAACGTCTGCGAC CTGAGCTC |

*The E. coli hya promoter, including the ATG protein translation initiation site is indicated in boldface in the table. The region immediately after includes ggt (encoding a Glycine)/catcaccatcatcaccac(6x His tag)/ggctcgatcacaagtttgtacaaaaaagcaggctca (Gateway attB1 site, encoding GSITSLYKKAGS)/gaaaacct gtattttcaggga (encoding TEV protease recognition site: ENLYFQG, TEV protease cut between Q and G)/gga, encoding another Glycine (SEQ ID NO: 50). At the asterisk, P. furiosus genes are cloned without a start codon to create a fusion protein MGHHHHHHGSITSLYKKAG-SENLYFQGG-Pfu target gene (MGHHHHHHGSITSLYKKAGSENLYFQGG, SEQ ID NO: 51).

TABLE 3

Complete list of vectors constructed.
Plasmids Constructed

| plasmid | promoter | gene | Antibiotics |
|---|---|---|---|
| pHA-BC | hya | 0894-hybC | Amp |
| pHA-CS | hya | 0894-CS | Amp |
| pET-CAG | | Gateway plasmid, with promoter P-hya, Ampicillin resistant, | |

TABLE 3-continued

Complete list of vectors constructed.
Plasmids Constructed

| plasmid | promoter | gene | Antibiotics |
|---|---|---|---|
| pET-CXG | Gateway plasmid, with promoter P-xylA, Ampicillin resistant, | | |
| pEA-SH1 | hya | 0891-0894 | Amp |
| pDEST-C11 | T7 promoter, Gateway plasmid, from pDEST-C1, Streptomycin resistant | | |
| pDEST-C11A | hya, Gateway plasmid, from pDEST-C1, Streptomycin resistant | | |
| pDEST-C11A-hypABI | hya | PF0615-0617 | Sm |
| pC11A-CDABI | hya | PF0548-0549-0615-0616-0617 | Sm |
| pDEST-C3A | Gateway plasmid with P-hya promoter in front of Gateway cassette, Chloramphenicol resistant | | |
| pDEST-C3X | Gateway plasmid with P-xylA promoter in front of Gateway cassette, Chloramphenicol resistant | | |
| pDEST-C3-SH1 | T7 | PF0891-0894 | Cm |
| pDEST-C3A-SH1 | hya | PF0891-0894 | Cm |
| pDEST-C3A-lacZ | hya | lacZ | Cm |
| pDEST-C3X-lacZ | P-xylA | lacZ | Cm |
| pDEST-C3AR | derivative of plasmid pDEST-C3A, in Which RIL fragment inserted | | |
| pC3A-slyD | hya | PF1401 | Cm |
| pC3AR-slyD | hya | PF1401 | Cm |
| pRSF-CAG | Gateway plasmid, sequencing confirmed, | | |
| pRSF-CXG | Kanamycin resistant, done by JS | | |
| pRA-hypE | hya | PF0604 | Kan |
| pRA-hypF | hya | PF0559 | Kan |
| pRA-EF | hya | PF0604-0559 | Kan |
| pDONR/zeo-hycl | | PF0617 | Zeo |
| pDONR/zeo-hypCD-ABI | | PF0548-0549/0615-0617 | Zeo |
| pDONR/zeo-hypEF | | PF0604/0559 | Zeo |
| pDONR/zeo-slyD | | PF1401 | Zeo |
| pDONR/zeo-lacZ | | E. coli lacZ N-terminal sequence | Zeo |
| pDONR/zeo-hypCD | | PF0548-0549 | Zeo |
| pDONR/zeo-hypE | | PF0604 | Zeo |
| pDONR/zeo-hypF | | PF0559 | Zeo |

Amp, ampicillin resistance marker; Sm, streptomycin/spectinomycin resistance marker; Cm, chloramphenicol resistance marker; Kan, kanamycin resistance marker; Zeo, zeocin resistance marker.

TABLE 4

Compatible anaerobic expression vectors utilized to express functional P. furiosus cytoplasmic hydrogenase I in E. coli.

| Vector | Parent Vector | Antibiotic Resistance marker | P. furiosus gene products | P. furiosus gene number[6] |
|---|---|---|---|---|
| pC11A-CDABI[6] | pDEST-C1[2] | Strepto-mycin[R] | HypCDAB Hyc1 | PF0548, PF0549, PF0615-0617 |
| pC3AR-slyD[1] | pDEST-C3[3] | Chloram-phenicol[R] | SlyD | PF1401 |
| pEA-SH1 | pET23(+)[4] | Ampicillin[R] | Hydro-genase I | PF0891-PF0894 |
| pRA-EF[7] | pRSFDuet-1[5] | Kanamycin[R] | HypEF | PF0604 PF0559 |

[1]Also includes the region (SEQ ID NO: 28, see Table 2) of the Stratagene (La Jolla, CA) helper plasmid pRIL BL21-CodonPlus ® (DE3)-RIL competent cells, catalog number 230245. This strain carries the pRIL plasmid which expresses transfer RNAs that are rare in E. coli.
[2]Horanyi et al., (U.S. patent application 20060183193)
[3]Horanyi et al., (U.S. patent application 20060183193)
[4]EMD Chemicals Inc., Catalog Number 69771-3.
[5]EMD Chemicals Inc., Catalog Number 71341.
[6]An artificial intergenic sequence was introduced between the hypD and hypA coding regions to create a Shine-Dalgarno ribosome binding site for hypA. CD-ABI intergenic sequence: gaggtggaaa (SEQ ID NO: 52), there was an artificial Shine-dalgarno sequence (aggaggtg) in front of hypA gene. hypD's expression stops at TAG, while hypA starts with ATG: (hypD-tttacaaatatggcgccctgatgtaggaggtg gaaaATGcacgaatgggcgttggcagatgcaatagtaagg-hypA)(tttacaaatatg-gcgccctgatgt aggaggtggaaaATGcacgaatgggcgttggcagatgcaatagtaagg, SEQ ID NO: 53).
[7]An artificial intergenic sequence was introduced between the hypE and hypF coding regions to create a Shine-Dalgarno ribosome binding site for hypF. The hypE-hypF intergenic sequence is still gaggtggaaa (SEQ ID NO: 52), there was an same artificial Shine-dalgarno sequence (aggaggtg) in front of hypF gene. hypE's expression stops at tag, while hypF starts with ATG: hypE-gtgatcccgttcctagagtttgttaggaggtggaaa ATGatctggggagagaatgaaagcttatagaattcacg-hypF (gtgatcccgttc-ctagagtttgttaggaggtggaaaAT-Gatctggggagagaatgaaagcttatagaattcacg; SEQ ID NO: 54).

In addition, one of the vectors, pC3AR-slyD (Table 3) has been further modified to include a region (SEQ ID NO: 28) of the Stratagene (La Jolla, Calif.) helper plasmid pRIL. This plasmid was purified from E. coli BL21-CodonPlus cells from Stratagene (La Jolla, Calif. catalog #230240). This over-expresses transfer RNAs that are rare in E. coli but are required for efficient expression of P. furiosus proteins due to differences in codon usage between the two organisms. This eliminates the need for yet another vector (containing pRIL) and yet another antibiotic resistance marker. The following sequence was amplified from pRIL by PCR, and inserted into pDEST-C3A to create destination plasmid pC3A-RIL, which was used to make expression plasmid pC3AR-slyD (ggatc-cccgtcaccctggatgctgtacaat-tgacgacgacaagggcccgggcaaactagtaatcagac gcggtcgttcacttgt-tcagcaaccagatcaaaagccattgactcagcaagggttgaccgtataattcacg cgattacaccgcattgcggtat-caacgcgccctagctcagttggatagagcaacgaccttctaagtcgtg ggccg-caggttcgaatcctgcagggcgcgccat-tacaattcaatcagttacgccttctttatatcctccagc catggccttgaaatggcgttagtcat-gaaatatagaccgccatcgagtacccttgtacccttaactcttcct gatacg-taaataatgatttggtggcccttgctg-gacttgaaccagcgaccaagcgattatgagtcgcctgc tctaaccactgagctaaagggcct-tgagtgtgcaataacaatacttataaaccacgcaataaacatgatga tcta-gagaatcccgtcgtagccac-catcttttttgcgggagtggcgaaattggtagacgcaccagatttag gttctggcgccgctaggtgtgcgagt-tcaagtcgcctcccgcaccattcaccagaaagcgttgatcgg atgccctc-gagtcgggcagcgttgggtcctggc-cacgggtgcgcatgatcgtgctcctgtcgttgagga cccggctaggctggcgggtttgcct-tactggttagcagaatgaatcaccgatacgcgagcgaacgtgaa gcgactgct-gctgcaaaacgtctgcgacctgagctc; SEQ ID NO:55). If all four vectors are used, there are seven possible cloning sites available, four Gateway™ recombination sites (Invitrogen, Carlsbad, Calif.) under control of four different anaerobic promoters, and three standard multiple cloning sites (under standard T7 promoter control), as these are derived from the Novagen Duet system vectors (EMD Chemicals, San Diego, Calif.), with the exception of pEA-SHI, which was derived from pET23, also from Novagen but not part of the Duet system of vectors. However, as many as five consecutive genes can be cloned in tandem under control of the P-hya promoter (plasmid pC11A-CDABI), and all were expressed as demonstrated by quantitative PCR, as described below. This means as many as twenty genes can potentially be coexpressed anaerobically using these compatible vectors and potentially more. Herein we used all four vectors to express 12 genes from *P. furiosus*. In each construct, a single gene, or the first gene (at the 5' end) of any group of genes had a poly His-tag which is cleavable with TEV protease.

Example 2

Growth of Recombinant *E. coli* and Production of Recombinant *P. furiosus* Hydrogenase The *E. coli* strain used for expression of the *P. furiosus* hydrogenase was MW1001, a derivative of the strain BW25113. This strain has the genotype (hyaB hybC hycE Δkan; defective in LSU of hydrogenases 1, 2, and 3, no antibiotic marker) m and lacks detectable *E. coli* hydrogenase activity (Maeda et al. 2007. BMC Biotechnol 7:25).

To obtain the recombinant form of *P. furiosus* cytoplasmic hydrogenase I, recombinant *E. coli* cells containing the four vectors (Table 4) were grown on an 8 L scale at 37° C. in 2×YT media (16 g Tryptone, 10 g Yeast Extract, 5 g NaCl) supplemented with 25 μM $NiCl_2$, 100 μM $FeCl_3$, 2 mM $MgSO_4$ and the antibiotics Ampicillin (50 μg/ml), Chloramphenicol (16.5, μg/ml), Streptomycin (25 μg/ml) and Kanamycin (25 μg/ml). Cloning the complete. *P. furiosus* SHI operon in *E. coli* resulted in low efficiency of transformation; however, all techniques used for cloning and transformations were standard molecular biology techniques as described (Sambrook et al., J., E. F. Fritsch, and T. Maniatis. 1989. Molecular cloning: a laboratory manual, 2nd ed. Cold Spring Harbor Laboratory Press, Cold Spring Harbor, N.Y.), and transformants were obtained. The culture was sparged with sterile, compressed air (3-5 L/min) until an $OD_{600}$ of ~0.3 was reached. At this time compressed air was turned off and the cells were sparged with sterile argon (~4 L/min) and 2% glucose and 30 mM sodium formate were added to supplement growth and induce hydrogenase-related genes in *E. coli*. The culture was allowed to ferment for five hours and the cells were then quickly harvested by centrifugation and frozen at −80° C. Frozen cells were then thawed and lysed at 25° C. in anaerobic 50 mM Tris buffer pH 8.0, 2 mM sodium dithionite, 0.5 mg/mL lysozyme, 50 μg/mL DNase at a ratio of 1 g/3 mL in an anaerobic chamber under an atmosphere of 5% hydrogen/95% argon overnight.

A hydrogen evolution assay was used to measure hydrogenase activity using an artificial (methyl viologen) electron carrier with sodium dithionite as the electron donor as described (Ma and Adams. 2001. Methods Enzymol 331:208-16). Briefly, this was carried out using 5 mL stoppered vials containing 2 mL of anaerobic 100 mM EPPS buffer pH 8.4, 10 mM sodium dithionite, and 1 mM Methyl Viologen under an atmosphere of argon. Vials were preheated at 80° C. for 1 min and then 200 μL of sample was injected. Samples (100 μL) of the headspace of the sealed vial were removed with a gas-tight syringe and injected into a gas chromatograph after the reaction had proceeded for 6 min. The resulting hydrogen peak was compared to a known standard curve to calculate micromoles of hydrogen produced per mL of assay solution. Specific activity is defined as micromoles $H_2$ produced $min^{-1}$ mg $protein^{-1}$. After cell lysis the following samples were analyzed for hydrogen evolution at 80° C.: Whole cell extracts (WCEs), the cytoplasmic extract after a 100,000×g centrifugation (S100), and heat-treated (at 80° C. for 30 min) and re-centrifuged S100. The data are summarized in Table 5.

TABLE 5

MV-linked $H_2$-evolving activity of recombinant *P. furiosus* cytoplasmic hydrogenase I.

| Step | BW25113[1] | | MW1001[2] | |
|---|---|---|---|---|
| | Total Units | Specific Activity[3] | Total Units | Specific Activity[3] |
| WCE | 891 | 2.7 | ND[4] | ND[4] |
| S100 | 2 | 0.02 | ND[4] | ND[4] |
| 80° C. treated S100 | ND[4] | ND[4] | ND[4] | ND[4] |

| Step | MW1001 + SHI[5] | | MW1001 + SHI + Pf Plasmids[6] | |
|---|---|---|---|---|
| | Total Units | Specific Activity[3] | Total Units | Specific Activity[3] |
| WCE | ND[4] | ND[4] | 2.9 | 0.008 |
| S100 | ND[4] | ND[4] | 3.8 | 0.04 |
| 80° C. treated S100 | ND[4] | ND[4] | 4.9 | 0.31 |

[1]Obtained from T. K. Wood, Texas A&M University, College Station, TX.
[2]See reference (Maeda et al. 2007. Appl Microbiol Biotechnol 76: 1035-1042).
[3]Specific activity is defined as μmol $H_2$ produced $min^{-1}$ mg $protein^{-1}$.
[4]Not detected (below detection limit of 0.017 Units (measured with 0.5 mg protein after 2 minutes).
[5]Contains one plasmid expressing the four structural genes that encode *P. furiosus* hydrogenase: pEA-SH1 (PF0891-0894).
[6]Contains all four plasmids expressing *P. furiosus* hydrogenase genes including structural and processing genes: pEA-SH1 (PF0891-0894), pC11A-CDABI (PF0548-0549, PF0615-0617), pRA-EF (PF0604, PF0559), pC3AR-slyD (PF1401).

Figure 5:
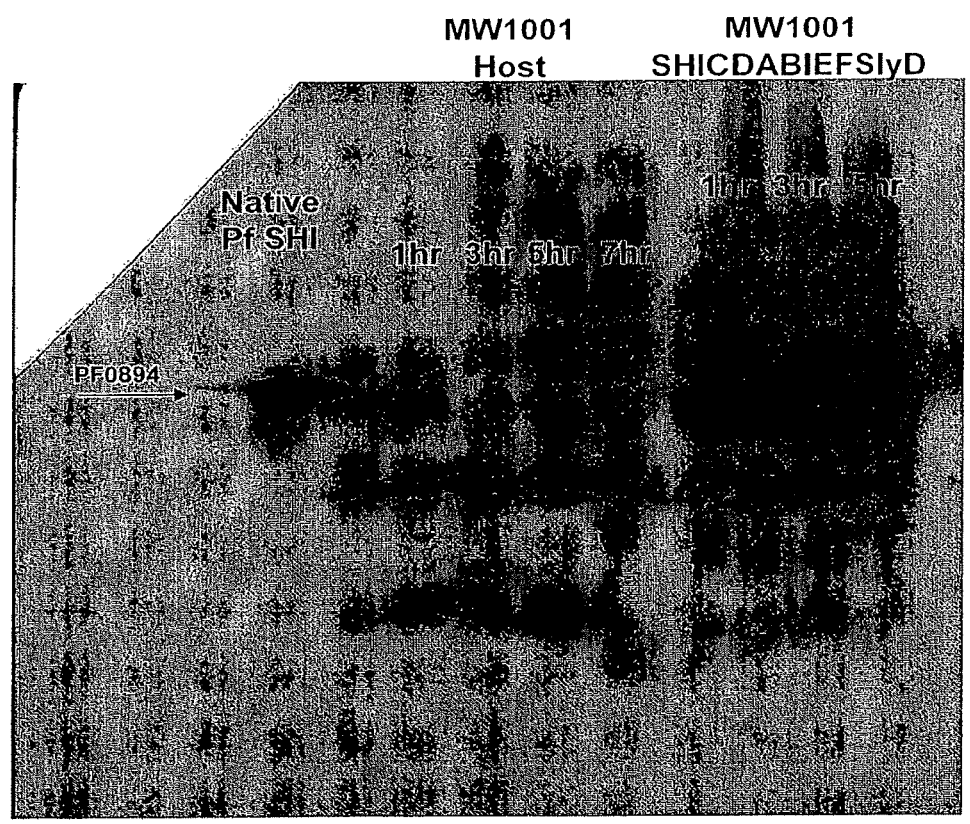
FIG. 5. Immunoanalysis using antibodies to the catalytic subunit (PF0894). MW 1001 SHICDABIEFSlyD, MW 1001 containing the coding regions HypC, HypD, HypF, HypE, HypA, HypB, HycI, and SlyD. Native PfSHI, native *P. furiosus* SH0I hydrogenase.
Figure 6:
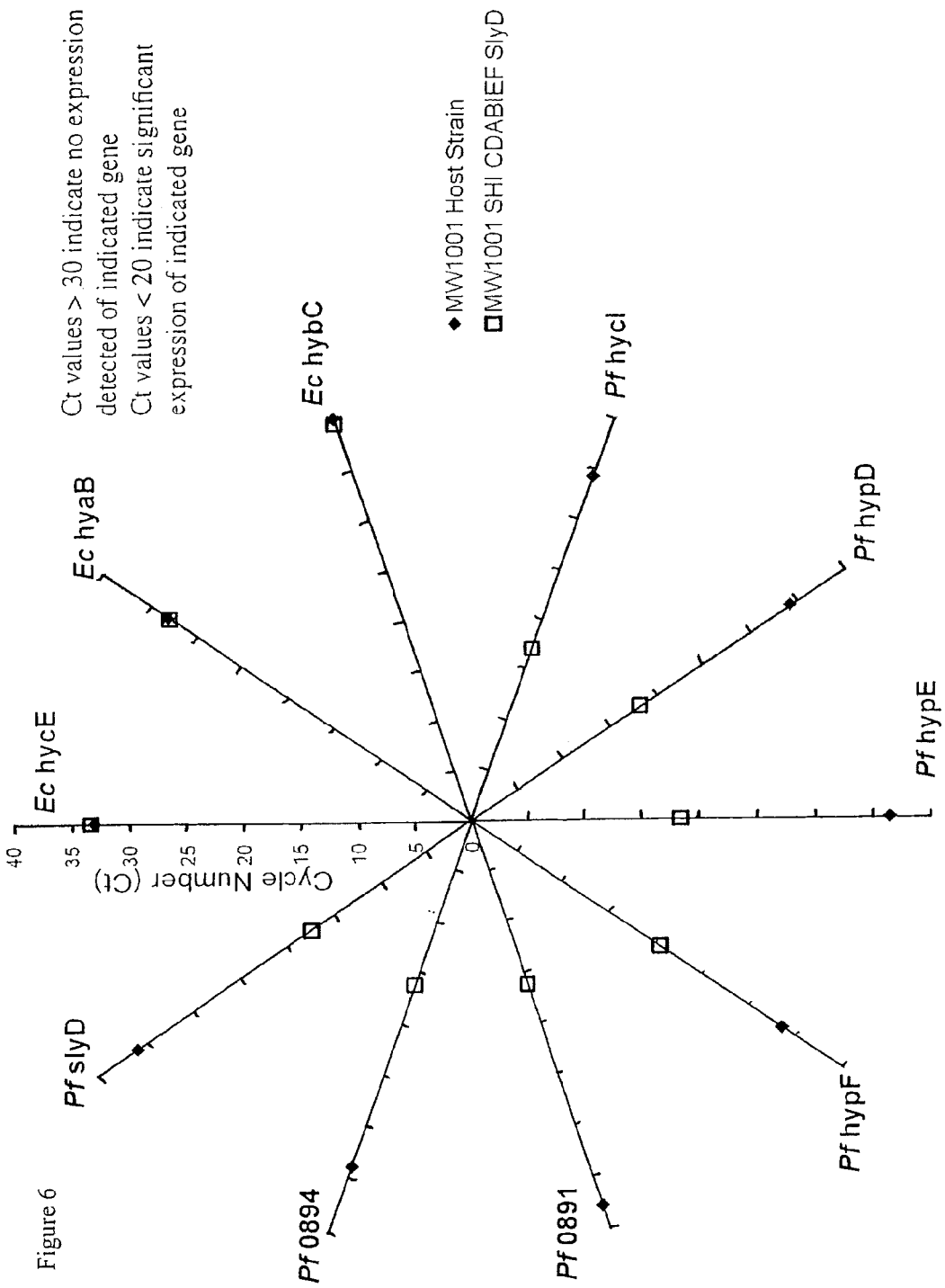
FIG. 6. QPCR analysis of the expression of exogenous coding regions in *E. coli*.
Figure 9:
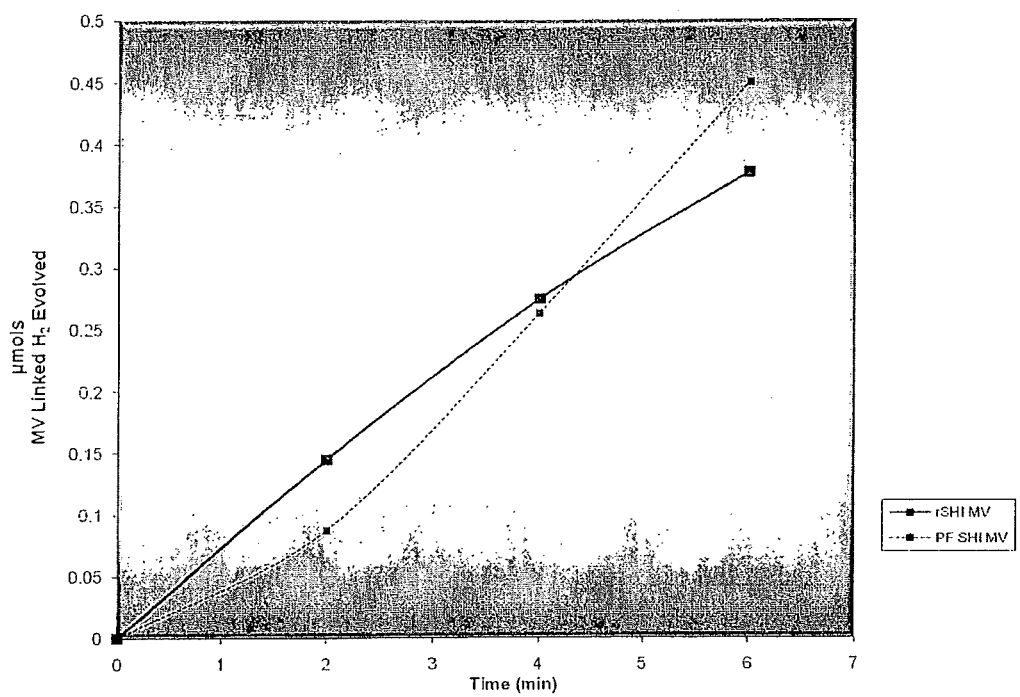
FIG. 9. MV (methyl viologen)-linked hydrogenase activity of native versus recombinant *P. furiosus* soluble hydrogenase I.

The data clearly demonstrate $H_2$ evolution from cells expressing the genes encoding *P. furiosus* hydrogenase, with no detectable $H_2$ produced by the control strain lacking any gene from *P. furiosus*. The form of the *P. furiosus* enzyme responsible for this activity was not only stable at 80° C. for 30 min, but it was activated by this heat treatment, a step that also precipitates heat-labile *E. coli* proteins. This increase was unexpected and, at 28%, significant. Production of protein corresponding to the catalytic subunit of hydrogenase I (encoded by PF0894) has been confirmed by immunoanalyis (FIG. 5). In addition, expression of the *P. furiosus* genes in *E. coli* using these constructs at the level of mRNA has been confirmed by quantitative PCR (FIG. 6). In comparison to the natively purified *P. furiosus* hydrogenase, FIG. 9 demonstrates that the MV-linked $H_2$ evolution activity was virtually identical. The expression of coding regions PF0891-0894 resulted in a his-tag present at the amino terminal end of the polypeptide encoded by PF0891, the beta subunit. This tag did not result in a hydrogenase polypeptide that could be affinity purified; however, the hydrogenase polypeptide was active, suggesting the hydrogenase polypeptide is permissive for mutations.

We have therefore demonstrated that heterologous gene expression of the hydrogenase was achieved in *E. coli*. This was shown by analysis of cell-extracts for mRNA (by PCR) and for protein (by western blot) and that this gene expression leads to the production of a functional recombinant hydrogenase that is catalytically active at 80° C. (by hydrogen production measurements) and is also heat stable at 80° C. (for at least 30 min).

Example 3

Production of Hydrogenase by *E. coli*

Figure 10:
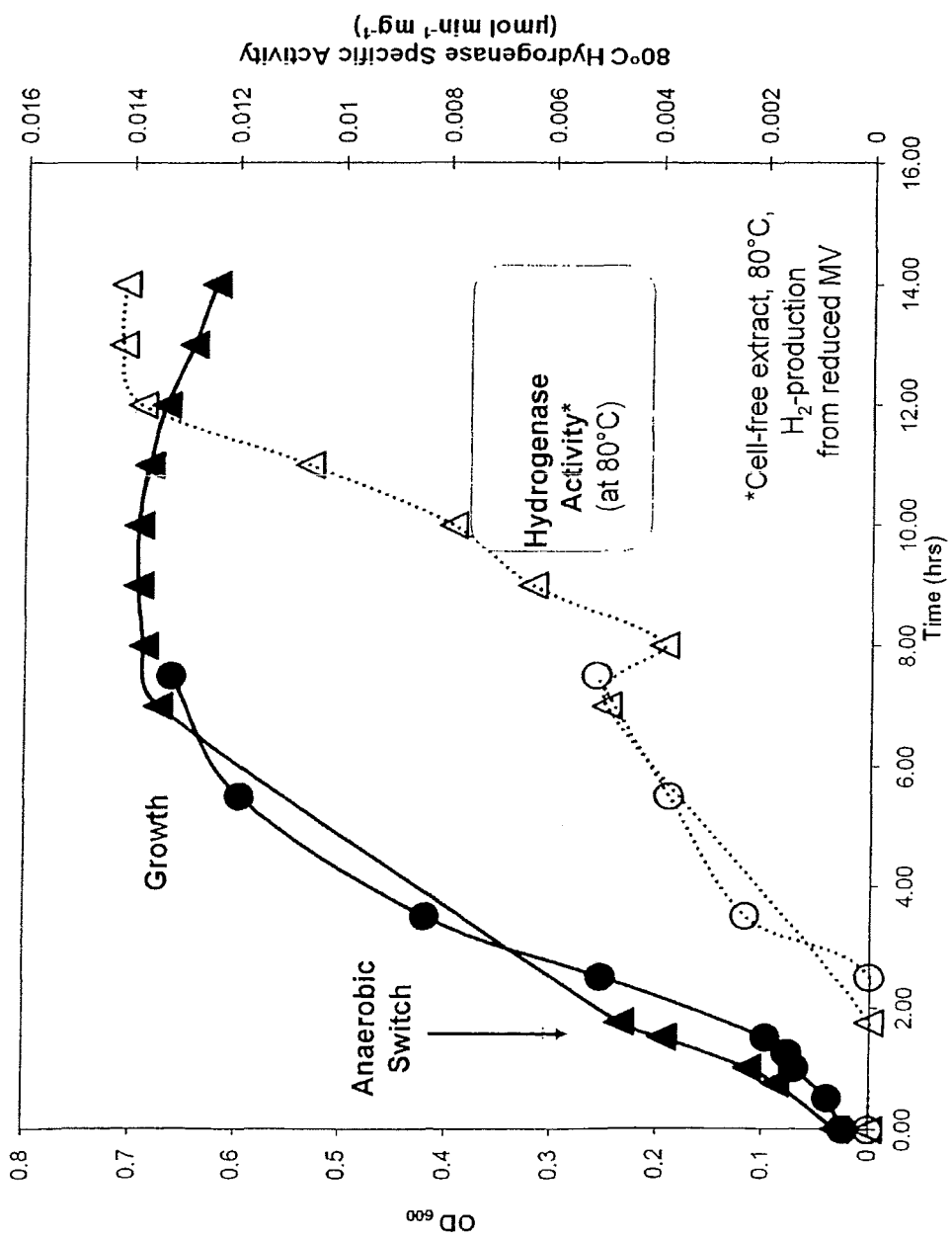
FIG. 10. Production of MV-Linked Hydrogenase activity at 80° C. in recombinant *E. coli* MW/rSHI-C. The results from two separate cultures (one indicated by circles, one by triangles) are shown. The growth curves are shown by solid symbols.

The ability of *E. coli* containing the four compatible vectors, termed strain MW/rSHI-C, to produce the recombinant hydrogenase was investigated throughout the growth phase (FIG. 10). The strain was grown on an 8-liter scale in carboys in 2×YT growth media (16 g tryptone, 10 g yeast extract and 5 g NaCl per liter) supplemented with 1% glucose, 2 mM MgSO4, Amp (50 μg/ml), Cm (16 μg/ml), Sm (25 μg/ml) and Kan (25 μg/mL), see Table 4. FIG. 10 summarizes the results from two separate cultures (one indicated by circles, one by triangles). At an $OD_{600}$ of 0.2-0.3, 100 μM FeCl3 and 25 μM NiSO4 were added, the culture was then sealed and allowed to ferment anaerobically (indicated by the arrow in FIG. 10). The growth curves are shown by solid symbols. Samples of the culture were taken every hour after the anaerobic switch. The cells were harvested by centrifugation, lysed, and analyzed for MV linked hydrogenase activity at 80° C. (shown by open symbols). The results show that hydrogenase activity is not detected in *E. coli* MW/rSHI-C until the cells are switched to anaerobic growth, which is expected since expression of the *P. furiosus* genes is induced by the so-called anaerobic hya promoter. FIG. 10 also shows that the amount of 80° C. hydrogenase activity, and thus production of the recombinant hydrogenase, increases with cell growth until late stationary phase.

Figure 11:
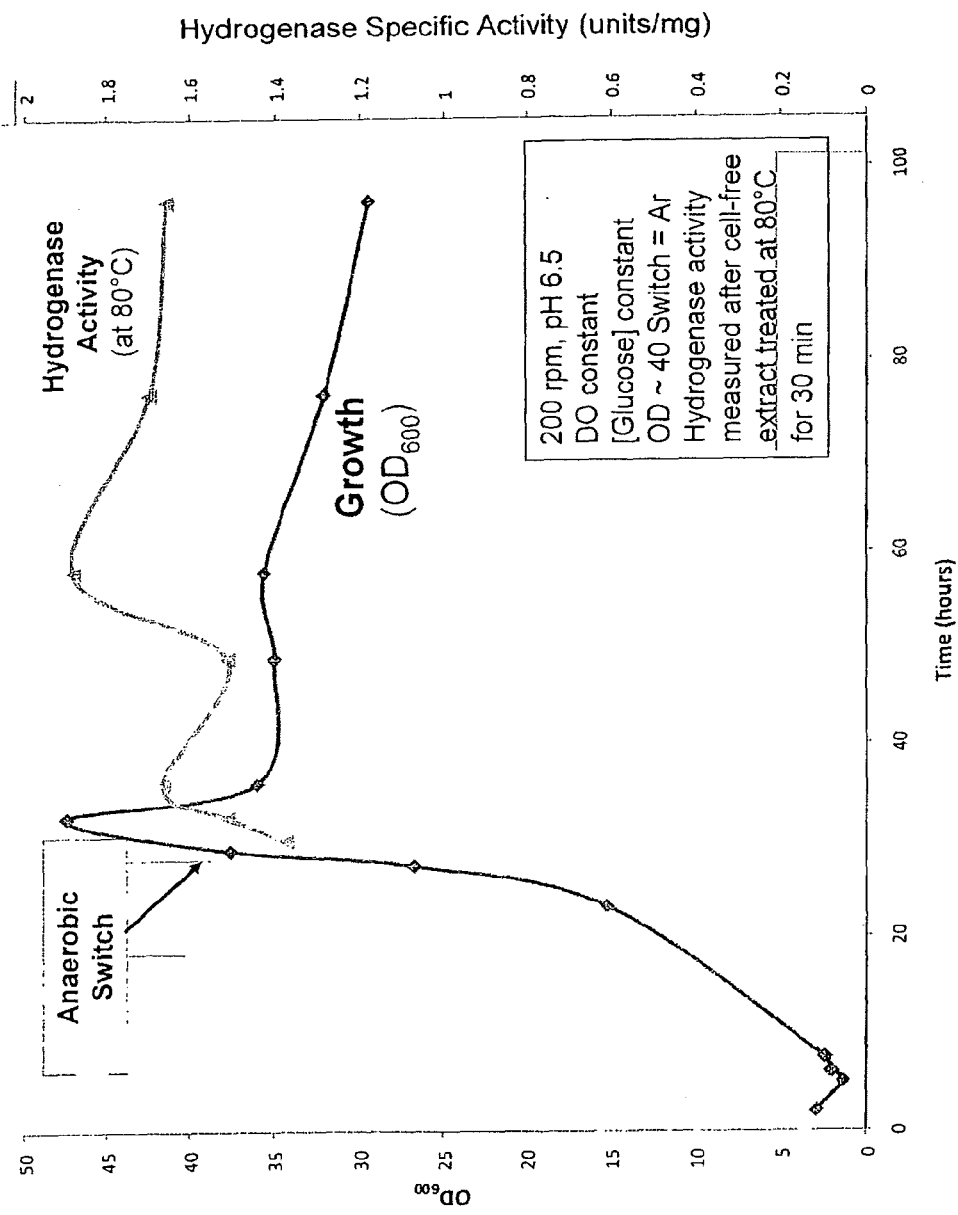
FIG. 11. High Density 5-Liter Controlled Fermentation of *E. coli* MW/rSHI-C.

Cell yields of recombinant *E. coli* MW/rSHI-C approached 1 gram (wet weight)/liter when grown on the 8-liter scale in carboys. We also demonstrated that the same strain could be grown to extremely high cell densities under anaerobic conditions and under such conditions produced the recombinant hydrogenase, as measured by hydrogenase activity at 80° C. Cells were grown in a 5-liter controlled fermentation system (New Brunswick) on same medium that was used in the carboys but with controlled a) pH (6.5), b) dissolved oxygen, and c) glucose concentration. As shown in FIG. 11, cells were grown to an $OD_{600}$ of 38 before switching to anaerobic conditions, in this case by replacing the air with Argon, and this induced the production of the recombinant hydrogenase activity to approximately the same level as in the 8-liter carboy cultures (~0.1 unit/mg before heat treatment). The cell yield in this case was ~40 gram (wet weight)/liter.

Example 4

Purification of Hydrogenase

Figure 12:
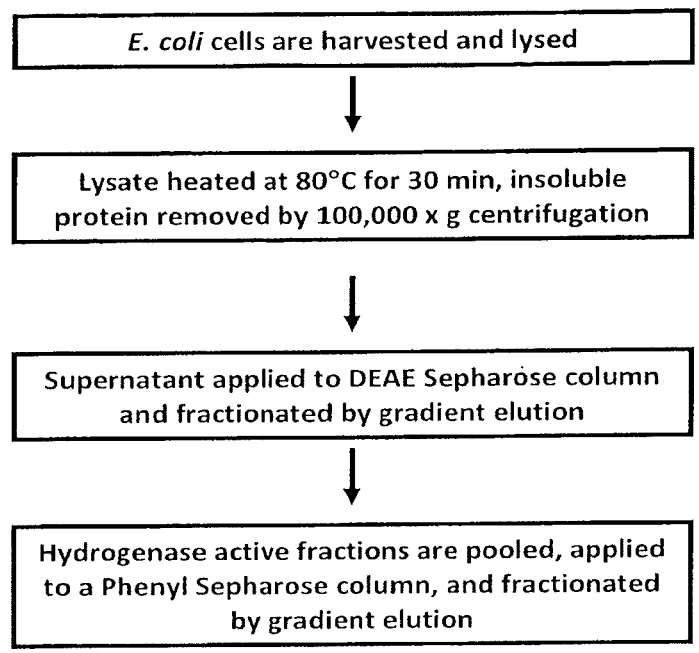
FIG. 12. Recombinant Hydrogenase Purification Scheme.

A method for purifying the recombinant hydrogenase was developed that enabled confirmation of the production of the recombinant forms of all four of the protein subunits of *P. furiosus* hydrogenase. The scheme is summarized in FIG. 12, and involves two standard column chromatography steps using DEAE-Sepharose and Phenyl Sepharose (GE Healthcare). In brief, the *E. coli* cells (154 gram, wet weight) were broken by thawing them in 3 mL of anaerobic 50 mM Tris, pH 8.0 (3 mL per gram of frozen cells) containing 0.5 mg/mL lysozyme, 50 μg/mL DNase, 1 mM phenylmethylsulfonyl fluoride, and 2 mM sodium dithionite. The suspension was incubated at room temperature in an anaerobic chamber under an atmosphere of 5% $H_2$/95% Ar for 4 hours to allow the cells to break. The sample was then sealed in an anaerobic flask and heat-treated at 80° C. for 30 min by immersion of the flask in a hot water bath. Samples were then anaerobically centrifuged at 100,000×g for 30 min. The supernatant (650 mls) was then diluted 5-fold with Buffer A (50 mM Tris, 2 mM sodium dithionite, pH 8.0) at a sample/Buffer A ratio and loaded onto a column of DEAE Sepharose (300 ml; GE Healthcare) equilibrated in Buffer A. The column was then washed with 5 column volumes of Buffer A and eluted with a 20-column volume gradient from 0 to 25% gradient of Buffer B (Buffer A+2M NaCl) in 40 ml fractions. Those that contained hydrogenase activity in the standard assay (at 80° C. using reduced methyl viologen as the electron donor) were combined and Buffer A containing 2.0 M ammonium sulfate $(NH_4)_2SO_4$ was added to a final concentration of 0.8 M. The sample was then loaded on to a column of Phenyl Sepharose (45 ml) equilibrated in Buffer C (Buffer A containing 0.8M $(NH_4)_2SO_4$). The column was washed with 5-column volumes of Buffer C and eluted with a 20 column volume gradient from 100% Buffer C to 100% Buffer A in 10 ml fractions. Those containing hydrogenase activity were combined.

Figure 13:
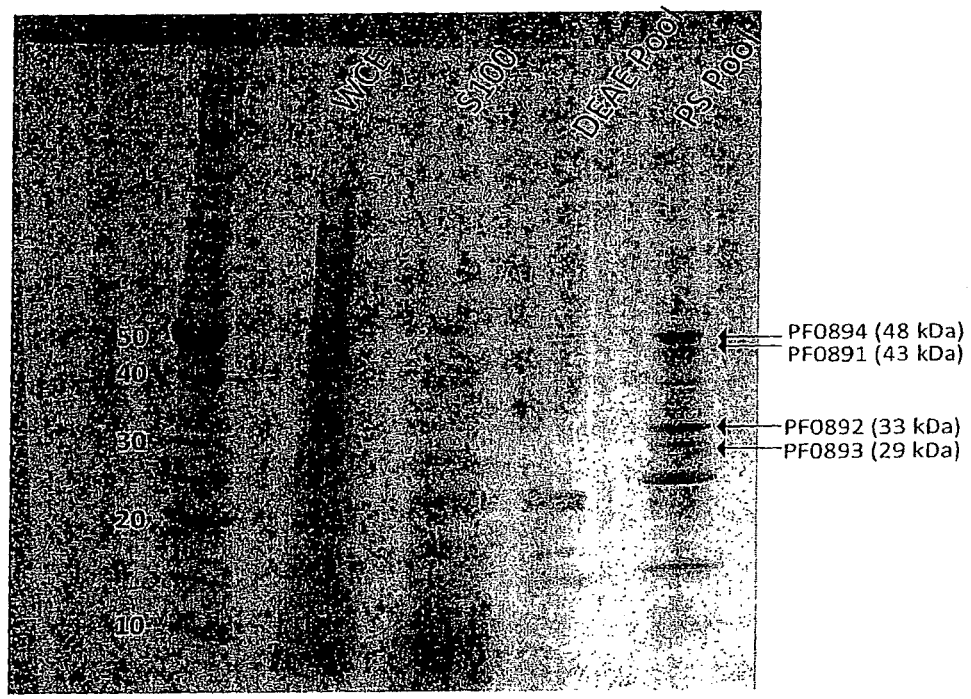
FIG. 13. SDS Gel Analysis of Recombinant Hydrogenase Purification. WCE, whole cell extract; S100, cytoplasmic extract after a 100,000×g centrifugation; DEAE pool, pool from DEAE Sepharose column; and PS pool, pool from Phenyl Sepharose column. The PF numbers and the calculated molecular weights for the four subunits of the hydrogenase are indicated.

Typical results of this two-column purification are shown in Table 6. The enzyme was purified almost 60-fold, about 20% of the total activity was recovered with a specific activity in the standard 80° C. assay of 6 units/mg. SDS gel analysis of the hydrogenase active fractions obtained at the different purification steps is shown in FIG. 13. The most purified fractions (the PS Pool from the Phenyl Sepharose column) contain six or so major bands on SDS gels. Analysis of the bands that migrated at the expected molecular weights for the four subunits of the recombinant hydrogenase (see FIG. 11) by standard tryptic digestion/mass spectrometry (MALDI) confirmed unambiguously that those were the four subunits of the *P. furiosus* hydrogenase enzyme.

TABLE 6

Isolation of recombinant hydrogenase.

| Step | Total Units[a] (μmol min−1) | Total Protein (mg) | Specific Activity | % Yield | Fold Purification |
|---|---|---|---|---|---|
| Cell Lysate | 1349 | 13059 | 0.1 | 100 | 1 |
| S100 (after 80° C./30 min) | 1380 | 1231 | 1 | 102 | 11 |
| DEAE Sepharose | 640 | 301 | 2 | 47 | 21 |
| Phenyl Sepharose | 239 | 41 | 6 | 18 | 56 |

[a]Hydrogenase activity was measured at 80° C. using reduced MV as the electron donor. One unit of activity is equivalent to the production of 1 μmole of hydrogen per minute.

Example 5

Purification of Hydrogenase

Figure 14:
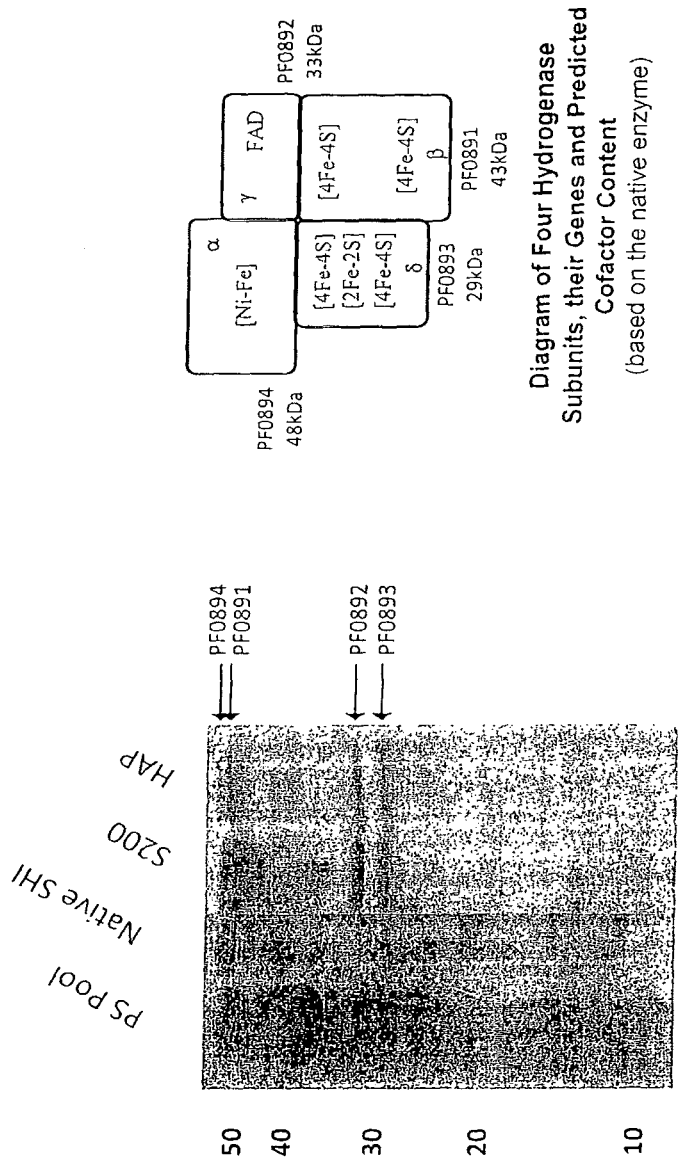
FIG. 14. SDS Gel Analysis of Highly Purified Recombinant Hydrogenase. PS pool, pool from Phenyl Sepharose column; native SHI, native hydrogenase purified from *P. furiosus*; 5200, Sepharcryl S-200 eluate; HAP, Hydroxyapatite eluate.

A method to obtain highly purified preparations of the hydrogenase that are near homogeneous was devised. This involves two subsequent steps of conventional column chromatography. In brief, the PS Pool (see Table 6) was concentrated by ultrafiltration (Amicon, PM-30 membrane), and applied to a column of Sepharcryl S-200 (GE Healthcare) equilibrated with Buffer A. The same buffer was used to elute the column. Fractions that contained hydrogenase activity in the standard assay were combined and applied directly to a column of Hydroxyapatite (Life Science Research, Hercules, Calif.) equilibrated in Buffer A. The column was washed with 5 column volumes of Buffer A and eluted with a 20-column volume gradient from 0 to 50% gradient of Buffer D (Buffer A+0.5 M potassium phosphate). Samples containing hydrogenase activity were combined. As shown in FIG. 14, the fractions from the Hydroxyapatite column contain highly purified hydrogenase containing four major proteins. These corresponded to the protein bands found in the native hydrogenase purified from P. furiosus. The four protein bands in the purified recombinant hydrogenase were unambiguously shown by tryptic digest/MADI analysis to correspond to the four subunits of the recombinant form of P. furiosus hydrogenase. In addition, the hydrogenase activity from the Sephacryl S-200 column eluted a single band with a molecular weight of approximately 150,000, showing that it was a homogeneous species whose size corresponds to that of the native enzyme, which consists of a heterotetramer of four different polypeptides (see FIG. 14).

Example 6

Metal Analysis

Figure 15:
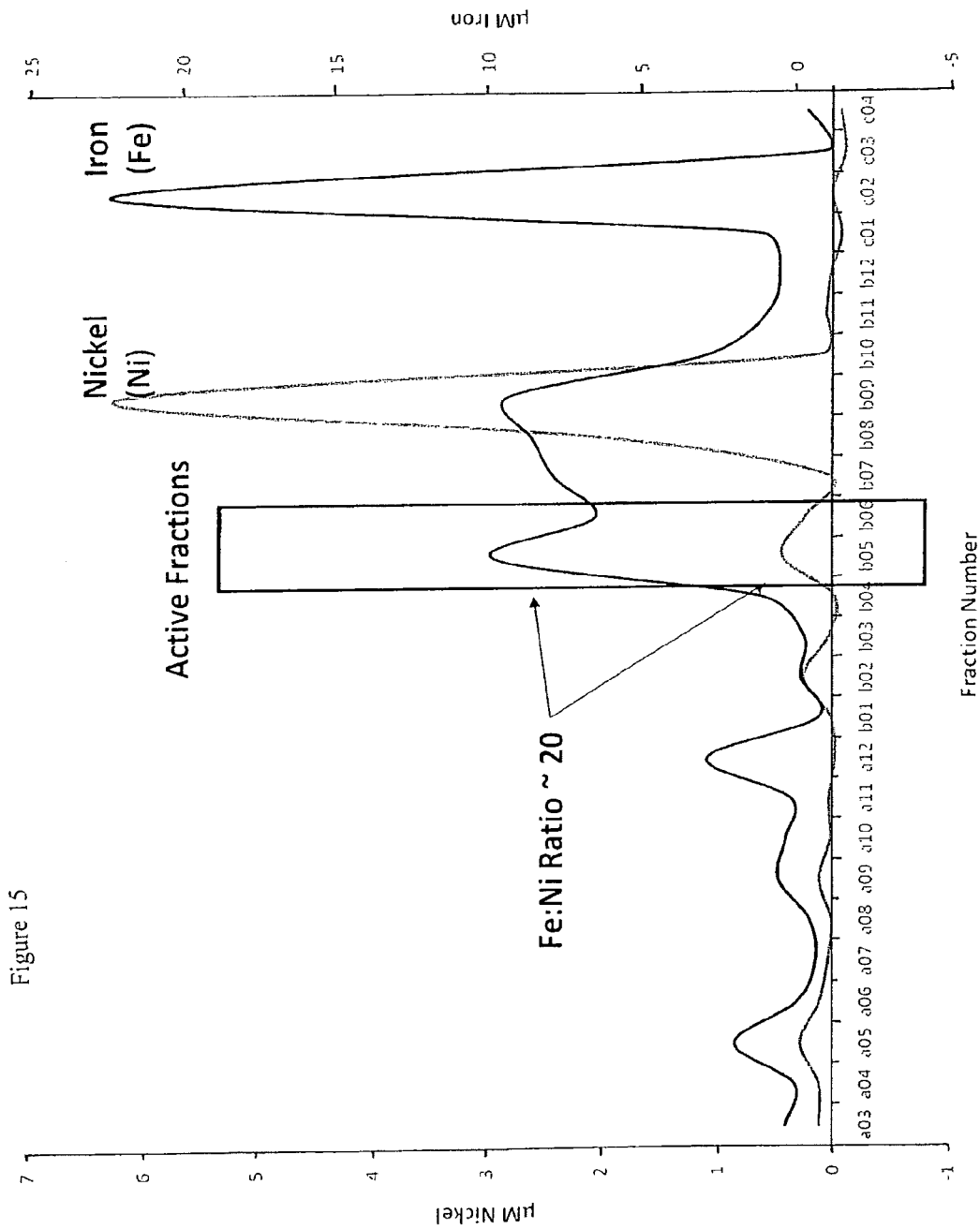
FIG. 15. Metal Analysis of Phenyl Sepharose fractions.

The purified recombinant hydrogenase has hydrogen-evolving activity and must therefore contain a nickel-iron catalytic site. This is demonstrated by a metal analysis of the fractions eluting from the Phenyl Sepharose column using the technique of ICP-MS (Model 7500ce, Agilent Technologies). As shown in FIG. 15, fractions that contained hydrogenase activity also contained both nickel and iron. Moreover, the Fe:Ni ratio was approximately 20, which is almost identical to the value (Fe:Ni=19) proposed to be in the native P. furiosus enzyme (see proposed cofactor content in FIG. 14). Therefore, the recombinant hydrogenase has the expected metal content, consistent with a fully functional enzyme.

FIG. 15 shows a major additional peak of nickel that is not associated with the enzyme. We propose that this nickel is not inserted into the hydrogenase protein because of a limiting growth factor for hydrogenase biosynthesis in E. coli, but that this would occur when E. coli is grown under the appropriate conditions. As an example, nickel may not be processed completely due to the availability of the cyanide and carbon monoxide ligands that are coordinated to the nickel-iron catalytic site. Others have shown that carbamoyl phosphate is the source of the cyanide (Paschos et al. 2001. FEBS Lett 488:9-12). E. coli cells deficient in carbamoyl phosphate (CP) synthesis (by lesion the carAB locus) lose the ability to synthesize active hydrogenase enzymes (Blokesch and Bock. 2002. Journal of Molecular Biology 324:287-296). It was shown that the ΔcarAB strain contained a stable HypC-HypD complex but that processing of hydrogenase does not occur. The complex disappeared and processing and hydrogenase production was restored when a source of CP (L-citrulline) was added to the E. coli growth media. It is anticipated that the addition of this or similar sources of key nutrients will dramatically increase the yield of active recombinant P. furiosus hydrogenase produced in E. coli.

Example 7

Figure 16:
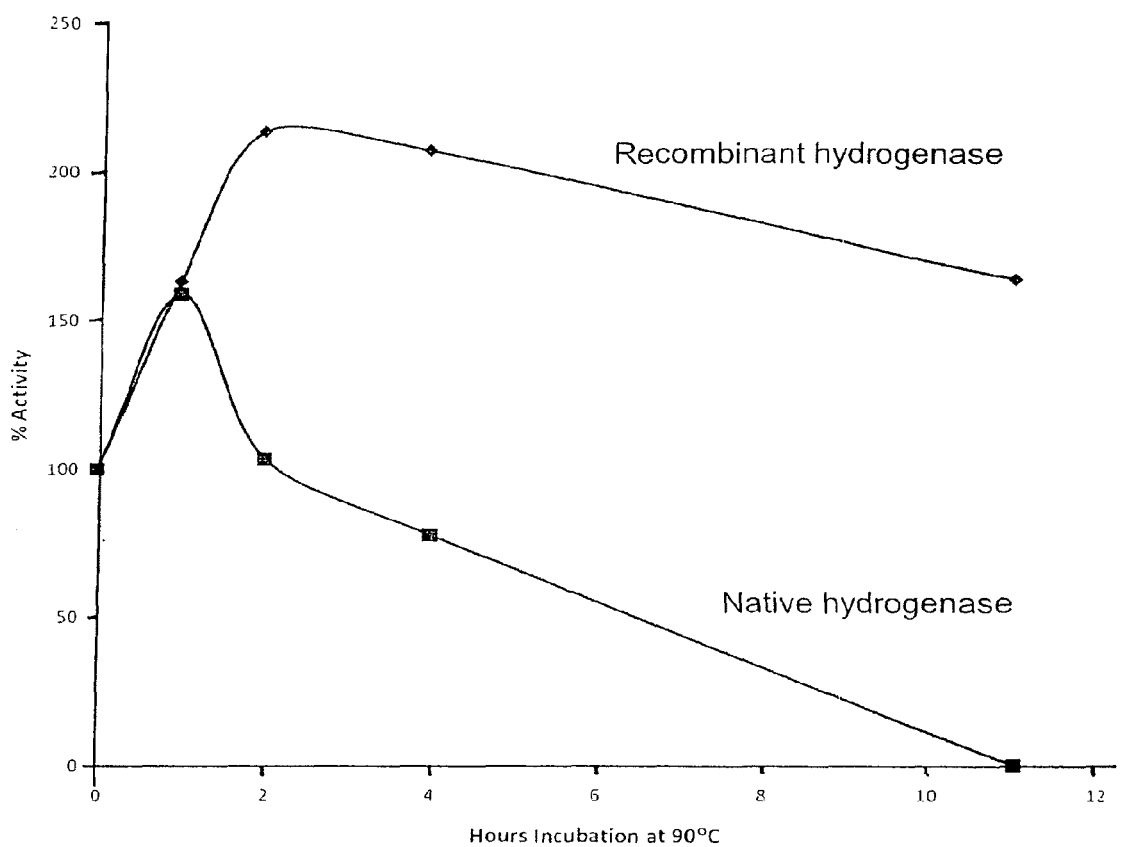
FIG. 16. Thermal Sensitivity of Recombinant Hydrogenase.

Temperature and Oxygen Sensitivity and Electron Donor Specificity of Recombinant Hydrogenase Purified recombinant hydrogenase is as stable to incubation at high temperature (90° C.) and as sensitive to oxygen as the native form of the enzyme purified from P. furiosus native biomass. For example, as shown in FIG. 16, the thermal stability of purified recombinant hydrogenase (7.5 mg/ml) and the native hydrogenase (0.4 mg/ml) were analyzed by incubating samples anaerobically under Argon in 100 mM EPPS buffer, pH 8.4, containing 2 mM sodium dithionite in a sealed 8-ml serum vials in a 90° C. water bath. Samples were analyzed for 80° C. MV linked hydrogen evolution activity periodically during the incubation. Both enzyme preparations showed an initial activation to over 150% of the initial activity, as originally reported with the native enzyme (Bryant and Adams, 1989. 1989. J Biol Chem 264:5070-5079). Moreover, the recombinant enzyme continued to exhibit an activity above 150% of the initial value even after 11 hours at 90° C., while that of native enzyme decreased (FIG. 16). However, such stability is dependent upon the protein concentration and increases as the concentration increases. Given the 37-fold higher protein concentration of the recombinant enzyme, it can be concluded that the stabilities of the two forms are comparable.

Figure 17:
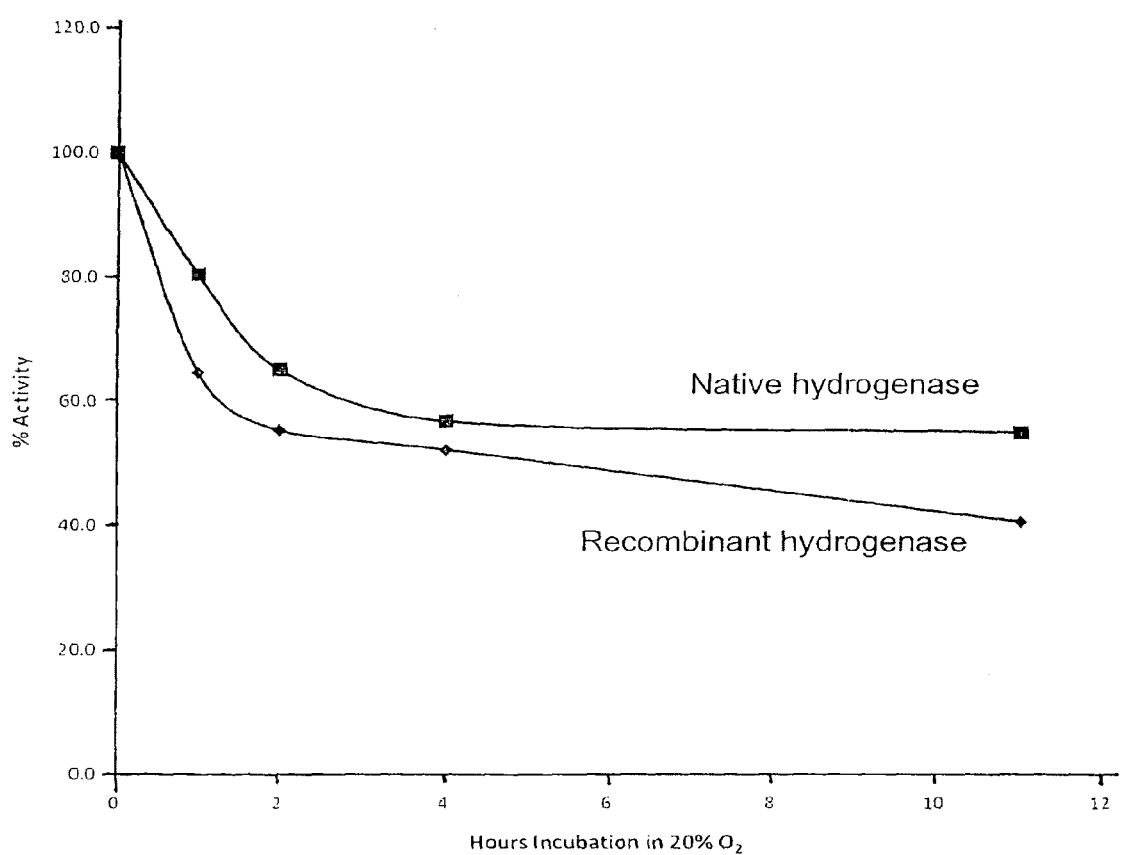
FIG. 17. Oxygen Sensitivity of Recombinant Hydrogenase.

FIG. 17 shows the results of incubating the purified recombinant hydrogenase (7.5 mg/ml) and the native hydrogenase (0.4 mg/ml) in 100 mM EPPS buffer, pH 8.4, in 8-ml serum vials at room temperature that were exposed at zero time to 20% oxygen (air). The sensitivities of the two forms to oxygen, a property that is not dependent upon protein concentration, was virtually identical.

The recombinant hydrogenase, like the native enzyme, is also able to use NADPH as an electron donor for hydrogen production at 80° C. As shown in Table 7, the two forms exhibit between 3 and 12% of the activity with MV as the electron donor when it is replaced by NADPH (1 mM) under the same assay conditions. The activity, oxygen and thermal stability data, summarized in Table 7, indicate that the structural and catalytic integrity of the recombinant hydrogenase is comparable to that of the native enzyme.

TABLE 7

Subunit Structure and Electron Donor Specificity of Native and Recombinant Forms of Hydrogenase

| Enzyme Type | MV-Linked (units/mg) | NADPH-linked (units/mg) | Ratio (%) | Stability at 90° C. ($t_{1/2}$, hr) | Stability in Air ($t_{1/2}$, hour) |
|---|---|---|---|---|---|
| Native hydrogenase (from P. furiosus biomass) | 109 | 12.7 | 12 | 7 | >12 |
| Recombinant Hydrogenase (αβγδ)[a] | 5.7 | 0.15 | 3 | >12 | 6 |
| Dimeric Recombinant Hydrogenase (αδ)[b] | 0.4 | 0 | — | ~1 | ~1 |

Activities were measured using either 1 mM MV or 1 mM NADPH as the electron donor at 80° C. The stability values for the native and recombinant (αβγδ) enzymes are estimates from FIG. 17. The data used to estimate the values for the dimeric form (αδ) is not shown.
[a] The form of the tetrameric recombinant hydrogenase (αβγδ) used in this experiment was obtained after two chromatography steps (see Table 6).
[b] The form of the dimeric recombinant hydrogenase (αδ) used in this experiment was after the cell-free extract was clarified by centrifugation (the S-100 fraction). The dimeric form of the hydrogenase is described below.

Example 8

Production of a Dimeric Hydrogenase

Figure 18:
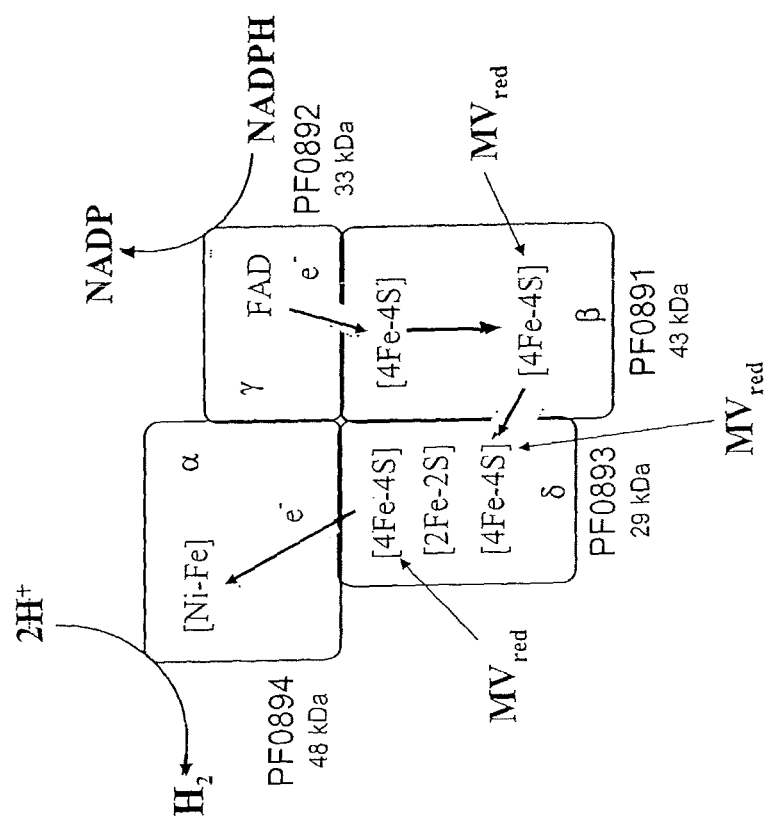
FIG. 18. Expected Interactions Between Tetrameric Recombinant Hydrogenase and MV and NADPH.
Figure 19:
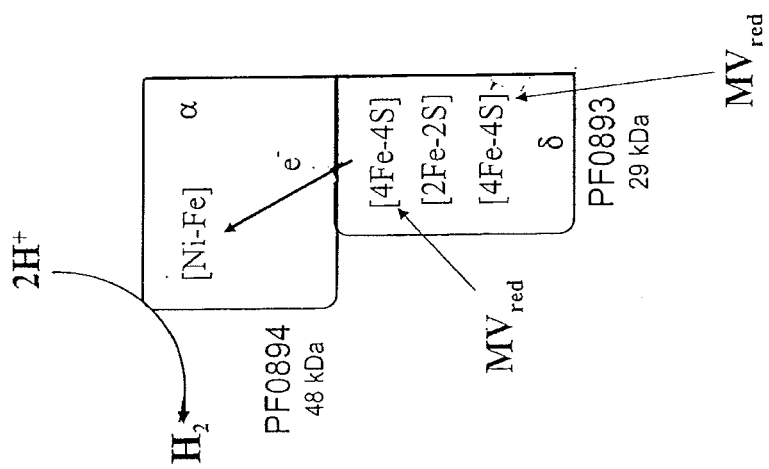
FIG. 19. Expected Interactions Between Dimeric Recombinant Hydrogenase and MV and NADPH.

The ability to generate the recombinant form of the hydrogenase opens up a complete spectrum of possibilities to produce mutant forms with very different properties from that of the native form. For example, FIG. 18 shows the proposed electron pathway from NADPH through the four subunits of the enzyme and the electron-carrying cofactors (FAD and then multiple [2Fe-2S] and [4Fe-4S] clusters) to the NiFe catalytic site, which catalyzes hydrogen ($H_2$) production. It is assumed that the artificial electron carrier, MV, can donate electrons directly to one or more of the [2Fe-2S] and [4Fe-4S] clusters directly, by-passing the FAD, see FIG. 18. Consequently, the native heterotetrameric ($\alpha\beta\gamma\delta$) enzyme produced from 4 genes (PF0891-PF0894) evolves hydrogen from both MV and NADPH (Table 7). However, as shown in FIG. 19, a heterodimeric ($\alpha\delta$) enzyme produced by expression of only PF0893 and PF0894 would lack the proposed NADPH-interacting and FAD-containing $\gamma$-subunit (PF0892). This dimeric form would not be expected to evolve hydrogen from NADPH, but may from MV (FIG. 19).

Figure 20A:
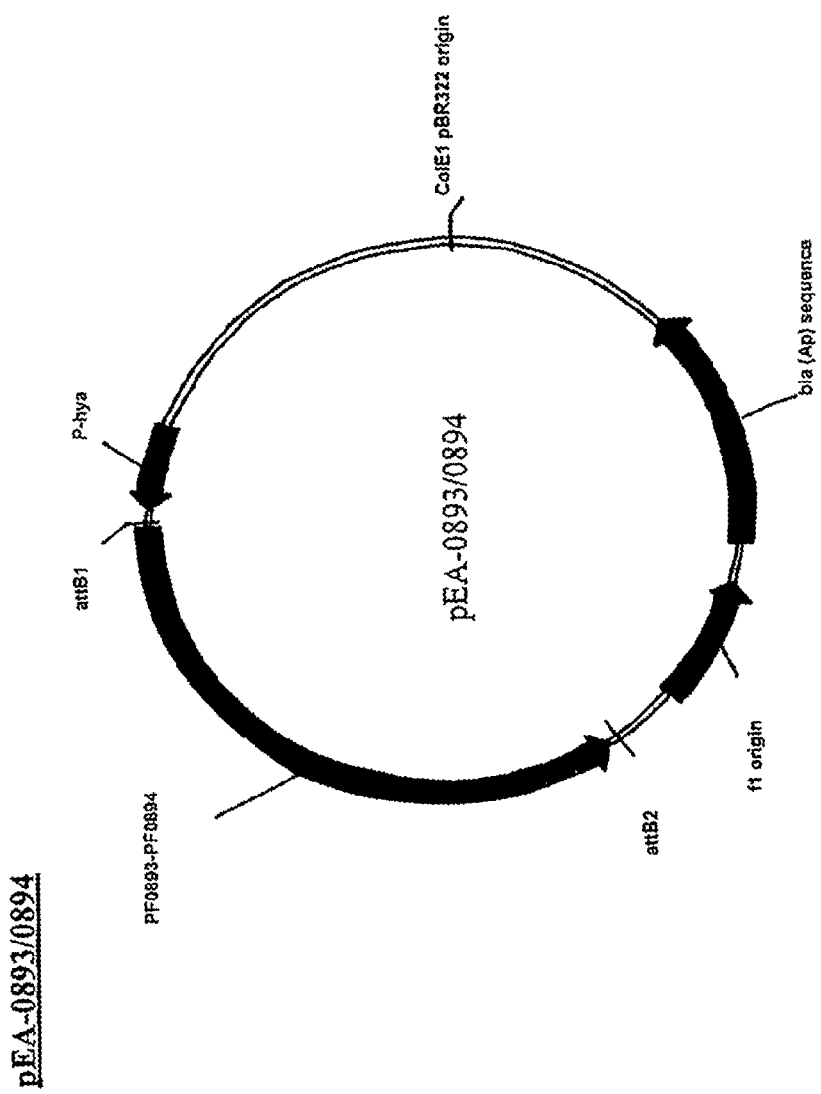
FIG. 20. pEA-0893/0894 (plasmid map and nucleotide sequence, SEQ ID NO:33).

To test this idea and to generate the first mutant form of recombinant *P. furiosus* hydrogenase, a plasmid, pEA-0893-0894, was constructed that contained only two of the four hydrogenase subunits encoded by PF0893 and PF0894 (FIG. 20). This was based on the plasmid that contains the four genes that encode all four subunits (pEA-SH1, FIG. 8); however, the P-hya promoter in this plasmid did not include the sequences encoding a his-tag. The dimeric ($\alpha\delta$) recombinant enzyme was produced in *E. coli* strain MW 1001 under the same anaerobic expression conditions that were used to produce the recombinant heterotetrameric ($\alpha\beta\gamma\delta$) enzyme (see FIG. 10) except that pEA-SH1 plasmid was replaced by the pEA-0893-0894 plasmid and that the culture was grown in a 1-liter flask rather than an 8-liter carboy. The recombinant cells (1.5 grams wet weight) were harvested by centrifugation and were lysed by resuspending them in 3 mls (per gram wet weight of cells) of anaerobic 50 mM Tris, pH 8.0, containing 0.5 mg/mL lysozyme, 50 ug/mL DNase, 1 mM phenylmethylsulfonyl fluoride, and 2 mM sodium dithionite. Samples were lysed by incubation at room temperature in an anaerobic chamber under an atmosphere of 5% $H_2$/95% Ar for 4 hours. The protein content of the cell-free extract was 8.9 mg/mL as determined by the standard protein assay and 5.2 units of hydrogenase activity measured using MV as the electron donor at 80° C. The specific activity was 0.078 U/mg, which is comparable to that obtained with the tetrameric ($\alpha\beta\gamma\delta$) recombinant enzyme (Table 6). However, as indicated in Table 7, the dimeric ($\alpha\delta$) recombinant form had no detectable hydrogen production activity using NADPH (1 mM) as the electron donor, as was predicted (FIG. 19). Also, the structural as well as the catalytic integrity of the recombinant dimeric hydrogenase differed from that of both the recombinant and native forms of tetrameric holoenzyme. As shown in Table 7, the dimeric form was much more sensitive to oxygen and was much less stable at 90° C. However, the fact that this mutated form of the enzyme containing only two subunits still had an approximate half-life at 90° C. of 1 hour shows the great advantage of using a hyperthermophilic enzyme as the starting material for any manipulation of enzyme structure. The resulting protein was expected to be considerably less stable than its native counterpart, but the extreme stability of the native means that an 'unstable' form can still retain remarkably stability and activity, relative to conventional enzymes found in organisms growing at conventional temperatures. Moreover, with the demonstration here of an extremely stable dimeric mutant form with catalytic properties, the means to generate a wide variety of mutant forms, for example, with various tags for purification and immobilization, is now possible.

In summary, a series of four compatible vectors have been constructed that will express a functional hydrogenase in *E. coli*. It was shown that recombinant hydrogenase was produced when cells were switched to anaerobic growth and that the amount of the enzyme produced increased with cell growth until late stationary phase. Recombinant hydrogenase was also produced in recombinant *E. coli* cells grown to exceedingly high densities (OD ~40). A method for purifying the recombinant hydrogenase to a high level of purity is described, and analysis of the protein components of the recombinant enzyme by a standard mass spectrometry technique established unambiguously that it contained the four hydrogenase subunits encoded by the four cloned genes that were heterologously expressed. It was also demonstrated that the recombinant enzyme has approximately the same molecular weight (~150 kDa) and metal content (20 Fe: 1 Ni) as the native enzyme purified from *P. furiosus* biomass, it is similarly stable to high temperature (half life at 90° C. of ~12 hr) and sensitive to inactivation by oxygen (half life of ~6 hr in air) and, like the native enzyme, uses NADPH as an electron donor for hydrogen production at 80° C. The ability to generate mutant or modified forms of the hydrogenase was demonstrated by the production of a heterodimer form containing two subunits rather than the four subunits of the heterotetrameric enzyme. The dimeric form was still catalytically active at 80° C. with the artificial electron donor MV, but it did not use NADPH as an electron donor. The dimeric form was still very thermostable (half-life at 90° C. of ~1 hr). This demonstrates the great advantage of using a hyperthermophilic enzyme as the starting material for any manipulation of enzyme structure.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A genetically modified microbe comprising four exogenous polynucleotides, wherein the exogenous polynucleotides each encode a subunit, wherein a first subunit comprises an amino acid sequence, and the amino acid sequence of the first subunit and the amino acid sequence of SEQ ID NO:6 have at least 80% identity, wherein a second subunit comprises an amino acid sequence, and the amino acid sequence of the second subunit and the amino acid sequence of SEQ ID NO:8 have at least 80% identity, wherein a third subunit comprises an amino acid sequence, and the amino acid sequence of the third subunit and the amino acid sequence of SEQ ID NO:2 have at least 80% identity, wherein a fourth subunit comprises an amino acid sequence, and the amino acid sequence of the fourth subunit and the amino acid sequence of SEQ ID NO:4 have at least 80% identity, and wherein the four subunits form a tetrameric polypeptide having hydrogenase activity, wherein the four subunits are expressed during growth in anaerobic conditions.

2. The genetically modified microbe of claim 1 wherein at least one subunit is a fusion comprising a heterologous amino acid sequence.

3. The genetically modified microbe of claim 1 wherein the microbe is *E. coli*.

4. The genetically modified microbe of claim 1 wherein the microbe is *P. furiosus*.

5. The genetically modified microbe of claim 1 wherein at least one exogenous polynucleotide is integrated into a chromosome of the microbe.

6. The genetically modified microbe of claim 1 wherein an exogenous polynucleotide comprises a heterologous promoter operably linked to the coding region encoding a subunit.

7. The genetically modified microbe of claim 2 wherein the heterologous amino acid sequence is present at the amino terminal end of a subunit.

8. The genetically modified microbe of claim 2 wherein the heterologous amino acid sequence is present at the carboxy terminal end of a subunit.

9. The genetically modified microbe of claim 2 wherein the heterologous amino acid sequence is a histidine-tag.

10. A method for using a genetically modified microbe comprising:

providing the genetically modified microbe of claim 1; and incubating the genetically modified microbe under conditions suitable for expression of the exogenous polypeptides.

11. The method of claim 10 wherein the genetically modified microbe produces $H_2$, the method further comprising collecting the produced $H_2$.

12. The method of claim 10 wherein the genetically modified microbe produces NADPH, the method further comprising collecting the produced NADPH.

13. The method of claim 10 wherein the incubating comprises conditions that comprise a polysaccharide.

14. The method of claim 13 wherein the polysaccharide comprises starch.

15. The method of claim 10 wherein the conditions comprise a temperature of at least 70° C.

16. The method of claim 10 wherein the conditions comprise a temperature of at least 37° C.

* * * * *

```
                              SEQUENCE LISTING

<160> NUMBER OF SEQ ID NOS: 59

<210> SEQ ID NO 1
<211> LENGTH: 1104
<212> TYPE: DNA
<213> ORGANISM: Pyrococcus furiosus

<400> SEQUENCE: 1
gtgaggtatg ttaagttacc caaggaaaac acttacgagt ttttggaaag acttaaagac      60
tgggggaagc tttacgctcc agtaaaaatt tcggacaagt tctatgactt cagggagatt     120
gatgatgtta gaaagataga attccactac aacaggacaa taatgccacc taagaagttc     180
ttcttcaagc cgagggaaaa gctctttgag ttcgacattt caaaaccaga atacagggag     240
gtaatagagg aagttgaacc atttattata tttggagtcc acgcgtgtga catatatggc     300
ctaaagatcc tagacacggt ataccttgat gagttccccg acaagtacta caaggtgagg     360
agagagaagg ggataatcat tggaataagc tgtatgccag atgaatattg cttctgtaac     420
ttaagagaaa cagacttcgc tgatgatggt tttgacttgt tcttccatga actgcccgat     480
ggatggttga taagggttgg cactccaact gggcacaggc ttgttgacaa gaacataaag     540
ctctttgaag aggtaacgga caaggatatc tgtgcattta gagattttga aaagaggaga     600
cagcaagcat tcaaatacca cgaagactgg ggcaacttga ggtatcttct cgagttggaa     660
atggaacatc caatgtggga tgaggaggca gataagtgct tggcttgtgg aatatgtaac     720
accacatgcc aacgtgtag atgctatgaa gttcaggata ttgtaaacct agatggagtt     780
actggataca gggaaagaag atgggattct tgtcagttca gaagtcatgg cttagttgct     840 ggggggccaca acttcaggcc cacaaagaag gatcgcttta ggaacagata cctctgtaag     900
aacgcatata acgaaaagct tggattaagc tactgtgtcg gttgtggaag gtgtactgca     960
ttctgtccag ccaatataag ttttgtaggc aatcttagaa ggattttagg acttgaggag    1020
aacaaatgtc ccccaacggt tagtgaggag attccaaaga gaggatttgc atattcctct    1080
aacattagag gtgatggagt atga                                           1104

<210> SEQ ID NO 2
<211> LENGTH: 367
<212> TYPE: PRT
<213> ORGANISM: Pyrococcus furiosus

<400> SEQUENCE: 2

Met Arg Tyr Val Lys Leu Pro Lys Glu Asn Thr Tyr Glu Phe Leu Glu
1               5                   10                  15

Arg Leu Lys Asp Trp Gly Lys Leu Tyr Ala Pro Val Lys Ile Ser Asp
            20                  25                  30

Lys Phe Tyr Asp Phe Arg Glu Ile Asp Asp Val Arg Lys Ile Glu Phe
        35                  40                  45

His Tyr Asn Arg Thr Ile Met Pro Pro Lys Lys Phe Phe Lys Pro
    50                  55                  60

Arg Glu Lys Leu Phe Glu Phe Asp Ile Ser Lys Pro Glu Tyr Arg Glu
65                  70                  75                  80

Val Ile Glu Glu Val Glu Pro Phe Ile Ile Phe Gly Val His Ala Cys
                85                  90                  95
```

```
Asp Ile Tyr Gly Leu Lys Ile Leu Asp Thr Val Tyr Leu Asp Glu Phe
            100                 105                 110

Pro Asp Lys Tyr Tyr Lys Val Arg Arg Glu Lys Gly Ile Ile Ile Gly
        115                 120                 125

Ile Ser Cys Met Pro Asp Glu Tyr Cys Phe Cys Asn Leu Arg Glu Thr
    130                 135                 140

Asp Phe Ala Asp Asp Gly Phe Asp Leu Phe His Glu Leu Pro Asp
145                 150                 155                 160

Gly Trp Leu Val Arg Val Gly Thr Pro Thr Gly His Arg Leu Val Asp
                165                 170                 175

Lys Asn Ile Lys Leu Phe Glu Glu Val Thr Asp Lys Asp Ile Cys Ala
            180                 185                 190

Phe Arg Asp Phe Glu Lys Arg Arg Gln Gln Ala Phe Lys Tyr His Glu
        195                 200                 205

Asp Trp Gly Asn Leu Arg Tyr Leu Leu Glu Leu Glu Met Glu His Pro
    210                 215                 220

Met Trp Asp Glu Glu Ala Asp Lys Cys Leu Ala Cys Gly Ile Cys Asn
225                 230                 235                 240

Thr Thr Cys Pro Thr Cys Arg Cys Tyr Glu Val Gln Asp Ile Val Asn
                245                 250                 255

Leu Asp Gly Val Thr Gly Tyr Arg Glu Arg Arg Trp Asp Ser Cys Gln
            260                 265                 270

Phe Arg Ser His Gly Leu Val Ala Gly Gly His Asn Phe Arg Pro Thr
        275                 280                 285

Lys Lys Asp Arg Phe Arg Asn Arg Tyr Leu Cys Lys Asn Ala Tyr Asn
    290                 295                 300

Glu Lys Leu Gly Leu Ser Tyr Cys Val Gly Cys Gly Arg Cys Thr Ala
305                 310                 315                 320

Phe Cys Pro Ala Asn Ile Ser Phe Val Gly Asn Leu Arg Arg Ile Leu
                325                 330                 335

Gly Leu Glu Glu Asn Lys Cys Pro Pro Thr Val Ser Glu Glu Ile Pro
            340                 345                 350

Lys Arg Gly Phe Ala Tyr Ser Ser Asn Ile Arg Gly Asp Gly Val
        355                 360                 365

<210> SEQ ID NO 3
<211> LENGTH: 879
<212> TYPE: DNA
<213> ORGANISM: Pyrococcus furiosus

<400> SEQUENCE: 3
atgatgttgc aaaagagat tatgatgcca atgataatc cgtatgccct tcatagagtc      60
aaagttctaa aggtttactc cttgacggaa acggaaaagc ttttcctctt tagatttgag     120
gatcccgagt tggcagagaa gtggacgttc aaacctggac agtttgtcca gctgacgata     180
cctggagttg gagaggttcc cataagtata tgctcttctc caatgaggaa aggattcttt     240
gagctctgta taagaaaggc aggaagggtc acaactgttg tccatagact aaagcctggc     300
gatactgttc ttgtgagagg gccttacggt aatggattcc cagtggatga gtgggaagga     360
atggatctac tattaatagc tgctggcctt ggaactgcac ctcttaggag cgtctttctc     420
tatgcaatgg acaacaggtg gaagtatgga acattacct tcataaacac cgcacgttat     480
gggaaggatc cctcttcta caaggagctg gaggcaatga agacctagc tgaggctgaa     540 aacgtgaaaa tcatccagag cgtcactagg gatccaaact ggccgggcct aaagggtagg     600
```

-continued

```
ccacagcagt tcatcgttga ggccaacaca atccaaaga acactgcagt tgcaatctgt    660
gggcctccta gaatgtataa gtcagtgttt gaggccctca tcaactacgg ttatcgccca    720
gagaacatct tcgtgacatt ggagagaaga atgaaatgtg gaatcgggaa gtgcggccac    780
tgcaacgtcg aacgagcac gagctggaag tacatctgta aagatggacc agtcttcacg    840
tacttcgaca tagtttcaac cccaggactg ctggactga                          879
```

<210> SEQ ID NO 4
<211> LENGTH: 292
<212> TYPE: PRT
<213> ORGANISM: Pyrococcus furiosus

<400> SEQUENCE: 4

```
Met Met Leu Pro Lys Glu Ile Met Met Pro Asn Asp Asn Pro Tyr Ala
1               5                   10                  15

Leu His Arg Val Lys Val Leu Lys Val Tyr Ser Leu Thr Glu Thr Glu
            20                  25                  30

Lys Leu Phe Leu Phe Arg Phe Glu Asp Pro Glu Leu Ala Glu Lys Trp
        35                  40                  45

Thr Phe Lys Pro Gly Gln Phe Val Gln Leu Thr Ile Pro Gly Val Gly
    50                  55                  60

Glu Val Pro Ile Ser Ile Cys Ser Ser Pro Met Arg Lys Gly Phe Phe
65                  70                  75                  80

Glu Leu Cys Ile Arg Lys Ala Gly Arg Val Thr Val Val His Arg
                85                  90                  95

Leu Lys Pro Gly Asp Thr Val Leu Val Arg Gly Pro Tyr Gly Asn Gly
            100                 105                 110

Phe Pro Val Asp Glu Trp Glu Gly Met Asp Leu Leu Leu Ile Ala Ala
        115                 120                 125

Gly Leu Gly Thr Ala Pro Leu Arg Ser Val Phe Leu Tyr Ala Met Asp
    130                 135                 140

Asn Arg Trp Lys Tyr Gly Asn Ile Thr Phe Ile Asn Thr Ala Arg Tyr
145                 150                 155                 160

Gly Lys Asp Leu Leu Phe Tyr Lys Glu Leu Glu Ala Met Lys Asp Leu
                165                 170                 175

Ala Glu Ala Glu Asn Val Lys Ile Ile Gln Ser Val Thr Arg Asp Pro
            180                 185                 190

Asn Trp Pro Gly Leu Lys Gly Arg Pro Gln Gln Phe Ile Val Glu Ala
        195                 200                 205

Asn Thr Asn Pro Lys Asn Thr Ala Val Ala Ile Cys Gly Pro Pro Arg
    210                 215                 220

Met Tyr Lys Ser Val Phe Glu Ala Leu Ile Asn Tyr Gly Tyr Arg Pro
225                 230                 235                 240

Glu Asn Ile Phe Val Thr Leu Glu Arg Arg Met Lys Cys Gly Ile Gly
                245                 250                 255

Lys Cys Gly His Cys Asn Val Gly Thr Ser Thr Ser Trp Lys Tyr Ile
            260                 265                 270

Cys Lys Asp Gly Pro Val Phe Thr Tyr Phe Asp Ile Val Ser Thr Pro
        275                 280                 285

Gly Leu Leu Asp
    290
```

<210> SEQ ID NO 5
<211> LENGTH: 786
<212> TYPE: DNA

<213> ORGANISM: Pyrococcus furiosus

<400> SEQUENCE: 5

| | |
|---|---:|
| atgggaaaag ttaggattgg attttacgca ttaacctcgt gctacggctg tcaattgcag | 60 |
| ctagctatga tggacgagtt attacaactt atcccaaatg ctgaaatagt ttgctggttc | 120 |
| atgattgata gagatagcat tgaggatgaa aaggtcgaca tagctttat agaaggaagc | 180 |
| gtttcaactg aggaagaagt tgaactcgtg aaaaaaatta gggagaatgc aaagatcgtc | 240 |
| gttgcggttg gagcttgtgc tgttcaagga ggagttcaga gctggagtga aaagccatta | 300 |
| gaagagctct ggaagaaggt ttatggagac gcaaaagtca agttccaacc gaagaaggct | 360 |
| gaaccagttt caaaatacat aaaagttgac tacaacatct acggttgccc accagagaag | 420 |
| aaggacttcc tctacgccct gggaacattc ttgattggtt catggccaga ggatatagat | 480 |
| tatccagttt gtctagaatg taggctcaat ggacatccat gtatccttct tgagaaagga | 540 |
| gaaccctgtc taggtccagt aacaagggca ggatgtaacg cgagatgtcc aggatttgga | 600 |
| gttgcgtgta taggatgcag aggggcaata gggtacgatg tagcttggtt cgactctcta | 660 |
| gctaaggtgt tcaaggagaa ggggatgaca aagaggaga taattgagag aatgaaaatg | 720 |
| ttcaatggac atgatgagag ggttgagaaa atggttgaaa aatattctc aggtggtgaa | 780 |
| caatga | 786 |

<210> SEQ ID NO 6
<211> LENGTH: 261
<212> TYPE: PRT
<213> ORGANISM: Pyrococcus furiosus

<400> SEQUENCE: 6

```
Met Gly Lys Val Arg Ile Gly Phe Tyr Ala Leu Thr Ser Cys Tyr Gly
1               5                   10                  15

Cys Gln Leu Gln Leu Ala Met Met Asp Glu Leu Leu Gln Leu Ile Pro
            20                  25                  30

Asn Ala Glu Ile Val Cys Trp Phe Met Ile Asp Arg Asp Ser Ile Glu
        35                  40                  45

Asp Glu Lys Val Asp Ile Ala Phe Ile Glu Gly Ser Val Ser Thr Glu
    50                  55                  60

Glu Glu Val Glu Leu Val Lys Lys Ile Arg Glu Asn Ala Lys Ile Val
65                  70                  75                  80

Val Ala Val Gly Ala Cys Ala Val Gln Gly Gly Val Gln Ser Trp Ser
                85                  90                  95

Glu Lys Pro Leu Glu Glu Leu Trp Lys Lys Val Tyr Gly Asp Ala Lys
            100                 105                 110

Val Lys Phe Gln Pro Lys Lys Ala Glu Pro Val Ser Lys Tyr Ile Lys
        115                 120                 125

Val Asp Tyr Asn Ile Tyr Gly Cys Pro Pro Glu Lys Lys Asp Phe Leu
    130                 135                 140

Tyr Ala Leu Gly Thr Phe Leu Ile Gly Ser Trp Pro Glu Asp Ile Asp
145                 150                 155                 160

Tyr Pro Val Cys Leu Glu Cys Arg Leu Asn Gly His Pro Cys Ile Leu
                165                 170                 175

Leu Glu Lys Gly Glu Pro Cys Leu Gly Pro Val Thr Arg Ala Gly Cys
            180                 185                 190

Asn Ala Arg Cys Pro Gly Phe Gly Val Ala Cys Ile Gly Cys Arg Gly
        195                 200                 205
```

Ala Ile Gly Tyr Asp Val Ala Trp Phe Asp Ser Leu Ala Lys Val Phe
    210                 215                 220

Lys Glu Lys Gly Met Thr Lys Glu Glu Ile Ile Glu Arg Met Lys Met
225                 230                 235                 240

Phe Asn Gly His Asp Glu Arg Val Glu Lys Met Val Glu Lys Ile Phe
                245                 250                 255

Ser Gly Gly Glu Gln
            260

<210> SEQ ID NO 7
<211> LENGTH: 1287
<212> TYPE: DNA
<213> ORGANISM: Pyrococcus furiosus

<400> SEQUENCE: 7

```
atgaagaacc tctatcttcc aatcaccatt gatcatatag caagagttga ggggaagggt      60
ggtgtggaga taataattgg ggatgatgga gtcaaggagg tcaagctaaa cataattgaa     120
gggcccagat tctttgaggc cataactatt ggaagaagc ttgaggaagc tctggccatt     180
tacccgagaa tatgctcatt ctgttcagcc gcccacaagt taaccgcatt agaggctgca     240
gaaaaggccg tcggttttgt cccaagggaa gagatacagg cccttagaga agtactatac     300
atcggagaca tgatagagag tcatgccctt cacctatatc ttctagttct tcccgactac     360
aggggctact cgagcccact aagatggtg aatgaataca agaggagat agagatagcc      420
cttaagctga gaaccttgg cacctggatg atggacattc tagggtcaag agccatacac     480
caagaaaatg cggttttggg cggattcgga agctccctg agaagagtgt ccttgagaaa     540
atgaaagccg agcttaggga agccctacca cttgccgagt atactttga gttatttgca     600
aagcttgagc agtacagcga agttgaaggg ccaataacac acttggccgt gaagccgagg     660
ggagatgctt atggaattta tggagattac ataaaggcaa gtgatgggga ggagttccca     720
agtgaaaagt acagagatta tataaaggag ttcgtcgttg aacacagttt tgcaaagcac     780
agtcactaca agggcagacc cttcatggtt ggggctatat ctagagttat taacaatgct     840
gacctcctat acggcaaggc caaggagctg tatgaggcaa acaaagacct attaaaggga     900
acaaatccgt ttgcaaataa cttagcccag gccctcgaaa tagtttactt tatagagagg     960
gcaatagatc tgctcgacga ggctctcgcc aagtggccaa ttaagcccag ggatgaagtt    1020
gagataaagg acggctttgg tgtctcaacg actgaggctc aaggggaat cttagtctat    1080
gccctcaaag ttgagaatgg aagggttttct tatgccgaca taataccac tacagcattc    1140
aacttggcaa tgatggaaga acatgtaaga atgatggcag aaaagcacta caatgacgat    1200
ccagaaaggt taaagatact ggctgagatg gttgttaggg cttatgatcc atgcatatct    1260
tgctcagtcc acgtggttag actttaa                                         1287
```

<210> SEQ ID NO 8
<211> LENGTH: 428
<212> TYPE: PRT
<213> ORGANISM: Pyrococcus furiosus

<400> SEQUENCE: 8

Met Lys Asn Leu Tyr Leu Pro Ile Thr Ile Asp His Ile Ala Arg Val
1               5                   10                  15

Glu Gly Lys Gly Gly Val Glu Ile Ile Ile Gly Asp Asp Gly Val Lys
                20                  25                  30

Glu Val Lys Leu Asn Ile Ile Glu Gly Pro Arg Phe Phe Glu Ala Ile

```
                35                  40                  45
Thr Ile Gly Lys Lys Leu Glu Glu Ala Leu Ala Ile Tyr Pro Arg Ile
 50                  55                  60
Cys Ser Phe Cys Ser Ala Ala His Lys Leu Thr Ala Leu Glu Ala Ala
 65                  70                  75                  80
Glu Lys Ala Val Gly Phe Val Pro Arg Glu Ile Gln Ala Leu Arg
                 85                  90                  95
Glu Val Leu Tyr Ile Gly Asp Met Ile Glu Ser His Ala Leu His Leu
                100                 105                 110
Tyr Leu Val Leu Pro Asp Tyr Arg Gly Tyr Ser Ser Pro Leu Lys
            115                 120                 125
Met Val Asn Glu Tyr Lys Arg Glu Ile Glu Ile Ala Leu Lys Leu Lys
            130                 135                 140
Asn Leu Gly Thr Trp Met Met Asp Ile Leu Gly Ser Arg Ala Ile His
145                 150                 155                 160
Gln Glu Asn Ala Val Leu Gly Gly Phe Gly Lys Leu Pro Glu Lys Ser
                165                 170                 175
Val Leu Glu Lys Met Lys Ala Glu Leu Arg Glu Ala Leu Pro Leu Ala
            180                 185                 190
Glu Tyr Thr Phe Glu Leu Phe Ala Lys Leu Glu Gln Tyr Ser Glu Val
            195                 200                 205
Glu Gly Pro Ile Thr His Leu Ala Val Lys Pro Arg Gly Asp Ala Tyr
210                 215                 220
Gly Ile Tyr Gly Asp Tyr Ile Lys Ala Ser Asp Gly Glu Glu Phe Pro
225                 230                 235                 240
Ser Glu Lys Tyr Arg Asp Tyr Ile Lys Glu Phe Val Glu His Ser
                245                 250                 255
Phe Ala Lys His Ser His Tyr Lys Gly Arg Pro Phe Met Val Gly Ala
            260                 265                 270
Ile Ser Arg Val Ile Asn Asn Ala Asp Leu Leu Tyr Gly Lys Ala Lys
            275                 280                 285
Glu Leu Tyr Glu Ala Asn Lys Asp Leu Leu Lys Gly Thr Asn Pro Phe
290                 295                 300
Ala Asn Asn Leu Ala Gln Ala Leu Glu Ile Val Tyr Phe Ile Glu Arg
305                 310                 315                 320
Ala Ile Asp Leu Leu Asp Glu Ala Leu Ala Lys Trp Pro Ile Lys Pro
                325                 330                 335
Arg Asp Glu Val Glu Ile Lys Asp Gly Phe Gly Val Ser Thr Thr Glu
            340                 345                 350
Ala Pro Arg Gly Ile Leu Val Tyr Ala Leu Lys Val Glu Asn Gly Arg
            355                 360                 365
Val Ser Tyr Ala Asp Ile Ile Thr Pro Thr Ala Phe Asn Leu Ala Met
            370                 375                 380
Met Glu Glu His Val Arg Met Met Ala Glu Lys His Tyr Asn Asp Asp
385                 390                 395                 400
Pro Glu Arg Leu Lys Ile Leu Ala Glu Met Val Val Arg Ala Tyr Asp
                405                 410                 415
Pro Cys Ile Ser Cys Ser Val His Val Val Arg Leu
            420                 425

<210> SEQ ID NO 9
<211> LENGTH: 228
<212> TYPE: DNA
<213> ORGANISM: Pyrococcus furiosus
```

<400> SEQUENCE: 9

```
atgtgccttg caatcccagg gaaagtggtg gagattaaag gtaacgttgg aatagtggat    60
tttggaggaa tacggagaga ggtaaggtta gatcttttga gtgatgttaa agttggcgat   120
tacgttatag ttcacactgg ctttgctata gaaaagttag atgagaggag agctagagaa   180
attcttgaag cctgggaaga agtttttctca gtaattgggg gtgagtaa              228
```

<210> SEQ ID NO 10
<211> LENGTH: 75
<212> TYPE: PRT
<213> ORGANISM: Pyrococcus furiosus

<400> SEQUENCE: 10

```
Met Cys Leu Ala Ile Pro Gly Lys Val Val Glu Ile Lys Gly Asn Val
1               5                   10                  15

Gly Ile Val Asp Phe Gly Gly Ile Arg Arg Glu Val Arg Leu Asp Leu
            20                  25                  30

Leu Ser Asp Val Lys Val Gly Asp Tyr Val Ile Val His Thr Gly Phe
        35                  40                  45

Ala Ile Glu Lys Leu Asp Glu Arg Arg Ala Arg Glu Ile Leu Glu Ala
    50                  55                  60

Trp Glu Glu Val Phe Ser Val Ile Gly Gly Glu
65                  70                  75
```

<210> SEQ ID NO 11
<211> LENGTH: 1104
<212> TYPE: DNA
<213> ORGANISM: Pyrococcus furiosus

<400> SEQUENCE: 11

```
atgcttgaaa aatttggaga caaagctgta gctcaaaaga ttttagaaaa aattaaagag    60
gaagctaaag ggatagaaga gctacgattt atgcacgttt gtgggactca tgaggacaca   120
gtaactagga gtggaatcag atcacttctt ccagaaaatg taaaaatcat gagtggccca   180
ggatgtcccg tctgtataac ccccgttgag gacatagtga agatgatgga aattatgaaa   240
gttgcgagag aggagaggga gaaattatt ctcactactt ttggtgacat gtatagaatt   300
ccaactccaa taggaagctt tgcagactta aagagtcagg gttacgatgt gaggatagtt   360
tactctatat acgactccta aaaatagcc aaggaaaatc cagataagct tgtagtgcac   420
ttttctcctg ggttttgagac taccgccgct ccaacagctg gaatgcttga gagcattgtg   480
gaagaggggc tagagaactt taagatttat tccgttcata ggttaacccc tcctgcagtt   540
gaagctctcc taaatgcggg gactgttttt cacggtttaa tagatcctgg tcatgtctct   600
acaataattg gggtgaaagg atgggcgtat ctcacagaaa agtttggaat tcctcaagtt   660
gtggctggct ttgagccagt tgatgtttta ctcggaatac ttattctcat taggcttgtg   720
aagaggggcg aagcgaaaat aatcaacgag tataatagag ttgtaaagtg ggaaggaaat   780
gtcaaggccc aagaactgat ttggaagtac tttgaagtta agatgcaaa gtggagggcc   840
ctaggagtaa ttccaaggag cggattggaa cttaagaaag agtggaagga gctagaaatt   900
agaacttatt acaatcccga ggttccaaag ctcccagatc ttgaaaaagg atgtctctgt   960
ggggcagtcc ttagaggatt agccttaccg acccagtgcc aacactttgg aaagacatgt  1020
acaccaagac atccggtagg tccttgtatg gtttcgtacg aaggaacttg tcacatattt  1080
tacaaatatg gcgccctgat gtag                                         1104
```

<210> SEQ ID NO 12
<211> LENGTH: 367
<212> TYPE: PRT
<213> ORGANISM: Pyrococcus furiosus

<400> SEQUENCE: 12

```
Met Leu Glu Lys Phe Gly Asp Lys Ala Val Ala Gln Lys Ile Leu Glu
1               5                   10                  15

Lys Ile Lys Glu Glu Ala Lys Gly Ile Glu Leu Arg Phe Met His
            20                  25                  30

Val Cys Gly Thr His Glu Asp Thr Val Thr Arg Ser Gly Ile Arg Ser
            35                  40                  45

Leu Leu Pro Glu Asn Val Lys Ile Met Ser Gly Pro Gly Cys Pro Val
        50                  55                  60

Cys Ile Thr Pro Val Glu Asp Ile Val Lys Met Met Glu Ile Met Lys
65                  70                  75                  80

Val Ala Arg Glu Glu Arg Glu Glu Ile Ile Leu Thr Thr Phe Gly Asp
                85                  90                  95

Met Tyr Arg Ile Pro Thr Pro Ile Gly Ser Phe Ala Asp Leu Lys Ser
            100                 105                 110

Gln Gly Tyr Asp Val Arg Ile Val Tyr Ser Ile Tyr Asp Ser Tyr Lys
        115                 120                 125

Ile Ala Lys Glu Asn Pro Asp Lys Leu Val Val His Phe Ser Pro Gly
130                 135                 140

Phe Glu Thr Thr Ala Ala Pro Thr Ala Gly Met Leu Glu Ser Ile Val
145                 150                 155                 160

Glu Glu Gly Leu Glu Asn Phe Lys Ile Tyr Ser Val His Arg Leu Thr
                165                 170                 175

Pro Pro Ala Val Glu Ala Leu Leu Asn Ala Gly Thr Val Phe His Gly
            180                 185                 190

Leu Ile Asp Pro Gly His Val Ser Thr Ile Ile Gly Val Lys Gly Trp
        195                 200                 205

Ala Tyr Leu Thr Glu Lys Phe Gly Ile Pro Gln Val Val Ala Gly Phe
210                 215                 220

Glu Pro Val Asp Val Leu Leu Gly Ile Leu Ile Leu Ile Arg Leu Val
225                 230                 235                 240

Lys Arg Gly Glu Ala Lys Ile Ile Asn Glu Tyr Asn Arg Val Val Lys
                245                 250                 255

Trp Glu Gly Asn Val Lys Ala Gln Glu Leu Ile Trp Lys Tyr Phe Glu
            260                 265                 270

Val Lys Asp Ala Lys Trp Arg Ala Leu Gly Val Ile Pro Arg Ser Gly
        275                 280                 285

Leu Glu Leu Lys Lys Glu Trp Lys Glu Leu Glu Ile Arg Thr Tyr Tyr
290                 295                 300

Asn Pro Glu Val Pro Lys Leu Pro Asp Leu Glu Lys Gly Cys Leu Cys
305                 310                 315                 320

Gly Ala Val Leu Arg Gly Leu Ala Leu Pro Thr Gln Cys Gln His Phe
                325                 330                 335

Gly Lys Thr Cys Thr Pro Arg His Pro Val Gly Pro Cys Met Val Ser
            340                 345                 350

Tyr Glu Gly Thr Cys His Ile Phe Tyr Lys Tyr Gly Ala Leu Met
        355                 360                 365
```

<210> SEQ ID NO 13
<211> LENGTH: 2340
<212> TYPE: DNA
<213> ORGANISM: Pyrococcus furiosus

<400> SEQUENCE: 13

```
atgtatctgg gggagagaat gaaagcttat agaattcacg ttcagggaat agttcaggcc    60
gtgggattta ggcccttcgt ttatagaata gctcatgctc acaacttgag gggatacgtt   120
aggaacttag gcgatgctgg agttgaaatt gttgtcgagg gaagggagga agacatagag   180
gcattcatca aggatttata caagaagaaa cccccacttg caaggattga taaggttgag   240
agggaggaaa ttcctcttca gggctttgac agatttttaca tagagaaaag ctcgacggaa   300
aagaaggggg agggagattc aataatccct ccggacatag ctatttgtga ggactgtctt   360
agggagttat ttaatccaac tgacaagcgc tacatgtatc ctttcatagt atgtacaaac   420
tgtgggccga ggttcacgat aattgaagat cttccctacg atagggagaa cacagcgatg   480
agagaattcc cgatgtgcga gttctgtagg agtgaatacg aggatcccct gaataggagg   540
tatcatgcag agccggttgc atgtccaact tgtgggccga gctataggct ttacacgagc   600
gatgaaaatg agataattgg agaccccctg agaaaggcgg caaaactaat cgataaggga   660
tacatagttg cgataaaggg tataggtgga attcatttgg cctgcgatgc tacaagagag   720
gatgtggtgg ccgagcttag gaagaggatt tttaggcctc agaagccttt cgccattatg   780
gccaaagatt tagaaactgt aaggactttt gcctatattt ctcccgaaga ggaggaagaa   840
ttaacaagct atagaaggcc aatagtggct tgaagaagaa aggagccctt cccacttccc   900
gaaaacctcg ctcctgggct tcacacaatt ggggtaatgc ttcctatgc tggaacccac   960
tacatattat ccactggag caagactcca gtttacgtta tgacttccgc aaacttccca  1020
gggatgccga tgataaagga caatgaagag gcatttgaaa agcttaggga cgttgctgac  1080
tacctcttgc tccacaatag gagaattcca aatagagctg acgatagcgt tgttcgcttt  1140
gtagatggta aagagctgt tattaggagg agcagaggat ttgttccact tggaatagag  1200
attccatttg agtacaaagg attggcagtt ggtgctgagt taatgaatgc tttcggagtt  1260
gttaagaatg aaaagtttta tccaagtcag tacataggg atacatcaaa gattgaagtt  1320
ttagagttta tgagggaagc cgtgaggcac ttcttcaaga tattgagagt tgataactta  1380
gatctagttg ttgcagattt gcatccaagc tacaacacaa ctaagctggg aatggagatc  1440
gctgaggaat tggggcaga attccttcaa gttcaacatc actacgctca cgtggcctct  1500
gtaatggctg agcacaactt ggaggaagtt gttggaattg ctctagatgg tgttgggtat  1560
ggaaccgacg gaaaaacttg gggtgggaa gtaatatatc taagctatga agatgtggag  1620
aggttggccc acatagagta ttatccactc ccaggagggg atttggccag ctactatccc  1680
ttgagggcct taattggaat actcagctta aaccacgact tagaggaagt tgagaaaatc  1740
ataagggagt tctgtccaaa tgcaataaag agcttaaagt atggggaaac agagtttagg  1800
gtaattatga ggcaactcag cagcgggata aacgttgcct atgcctcttc aacgggaagg  1860
gtgcttgatg ccttctcggt acttttgaac gtttcctaca ggaggcacta tgagggagag  1920
cctgcgatga agctggagag ctttgcatac caaggaaaga acgatctaaa gctcacggct  1980
ccaattgaag gtgaggaaat aaaggtttca gagttgtttg aggaagttct tgagctgatg  2040
ggcaaggcca atcctaaaga catagcttac tccgttcact tagccttagc tagggcatttt  2100
gctgaagtta gcgtggagaa agctaaggag tttggagcta aaactgtcgt tttgggtggg  2160
```

```
ggagtagggt acaatgagct aatagttaag acgataagaa agatagtaga ggggagaggg    2220
ctaaggttct taacaactta cgaagttccc aggggagata atggaattaa tgtaggccag    2280
gccttcctgg gaggattgta cttggaagga tacttaaata gggaagattt gagcatttag    2340
```

<210> SEQ ID NO 14
<211> LENGTH: 779
<212> TYPE: PRT
<213> ORGANISM: Pyrococcus furiosus

<400> SEQUENCE: 14

```
Met Tyr Leu Gly Glu Arg Met Lys Ala Tyr Arg Ile His Val Gln Gly
  1               5                  10                  15

Ile Val Gln Ala Val Gly Phe Arg Pro Phe Val Tyr Arg Ile Ala His
                 20                  25                  30

Ala His Asn Leu Arg Gly Tyr Val Arg Asn Leu Gly Asp Ala Gly Val
             35                  40                  45

Glu Ile Val Val Glu Gly Arg Glu Asp Ile Glu Ala Phe Ile Lys
         50                  55                  60

Asp Leu Tyr Lys Lys Lys Pro Pro Leu Ala Arg Ile Asp Lys Val Glu
 65                  70                  75                  80

Arg Glu Glu Ile Pro Leu Gln Gly Phe Asp Arg Phe Tyr Ile Glu Lys
                 85                  90                  95

Ser Ser Thr Glu Lys Lys Gly Gly Asp Ser Ile Ile Pro Pro Asp
            100                 105                 110

Ile Ala Ile Cys Glu Asp Cys Leu Arg Glu Leu Phe Asn Pro Thr Asp
            115                 120                 125

Lys Arg Tyr Met Tyr Pro Phe Ile Val Cys Thr Asn Cys Gly Pro Arg
        130                 135                 140

Phe Thr Ile Ile Glu Asp Leu Pro Tyr Asp Arg Glu Asn Thr Ala Met
145                 150                 155                 160

Arg Glu Phe Pro Met Cys Glu Phe Cys Arg Ser Glu Tyr Glu Asp Pro
                165                 170                 175

Leu Asn Arg Arg Tyr His Ala Glu Pro Val Ala Cys Pro Thr Cys Gly
            180                 185                 190

Pro Ser Tyr Arg Leu Tyr Thr Ser Asp Gly Asn Glu Ile Ile Gly Asp
        195                 200                 205

Pro Leu Arg Lys Ala Ala Lys Leu Ile Asp Lys Gly Tyr Ile Val Ala
    210                 215                 220

Ile Lys Gly Ile Gly Gly Ile His Leu Ala Cys Asp Ala Thr Arg Glu
225                 230                 235                 240

Asp Val Val Ala Glu Leu Arg Lys Arg Ile Phe Arg Pro Gln Lys Pro
                245                 250                 255

Phe Ala Ile Met Ala Lys Asp Leu Glu Thr Val Arg Thr Phe Ala Tyr
            260                 265                 270

Ile Ser Pro Glu Glu Glu Glu Leu Thr Ser Tyr Arg Arg Pro Ile
        275                 280                 285

Val Ala Leu Lys Lys Lys Glu Pro Phe Pro Leu Pro Glu Asn Leu Ala
    290                 295                 300

Pro Gly Leu His Thr Ile Gly Val Met Leu Pro Tyr Ala Gly Thr His
305                 310                 315                 320

Tyr Ile Leu Phe His Trp Ser Lys Thr Pro Val Tyr Val Met Thr Ser
                325                 330                 335

Ala Asn Phe Pro Gly Met Pro Met Ile Lys Asp Asn Glu Glu Ala Phe
            340                 345                 350
```

```
Glu Lys Leu Arg Asp Val Ala Asp Tyr Leu Leu His Asn Arg Arg
        355                 360                 365

Ile Pro Asn Arg Ala Asp Asp Ser Val Val Arg Phe Val Asp Gly Arg
    370                 375                 380

Arg Ala Val Ile Arg Arg Ser Arg Gly Phe Val Pro Leu Gly Ile Glu
385                 390                 395                 400

Ile Pro Phe Glu Tyr Lys Gly Leu Ala Val Gly Ala Glu Leu Met Asn
                405                 410                 415

Ala Phe Gly Val Val Lys Asn Gly Lys Val Tyr Pro Ser Gln Tyr Ile
                420                 425                 430

Gly Asp Thr Ser Lys Ile Glu Val Leu Glu Phe Met Arg Glu Ala Val
            435                 440                 445

Arg His Phe Phe Lys Ile Leu Arg Val Asp Asn Leu Asp Leu Val Val
    450                 455                 460

Ala Asp Leu His Pro Ser Tyr Asn Thr Thr Lys Leu Gly Met Glu Ile
465                 470                 475                 480

Ala Glu Glu Phe Gly Ala Glu Phe Leu Gln Val Gln His His Tyr Ala
                485                 490                 495

His Val Ala Ser Val Met Ala Glu His Asn Leu Glu Glu Val Val Gly
            500                 505                 510

Ile Ala Leu Asp Gly Val Gly Tyr Gly Thr Asp Gly Lys Thr Trp Gly
        515                 520                 525

Gly Glu Val Ile Tyr Leu Ser Tyr Glu Asp Val Glu Arg Leu Ala His
    530                 535                 540

Ile Glu Tyr Tyr Pro Leu Pro Gly Gly Asp Leu Ala Ser Tyr Tyr Pro
545                 550                 555                 560

Leu Arg Ala Leu Ile Gly Ile Leu Ser Leu Asn His Asp Leu Glu Glu
                565                 570                 575

Val Glu Lys Ile Ile Arg Glu Phe Cys Pro Asn Ala Ile Lys Ser Leu
                580                 585                 590

Lys Tyr Gly Glu Thr Glu Phe Arg Val Ile Met Arg Gln Leu Ser Ser
            595                 600                 605

Gly Ile Asn Val Ala Tyr Ala Ser Ser Thr Gly Arg Val Leu Asp Ala
        610                 615                 620

Phe Ser Val Leu Leu Asn Val Ser Tyr Arg Arg His Tyr Glu Gly Glu
625                 630                 635                 640

Pro Ala Met Lys Leu Glu Ser Phe Ala Tyr Gln Gly Lys Asn Asp Leu
                645                 650                 655

Lys Leu Thr Ala Pro Ile Glu Gly Glu Ile Lys Val Ser Glu Leu
                660                 665                 670

Phe Glu Glu Val Leu Glu Leu Met Gly Lys Ala Asn Pro Lys Asp Ile
            675                 680                 685

Ala Tyr Ser Val His Leu Ala Leu Ala Arg Ala Phe Ala Glu Val Ser
        690                 695                 700

Val Glu Lys Ala Lys Glu Phe Gly Ala Lys Thr Val Val Leu Gly Gly
705                 710                 715                 720

Gly Val Gly Tyr Asn Glu Leu Ile Val Lys Thr Ile Arg Lys Ile Val
                725                 730                 735

Glu Gly Arg Gly Leu Arg Phe Leu Thr Thr Tyr Glu Val Pro Arg Gly
            740                 745                 750

Asp Asn Gly Ile Asn Val Gly Gln Ala Phe Leu Gly Gly Leu Tyr Leu
        755                 760                 765
```

Glu Gly Tyr Leu Asn Arg Glu Asp Leu Ser Ile
        770                 775

<210> SEQ ID NO 15
<211> LENGTH: 972
<212> TYPE: DNA
<213> ORGANISM: Pyrococcus furiosus

<400> SEQUENCE: 15

| | | |
|---|---|---|
| atggaagaac taattaggga ggtaatcctc aagaatttaa cccttaattc tgctggagga | 60 |
| ataggattag aggagcttga tgacggagct acaatccccc ttggagataa gcatttagtg | 120 |
| tttacaatag atgggcatac agtaaagccg atattcttcc cagggggaga catcggaagg | 180 |
| ttggccgtta gcggaactgt aaacgatttg gctgtcatgg gagctcaacc cttggcaatt | 240 |
| gcaagctcgt tgataatcga ggaagggttt gaagttagtg agctggaaaa gattctgaag | 300 |
| tcgatggacg aaacagctaa agaggttcca gttccaattg ttactggaga cacaaaagtc | 360 |
| gttgaagaca ggataggaat cttcgttata acagctggag tggggtagc tgagaggccg | 420 |
| ataagcgatg ccggcgcaaa agttggggat gtcgttttag tgagtggaac aattggagac | 480 |
| cacggaatag cactaatgag ccatagagag gggatctcct ttgagacaga gcttaagagc | 540 |
| gatgtagctc caatttggga tgtcgtaaag gccgttgcag atgccattgg ttgggagaac | 600 |
| atccacgcaa tgaaagatcc cacaagagga ggattgagca acgcactaaa cgagatggca | 660 |
| agaaaggcaa acgttggaat tttggtaaga gaggaggcaa taccaattag gccagaagta | 720 |
| aaagctgcca gcgaaatgct tggaataagt ccctatgaag ttgcaaacga ggaaaagtt | 780 |
| gtaatgatag tggcgaagga gtatgcggag gaggcacttg aggccatgaa gaagacagaa | 840 |
| aagggtaggg atgccgcaat aataggagaa gttattggtg aatacagagg aaaagttatt | 900 |
| ctggagacgg gaattggtgg aagaagattt ttagagccgc ctctcggtga tcccgttcct | 960 |
| agagtttgtt ag | 972 |

<210> SEQ ID NO 16
<211> LENGTH: 323
<212> TYPE: PRT
<213> ORGANISM: Pyrococcus furiosus

<400> SEQUENCE: 16

Met Glu Glu Leu Ile Arg Glu Val Ile Leu Lys Asn Leu Thr Leu Asn
1               5                   10                  15

Ser Ala Gly Gly Ile Gly Leu Glu Glu Leu Asp Asp Gly Ala Thr Ile
            20                  25                  30

Pro Leu Gly Asp Lys His Leu Val Phe Thr Ile Asp Gly His Thr Val
        35                  40                  45

Lys Pro Ile Phe Phe Pro Gly Gly Asp Ile Gly Arg Leu Ala Val Ser
    50                  55                  60

Gly Thr Val Asn Asp Leu Ala Val Met Gly Ala Gln Pro Leu Ala Ile
65                  70                  75                  80

Ala Ser Ser Leu Ile Ile Glu Glu Gly Phe Glu Val Ser Glu Leu Glu
                85                  90                  95

Lys Ile Leu Lys Ser Met Asp Glu Thr Ala Lys Glu Val Pro Val Pro
            100                 105                 110

Ile Val Thr Gly Asp Thr Lys Val Val Glu Asp Arg Ile Gly Ile Phe
        115                 120                 125

Val Ile Thr Ala Gly Val Gly Val Ala Glu Arg Pro Ile Ser Asp Ala
    130                 135                 140

Gly Ala Lys Val Gly Asp Val Leu Val Ser Gly Thr Ile Gly Asp
145                 150                 155                 160

His Gly Ile Ala Leu Met Ser His Arg Glu Gly Ile Ser Phe Glu Thr
            165                 170                 175

Glu Leu Lys Ser Asp Val Ala Pro Ile Trp Asp Val Lys Ala Val
        180                 185                 190

Ala Asp Ala Ile Gly Trp Glu Asn Ile His Ala Met Lys Asp Pro Thr
        195                 200                 205

Arg Gly Gly Leu Ser Asn Ala Leu Asn Glu Met Ala Arg Lys Ala Asn
        210                 215                 220

Val Gly Ile Leu Val Arg Glu Glu Ala Ile Pro Ile Arg Pro Glu Val
225                 230                 235                 240

Lys Ala Ala Ser Glu Met Leu Gly Ile Ser Pro Tyr Glu Val Ala Asn
                245                 250                 255

Glu Gly Lys Val Val Met Ile Val Ala Lys Glu Tyr Ala Glu Glu Ala
            260                 265                 270

Leu Glu Ala Met Lys Lys Thr Glu Lys Gly Arg Asp Ala Ala Ile Ile
        275                 280                 285

Gly Glu Val Ile Gly Glu Tyr Arg Gly Lys Val Ile Leu Glu Thr Gly
        290                 295                 300

Ile Gly Gly Arg Arg Phe Leu Glu Pro Pro Leu Gly Asp Pro Val Pro
305                 310                 315                 320

Arg Val Cys

<210> SEQ ID NO 17
<211> LENGTH: 420
<212> TYPE: DNA
<213> ORGANISM: Pyrococcus furiosus

<400> SEQUENCE: 17
atgcacgaat gggcgttggc agatgcaata gtaaggactg ttttagatta cgctcaaaag     60
gagggtgcaa gtagggtaaa ggccgtcaag gtagtcctcg agaactccag agatgttggg    120
gaggatatag taaagtttgc catggaagag ctcttcaggg gaacaatagc ggaaggggca    180
gagataatat cgaagagga agaggccgtc tttaagtgcc gcaactgcgg gcatgtatgg    240
aagcttaagg aagtcaaaga taagttggat gagaggataa agaggacat ccactttatt    300
ccagaggtcg ttcatgcatt tctatcctgt ccaaaatgtg aagccatga ttttgaagtg    360
gtgaagggaa gggagtttta catttctgga ataatgatcg agaaggaggg agaagaatga    420

<210> SEQ ID NO 18
<211> LENGTH: 139
<212> TYPE: PRT
<213> ORGANISM: Pyrococcus furiosus

<400> SEQUENCE: 18

Met His Glu Trp Ala Leu Ala Asp Ala Ile Val Arg Thr Val Leu Asp
1               5                   10                  15

Tyr Ala Gln Lys Glu Gly Ala Ser Arg Val Lys Ala Val Lys Val Val
            20                  25                  30

Leu Gly Glu Leu Gln Asp Val Gly Glu Asp Ile Val Lys Phe Ala Met
        35                  40                  45

Glu Glu Leu Phe Arg Gly Thr Ile Ala Glu Gly Ala Glu Ile Ile Phe
    50                  55                  60

Glu Glu Glu Glu Ala Val Phe Lys Cys Arg Asn Cys Gly His Val Trp

```
                    65                  70                  75                  80
Lys Leu Lys Glu Val Lys Asp Lys Leu Asp Glu Arg Ile Arg Glu Asp
                85                  90                  95

Ile His Phe Ile Pro Glu Val Val His Ala Phe Leu Ser Cys Pro Lys
            100                 105                 110

Cys Gly Ser His Asp Phe Glu Val Lys Gly Arg Gly Val Tyr Ile
        115                 120                 125

Ser Gly Ile Met Ile Glu Lys Glu Gly Glu Glu
    130                 135
```

<210> SEQ ID NO 19
<211> LENGTH: 726
<212> TYPE: DNA
<213> ORGANISM: Pyrococcus furiosus

<400> SEQUENCE: 19

```
atgatagatc ccagagaact cgcaatttca gcgaagcttg agggagtaaa aagaataatc      60
ccagttgtaa gtgggaaggg aggagtagga aaatccctaa tctccacaac tcttgcccta     120
gttctatcag aacaaaaata caaagttgga cttctcgact ggatttcca tggagcaagt      180
gaccacgtca tcctgggatt tgaacccaaa gaacttcccg aggaagacaa aggagttatt     240
cccccaacgg ttcacggaat aaagttcatg acaatagcgt attacaccga ggacaggcca     300
actcctttaa gaggaaagga gattagcgac gccctaatag agctactaac aataaccagg     360
tgggatgagc tcgactttt agttgttgac atgcccctg gatgggaga tcagttctta       420
gacgttttaa agtacttcaa gaggggagaa ttcttgatag tcgcaactcc gtcaaagctc     480
tctcttaatg ttgttaggaa gcttatagag ttgctaaaag aagagaagca tcagatactt     540
ggaatagttg agaatatgaa gctggatgaa gaggaagatg ttatgagaat tgcccaggaa     600
tatgggatta ggtatcttgg aggaatacct ctgtacaggg atctagagag taaagttgga   660
aatgttaatg aacttttagc cacagagttt gccgagaaaa ttagaggaat agctaaaaag     720
atttga                                                                726
```

<210> SEQ ID NO 20
<211> LENGTH: 241
<212> TYPE: PRT
<213> ORGANISM: Pyrococcus furiosus

<400> SEQUENCE: 20

```
Met Ile Asp Pro Arg Glu Leu Ala Ile Ser Ala Lys Leu Glu Gly Val
1               5                   10                  15

Lys Arg Ile Ile Pro Val Val Ser Gly Lys Gly Gly Val Gly Lys Ser
            20                  25                  30

Leu Ile Ser Thr Thr Leu Ala Leu Val Leu Ser Glu Gln Lys Tyr Lys
        35                  40                  45

Val Gly Leu Leu Asp Leu Asp Phe His Gly Ala Ser Asp His Val Ile
    50                  55                  60

Leu Gly Phe Glu Pro Lys Glu Leu Pro Glu Glu Asp Lys Gly Val Ile
65                  70                  75                  80

Pro Pro Thr Val His Gly Ile Lys Phe Met Thr Ile Ala Tyr Tyr Thr
                85                  90                  95

Glu Asp Arg Pro Thr Pro Leu Arg Gly Lys Glu Ile Ser Asp Ala Leu
            100                 105                 110

Ile Glu Leu Leu Thr Ile Thr Arg Trp Asp Glu Leu Asp Phe Leu Val
        115                 120                 125
```

Val Asp Met Pro Pro Gly Met Gly Asp Gln Phe Leu Asp Val Leu Lys
            130                 135                 140

Tyr Phe Lys Arg Gly Glu Phe Leu Ile Val Ala Thr Pro Ser Lys Leu
145                 150                 155                 160

Ser Leu Asn Val Val Arg Lys Leu Ile Glu Leu Leu Lys Glu Glu Lys
                165                 170                 175

His Gln Ile Leu Gly Ile Val Glu Asn Met Lys Leu Asp Glu Glu Glu
                180                 185                 190

Asp Val Met Arg Ile Ala Gln Glu Tyr Gly Ile Arg Tyr Leu Gly Gly
            195                 200                 205

Ile Pro Leu Tyr Arg Asp Leu Glu Ser Lys Val Gly Asn Val Asn Glu
            210                 215                 220

Leu Leu Ala Thr Glu Phe Ala Glu Lys Ile Arg Gly Ile Ala Lys Lys
225                 230                 235                 240

Ile

<210> SEQ ID NO 21
<211> LENGTH: 477
<212> TYPE: DNA
<213> ORGANISM: Pyrococcus furiosus

<400> SEQUENCE: 21
atggaagagc tgagagaagc tctaaaaaat gctaagagaa ttgtaatatg tggaataggg     60
aatgacatca ggggagacga cagcttcggg gtttatattg cagaaaaatt aaagagagtt   120
ataaagaagg caaacattct agtcctcaac tgtggagagg ttccagagaa ctacacaggg   180
aagatactaa actttcaccc tgatttaatc attttttatag acgcagtaaa cttcggagga   240
aagcctggag aaataataat tacagatcca gaaatactg aaggggccgg agtttccacc   300
cacagtcttc ccctcaagtt tttggccact tatctcaaag ctaatacaaa tgccaagaca   360
atcttaatag gatgccagcc aaagaacatt gggctttttg aagatatgag cgaagaagta   420
aaagccgttg cggaagtctt attaaaattc ctttatgaaa gtcttgagct ttcttag     477

<210> SEQ ID NO 22
<211> LENGTH: 158
<212> TYPE: PRT
<213> ORGANISM: Pyrococcus furiosus

<400> SEQUENCE: 22

Met Glu Glu Leu Arg Glu Ala Leu Lys Asn Ala Lys Arg Ile Val Ile
1               5                   10                  15

Cys Gly Ile Gly Asn Asp Ile Arg Gly Asp Asp Ser Phe Gly Val Tyr
                20                  25                  30

Ile Ala Glu Lys Leu Lys Arg Val Ile Lys Ala Asn Ile Leu Val
            35                  40                  45

Leu Asn Cys Gly Glu Val Pro Glu Asn Tyr Thr Gly Lys Ile Leu Asn
    50                  55                  60

Phe His Pro Asp Leu Ile Ile Phe Ile Asp Ala Val Asn Phe Gly Gly
65                  70                  75                  80

Lys Pro Gly Glu Ile Ile Thr Asp Pro Glu Asn Thr Glu Gly Ala
                85                  90                  95

Gly Val Ser Thr His Ser Leu Pro Leu Lys Phe Leu Ala Thr Tyr Leu
                100                 105                 110

Lys Ala Asn Thr Asn Ala Lys Thr Ile Leu Ile Gly Cys Gln Pro Lys
            115                 120                 125

Asn Ile Gly Leu Phe Glu Asp Met Ser Glu Glu Val Lys Ala Val Ala
        130                 135                 140

Glu Val Leu Leu Lys Phe Leu Tyr Glu Ser Leu Glu Leu Ser
145                 150                 155

<210> SEQ ID NO 23
<211> LENGTH: 777
<212> TYPE: DNA
<213> ORGANISM: Pyrococcus furiosus

<400> SEQUENCE: 23
atgaaagtag agaaaggaga tgtcataaga cttcattaca ctggaaaggt taaagaaact      60
ggagaaatct tcgacacaac ttatgaggat gttgcaaaag aagctagaat atacaatcca    120
aacggaatct atgggccagt ccctatagcg gttggagcgg gacacgtatt gcccggacta    180
gacaagagac ttatagggct tgaagttaag aaaaaatacg tcattgaagt tccacccgaa    240
gaaggctttg gattgagaga tccaggaaaa attaagatta tcccacttgg aaagttcaga    300
aaatctggaa taatcccgta ccctgggcta gaaattgaag ttgaaacaga aatgggaga     360 aaaatgagag gtagggttct tacagttagc ggaggaagag ttagagtaga cttcaatcat    420
ccattagcag gaaagactct cgtatatgaa gttgaagttg ttgagaaaat tgaagatcca    480
atagaaaaga ttaaggcact aatagaacta agactgccaa tgattgacaa agataaggtt    540
attattgaga ttagtgaaaa agatgtaaag ctaaacttca agacgttga tattgatcca    600 aagcactaa ttttgggcga aattcttctc gaaagtgact tgaaatttat aggatatgag    660
aaagttgaat ttgagccaac cattgaagag ttattaaagc ccaagtctgc cgaggagcaa    720
gagtctccta acgaagaaca gcaagaggag agtgagtcta agcggaaga atcttaa       777

<210> SEQ ID NO 24
<211> LENGTH: 258
<212> TYPE: PRT
<213> ORGANISM: Pyrococcus furiosus

<400> SEQUENCE: 24

Met Lys Val Glu Lys Gly Asp Val Ile Arg Leu His Tyr Thr Gly Lys
1               5                   10                  15

Val Lys Glu Thr Gly Glu Ile Phe Asp Thr Thr Tyr Glu Asp Val Ala
            20                  25                  30

Lys Glu Ala Arg Ile Tyr Asn Pro Asn Gly Ile Tyr Gly Pro Val Pro
        35                  40                  45

Ile Ala Val Gly Ala Gly His Val Leu Pro Gly Leu Asp Lys Arg Leu
    50                  55                  60

Ile Gly Leu Glu Val Lys Lys Lys Tyr Val Ile Glu Val Pro Pro Glu
65                  70                  75                  80

Glu Gly Phe Gly Leu Arg Asp Pro Gly Lys Ile Lys Ile Ile Pro Leu
                85                  90                  95

Gly Lys Phe Arg Lys Ser Gly Ile Ile Pro Tyr Pro Gly Leu Glu Ile
            100                 105                 110

Glu Val Glu Thr Glu Asn Gly Arg Lys Met Arg Gly Arg Val Leu Thr
        115                 120                 125

Val Ser Gly Gly Arg Val Arg Val Asp Phe Asn His Pro Leu Ala Gly
    130                 135                 140

Lys Thr Leu Val Tyr Glu Val Glu Val Val Glu Lys Ile Glu Asp Pro
145                 150                 155                 160

```
Ile Glu Lys Ile Lys Ala Leu Ile Glu Leu Arg Leu Pro Met Ile Asp
            165                 170                 175

Lys Asp Lys Val Ile Glu Ile Ser Glu Lys Asp Val Lys Leu Asn
        180                 185                 190

Phe Lys Asp Val Asp Ile Asp Pro Lys Thr Leu Ile Leu Gly Glu Ile
            195                 200                 205

Leu Leu Glu Ser Asp Leu Lys Phe Ile Gly Tyr Glu Lys Val Glu Phe
    210                 215                 220

Glu Pro Thr Ile Glu Glu Leu Leu Lys Pro Lys Ser Ala Glu Glu Gln
225                 230                 235                 240

Glu Ser Pro Asn Glu Glu Gln Gln Glu Glu Ser Glu Ser Lys Ala Glu
                245                 250                 255

Glu Ser
```

<210> SEQ ID NO 25
<211> LENGTH: 386
<212> TYPE: DNA
<213> ORGANISM: Escherichia coli

<400> SEQUENCE: 25

```
ctcgaattcc ttctctttta ctcgtttagc aaccggctaa acatccccac cgcccggcca      60
aaagaaaata ggtccatttt tatcgctaaa agataaatcc acacagtttg tattgttttg     120
tgcaaaagtt tcactacgct ttattaacaa tactttctgg cgacgtgcgc cagtgcagaa     180
ggatgagctt tcgttttcag catctcacgt gaagcgatgg tttgccttgc tacagggacg     240
tcgcttgccg accataagcg cccggtgtcc tgccggtgtc gcaaggagga gagacgtgcg     300
atatgggtca tcaccatcat caccacggct cgatcacaag tttgtacaaa aaagcaggct     360
cagaaaacct gtattttcag ggagga                                          386
```

<210> SEQ ID NO 26
<211> LENGTH: 637
<212> TYPE: DNA
<213> ORGANISM: Escherichia coli

<400> SEQUENCE: 26

```
ctcgaattct gcagcatgtc accatgacac tgtggacagc ggcggacgcg ctgggtcagt      60
agcgtcacat actgttggca tgtttcacac cagcattcgg cctcttgttc ttcgaggtgc     120
agtttacaac cttccgccac gctgccgcgg caaaccagat caaaacaaaa ggcaagagag     180
ctggtttcga cacaagaaaa tgcgccaatt ttgagccaga ccccagttac gcgttttgcg     240
ccgtgttttg cggcctgctg ttcgatcaat tccagtgccc gttggcagag ggttatttcg     300
tgcatatcgc ctcccattaa ctattgccag ctacaagcaa taattgtgcc agtgttgatt     360
atccctgcgg tgaataatgt cgatgatgtc gaaatgacac gtcgacacgg cgacgaaatt     420
catctttagc ttaaaaatct ctttaataac aataaattaa agttggcac aaaaaatgct     480
taaagctggc atctctgtta aacgggtaac ctgacaatga ctatttggga aataagcgag     540
aaagccgatt acatcgcaca gcggcatcgt cgcctacagg accagtggca catctactgc     600
aattcgctgg ttcaggggag aggaggaata aaaaatg                              637
```

<210> SEQ ID NO 27
<211> LENGTH: 179
<212> TYPE: DNA
<213> ORGANISM: Bacillus megaterium

<400> SEQUENCE: 27

```
gaattctaga atctaatatt ataactaaat tttctaaaaa aaacattgga atagacattt      60
attttgtata tgatgaaata aagttagttt attggataaa caaactaact ttattaaggt     120
agttgatgga taaacttgtt cacttaaatc aacccgggaa caaggaggaa taaaaaatg      179
```

<210> SEQ ID NO 28
<211> LENGTH: 813
<212> TYPE: DNA
<213> ORGANISM: Escherichia coli

<400> SEQUENCE: 28

```
ggatccccgt caccctggat gctgtacaat tgacgacgac aagggcccgg gcaaactagt      60
aatcagacgc ggtcgttcac ttgttcagca accagatcaa aagccattga ctcagcaagg     120
gttgaccgta taattcacgc gattacaccg cattgcggta tcaacgcgcc cttagctcag     180
ttggatagag caacgacctt ctaagtcgtg gccgcaggt tcgaatcctg cagggcgcgc      240
cattacaatt caatcagtta cgccttcttt atatcctcca gccatggcct tgaaatggcg     300
ttagtcatga atatagacc gccatcgagt accccttgta cccttaactc ttcctgatac      360
gtaaataatg atttggtggc ccttgctgga cttgaaccag cgaccaagcg attatgagtc     420
gcctgctcta accactgagc taagggcct tgagtgtgca ataacaatac ttataaacca      480
cgcaataaac atgatgatct agagaatccc gtcgtagcca ccatcttttt ttgcgggagt     540
ggcgaaattg gtagacgcac cagatttagg ttctggcgcc gctaggtgtg cgagttcaag     600
tctcgcctcc cgcaccattc accagaaagc gttgatcgga tgccctcgag tcgggcagcg     660
ttgggtcctg gccacgggtg cgcatgatcg tgctcctgtc gttgaggacc cggctaggct     720
ggcggggttg ccttactggt tagcagaatg aatcaccgat acgcgagcga acgtgaagcg     780
actgctgctg caaaacgtct gcgacctgag ctc                                  813
```

<210> SEQ ID NO 29
<211> LENGTH: 8123
<212> TYPE: DNA
<213> ORGANISM: artificial
<220> FEATURE:
<223> OTHER INFORMATION: expression vector sequence

<400> SEQUENCE: 29

```
ttgtacaaac ttgtgatcga gccgtggtga tgatggtgat gacccatatc gcacgtctct      60
cctccttgcg acaccggcag gacaccgggc gcttatggtc ggcaagcgac gtccctgtag     120
caaggcaaac catcgcttca cgtgagatgc tgaaaacgaa agctcatcct tctgcactgg     180
cgcacgtcgc cagaaagtat tgttaataaa gcgtagtgaa acttttgcac aaaacaatac     240
aaactgtgtg gatttatctt ttagcgataa aaatggacct attttttctt tggccgggcg     300
gtggggatgt ttagccggtt gctaaacgag taaaagagaa ggaattcgag ctcgaattcg     360
gatcctagag ggaaaccgtt gtggtctccc tatagtgagt cgtattaatt tcgcgggatc     420
gagatctcgg gcagcgttgg gtcctggcca cgggtgcgca tgatcgtgct cctgtcgttg     480
aggacccggc taggctggcg ggttgccctt actggttagc agaatgaatc accgatacgc     540
gagcgaacgt gaagcgactg ctgctgcaaa acgtctgcga cctgagcaac aacatgaatg     600
gtcttcggtt tccgtgtttc gtaaagtctg gaaacgcgga agtcagcgcc ctgcaccatt     660
atgttccgga tctgcatcgc aggatgctgc tggctaccct gtggaacacc tacatctgta     720
ttaacgaagc gctggcattg accctgagtg atttttctct ggtcccgccg catccatacc     780
```

```
gccagttgtt taccctcaca acgttccagt aaccgggcat gttcatcatc agtaacccgt    840
atcgtgagca tcctctctcg tttcatcggt atcattaccc ccatgaacag aaatccccct    900
tacacggagg catcagtgac caaacaggaa aaaaccgccc ttaacatggc ccgctttatc    960
agaagccaga cattaacgct tctggagaaa ctcaacgagc tggacgcgga tgaacaggca   1020
gacatctgtg aatcgcttca cgaccacgct gatgagcttt accgcagctg cctcgcgcgt   1080
ttcggtgatg acggtgaaaa cctctgacac atgcagctcc cggagacggt cacagcttgt   1140
ctgtaagcgg atgccgggag cagacaagcc cgtcagggcg cgtcagcggg tgttggcggg   1200
tgtcggggcg cagccatgac ccagtcacgt agcgatagcg gagtgtatac tggcttaact   1260
atgcggcatc agagcagatt gtactgagag tgcaccatat atgcggtgtg aaataccgca   1320
cagatgcgta aggagaaaat accgcatcag gcgctcttcc gcttcctcgc tcactgactc   1380
gctgcgctcg gtcgttcggc tgcggcgagc ggtatcagct cactcaaagg cggtaatacg   1440
gttatccaca gaatcagggg ataacgcagg aaagaacatg tgagcaaaag gccagcaaaa   1500
ggccaggaac cgtaaaaagg ccgcgttgct ggcgtttttc cataggctcc gcccccctga   1560
cgagcatcac aaaaatcgac gctcaagtca gaggtggcga aacccgacag gactataaag   1620
ataccaggcg tttccccctg gaagctccct cgtgcgctct cctgttccga ccctgccgct   1680
taccggatac ctgtccgcct ttctcccttc gggaagcgtg gcgctttctc atagctcacg   1740
ctgtaggtat ctcagttcgg tgtaggtcgt tcgctccaag ctgggctgtg tgcacgaacc   1800
ccccgttcag cccgaccgct gcgccttatc cggtaactat cgtcttgagt ccaacccggt   1860
aagacacgac ttatcgccac tggcagcagc cactggtaac aggattagca gagcgaggta   1920
tgtaggcggt gctacagagt tcttgaagtg gtggcctaac tacggctaca ctagaaggac   1980
agtatttggt atctgcgctc tgctgaagcc agttaccttc ggaaaaagag ttggtagctc   2040
ttgatccggc aaacaaacca ccgctggtag cggtggtttt tttgtttgca agcagcagat   2100
tacgcgcaga aaaaaaggat ctcaagaaga tcctttgatc ttttctacgg ggtctgacgc   2160
tcagtggaac gaaaactcac gttaagggat tttggtcatg agattatcaa aaaggatctt   2220
cacctagatc cttttaaatt aaaaatgaag ttttaaatca atctaaagta tatatgagta   2280
aacttggtct gacagttacc aatgcttaat cagtgaggca cctatctcag cgatctgtct   2340
atttcgttca tccatagttg cctgactccc cgtcgtgtag ataactacga tacgggaggg   2400
cttaccatct ggccccagtg ctgcaatgat accgcgagac ccacgctcac cggctccaga   2460
tttatcagca ataaaccagc cagccggaag ggccgagcgc agaagtggtc ctgcaacttt   2520
atccgcctcc atccagtcta ttaattgttg ccgggaagct agagtaagta gttcgccagt   2580
taatagtttg cgcaacgttg ttgccattgc tgcaggcatc gtggtgtcac gctcgtcgtt   2640
tggtatggct tcattcagct ccggttccca acgatcaagg cgagttacat gatccccat   2700 gttgtgcaaa aaagcggtta gctccttcgg tcctccgatc gttgtcagaa gtaagttggc   2760
cgcagtgtta tcactcatgg ttatggcagc actgcataat tctcttactg tcatgccatc   2820
cgtaagatgc ttttctgtga ctggtgagta ctcaaccaag tcattctgag aatagtgtat   2880
gcggcgaccg agttgctctt gcccggcgtc aatacgggat aataccgcgc cacatagcag   2940
aactttaaaa gtgctcatca ttggaaaacg ttcttcgggg cgaaaactct caaggatctt   3000
accgctgttg agatccagtt cgatgtaacc cactcgtgca cccaactgat cttcagcatc   3060
ttttactttc accagcgttt ctgggtgagc aaaaacagga aggcaaaatg ccgcaaaaaa   3120
gggaataagg gcgacacgga aatgttgaat actcatactc ttcctttttc aatattattg   3180
```

```
aagcatttat cagggttatt gtctcatgag cggatacata tttgaatgta tttagaaaaa   3240
taaacaaata ggggttccgc gcacatttcc ccgaaaagtg ccacctgaaa ttgtaaacgt   3300
taatattttg ttaaaattcg cgttaaattt ttgttaaatc agctcatttt ttaaccaata   3360
ggccgaaatc ggcaaaatcc cttataaatc aaaagaatag accgagatag ggttgagtgt   3420
tgttccagtt tggaacaaga gtccactatt aaagaacgtg gactccaacg tcaagggcg    3480 aaaaaccgtc tatcagggcg atgggcccact acgtgaacca tcaccctaat caagttttt   3540 ggggtcgagg tgccgtaaag cactaaatcg gaaccctaaa gggagccccc gatttagagc   3600
ttgacgggga aagccggcga acgtggcgag aaggaaggg aagaaagcga aggagcggg    3660 cgctagggcg ctggcaagtg tagcggtcac gctgcgcgta accaccacac ccgccgcgct   3720
taatgcgccg ctacagggcg cgtcccattc gccaatccgg atatagttcc tcctttcagc   3780
aaaaaacccc tcaagacccg tttagaggcc ccaaggggtt atgctagtta ttgctcagcg   3840
gtggcagcag ccaactcagc ttcctttcgg gctttgttag cagccggatc tcagtggtgg   3900
tggtggtggt gctcgagtgc ggccgcaagc ttgtcgacgg agcgcaagct tagcagccgg   3960
atctgatctt aattaattat caccactttg tacaagaaag ctgggtctcc tccctgaaaa   4020
tacaggtttt cctaaagtct aaccacgtgg actgagcaag atatgcatgg atcataagcc   4080
ctaacaacca tctcagccag tatctttaac ctttctggat cgtcattgta gtgcttttct   4140
gccatcattc ttacatgttc ttccatcatt gccaagttga atgctgtagg tgttattatg   4200
tcggcataag aaacccttcc attctcaact ttgagggcat agactaagat tccccttgga   4260
gcctcagtcg ttgagacacc aaagccgtcc tttatctcaa cttcatccct gggcttaatt   4320
ggccacttgg cgagagcctc gtcgagcaga tctattgccc tctctataaa gtaaactatt   4380
tcgagggcct gggctaagtt atttgcaaac ggatttgttc cctttaatag gtctttgttt   4440
gcctcataca gctccttggc cttgccgtat aggaggtcag cattgttaat aactctagat   4500
atagccccaa ccatgaaggg tctgcccttg tagtgactgt gctttgcaaa actgtgttca   4560
acgacgaact cctttatata atctctgtac ttttcacttg gaactcctc cccatcactt    4620 gcctttatgt aatctccata aattccataa gcatctcccc tcggcttcac ggccaagtgt   4680
gttattggcc cttcaacttc gctgtactgc tcaagctttg caaataactc aaaagtatac   4740
tcggcaagtg gtagggcttc cctaagctcg gctttcattt tctcaaggac actcttctca   4800
gggagctttc cgaatccgcc caaaaccgca ttttcttggt gtatggctct tgaccctaga   4860
atgtccatca tccaggtgcc aaggttcttc agcttaaggg ctatctctat ctccctcttg   4920
tattcattca ccatcttaag tgggctcgag tagcccctgt agtcgggaag aactagaaga   4980
tataggtgaa gggcatgact ctctatcatg tctccgatgt atagtacttc tctaagggcc   5040
tgtatctctt cccttgggac aaaaccgacg gccttttctg cagcctctaa tgcggttaac   5100
ttgtgggcgg ctgaacagaa tgagcatatt ctcgggtaaa tggccagagc ttcctcaagc   5160
ttcttcccaa tagttatggc ctcaaagaat ctgggccctt caattatgtt tagcttgacc   5220
tccttgactc catcatcccc aattattatc tccacaccac ccttccctc aactcttgct    5280 atatgatcaa tggtgattgg aagatagagg ttcttcattg ttcaccacct gagaatattt   5340
tttcaaccat tttctcaacc ctctcatcat gtccattgaa catttcatt ctctcaatta    5400 tctcctcttt tgtcatcccc ttctccttga cacccttagc tagagagtcg aaccaagcta   5460
catcgtaccc tattgcccct ctgcatccta tacacgcaac tccaaatcct ggacatctcg   5520
```

```
cgttacatcc tgcccttgtt actggaccta gacagggttc tcctttctca agaaggatac    5580
atggatgtcc attgagccta cattctagac aaactggata atctatatcc tctggccatg    5640
aaccaatcaa gaatgttccc agggcgtaga ggaagtcctt cttctctggt gggcaaccgt    5700
agatgttgta gtcaactttt atgtattttg aaactggttc agccttcttc ggttggaact    5760
tgacttttgc gtctccataa accttcttcc agagctcttc taatggcttt tcactccagc    5820
tctgaactcc tccttgaaca gcacaagctc caaccgcaac gacgatcttt gcattctccc    5880 taatttttt cacgagttca acttcttcct cagttgaaac gcttccttct ataaaagcta    5940
tgtcgacctt ttcatcctca atgctatctc tatcaatcat gaaccagcaa actatttcag    6000
catttgggat aagttgtaat aactcgtcca tcatagctag ctgcaattga cagccgtagc    6060
acgaggttaa tgcgtaaaat ccaatcctaa ctttttcccat tttcctcacc tcagtccagc    6120
agtcctgggg ttgaaactat gtcgaagtac gtgaagactg gtccatcttt acagatgtac    6180
ttccagctcg tgctcgttcc gacgttgcag tggccgcact tcccgattcc acatttcatt    6240
cttctctcca atgtcacgaa gatgttctct gggcgataac cgtagttgat gagggcctca    6300
aacactgact tatacattct aggaggccca cagattgcaa ctgcagtgtt ctttggattt    6360
gtgttggcct caacgatgaa ctgctgtggc ctacccttta ggcccggcca gtttggatcc    6420
ctagtgacgc tctggatgat tttcacgttt tcagcctcag ctaggtcttt cattgcctcc    6480
agctccttgt agaagaggag atccttccca taacgtgcgg tgtttatgaa ggtaatgttt    6540
ccatacttcc acctgttgtc cattgcatag agaaagacgc tcctaagagg tgcagttcca    6600
aggccagcag ctattaatag tagatccatt ccttcccact catccactgg gaatccatta    6660
ccgtaaggcc ctctcacaag aacagtatcg ccaggcttta gtctatggac aacagttgtg    6720
acccttcctg cctttcttat acagagctca agaatccttt tcctcattgg agaagagcat    6780
atacttatgg gaacctctcc aactccaggt atcgtcagct ggacaaactg tccaggtttg    6840
aacgtccact tctctgccaa ctcgggatcc tcaaatctaa agaggaaaag ctttccgtt    6900 tccgtcaagg agtaaacctt tagaactttg actctatgaa gggcatacgg attatcattt    6960
ggcatcataa tctcttttgg caacatcata ctccatcacc tctaatgtta gaggaatatg    7020
caaatcctct ctttggaatc tcctcactaa ccgttggggg acatttgttc tcctcaagtc    7080
ctaaaatcct tctaagattg cctacaaaac ttatattggc tggacagaat gcagtacacc    7140
ttccacaacc gacacagtag cttaatccaa gcttttcgtt atatgcgttc ttacagaggt    7200
atctgttcct aaagcgatcc ttctttgtgg gcctgaagtt gtggcccca gcaactaagc    7260 catgacttct gaactgacaa gaatcccatc ttctttccct gtatccagta actccatcta    7320
ggtttacaat atcctgaact tcatagcatc tacacgttgg gcatgtggtg ttacatattc    7380
cacaagccaa gcacttatct gcctcctcat cccacattgg atgttccatt tccaactcga    7440
gaagatacct caagttgccc cagtcttcgt ggtatttgaa tgcttgctgt ctcctctttt    7500
caaaatctct aaatgcacag atatccttgt ccgttacctc ttcaaagagc tttatgttct    7560
tgtcaacaag cctgtgccca gttggagtgc caacccttac caaccatcca tcgggcagtt    7620
catggaagaa caagtcaaaa ccatcatcag cgaagtctgt ttctcttaag ttacagaagc    7680
aatattcatc tggcatacag cttattccaa tgattatccc cttctctctc ctcaccttgt    7740
agtacttgtc ggggaactca tcaaggtata ccgtgtctag gatctttagg ccatatatgt    7800
cacacgcgtg gactccaaat ataataaatg gttcaacttc ctctattacc tccctgtatt    7860
ctggttttga aatgtcgaac tcaaagagct tttccctcgg cttgaagaag aacttcttag    7920
```

-continued

| | |
|---|---|
| gtggcattat tgtcctgttg tagtggaatt ctatctttct aacatcatca atctccctga | 7980 |
| agtcatagaa cttgtccgaa atttttactg gagcgtaaag cttcccccag tctttaagtc | 8040 |
| tttccaaaaa ctcgtaagtg ttttccttgg gtaacttaac ataccttcct ccctgaaaat | 8100 |
| acaggttttc tgagcctgct ttt | 8123 |

<210> SEQ ID NO 30
<211> LENGTH: 7025
<212> TYPE: DNA
<213> ORGANISM: artificial
<220> FEATURE:
<223> OTHER INFORMATION: expression vector sequence

<400> SEQUENCE: 30

| | |
|---|---|
| ttgtacaaag tggttgatga gtccggatcc caattgggag ctcgtgtaca cggcgcgcct | 60 |
| gcaggtcgac aagcttgcgg ccgcactcga gtctggtaaa gaaaccgctg ctgcgaaatt | 120 |
| tgaacgccag cacatggact cgtctactag cgcagcttaa ttaacctagg ctgctgccac | 180 |
| cgctgagcaa taactagcat aaccccttgg ggcctctaaa cgggtcttga ggggtttttt | 240 |
| gctgaaacct caggcatttg agaagcacac ggtcacactg cttccggtag tcaataaacc | 300 |
| ggtaaaccag caatagacat aagcggctat ttaacgaccc tgccctgaac cgacgaccgg | 360 |
| gtcatcgtgg ccggatcttg cggccccctcg gcttgaacga attgttagac attatttgcc | 420 |
| gactaccttg gtgatctcgc cttttcacgta gtggacaaat tcttccaact gatctgcgcg | 480 |
| cgaggccaag cgatcttctt cttgtccaag ataagcctgt ctagcttcaa gtatgacggg | 540 |
| ctgatactgg gccggcaggc gctccattgc ccagtcggca gcgacatcct tcggcgcgat | 600 |
| tttgccggtt actgcgctgt accaaatgcg ggacaacgta agcactacat ttcgctcatc | 660 |
| gccagcccag tcgggcggcg agttccatag cgttaaggtt tcatttagcg cctcaaatag | 720 |
| atcctgttca ggaaccggat caaagagttc ctccgccgct ggacctacca aggcaacgct | 780 |
| atgttctctt gcttttgtca gcaagatagc cagatcaatg tcgatcgtgg ctggctcgaa | 840 |
| gatacctgca agaatgtcat tgcgctgcca ttctccaaat tgcagttcgc gcttagctgg | 900 |
| ataacgccac ggaatgatgt cgtcgtgcac aacaatggtg acttctacag cgcggagaat | 960 |
| ctcgctctct ccaggggaag ccgaagtttc caaaaggtcg ttgatcaaag ctcgccgcgt | 1020 |
| tgtttcatca agccttacgg tcaccgtaac cagcaaatca atatcactgt gtggcttcag | 1080 |
| gccgccatcc actgcggagc cgtacaaatg tacggccagc aacgtcggtt cgagatggcg | 1140 |
| ctcgatgacg ccaactacct ctgatagttg agtcgtatact tcggcgatca ccgcttccct | 1200 |
| catactcttc cttttcaat attattgaag catttatcag ggttattgtc tcatgagcgg | 1260 |
| atacatattt gaatgtattt agaaaaataa acaatagct agctcactcg gtcgctacgc | 1320 |
| tccgggcgtg agactgcggc gggcgctgcg gacacataca aagttaccca cagattccgt | 1380 |
| ggataagcag gggactaaca tgtgaggcaa acagcaggg ccgcgccggt ggcgtttttc | 1440 |
| cataggctcc gccctcctgc cagagttcac ataaacagac gcttttccgg tgcatctgtg | 1500 |
| ggagccgtga ggctcaacca tgaatctgac agtacgggcg aaaccccgaca ggacttaaag | 1560 |
| atccccaccg ttccggcggg tcgctccctc ttgcgctctc ctgttccgac cctgccgttt | 1620 |
| accggatacc tgttccgcct ttctccctta cgggaagtgt ggcgctttct catagctcac | 1680 |
| acactggtat ctcggctcgg tgtaggtcgt tcgctccaag ctgggctgta agcaagaact | 1740 |
| ccccgttcag cccgactgct gcgccttatc cggtaactgt tcacttgagt ccaacccgga | 1800 |

-continued

```
aaagcacggt aaaacgccac tggcagcagc cattggtaac tgggagttcg cagaggattt    1860
gtttagctaa acacgcggtt gctcttgaag tgtgcgccaa agtccggcta cactggaagg    1920
acagatttgg ttgctgtgct ctgcgaaagc cagttaccac ggttaagcag ttccccaact    1980
gacttaacct tcgatcaaac cacctcccca ggtggttttt tcgtttacag gcaaaagat     2040 tacgcgcaga aaaaaggat ctcaagaaga tcctttgatc ttttctactg aaccgctcta     2100
gatttcagtg caatttatct cttcaaatgt agcacctgaa gtcagcccca tacgatataa    2160
gttgtaattc tcatgttagt catgccccgc gcccaccgga aggagctgac tgggttgaag    2220
gctctcaagg gcatcggtcg agatcccggt gcctaatgag tgagctaact tacattaatt    2280
gcgttgcgct cactgcccgc tttccagtcg ggaaacctgt cgtgccagct gcattaatga    2340
atcggccaac gcgcgggag aggcggtttg cgtattgggc gccagggtgg ttttttcttt     2400
caccagtgag acgggcaaca gctgattgcc cttcaccgcc tggccctgag agagttgcag    2460
caagcggtcc acgctggttt gccccagcag gcgaaaatcc tgtttgatgg tggttaacgg    2520
cgggatataa catgagctgt cttcggtatc gtcgtatccc actaccgaga tgtccgcacc    2580
aacgcgcagc ccggactcgg taatggcgcg cattgcgccc agcgccatct gatcgttggc    2640
aaccagcatc gcagtgggaa cgatgccctc attcagcatt tgcatggttt gttgaaaacc    2700
ggacatggca ctccagtcgc cttcccgttc cgctatcggc tgaatttgat tgcgagtgag    2760
atatttatgc cagccagcca gacgcagacg cgccgagaca gaacttaatg ggcccgctaa    2820
cagcgcgatt tgctggtgac ccaatgcgac cagatgctcc acgcccagtc gcgtaccgtc    2880
ttcatgggag aaaataatac tgttgatggg tgtctggtca gagacatcaa gaaataacgc    2940
cggaacatta gtgcaggcag cttccacagc aatggcatcc tggtcatcca gcggatagtt    3000
aatgatcagc ccactgacgc gttgcgcgag aagattgtgc accgccgctt tacaggcttc    3060
gacgccgctt cgttctacca tcgacaccac cacgctggca cccagttgat cggcgcgaga    3120
tttaatcgcc gcgacaattt gcgacggcgc gtgcagggcc agactggagg tggcaacgcc    3180
aatcagcaac gactgtttgc ccgccagttg ttgtgccacg cggttgggaa tgtaattcag    3240
ctccgccatc gccgcttcca cttttttcccg cgttttcgca gaaacgtggc tggcctggtt    3300
caccacgcgg gaaacggtct gataagagac accggcatac tctgcgacat cgtataacgt    3360
tactggtttc acattcacca ccctgaattg actctcttcc gggcgctatc atgccatacc    3420
gcgaaaggtt ttgcgccatt cgatggtgtc cgggatctcg acgctctccc ttatgcgact    3480
cctgcattag gaaattaata cgactcacta tagggggaatt gtgagcggat aacaattccc    3540
ctgtagaaat aattttgttt aactttaata aggagatata ccatggcaca tcaccaccac    3600
catcacgtgg gtaccggttc gaatgatctc gaattccttc tcttttactc gtttagcaac    3660
cggctaaaca tccccaccgc ccggccaaaa gaaaaatagg tccattttta tcgctaaaag    3720
ataaatccac acagtttgta ttgttttgtg caaaagtttc actacgcttt attaacaata    3780
ctttctggcg acgtgcgcca gtgcagaagg atgagctttc gttttcagca tctcacgtga    3840
agcgatggtt tgccttgcta cagggacgtc gcttgccgac cataagcgcc cggtgtcctg    3900
ccggtgtcgc aaggaggaga gacgtgcgat atgggtcatc accatcatca ccacatcgac    3960
gacaaatcaa caagtttgta caaaaaagca ggctcagaaa acctgtattt tcagggagga    4020
tgccttgcaa tcccagggaa agtggtggag attaaaggta acgttggaat agtggatttt    4080
ggaggaatac ggagagaggt aaggttagat cttttgagtg atgttaaagt tggcgattac    4140
gttatagttc acactggctt tgctatagaa aagttagatg agaggagagc tagagaaatt    4200
```

```
cttgaagcct gggaagaagt tttctcagta attgggggtg agtaaatgct tgaaaaattt    4260
ggagacaaag ctgtagctca aaagatttta gaaaaaatta agaggaagc taaagggata    4320 gaagagctac gatttatgca cgtttgtggg actcatgagg acacagtaac taggagtgga    4380
atcagatcac ttcttccaga aaatgtaaaa atcatgagtg gcccaggatg tcccgtctgt    4440 ataaccccg ttgaggacat agtgaagatg atggaaatta tgaaagttgc gagagaggag    4500
agggaagaaa ttattctcac tactttggt gacatgtata gaattccaac tccaatagga    4560
agctttgcag acttaaagag tcagggttac gatgtgagga tagtttactc tatatacgac    4620
tcctataaaa tagccaagga aaatccagat aagcttgtag tgcacttttc tcctgggttt    4680
gagactaccg ccgctccaac agctggaatg cttgagagca ttgtggaaga ggggctagag    4740
aactttaaga tttattccgt tcataggtta accccctcctg cagttgaagc tctcctaaat    4800
gcggggactg ttttcacgg tttaatagat cctggtcatg tctctacaat aattggggtg    4860
aaaggatggg cgtatctcac agaaaagttt ggaattcctc aagttgtggc tggctttgag    4920
ccagttgatg ttttactcgg aatacttatt ctcattaggc ttgtgaagag gggcgaagcg    4980
aaaataatca acgagtataa tagagttgta aagtgggaag gaaatgtcaa ggcccaagaa    5040
ctgatttgga agtactttga agttaaagat gcaaagtgga gggccctagg agtaattcca    5100
aggagcggat tggaacttaa gaaagagtgg aaggagctag aaattagaac ttattacaat    5160
cccgaggttc caaagctccc agatcttgaa aaaggatgtc tctgtggggc agtccttaga    5220
ggattagcct taccgaccca gtgccaacac tttggaaaga catgtacacc aagacatccg    5280
gtaggtcctt gtatggtttc gtacgaagga acttgtcaca tattttacaa atatggcgcc    5340
ctgatgtagg aggtggaaaa tgcacgaatg ggcgttggca gatgcaatag taaggactgt    5400
tttagattac gctcaaaagg agggtgcaag tagggtaaag gccgtcaagg tagtcctcgg    5460
agaactccaa gatgttgggg aggatatagt aaagtttgcc atggaagagc tcttcagggg    5520
aacaatagcg gaagggcag agataatatt cgaagaggaa gaggccgtct ttaagtgccg    5580
caactgcggg catgtatgga agcttaagga agtcaaagat aagttggatg agaggataag    5640
agaggacatc cactttattc cagaggtcgt tcatgcattt ctatcctgtc caaaatgtgg    5700
aagccatgat tttgaagtgg tgaagggaag gggagtttac atttctggaa taatgatcga    5760
gaaggaggga gaagaatgat agatcccaga gaactcgcaa tttcagcgaa gcttgaggga    5820 gtaaaagaa taatcccagt tgtaagtggg aagggaggag taggaaaatc cctaatctcc    5880
acaactcttg ccctagttct atcagaacaa aaatacaaag ttggacttct cgacttggat    5940
ttccatgagc aagtgaccac gtcatcctgg gatttgaacc caaagaactt cccgaggaag    6000
acaaaggagt tattcccca acggttcacg gaataaagtt catgacaata gcgtattaca    6060
ccgaggacag gccaactcct ttaagaggaa aggagattag cgacgcccta atagagctac    6120
taacaataac caggtgggat gagctcgact ttttagttgt tgacatgccc cctgggatgg    6180
gagatcagtt cttagacgtt ttaaagtact tcaagagggg agaattcttg atagtcgcaa    6240
ctccgtcaaa gctctctctt aatgttgtta ggaagcttat agagttgcta aaagaagaga    6300
agcatcagat acttggaata gttgagaata tgaagctgga tgaagaggaa gatgttatga    6360
gaattgccca ggaatatggg attaggtatc ttggaggaat acctctgtac agggatctag    6420
agagtaaagt tggaaatgtt aatgaacttt tagccacaga gtttgccgag aaaattagag    6480
gaatagctaa aaagatttga ctggtgcaag ctatggaaga gctgagagaa gctctaaaaa    6540
```

| | |
|---|---|
| atgctaagag aattgtaata tgtggaatag ggaatgacat caggggagac gacagcttcg | 6600 |
| gggtttatat tgcagaaaaa ttaaagagag ttataaagaa ggcaaacatt ctagtcctca | 6660 |
| actgtggaga ggttccagag aactacacag ggaagatact aaactttcac cctgatttaa | 6720 |
| tcattttat agacgcagta aacttcggag gaaagcctgg agaaataata attacagatc | 6780 |
| cagaaaatac tgaaggggcc ggagtttcca cccacagtct tcccctcaag ttttttggcca | 6840 |
| cttatctcaa agctaataca aatgccaaga caatcttaat aggatgccag ccaaagaaca | 6900 |
| ttgggctttt tgaagatatg agcgaagaag taaaagccgt tgcggaagtc ttattaaaat | 6960 |
| tcctttatga aagtcttgag ctttcttagg aaaacctgta ttttcaggga ggagacccag | 7020 |
| ctttc | 7025 |

<210> SEQ ID NO 31
<211> LENGTH: 7623
<212> TYPE: DNA
<213> ORGANISM: artificial
<220> FEATURE:
<223> OTHER INFORMATION: expression vector sequence

<400> SEQUENCE: 31

| | |
|---|---|
| ttgtacaaag tggtgataat taattaagat cagatccggc tgctaagctt gcgctcggcg | 60 |
| cgcctgcagg tcgacaagct tgcggccgca taatgcttaa gtcgaacaga aagtaatcgt | 120 |
| attgtacacg gccgcataat cgaaattaat acgactcact ataggggaat gtgagcggga | 180 |
| taacaattcc ccatcttagt atattagtta gtataagaa ggagatatac atatggcaga | 240 |
| tctcaattgg atatcggccg gccacgcgat cgctgacgtc ggtaccctcg agtctggtaa | 300 |
| agaaaccgct gctgcgaaat ttgaacgcca gcacatggac tcgtctacta gcgcagctta | 360 |
| attaacctag gctgctgcca ccgctgagca ataactagca taaccccttg gggcctctaa | 420 |
| acgggtcttg aggggttttt tgctgaaacc tcaggcattt gagaagcaca cggtcacact | 480 |
| gcttccggta gtcaataaac cggtaaacca gcaatagaca taagcggcta tttaacgacc | 540 |
| ctgccctgaa ccgacgacaa gctgacgacc gggtctccgc aagtggcact tttcggggaa | 600 |
| atgtgcgcgg aacccctatt tgtttatttt tctaaataca ttcaaatatg tatccgctca | 660 |
| tgaattaatt cttagaaaaa ctcatcgagc atcaaatgaa actgcaattt attcatatca | 720 |
| ggattatcaa taccatattt ttgaaaaagc cgtttctgta atgaaggaga aaactcaccg | 780 |
| aggcagttcc ataggatggc aagatcctgg tatcggtctg cgattccgac tcgtccaaca | 840 |
| tcaatacaac ctattaattt cccctcgtca aaaataaggt tatcaagtga gaaatcacca | 900 |
| tgagtgacga ctgaatccgg tgagaatggc aaaagtttat gcatttcttt ccagacttgt | 960 |
| tcaacaggcc agccattacg ctcgtcatca aaatcactcg catcaaccaa accgttattc | 1020 |
| attcgtgatt gcgcctgagc gagacgaaat acgcggtcgc tgttaaaagg acaattacaa | 1080 |
| acaggaatcg aatgcaaccg gcgcaggaac actgccagcg catcaacaat attttcacct | 1140 |
| gaatcaggat attcttctaa tacctggaat gctgttttcc cggggatcgc agtggtgagt | 1200 |
| aaccatgcat catcaggagt acggataaaa tgcttgatgg tcggaagagg cataaattcc | 1260 |
| gtcagccagt ttagtctgac catctcatct gtaacatcat tggcaacgct acctttgcca | 1320 |
| tgtttcagaa acaactctgg cgcatcgggc ttcccataca atcgatagat tgtcgcacct | 1380 |
| gattgcccga cattatcgcg agcccattta tacccatata aatcagcatc catgttggaa | 1440 |
| tttaatcgcg gcctagagca agacgtttcc cgttgaatat ggctcatact cttcctttc | 1500 |
| aatattattg aagcatttat cagggttatt gtctcatgag cggatacata tttgaatgta | 1560 |

```
tttagaaaaa taaacaaata ggcatgcagc gctcttccgc ttcctcgctc actgactcgc   1620
tacgctcggt cgttcgactg cggcgagcgg tgtcagctca ctcaaaagcg gtaatacggt   1680
tatccacaga atcaggggat aaagccggaa agaacatgtg agcaaaaagc aaagcaccgg   1740
aagaagccaa cgccgcaggc gttttttccat aggctccgcc cccctgacga gcatcacaaa   1800
aatcgacgct caagccagag gtggcgaaac ccgacaggac tataaagata ccaggcgttt   1860 cccccctggaa gctccctcgt gcgctctcct gttccgaccc tgccgcttac cggatacctg   1920
tccgcctttc tcccttcggg aagcgtggcg ctttctcata gctcacgctg ttggtatctc   1980
agttcggtgt aggtcgttcg ctccaagctg ggctgtgtgc acgaaccccc cgttcagccc   2040
gaccgctgcg ccttatccgg taactatcgt cttgagtcca acccggtaag acacgactta   2100
tcgccactgg cagcagccat tggtaactga tttagaggac tttgtcttga agttatgcac   2160
ctgttaaggc taaactgaaa gaacagattt tggtgagtgc ggtcctccaa cccacttacc   2220
ttggttcaaa gagttggtag ctcagcgaac cttgagaaaa ccaccgttgg tagcggtggt   2280
ttttctttat ttatgagatg atgaatcaat cggtctatca agtcaacgaa cagctattcc   2340
gttactctag atttcagtgc aatttatctc ttcaaatgta gcacctgaag tcagccccat   2400
acgatataag ttgtaattct catgttagtc atgccccgcg cccaccggaa ggagctgact   2460
gggttgaagg ctctcaaggg catcggtcga gatcccggtg cctaatgagt gagctaactt   2520
acattaattg cgttgcgctc actgcccgct ttccagtcgg gaaacctgtc gtgccagctg   2580
cattaatgaa tcggccaacg cgcggggaga ggcggtttgc gtattgggcg ccagggtggt   2640
ttttcttttc accagtgaga cgggcaacag ctgattgccc ttcaccgcct ggccctgaga   2700
gagttgcagc aagcggtcca cgctggtttg ccccagcagg cgaaaatcct gtttgatggt   2760
ggttaacggc gggatataac atgagctgtc ttcggtatcg tcgtatccca ctaccgagat   2820
gtccgcacca acgcgcagcc cggactcggt aatggcgcgc attgcgccca cgcgcatctg   2880
atcgttggca accagcatcg cagtgggaac gatgccctca ttcagcattt gcatggtttg   2940
ttgaaaaccg gacatggcac tccagtcgcc ttcccgttcc gctatcggct gaatttgatt   3000
gcgagtgaga tatttatgcc agccagccag acgcagacgc gccgagacag aacttaatgg   3060
gcccgctaac agcgcgattt gctggtgacc caatgcgacc agatgctcca cgcccagtcg   3120
cgtaccgtct tcatgggaga aaataatact gttgatgggt gtctggtcag agacatcaag   3180
aaataacgcc ggaacattag tgcaggcagc ttccacagca atggcatcct ggtcatccag   3240
cggatagtta atgatcagcc cactgacgcg ttgcgcgaga agattgtgca ccgccgcttt   3300
acaggcttcg acgccgcttc gttctaccat cgacaccacc acgctggcac ccagttgatc   3360
ggcgcgagat ttaatcgccg cgacaatttg cgacggcgcg tgcagggcca gactggaggt   3420
ggcaacgcca atcagcaacg actgtttgcc cgccagttgt tgtgccacgc ggttgggaat   3480
gtaattcagc tccgccatcg ccgcttccac ttttcccgc gttttcgcag aaacgtggct   3540
ggcctggttc accacgcggg aaacggtctg ataagagaca ccggcatact ctgcgacatc   3600
gtataacgtt actggtttca cattcaccac cctgaattga ctctcttccg ggcgctatca   3660
tgccataccg cgaaaggttt tgcgccattc gatggtgtcc gggatctcga cgctctccct   3720
tatgcgactc ctgcattagg aaattaatac gactcactat aggggaattg tgagcggata   3780
acaattcccc tgtagaaata ttttgttta actttaataa ggagatatac catgggcagc   3840
agccatcacc atcatcacca cagccaggat ccgaattcga gctcgaattc cttctctttt   3900
```

```
actcgtttag caaccggcta aacatcccca ccgcccggcc aaaagaaaaa taggtccatt    3960
tttatcgcta aaagataaat ccacacagtt tgtattgttt tgtgcaaaag tttcactacg    4020
ctttattaac aatactttct ggcgacgtgc gccagtgcag aaggatgagc tttcgttttc    4080
agcatctcac gtgaagcgat ggtttgcctt gctacaggga cgtcgcttgc cgaccataag    4140
cgcccggtgt cctgccggtg tcgcaaggag gagagacgtg cgatatgggt catcaccatc    4200
atcaccacgg ctcgatcaca agtttgtaca aaaaagcagg ctcagaaaac ctgtatttc    4260 agggaggaga agaactaatt agggaggtaa tcctcaagaa tttaacccttt aattctgctg    4320 gaggaatagg attagaggag cttgatgacg gagctacaat cccccttgga gataagcatt    4380
tagtgtttac aatagatggg catacagtaa agccgatatt cttcccaggg ggagacatcg    4440
gaaggttggc cgttagcgga actgtaaacg atttggctgt catgggagct caacccttgg    4500
caattgcaag ctcgttgata atcgaggaag ggtttgaagt tagtgagctg aaaagattc    4560 tgaagtcgat ggacgaaaca gctaagagag ttccagttcc aattgttact ggagacacaa    4620
aagtcgttga agacaggata ggaatcttcg ttataacagc tggagtgggg gtagctgaga    4680
ggccgataag cgatgccggc gcaaaagttg gggatgtcgt tttagtgagt ggaacaattg    4740
gagaccacgg aatagcacta atgagccata gagagggat ctccttttgag acagagctta    4800 agagcgatgt agctccaatt tgggatgtcg taaaggccgt tgcagatgcc attggttggg    4860
agaacatcca cgcaatgaaa gatcccacaa gaggaggatt gagcaacgca ctaaacgaga    4920
tggcaagaaa ggcaaacgtt ggaattttgg taagagagga ggcaatacca attaggccag    4980
aagtaaaagc tgccagcgaa atgcttggaa taagtcccta tgaagttgca aacgaaggaa    5040
aagttgtaat gatagtggcg aaggagtatg cggaggaggc acttgaggcc atgaagaaga    5100
cagaaaaggg tagggatgcc gcaataatag gagaagttat tggtgaatac agaggaaaag    5160
ttattctgga gacgggaatt ggtggaagaa gattttagga gccgcctctc ggtgatcccg    5220
ttcctagagt ttgttaggag gtggaaaatg tatctggggg agagaatgaa gcttatagaa    5280
attcacgttc agggaatagt tcaggccgtg ggatttaggc ccttcgttta tagaatagct    5340
catgctcaca acttgagggg atacgttagg aacttaggcg atgctggagt tgaaattgtt    5400
gtcgagggaa gggaggaaga catagaggca ttcatcaagg atttatacaa gaagaaaccc    5460
ccacttgcaa ggattgataa ggttgagagg gaggaaattc ctcttcaggg ctttgacaga    5520
ttttacatag agaaaagctc gacggaaaag aagggggagg gagattcaat aatccctccg    5580
gacatagcta tttgtgagga ctgtcttagg gagttattta atccaactga caagcgctac    5640
atgtatcctt tcatagtatg tacaaactgt gggccgaggt tcacgataat tgaagatctt    5700
ccctacgata gggagaacac agcgatgaga gaattcccga tgtgcgagtt ctgtaggagt    5760
gaatacgagg atcccctgaa taggaggtat catgcagagc cggttgcatg tccaacttgt    5820
gggccgagct ataggcttta cacgagcgat ggaaatgaga taattggaga ccccctgaga    5880
aaggcggcaa aactaatcga taagggatac atagttgcga taaagggtat aggtggaatt    5940
catttggcct gcgatgctac aagagaggat gtggtggccg agcttaggaa gaggattttt    6000
aggcctcaga agcctttcgc cattatggcc aaagatttag aaactgtaag gacttttgcc    6060
tatatttctc ccgaagagga ggaagaatta acaagctata gaaggccaat agtggctttg    6120
aagaagaagg agcccttccc acttcccgaa aacctcgctc ctgggcttca cacaattggg    6180
gtaatgcttc cctatgctgg aacccactac atattattcc actggagcaa gactccagtt    6240
tacgttatga cttccgcaaa cttcccaggg atgccgatga taaaggacaa tgaagaggca    6300
```

```
tttgaaaagc ttagggacgt tgctgactac ctcttgctcc acaataggag aattccaaat    6360
agagctgacg atagcgttgt tcgctttgta gatggtagaa gagctgttat taggaggagc    6420
agaggatttg ttccacttgg aatagagatt ccatttgagt acaaggatt  ggcagttggt    6480 gctgagttaa tgaatgcttt cggagttgtt aagaatggaa aagtttatcc aagtcagtac    6540
ataggggata catcaaagat tgaagtttta gagtttatga gggaagccgt gaggcacttc    6600
ttcaagatat tgagagttga taacttagat ctagttgttg cagatttgca tccaagctac    6660
aacacaacta agctgggaat ggagatcgct gaggaatttg gggcagaatt ccttcaagtt    6720
caacatcact acgctcacgt ggcctctgta atggctgagc acaacttgga ggaagttgtt    6780
ggaattgctc tagatggtgt tgggtatgga accgacggaa aaacttgggg tggggaagta    6840
atatatctaa gctatgaaga tgtggagagg ttggcccaca tagagtatta tccactccca    6900 ggagggatt  tggccagcta ctatcccttg agggccttaa ttggaatact cagcttaaac    6960
cacgacttag aggaagttga gaaaatcata agggagttct gtccaaatgc aataaagagc    7020
ttaaagtatg gggaaacaga gtttagggta attatgaggc aactcagcag cgggataaac    7080
gttgcctatg cctcttcaac gggaagggtg cttgatgcct tctcggtact tttgaacgtt    7140
tcctacagga ggcactatga gggagagcct gcgatgaagc tggagagctt tgcataccaa    7200
ggaaagaacg atctaaagct cacggctcca attgaaggtg aggaaataaa ggtttcagag    7260
ttgtttgagg aagttcttga gctgatgggc aaggccaatc ctaaagacat agcttactcc    7320
gttcacttag cctagctag  ggcatttgct gaagttagcg tggagaaagc taaggagttt    7380
ggagctaaaa ctgtcgtttt gggtggggga gtagggtaca atgagctaat agttaagacg    7440
ataagaaaga tagtagaggg gagagggcta aggttcttaa caacttacga agttcccagg    7500
ggagataatg gaattaatgt aggccaggcc ttcctgggag gattgtactt ggaaggatac    7560
ttaaataggg aagatttgag catttaggaa aacctgtatt tcagggagg  agacccagct    7620 ttc                                                                  7623
```

<210> SEQ ID NO 32
<211> LENGTH: 6020
<212> TYPE: DNA
<213> ORGANISM: artificial
<220> FEATURE:
<223> OTHER INFORMATION: expression vector sequence

<400> SEQUENCE: 32

```
ttgtacaaag tggtgataat taattaagat cagatccggc tgctaagctt gcggccgcat     60
aatgcttaag tcgaacagaa agtaatcgta ttgtacacgg ccgcataatc gaaattaata    120
cgactcacta tagggaatt  gtgagcggat aacaattccc catcttagta tattagttaa    180
gtataagaag gagatataca tatggcagat ctcaattgga tatcggccgg ccacgcgatc    240
gctgacgtcg gtaccctcga gtctggtaaa gaaaccgctg ctgcgaaatt tgaacgccag    300
cacatggact cgtctactag cgcagcttaa ttaacctagg ctgctgccac cgctgagcaa    360
taactagcat aaccccttgg ggcctctaaa cgggtcttga ggggttttt  gctgaaacct    420 caggcatttg agaagcacac ggtcacactg cttccggtag tcaataaacc ggtaaaccag    480
caatagacat aagcggctat ttaacgaccc tgccctgaac cgacgaccgg gtcgaatttg    540
ctttcgaatt tctgccattc atccgcttat tatcacttat tcaggcgtag caccaggcgt    600
ttaagggcac caataactgc cttaaaaaaa ttacgccccg ccctgccact catcgcagta    660
```

```
ctgttgtaat tcattaagca ttctgccgac atggaagcca tcacagacgg catgatgaac    720
ctgaatcgcc agcggcatca gcaccttgtc gccttgcgta taatatttgc ccatagtgaa    780
aacgggggcg aagaagttgt ccatattggc cacgtttaaa tcaaaactgg tgaaactcac    840
ccagggattg gctgagacga aaaacatatt ctcaataaac cctttaggga ataggccag     900 gttttcaccg taacacgcca catcttgcga atatatgtgt agaaactgcc ggaaatcgtc   960
gtggtattca ctccagagcg atgaaaacgt tcagtttgc tcatggaaaa cggtgtaaca   1020
agggtgaaca ctatcccata tcaccagctc accgtctttc attgccatac ggaactccgg   1080
atgagcattc atcaggcggg caagaatgtg aataaaggcc ggataaaact tgtgcttatt   1140
tttctttacg gtctttaaaa aggccgtaat atccagctga acggtctggt tataggtaca   1200
ttgagcaact gactgaaatg cctcaaaatg ttctttacga tgccattggg atatatcaac   1260
ggtggtatat ccagtgattt ttttctccat tttagcttcc ttagctcctg aaaatctcga   1320
taactcaaaa aatacgcccg gtagtgatct tatttcatta tggtgaaagt tggaacctct   1380
tacgtgccga tcaacgtctc attttcgcca aaagttggcc cagggcttcc cggtatcaac   1440
agggacacca ggatttattt attctgcgaa gtgatcttcc gtcacaggta tttattcggc   1500
gcaaagtgcg tcgggtgatg ctgccaactt actgatttag tgtatgatgg tgtttttgag   1560
gtgctccagt ggcttctgtt tctatcagct gtccctcctg ttcagctact gacggggtgg   1620
tgcgtaacgg caaaagcacc gccggacatc agcgctagcg gagtgtatac tggcttacta   1680
tgttggcact gatgagggtg tcagtgaagt gcttcatgtg caggagaaa aaaggctgca    1740 ccggtgcgtc agcagaatat gtgatacagg atatattccg cttcctcgct cactgactcg   1800
ctacgctcgg tcgttcgact gcggcgagcg gaaatggctt acgaacgggg cggagatttc   1860
ctggaagatg ccaggaagat acttaacagg gaagtgagag ggccgcggca aagccgtttt   1920
tccataggct ccgccccct gacaagcatc acgaaatctg acgctcaaat cagtggtggc    1980
gaaacccgac aggactataa agataccagg cgtttcccct gcggctccc tcgtgcgctc    2040 tcctgttcct gcctttcggt ttaccggtgt cattccgctg ttatggccgc gtttgtctca    2100
ttccacgcct gacactcagt tccgggtagg cagttcgctc caagctggac tgtatgcacg   2160 aacccccccgt tcagtccgac cgctgcgcct tatccggtaa ctatcgtctt gagtccaacc   2220
cggaaagaca tgcaaaagca ccactggcag cagccactgg taattgattt agaggagtta   2280
gtcttgaagt catgcgccgg ttaaggctaa actgaaagga caagttttgg tgactgcgct   2340
cctccaagcc agttacctcg gttcaaagag ttggtagctc agagaacctt cgaaaaaccg   2400
ccctgcaagg cggttttttc gttttcagag caagagatta cgcgcagacc aaaacgatct   2460
caagaagatc atcttattaa tcagataaaa tatttctaga tttcagtgca atttatctct   2520
tcaaatgtag cacctgaagt cagccccata cgatataagt tgtaattctc atgttagtca   2580
tgccccgcgc ccaccggaag gagctgactg ggttgaaggc tctcaagggc atcggtcgag   2640
atcccggtgc ctaatgagtg agctaactta cattaattgc gttgcgctca ctgcccgctt   2700
tccagtcggg aaacctgtcg tgccagctgc attaatgaat cggccaacgc gcgggagag    2760 gcggtttgcg tattgggcgc cagggtggtt tttcttttca ccagtgagac gggcaacagc   2820
tgattgccct tcaccgcctg gccctgagag agttgcagca agcggtccac gctggtttgc   2880
cccagcaggc gaaaatcctg tttgatggtg gttaacggcg ggatataaca tgagctgtct   2940
tcggtatcgt cgtatcccac taccgagatg tccgcaccaa cgcgcagccc ggactcgta    3000 atggcgcgca ttgcgcccag cgccatctga tcgttggcaa ccagcatcgc agtgggaacg   3060
```

```
atgccctcat tcagcatttg catggtttgt tgaaaaccgg acatggcact ccagtcgcct    3120
tcccgttccg ctatcggctg aatttgattg cgagtgagat atttatgcca gccagccaga    3180
cgcagacgcg ccgagacaga acttaatggg cccgctaaca gcgcgatttg ctggtgaccc    3240
aatgcgacca gatgctccac gcccagtcgc gtaccgtctt catgggagaa aataatactg    3300
ttgatgggtg tctggtcaga gacatcaaga aataacgccg gaacattagt gcaggcagct    3360
tccacagcaa tggcatcctg gtcatccagc ggatagttaa tgatcagccc actgacgcgt    3420
tgcgcgagaa gattgtgcac cgccgcttta caggcttcga cgccgcttcg ttctaccatc    3480
gacaccacca cgctggcacc cagttgatcg gcgcgagatt taatcgccgc gacaatttgc    3540
gacggcgcgt gcagggccag actggagtg gcaacgccaa tcagcaacga ctgtttgccc    3600
gccagttgtt gtgccacgcg gttgggaatg taattcagct ccgccatcgc cgcttccact    3660
ttttcccgcg ttttcgcaga aacgtggctg gcctggttca ccacgcggga aacggtctga    3720
taagagacac cggcatactc tgcgacatcg tataacgtta ctggtttcac attcaccacc    3780
ctgaattgac tctcttccgg gcgctatcat gccataccgc gaaaggtttt gcgccattcg    3840
atggtgtccg ggatctcgac gctctccctt atgcgactcc tgcattagga aattaatacg    3900
actcactata ggggaattgt gagcggataa caattcccct gtagaaataa ttttgtttaa    3960
ctttaataag gagatatacc atgggcagca gccatcacca tcatcaccac agccaggatc    4020
cgtcaccctg gatgctgtac aattgacgac gacaagggcc cgggcaaact agtaatcaga    4080
cgcggtcgtt cacttgttca gcaaccagat caaaagccat tgactcagca agggttgacc    4140
gtataattca cgcgattaca ccgcattgcg gtatcaacgc gcccttagct cagttggata    4200
gagcaacgac cttctaagtc gtgggccgca ggttcgaatc ctgcagggcg cgccattaca    4260
attcaatcag ttacgccttc tttatatcct ccagccatgg ccttgaaatg gcgttagtca    4320
tgaaatatag accgccatcg agtaccccctt gtacccttaa ctcttcctga tacgtaaata    4380
atgatttggt ggcccttgct ggacttgaac cagcgaccaa gcgattatga gtcgcctgct    4440
ctaaccactg agctaaaggg ccttgagtgt gcaataacaa tactataaa ccacgcaata    4500 aacatgatga tctagagaat cccgtcgtag ccaccatctt tttttgcggg agtggcgaaa    4560
ttggtagacg caccagattt aggttctggc gccgctaggt gtgcgagttc aagtctcgcc    4620
tcccgcacca ttcaccagaa agcgttgatc ggatgccctc gagtcgggca gcgttgggtc    4680
ctggccacgg gtgcgcatga tcgtgctcct gtcgttgagg acccggctag ctggcgggg    4740 ttgccttact ggttagcaga atgaatcacc gatacgcgag cgaacgtgaa gcgactgctg    4800
ctgcaaaacg tctgcgacct gagctcgaat tccttctctt ttactcgttt agcaaccggc    4860
taaacatccc caccgcccgg ccaaaagaaa aataggtcca tttttatcgc taaaagataa    4920
atccacacag tttgtattgt tttgtgcaaa agtttcacta cgctttatta acaatacttt    4980
ctggcgacgt gcgccagtgc agaaggatga gctttcgttt tcagcatctc acgtgaagcg    5040
atggtttgcc ttgctacagg gacgtcgctt gccgaccata agcgcccggt gtcctgccgg    5100
tgtcgcaagg aggagagacg tgcgatatgg gtcatcacca tcatcaccac ggctcgatca    5160
caagtttgta caaaaaagca ggctcagaaa acctgtattt tcaggagga aaagtagaga    5220 aaggagatgt cataagactt cattacactg gaaaggttaa agaaactgga gaaatcttcg    5280
acacaactta tgaggatgtt gcaaaagaag ctagaatata caatccaaac ggaatctatg    5340
ggccagtccc tatagcggtt ggagcgggac acgtattgcc cggactagac aagagactta    5400
```

| | |
|---|---|
| tagggcttga agttaagaaa aaatacgtca ttgaagttcc acccgaagaa ggctttggat | 5460 |
| tgagagatcc aggaaaaatt aagattatcc cacttggaaa gttcagaaaa tctggaataa | 5520 |
| tcccgtaccc tgggctagaa attgaagttg aaacagaaaa tgggagaaaa atgagaggta | 5580 |
| gggttcttac agttagcgga ggaagagtta gagtagactt caatcatcca ttagcaggaa | 5640 |
| agactctcgt atatgaagtt gaagttgttg agaaaattga agatccaata gaaaagatta | 5700 |
| aggcactaat agaactaaga ctgccaatga ttgacaaaga taaggttatt attgagatta | 5760 |
| gtgaaaaaga tgtaaagcta aacttcaaag acgttgatat tgatccaaag acactaatttt | 5820 |
| tgggcgaaat tcttctcgaa agtgacttga aatttatagg atatgagaaa gttgaatttg | 5880 |
| agccaaccat tgaagagtta ttaaagccca gtctgccga ggagcaagag tctcctaacg | 5940 |
| aagaacagca agaggagagt gagtctaaag cggaagaatc ttaggaaaac ctgtattttc | 6000 |
| agggaggaga cccagctttc | 6020 |

<210> SEQ ID NO 33
<211> LENGTH: 6058
<212> TYPE: DNA
<213> ORGANISM: artificial
<220> FEATURE:
<223> OTHER INFORMATION: plasmid sequence

<400> SEQUENCE: 33

| | |
|---|---|
| ttgtacaaac ttgtgatcga gccacccata tcgcacgtct ctcctccttg cgacaccggc | 60 |
| aggacaccgg gcgcttatgg tcggcaagcg acgtccctgt agcaaggcaa accatcgctt | 120 |
| cacgtgagat gctgaaaacg aaagctcatc cttctgcact ggcgcacgtc gccagaaagt | 180 |
| attgttaata aagcgtagtg aaacttttgc acaaacaat acaaactgtg tggatttatc | 240 |
| ttttagcgat aaaaatggac ctatttttct tttggccggg cggtggggat gtttagccgg | 300 |
| ttgctaaacg agtaaaagag aaggaattcg agctcgaatt cggatcctag agggaaaccg | 360 |
| ttgtggtctc cctatagtga gtcgtattaa tttcgcggga tcgagatctc gggcagcgtt | 420 |
| gggtcctggc cacgggtgcg catgatcgtg ctcctgtcgt tgaggacccg gctaggctgg | 480 |
| cggggttgcc ttactggtta gcagaatgaa tcaccgatac gcgagcgaac gtgaagcgac | 540 |
| tgctgctgca aaacgtctgc gacctgagca acaacatgaa tggtcttcgg tttccgtgtt | 600 |
| tcgtaaagtc tggaaacgcg gaagtcagcg ccctgcacca ttatgttccg gatctgcatc | 660 |
| gcaggatgct gctggctacc ctgtggaaca cctacatctg tattaacgaa gcgctggcat | 720 |
| tgaccctgag tgattttct ctggtcccgc cgcatccata ccgccagttg tttaccctca | 780 |
| caacgttcca gtaaccgggc atgttcatca tcagtaaccc gtatcgtgag catcctctct | 840 |
| cgtttcatcg gtatcattac ccccatgaac agaaatcccc cttacacgga ggcatcagtg | 900 |
| accaaacagg aaaaaaccgc ccttaacatg gcccgcttta tcagaagcca gacattaacg | 960 |
| cttctggaga aactcaacga gctggacgcg gatgaacagg cagacatctg tgaatcgctt | 1020 |
| cacgaccacg ctgatgagct ttaccgcagc tgcctcgcgc gtttcggtga tgacggtgaa | 1080 |
| aacctctgac acatgcagct cccggagacg gtcacagctt gtctgtaagc ggatgccggg | 1140 |
| agcagacaag cccgtcaggg cgcgtcagcg ggtgttggcg ggtgtcgggg cgcagccatg | 1200 |
| acccagtcac gtagcgatag cggagtgtat actggcttaa ctatgcggca tcagagcaga | 1260 |
| ttgtactgag agtgcaccat atatgcggtg tgaaataccg cacagatgcg taaggagaaa | 1320 |
| ataccgcatc aggcgctctt ccgcttcctc gctcactgac tcgctgcgct cggtcgttcg | 1380 |
| gctgcggcga gcggtatcag ctcactcaaa ggcggtaata cggttatcca cagaatcagg | 1440 |

```
ggataacgca ggaaagaaca tgtgagcaaa aggccagcaa aaggccagga accgtaaaaa   1500
ggccgcgttg ctggcgtttt tccataggct ccgcccccct gacgagcatc acaaaaatcg   1560
acgctcaagt cagaggtggc gaaacccgac aggactataa agataccagg cgtttccccc   1620
tggaagctcc ctcgtgcgct ctcctgttcc gaccctgccg cttaccggat acctgtccgc   1680
ctttctccct tcgggaagcg tggcgctttc tcatagctca cgctgtaggt atctcagttc   1740
ggtgtaggtc gttcgctcca agctgggctg tgtgcacgaa ccccccgttc agcccgaccg   1800
ctgcgcctta tccggtaact atcgtcttga gtccaacccg gtaagacacg acttatcgcc   1860
actggcagca gccactggta acaggattag cagagcgagg tatgtaggcg gtgctacaga   1920
gttcttgaag tggtggccta actacggcta cactagaagg acagtatttg gtatctgcgc   1980
tctgctgaag ccagttacct tcggaaaaag agttggtagc tcttgatccg gcaaacaaac   2040
caccgctggt agcggtggtt tttttgtttg caagcagcag attacgcgca gaaaaaaagg   2100
atctcaagaa gatcctttga tcttttctac ggggtctgac gctcagtgga acgaaaactc   2160
acgttaaggg attttggtca tgagattatc aaaaaggatc ttcacctaga tccttttaaa   2220
ttaaaaatga agttttaaat caatctaaag tatatatgag taaacttggt ctgacagtta   2280
ccaatgctta atcagtgagg cacctatctc agcgatctgt ctatttcgtt catccatagt   2340
tgcctgactc cccgtcgtgt agataactac gatacgggag ggcttaccat ctggccccag   2400
tgctgcaatg ataccgcgag acccacgctc accggctcca gatttatcag caataaacca   2460
gccagccgga agggccgagc gcagaagtgg tcctgcaact ttatccgcct ccatccagtc   2520
tattaattgt tgccgggaag ctagagtaag tagttcgcca gttaatagtt tgcgcaacgt   2580
tgttgccatt gctgcaggca tcgtggtgtc acgctcgtcg tttggtatgg cttcattcag   2640
ctccggttcc caacgatcaa ggcgagttac atgatccccc atgttgtgca aaaaagcggt   2700
tagctccttc ggtcctccga tcgttgtcag aagtaagttg gccgcagtgt tatcactcat   2760
ggttatggca gcactgcata attctcttac tgtcatgcca tccgtaagat gcttttctgt   2820
gactggtgag tactcaacca agtcattctg agaatagtgt atgcggcgac cgagttgctc   2880
ttgcccggcg tcaatacggg ataataccgc gccacatagc agaactttaa aagtgctcat   2940
cattggaaaa cgttcttcgg ggcgaaaact ctcaaggatc ttaccgctgt tgagatccag   3000
ttcgatgtaa cccactcgtg cacccaactg atcttcagca tcttttactt tcaccagcgt   3060
ttctgggtga gcaaaaacag gaaggcaaaa tgccgcaaaa aagggaataa gggcgacacg   3120
gaaatgttga atactcatac tcttcctttt tcaatattat tgaagcattt atcagggtta   3180
ttgtctcatg agcggataca tatttgaatg tatttagaaa aataaacaaa tagggggttcc   3240 gcgcacattt ccccgaaaag tgccacctga aattgtaaac gttaatattt tgttaaaatt   3300
cgcgttaaat ttttgttaaa tcagctcatt ttttaaccaa taggccgaaa tcggcaaaat   3360
cccttataaa tcaaaagaat agaccgagat agggttgagt gttgttccag tttggaacaa   3420
gagtccacta ttaaagaacg tggactccaa cgtcaaaggg cgaaaaaccg tctatcaggg   3480
cgatggccca ctacgtgaac catcacccta atcaagtttt tggggtcga ggtgccgtaa   3540 agcactaaat cggaacccta agggagcccc cgatttagag cttgacggg gaaagccggc   3600 gaacgtggcg agaaaggaag ggaagaaagc gaaaggagcg ggcgctaggg cgctggcaag   3660
tgtagcggtc acgctgcgcg taaccaccac acccgccgcg cttaatgcgc cgctacaggg   3720
cgcgtcccat tcgccaatcc ggatatagtt cctcctttca gcaaaaaacc cctcaagacc   3780
```

```
cgtttagagg cccccaaggggg ttatgctagt tattgctcag cggtggcagc agccaactca   3840
gcttcctttc gggctttgtt agcagccgga tctcagtggt ggtggtggtg gtgctcgagt   3900
gcggccgcaa gcttagcagc cggatctgat cttaattaat tatcaccact ttgtacaaga   3960
aagctgggtc tccctattaa agtctaacca cgtggactga gcaagatatg catggatcat   4020
aagccctaac aaccatctca gccagtatct ttaacctttc tggatcgtca ttgtagtgct   4080
tttctgccat cattcttaca tgttcttcca tcattgccaa gttgaatgct gtaggtgtta   4140
ttatgtcggc ataagaaacc cttccattct caactttgag ggcatagact aagattcccc   4200
ttggagcctc agtcgttgag acaccaaagc cgtcctttat ctcaacttca tccctgggct   4260
taattggcca cttggcgaga gcctcgtcga gcagatctat tgccctctct ataaagtaaa   4320
ctatttcgag ggcctgggct aagttatttg caaacggatt tgttcccttt aataggtctt   4380
tgtttgcctc atacagctcc ttggccttgc cgtataggag gtcagcattg ttaataactc   4440
tagatatagc cccaaccatg aagggtctgc ccttgtagtg actgtgcttt gcaaaactgt   4500
gttcaacgac gaactccttt atataatctc tgtacttttc acttgggaac tcctccccat   4560
cacttgcctt tatgtaatct ccataaaatc cataagcatc tcccctcggc ttcacggcca   4620
agtgtgttat tggcccttca acttcgctgt actgctcaag ctttgcaaat aactcaaaag   4680
tatactcggc aagtggtagg gcttccctaa gctcggcttt cattttctca aggacactct   4740
tctcagggag ctttccgaat ccgcccaaaa ccgcattttt tggtgtatg gctcttgacc     4800
ctagaatgtc catcatccag gtgccaaggt tcttcagctt aagggctatc tctatctccc   4860
tcttgtattc attcaccatc ttaagtgggc tcgagtagcc cctgtagtcg ggaagaacta   4920
gaagatatag gtgaagggca tgactctcta tcatgtctcc gatgtatagt acttctctaa   4980
gggcctgtat ctcttccctt gggacaaaac cgacggcctt ttctgcagcc tctaatgcgg   5040
ttaacttgtg ggcggctgaa cagaatgagc atattctcgg gtaaatggcc agagcttcct   5100
caagcttctt cccaatagtt atggcctcaa agaatctggg cccttcaatt atgtttagct   5160
tgacctcctt gactccatca tccccaatta ttatctccac accacccttc ccctcaactc   5220
ttgctatatg atcaatggtg attggaagat agaggttctt cattgttcac cacctgagaa   5280
tattttttca accattttct caaccctctc atcatgtcca ttgaacattt tcattctctc   5340
aattatctcc tcttttgtca tcccccttctc cttgaacacc ttagctagag agtcgaacca   5400
agctacatcg taccctattg cccctctgca tcctatacac gcaactccaa atcctggaca   5460
tctcgcgtta catcctgccc ttgttactgg acctagacag ggttctcctt tctcaagaag   5520
gatacatgga tgtccattga gcctacattc tagacaaact ggataatcta tatcctctgg   5580
ccatgaacca atcaagaatg ttcccagggc gtagaggaag tccttcttct ctggtgggca   5640
accgtagatg ttgtagtcaa cttttatgta ttttgaaact ggttcagcct tcttcggttg   5700
gaacttgact tttgcgtctc cataaacctt cttccagagc tcttctaatg cttttcact    5760
ccagctctga actcctcctt gaacagcaca agctccaacc gcaacgacga tctttgcatt   5820
ctccctaatt ttttttcacga gttcaacttc ttcctcagtt gaaacgcttc cttctataaa   5880
agctatgtcg acctttttcat cctcaatgct atctctatca atcatgaacc agcaaactat   5940
ttcagcattt gggataagtt gtaataactc gtccatcata gctagctgca attgacagcc   6000
gtagcacgag gttaatgcgt aaaatccaat cctaactttt cctcctgagc ctgcttttt     6058

<210> SEQ ID NO 34
<211> LENGTH: 367
```

<212> TYPE: PRT
<213> ORGANISM: Pyrococcus abyssi

<400> SEQUENCE: 34

Met Arg Tyr Val Lys Leu Pro Lys Glu Asn Val Tyr Thr Phe Leu Glu
1               5                   10                  15

Arg Leu Lys Asp Trp Gly Lys Leu Tyr Ala Pro Val Lys Ile Ser Glu
            20                  25                  30

Lys Phe Tyr Asp Phe Arg Glu Ile Asp Asp Val Arg Lys Val Glu Phe
        35                  40                  45

His Tyr Thr Arg Thr Ile Met Pro Pro Lys Lys Phe Phe Lys Pro
    50                  55                  60

Arg Glu Lys Leu Phe Glu Phe Asp Ile Ser Lys Pro Glu Tyr Arg Glu
65              70                  75                  80

Val Ile Glu Asp Val Glu Pro Phe Val Leu Phe Gly Val His Ala Cys
                85                  90                  95

Asp Ile Tyr Gly Leu Lys Leu Leu Asp Thr Val Tyr Leu Asp Glu Phe
            100                 105                 110

Pro Asp Lys Tyr Tyr Lys Val Arg Arg Glu Lys Gly Ile Ile Ile Gly
        115                 120                 125

Ile Ser Cys Met Pro Asp Glu Tyr Cys Phe Cys Asn Leu Arg Glu Thr
    130                 135                 140

Asp Phe Ala Asp Gly Phe Asp Leu Phe Leu His Glu Leu Pro Asp
145                 150                 155                 160

Gly Trp Leu Val Arg Val Gly Thr Pro Thr Gly His Arg Ile Val Asp
                165                 170                 175

Lys Asn Ile Lys Leu Phe Glu Glu Val Thr Asn Glu Asp Ile Cys Ala
            180                 185                 190

Phe Arg Glu Phe Glu Lys Lys Arg His Glu Ala Phe Lys Tyr His Glu
        195                 200                 205

Asp Trp Gly Asn Leu Arg Tyr Leu Leu Glu Leu Glu Met Glu His Pro
    210                 215                 220

Met Trp Asp Glu Glu Ala Glu Lys Cys Leu Ala Cys Gly Ile Cys Asn
225                 230                 235                 240

Thr Thr Cys Pro Thr Cys Arg Cys Tyr Glu Val Gln Asp Ile Val Asn
                245                 250                 255

Leu Asp Gly Val Thr Gly Tyr Arg Glu Arg Trp Asp Ser Cys Gln
            260                 265                 270

Phe Arg Ser His Gly Leu Val Ala Gly Gly His Asn Phe Arg Pro Thr
        275                 280                 285

Lys Lys Ser Arg Phe Leu Asn Arg Tyr Leu Cys Lys Asn Ser Tyr Asn
    290                 295                 300

Glu Lys Leu Gly Ile Ser Phe Cys Val Gly Cys Gly Arg Cys Thr Ala
305                 310                 315                 320

Phe Cys Pro Ala Gly Ile Ser Phe Val Arg Asn Leu Arg Arg Ile Leu
                325                 330                 335

Gly Leu Glu Glu Gln Lys Cys Pro Pro Ser Val Ser Glu Glu Ile Pro
            340                 345                 350

Lys Arg Gly Phe Ala Tyr Ser Pro Gly Val Gly Glu Glu Glu
        355                 360                 365

<210> SEQ ID NO 35
<211> LENGTH: 292
<212> TYPE: PRT
<213> ORGANISM: Pyrococcus abyssi

<400> SEQUENCE: 35

```
Met Thr Leu Pro Lys Glu Val Met Pro Asn Asp Asn Pro Tyr Ala
1               5                   10                  15

Leu His Arg Val Lys Val Leu Lys Val Tyr Asp Leu Thr Glu Arg Glu
            20                  25                  30

Lys Leu Phe Leu Phe Arg Phe Glu Asp Pro Lys Leu Ala Glu Thr Trp
            35                  40                  45

Thr Phe Lys Pro Gly Gln Phe Val Gln Leu Thr Ile Pro Gly Val Gly
        50                  55                  60

Glu Val Pro Ile Ser Ile Cys Ser Ser Pro Met Arg Lys Gly Phe Phe
65                  70                  75                  80

Glu Leu Cys Ile Arg Arg Ala Gly Arg Val Thr Thr Val Val His Arg
                85                  90                  95

Leu Lys Pro Gly Asp Thr Val Leu Val Arg Gly Pro Tyr Gly Asn Gly
            100                 105                 110

Phe Pro Val Asp Glu Trp Glu Gly Met Asp Leu Leu Ile Ala Ala
            115                 120                 125

Gly Leu Gly Thr Ala Pro Leu Arg Ser Val Phe Leu Tyr Ala Met Asp
130                 135                 140

Asn Arg Trp Lys Tyr Gly Asn Ile Thr Phe Ile Asn Thr Ala Arg Tyr
145                 150                 155                 160

Gly Lys Asp Leu Leu Phe Tyr Lys Glu Leu Glu Ala Met Lys Asp Leu
                165                 170                 175

Ala Glu Ala Glu Asn Val Lys Ile Ile Gln Ser Val Thr Arg Asp Pro
            180                 185                 190

Asp Trp Pro Gly Leu His Gly Arg Pro Gln Gln Phe Ile Val Glu Ala
        195                 200                 205

Asn Thr Asn Pro Lys Asn Thr Ala Val Ala Ile Cys Gly Pro Pro Arg
210                 215                 220

Met Tyr Lys Ala Val Phe Glu Ser Leu Ile Asn Tyr Gly Tyr Arg Pro
225                 230                 235                 240

Glu Asn Ile Tyr Val Thr Leu Glu Arg Arg Met Lys Cys Gly Ile Gly
                245                 250                 255

Lys Cys Gly His Cys Val Ala Gly Thr Ser Thr Ser Trp Lys Tyr Ile
            260                 265                 270

Cys Lys Asp Gly Pro Val Phe Thr Tyr Phe Asp Ile Val Ser Thr Pro
        275                 280                 285

Gly Leu Leu Asp
        290
```

<210> SEQ ID NO 36
<211> LENGTH: 258
<212> TYPE: PRT
<213> ORGANISM: Pyrococcus abyssi

<400> SEQUENCE: 36

```
Lys Leu Arg Ile Gly Phe Tyr Ala Leu Thr Ser Cys Tyr Gly Cys Gln
1               5                   10                  15

Leu Gln Leu Ala Met Met Asp Glu Leu Leu Lys Leu Ile Pro Asn Ala
            20                  25                  30

Glu Ile Val Cys Trp Tyr Met Leu Asp Arg Asp Ser Val Glu Asp Lys
        35                  40                  45

Pro Val Asp Ile Ala Phe Ile Glu Gly Ser Val Ser Thr Glu Glu Glu
    50                  55                  60
```

```
Val Glu Leu Val Lys Lys Ile Arg Glu Asn Ala Lys Ile Val Val Ala
 65                  70                  75                  80

Val Gly Ala Cys Ala Val Gln Gly Gly Val Gln Ser Trp Asp Lys Ser
                 85                  90                  95

Leu Glu Glu Leu Trp Lys Thr Val Tyr Gly Asp Ala Lys Val Lys Phe
            100                 105                 110

Gln Pro Lys Lys Ala Glu Pro Val Ser Lys Tyr Ile Lys Val Asp Tyr
        115                 120                 125

Asn Ile Tyr Gly Cys Pro Pro Glu Lys Arg Asp Phe Leu Tyr Ala Leu
130                 135                 140

Gly Thr Phe Leu Ile Gly Ser Trp Pro Glu Asp Ile Asp Tyr Pro Val
145                 150                 155                 160

Cys Leu Glu Cys Arg Leu Asn Gly Tyr Pro Cys Val Leu Leu Glu Lys
                165                 170                 175

Gly Glu Pro Cys Leu Gly Pro Ile Thr Arg Ala Gly Cys Asn Ala Arg
            180                 185                 190

Cys Pro Gly Phe Gly Ile Ala Cys Ile Gly Cys Arg Gly Ala Ile Gly
        195                 200                 205

Tyr Asp Val Ala Trp Phe Asp Ser Leu Ala Arg Val Phe Lys Glu Lys
210                 215                 220

Gly Leu Thr Lys Glu Glu Ile Leu Glu Arg Met Lys Ile Phe Asn Gly
225                 230                 235                 240

His Asp Glu Arg Ile Glu Lys Met Val Glu Lys Val Phe Gln Glu Val
                245                 250                 255

Lys Glu

<210> SEQ ID NO 37
<211> LENGTH: 428
<212> TYPE: PRT
<213> ORGANISM: Pyrococcus abyssi

<400> SEQUENCE: 37

Met Arg Asn Leu Tyr Ile Pro Ile Thr Val Asp His Ile Ala Arg Val
  1               5                  10                  15

Glu Gly Lys Gly Gly Val Glu Ile Ile Val Gly Asp Glu Gly Val Lys
                 20                  25                  30

Glu Val Lys Leu Asn Ile Ile Glu Gly Pro Arg Phe Phe Glu Ala Ile
             35                  40                  45

Thr Ile Gly Lys Lys Leu Glu Glu Ala Leu Ala Ile Tyr Pro Arg Ile
         50                  55                  60

Cys Ser Phe Cys Ser Ala Ala His Lys Leu Thr Ala Leu Glu Ala Ala
 65                  70                  75                  80

Glu Lys Ala Ile Gly Phe Thr Pro Arg Glu Glu Ile Gln Ala Leu Arg
                 85                  90                  95

Glu Val Leu Tyr Ile Gly Asp Met Ile Glu Ser His Ala Leu His Leu
            100                 105                 110

Tyr Leu Leu Val Leu Pro Asp Tyr Leu Gly Tyr Ser Ser Pro Leu Lys
        115                 120                 125

Met Val Asn Glu Tyr Lys Lys Glu Leu Glu Ile Ala Leu Lys Leu Lys
    130                 135                 140

Asn Leu Gly Ser Trp Met Met Asp Val Leu Gly Ser Arg Ala Ile His
145                 150                 155                 160

Gln Glu Asn Ala Ile Leu Gly Gly Phe Gly Lys Leu Pro Ser Lys Glu
                165                 170                 175
```

```
Thr Leu Glu Glu Met Lys Ala Lys Leu Arg Glu Ser Leu Ser Leu Ala
            180                 185                 190

Glu Tyr Thr Phe Glu Leu Phe Ala Lys Leu Glu Gln Tyr Arg Glu Val
        195                 200                 205

Glu Gly Glu Ile Thr His Leu Ala Val Lys Pro Arg Gly Asp Val Tyr
    210                 215                 220

Gly Ile Tyr Gly Asp Tyr Ile Lys Ala Ser Gly Glu Glu Phe Pro
225                 230                 235                 240

Ser Glu Asp Tyr Lys Glu His Ile Asn Glu Phe Val Val Glu His Ser
                245                 250                 255

Phe Ala Lys His Ser His Tyr Lys Gly Lys Pro Phe Met Val Gly Ala
            260                 265                 270

Ile Ser Arg Val Val Asn Asn Lys Asp Leu Leu Tyr Gly Arg Ala Lys
        275                 280                 285

Asp Leu Tyr Glu Ser His Lys Glu Leu Leu Lys Gly Thr Asn Pro Phe
    290                 295                 300

Ala Asn Asn Leu Ala Gln Ala Leu Glu Leu Val Tyr Phe Ile Glu Arg
305                 310                 315                 320

Ala Ile Asp Leu Ile Asp Glu Val Leu Ile Lys Trp Pro Val Lys Glu
                325                 330                 335

Arg Asp Lys Val Glu Val Arg Asp Gly Phe Gly Val Ser Thr Thr Glu
            340                 345                 350

Ala Pro Arg Gly Ile Leu Val Tyr Ala Leu Lys Val Glu Asn Gly Arg
        355                 360                 365

Val Ala Tyr Ala Asp Ile Ile Thr Pro Thr Ala Phe Asn Leu Ala Met
    370                 375                 380

Met Glu Glu His Val Arg Met Met Ala Glu Lys His Tyr Asn Asp Asp
385                 390                 395                 400

Pro Glu Arg Leu Lys Leu Leu Ala Glu Met Val Val Arg Ala Tyr Asp
                405                 410                 415

Pro Cys Ile Ser Cys Ser Val His Val Val Lys Leu
            420                 425

<210> SEQ ID NO 38
<211> LENGTH: 428
<212> TYPE: PRT
<213> ORGANISM: Thermococcus kodakaraensis

<400> SEQUENCE: 38

Met Lys Asn Val Tyr Leu Pro Ile Thr Val Asp His Ile Ala Arg Val
1               5                   10                  15

Glu Gly Lys Gly Gly Val Glu Ile Val Val Gly Asp Asp Gly Val Lys
            20                  25                  30

Glu Val Lys Leu Asn Ile Ile Glu Gly Pro Arg Phe Phe Glu Ala Ile
        35                  40                  45

Thr Leu Gly Lys Lys Leu Asp Glu Ala Leu Ala Ile Tyr Pro Arg Ile
    50                  55                  60

Cys Ser Phe Cys Ser Ala Ala His Lys Leu Thr Ala Val Glu Ala Ala
65                  70                  75                  80

Glu Lys Ala Ile Gly Phe Thr Pro Arg Glu Glu Ile Gln Ala Leu Arg
                85                  90                  95

Glu Val Leu Tyr Ile Gly Asp Met Ile Glu Ser His Ala Leu His Leu
            100                 105                 110

Tyr Leu Leu Val Leu Pro Asp Tyr Leu Gly Tyr Ser Gly Pro Leu His
```

-continued

```
            115                 120                 125
Met Ile Asp Glu Tyr Lys Lys Glu Met Ser Ile Ala Leu Asp Leu Lys
    130                 135                 140

Asn Leu Gly Ser Trp Met Met Asp Glu Leu Gly Ser Arg Ala Ile His
145                 150                 155                 160

Gln Glu Asn Ala Val Leu Gly Gly Phe Gly Lys Leu Pro Asp Lys Ser
                165                 170                 175

Val Leu Glu Asn Met Lys Arg Arg Leu Lys Glu Ala Leu Pro Lys Ala
            180                 185                 190

Glu Tyr Thr Phe Glu Leu Phe Thr Lys Leu Glu Gln Tyr Glu Glu Val
        195                 200                 205

Glu Gly Pro Ile Thr His Ile Ala Val Lys Pro Arg Asn Gly Val Tyr
    210                 215                 220

Gly Ile Tyr Gly Asp Tyr Leu Lys Ala Ser Asp Gly Asn Glu Phe Pro
225                 230                 235                 240

Ser Glu Glu Tyr Arg Glu His Ile Lys Glu Phe Val Val Glu His Ser
                245                 250                 255

Phe Ala Lys His Ser His Tyr His Gly Lys Pro Phe Met Val Gly Ala
            260                 265                 270

Ile Ser Arg Leu Val Asn Asn Ala Asp Thr Leu Tyr Gly Arg Ala Lys
        275                 280                 285

Glu Leu Tyr Glu Ser Tyr Lys Asp Leu Leu Arg Ser Thr Asn Pro Phe
    290                 295                 300

Ala Asn Asn Leu Ala Gln Ala Leu Glu Leu Val Tyr Phe Thr Glu Arg
305                 310                 315                 320

Ala Ile Asp Leu Ile Asp Glu Ala Leu Ala Lys Trp Pro Ile Arg Pro
                325                 330                 335

Arg Asp Glu Val Ala Leu Lys Asp Gly Phe Gly Val Ser Thr Thr Glu
            340                 345                 350

Ala Pro Arg Gly Val Leu Val Tyr Ala Leu Lys Val Glu Asn Gly Arg
        355                 360                 365

Val Ser Tyr Ala Asp Ile Ile Thr Pro Thr Ala Phe Asn Leu Ala Met
    370                 375                 380

Met Glu Gln His Val Arg Met Met Ala Glu Lys His Tyr Asn Asp Asp
385                 390                 395                 400

Pro Glu Lys Leu Lys Leu Leu Ala Glu Met Val Val Arg Ala Tyr Asp
                405                 410                 415

Pro Cys Ile Ser Cys Ser Val His Val Ala Arg Leu
            420                 425

<210> SEQ ID NO 39
<211> LENGTH: 264
<212> TYPE: PRT
<213> ORGANISM: Thermococcus kodakaraensis

<400> SEQUENCE: 39

Met Ser Glu Lys Lys Ile Arg Ile Gly Phe Tyr Ala Leu Thr Ser Cys
1               5                   10                  15

Tyr Gly Cys Gln Leu Gln Phe Ala Met Met Asp Glu Ile Leu Gln Leu
            20                  25                  30

Ile Pro Asn Val Glu Ile Ala Cys Trp Phe Met Leu Glu Arg Asp Ser
        35                  40                  45

Tyr Glu Asp Glu Pro Val Asp Ile Ala Phe Ile Glu Gly Ser Val Ser
    50                  55                  60
```

```
Thr Glu Glu Glu Ala Glu Leu Val Lys Lys Ile Arg Glu Asn Ala Lys
 65                  70                  75                  80

Ile Val Val Ala Val Gly Ser Cys Ala Val Gln Gly Gly Val Gln Ser
                 85                  90                  95

Trp Glu Lys Asp Lys Pro Leu Glu Glu Leu Trp Lys Thr Val Tyr Gly
            100                 105                 110

Asp Ala Lys Val Lys Phe Gln Pro Lys Met Ala Glu Pro Ile Ser Asn
        115                 120                 125

Tyr Ile Lys Val Asp Tyr Asn Ile Tyr Gly Cys Pro Glu Lys Arg
    130                 135                 140

Asp Phe Leu Tyr Thr Leu Gly Thr Leu Leu Ile Gly Ser Trp Pro Glu
145                 150                 155                 160

Asp Ile Asp Tyr Pro Val Cys Leu Glu Cys Arg Leu Arg Gly Asn Thr
                165                 170                 175

Cys Val Leu Leu Glu Arg Gly Glu Pro Cys Leu Gly Pro Val Thr Arg
            180                 185                 190

Ala Gly Cys Asp Ala Arg Cys Pro Ala Tyr Gly Ile Ala Cys Ile Gly
        195                 200                 205

Cys Arg Gly Ala Ile Gly Tyr Asp Val Ala Trp Phe Asp Ser Leu Ala
210                 215                 220

Arg Val Phe Arg Glu Lys Gly Leu Thr Lys Glu Ile Leu Glu Arg
225                 230                 235                 240

Met Arg Met Phe Asn Ala His Asn Pro Lys Leu Glu Glu Met Val Asn
                245                 250                 255

Lys Ile Phe Gln Glu Val Lys Glu
            260

<210> SEQ ID NO 40
<211> LENGTH: 294
<212> TYPE: PRT
<213> ORGANISM: Thermococcus kodakaraensis

<400> SEQUENCE: 40

Met Ser Met Val Leu Pro Lys Glu Ile Met Met Pro Asn Asp Asn Pro
1               5                   10                  15

Tyr Ala Leu His Arg Ala Lys Val Leu Arg Val Tyr Pro Leu Thr Glu
            20                  25                  30

Lys Glu Lys Leu Phe Leu Phe Arg Phe Glu Asp Ala Glu Leu Ala Glu
        35                  40                  45

Lys Trp Thr Phe Arg Pro Gly Gln Phe Val Gln Leu Thr Ile Pro Gly
    50                  55                  60

Val Gly Glu Val Pro Ile Ser Ile Cys Ser Ser Ala Met Arg Arg Gly
65                  70                  75                  80

Phe Phe Glu Leu Cys Ile Arg Lys Ala Gly Arg Val Thr Thr Val Val
                85                  90                  95

His Arg Leu Lys Pro Gly Asp Thr Val Leu Val Arg Gly Pro Tyr Gly
            100                 105                 110

Asn Gly Phe Pro Val Asp Glu Trp Glu Gly Met Asp Leu Leu Leu Ile
        115                 120                 125

Ala Ala Gly Leu Gly Thr Ala Pro Leu Arg Ser Val Phe Leu Tyr Ala
    130                 135                 140

Met Asp Asn Arg Trp Lys Tyr Gly Asn Ile Thr Phe Ile Asn Thr Ala
145                 150                 155                 160

Arg Tyr Gly Lys Asp Leu Leu Phe Tyr Lys Glu Leu Glu Ala Met Lys
                165                 170                 175
```

```
Asp Leu Ala Glu Ala Glu Asn Val Lys Ile Ile Gln Ser Val Thr Arg
            180                 185                 190

Asp Pro Asp Trp Pro Gly Leu His Gly Arg Pro Gln Asn Phe Ile Pro
        195                 200                 205

Glu Ala Asn Thr Asn Pro Lys Lys Thr Ala Val Ala Ile Cys Gly Pro
    210                 215                 220

Pro Arg Met Tyr Lys Ala Val Phe Glu Ala Leu Ile Asn Tyr Gly Tyr
225                 230                 235                 240

Arg Pro Glu Asn Ile Tyr Val Thr Leu Glu Arg Lys Met Lys Cys Gly
                245                 250                 255

Ile Gly Lys Cys Gly His Cys Asn Val Gly Thr Ser Thr Ser Trp Lys
            260                 265                 270

Tyr Val Cys Lys Asp Gly Pro Val Phe Gly Tyr Phe Asp Ile Ile Ser
        275                 280                 285

Thr Pro Gly Leu Leu Asp
    290

<210> SEQ ID NO 41
<211> LENGTH: 367
<212> TYPE: PRT
<213> ORGANISM: Thermococcus kodakaraensis

<400> SEQUENCE: 41

Met Arg Tyr Val Lys Leu Pro Lys Glu Asn Thr Tyr Thr Phe Leu Glu
1               5                   10                  15

Arg Leu Lys Glu Trp Gly Lys Leu Tyr Ala Pro Val Lys Ile Ser Glu
            20                  25                  30

Lys Phe Tyr Asp Phe Arg Glu Ile Asp Asp Val Arg Lys Val Glu Phe
        35                  40                  45

Asn Tyr Asn Arg Thr Ile Met Pro Pro Lys Lys Phe Phe Phe Leu Pro
    50                  55                  60

Arg Glu Lys Leu Phe Glu Phe Asp Leu Ser Arg Pro Glu Tyr Arg Glu
65                  70                  75                  80

Thr Ile Glu Asp Val Glu Pro Phe Val Ile Phe Gly Leu His Ala Cys
                85                  90                  95

Asp Ile His Gly Leu Lys Ile Leu Asp Thr Val Tyr Leu Asp Glu Leu
            100                 105                 110

Pro Asp Lys Tyr Tyr Lys Ala Arg Arg Glu Lys Gly Ile Ile Ile Gly
        115                 120                 125

Ile Ser Cys Met Pro Asp Glu Tyr Cys Phe Cys Asn Leu Arg Glu Thr
    130                 135                 140

Asp Phe Ala Asp Asp Gly Phe Asp Leu Phe Leu His Glu Leu Pro Asp
145                 150                 155                 160

Gly Trp Leu Val Arg Val Gly Ser Pro Thr Gly His Arg Ile Val Asp
                165                 170                 175

Lys Asn Met Glu Leu Phe Glu Glu Val Thr Thr Glu Asp Ile Cys Asn
            180                 185                 190

Phe Arg Glu Phe Glu Asn Lys Arg Ser Gln Ala Phe Lys Tyr His Glu
        195                 200                 205

Asp Trp Ser Asn Leu Arg Tyr Leu Leu Glu Leu Met Glu His Pro
    210                 215                 220

Met Trp Glu Glu Gln Ala Asp Leu Cys Leu Ala Cys Gly Ile Cys Asn
225                 230                 235                 240

Thr Thr Cys Pro Thr Cys Arg Cys Tyr Glu Val Gln Asp Ile Val Asn
```

```
                        245                 250                 255
Leu Asp Gly Asn Thr Gly Tyr Arg Glu Arg Arg Trp Asp Ser Cys Gln
            260                 265                 270

Phe Arg Ser His Gly Leu Val Ala Gly Gly His Asn Phe Arg Pro Thr
            275                 280                 285

Lys Lys Asp Arg Phe Arg Asn Arg Tyr Leu Cys Lys Asn Ser Tyr Asn
            290                 295                 300

Glu Lys Leu Gly Leu Ser Tyr Cys Val Gly Cys Gly Arg Cys Thr Tyr
305                 310                 315                 320

Phe Cys Pro Ala Gly Ile Ser Phe Val Arg Asn Leu Arg Thr Ile Leu
            325                 330                 335

Gly Leu Glu Glu Lys Ser Cys Pro Ser Glu Ile Thr Glu Glu Ile Pro
            340                 345                 350

Lys Arg Gly Phe Ala Tyr Ala Ser His Ile Arg Gly Asp Gly Leu
            355                 360                 365

<210> SEQ ID NO 42
<211> LENGTH: 372
<212> TYPE: PRT
<213> ORGANISM: Pyrococcus horikoshii

<400> SEQUENCE: 42

Met Glu Val Ile Leu Leu Arg Tyr Val Lys Leu Pro Lys Glu Asn Thr
1               5                   10                  15

Tyr Glu Phe Leu Glu Arg Leu Lys Glu Trp Gly Lys Leu Tyr Ala Pro
            20                  25                  30

Val Lys Ile Ser Glu Lys Phe Tyr Asp Phe Arg Glu Ile Asp Asp Val
            35                  40                  45

Arg Lys Val Glu Phe His Tyr Thr Arg Thr Ile Met Pro Pro Lys Lys
50                  55                  60

Phe Phe Phe Lys Pro Arg Glu Lys Met Phe Glu Phe Asp Leu Ser Lys
65                  70                  75                  80

Pro Glu Tyr Lys Glu Val Ile Glu Asp Val Glu Pro Phe Val Leu Phe
            85                  90                  95

Gly Val His Ala Cys Asp Ile Tyr Gly Leu Lys Ile Leu Asp Thr Ile
            100                 105                 110

Tyr Leu Asp Glu Leu Pro Asp Lys Tyr Lys Ile Arg Arg Glu Lys
            115                 120                 125

Gly Ile Ile Ile Gly Ile Ser Cys Met Pro Asp Glu Tyr Cys Phe Cys
130                 135                 140

Asn Leu Arg Lys Thr Asp Phe Ala Asp Asp Gly Phe Asp Leu Phe Leu
145                 150                 155                 160

His Glu Leu Pro Asp Gly Trp Leu Val Arg Val Gly Ser Pro Thr Gly
            165                 170                 175

His Arg Ile Val Asp Lys Asn Ile Lys Leu Phe Glu Glu Val Thr Asp
            180                 185                 190

Glu Asp Ile Cys Ala Phe Arg Glu Phe Glu Lys Lys Arg Gln Glu Ala
            195                 200                 205

Phe Lys Tyr His Glu Asp Trp Asp Asn Leu Arg Tyr Leu Leu Glu Leu
            210                 215                 220

Glu Met Glu His Pro Met Trp Glu Glu Glu Ala Asn Lys Cys Leu Ala
225                 230                 235                 240

Cys Gly Ile Cys Thr Leu Thr Cys Pro Thr Cys Arg Cys Tyr Glu Val
            245                 250                 255
```

Gln Asp Ile Val Asn Leu Asp Gly Ile Thr Gly Tyr Arg Glu Arg Arg
                    260                 265                 270

Trp Asp Ser Cys Gln Phe Arg Ser His Gly Leu Val Ala Gly Gly His
            275                 280                 285

Asn Phe Arg Pro Thr Lys Lys Asp Arg Phe Arg Asn Arg Tyr Leu Cys
        290                 295                 300

Lys Asn Ala Tyr Asn Glu Lys Leu Gly Leu Ser Tyr Cys Val Gly Cys
305                 310                 315                 320

Gly Arg Cys Thr Ala Phe Cys Pro Ala Gly Ile Ser Phe Val Arg Asn
                325                 330                 335

Leu Arg Val Ile Leu Gly Phe Glu Glu Gln Arg Cys Pro Pro Asn Val
            340                 345                 350

Ser Glu Glu Ile Pro Lys Lys Gly Phe Ala Tyr Ser Pro Gly Val Gly
        355                 360                 365

Gly Asp Glu Glu
    370

<210> SEQ ID NO 43
<211> LENGTH: 292
<212> TYPE: PRT
<213> ORGANISM: Pyrococcus horikoshii

<400> SEQUENCE: 43

Met Asn Leu Pro Lys Asp Val Met Pro Asn Asp Asn Pro Tyr Ala
1               5                   10                  15

Leu His Arg Val Lys Val Leu Lys Val Tyr Asp Leu Thr Glu Lys Glu
                20                  25                  30

Lys Leu Phe Leu Phe Arg Phe Glu Asp Pro Lys Leu Ala Glu Thr Trp
            35                  40                  45

Thr Phe Lys Pro Gly Gln Phe Val Gln Leu Thr Ile Pro Gly Val Gly
        50                  55                  60

Glu Val Pro Ile Ser Ile Cys Ser Ser Pro Met Arg Arg Gly Phe Phe
65                  70                  75                  80

Glu Leu Cys Ile Arg Arg Ala Gly Arg Val Thr Thr Val Val His Arg
                85                  90                  95

Leu Lys Pro Gly Asp Ile Val Leu Val Arg Gly Pro Tyr Gly Asn Gly
                100                 105                 110

Phe Pro Val Asp Glu Trp Glu Gly Met Asp Leu Leu Leu Ile Ala Ala
            115                 120                 125

Gly Leu Gly Ala Ala Pro Leu Arg Ser Val Phe Leu Tyr Ala Met Asp
        130                 135                 140

Asn Arg Trp Lys Tyr Gly Asn Ile Thr Phe Ile Asn Thr Ala Arg Tyr
145                 150                 155                 160

Gly Lys Asp Leu Leu Phe Tyr Lys Glu Leu Glu Ala Ile Lys Asp Leu
                165                 170                 175

Ala Glu Ala Glu Asn Val Lys Ile Ile Gln Ser Val Thr Arg Asp Pro
            180                 185                 190

Asn Trp Pro Gly Leu His Gly Arg Pro Gln Gln Phe Ile Val Glu Ala
        195                 200                 205

Asn Thr Asn Pro Lys Asn Thr Ala Val Ala Ile Cys Gly Pro Pro Arg
210                 215                 220

Met Tyr Lys Ser Val Phe Glu Ala Leu Ile Asn Tyr Gly Tyr Arg Pro
225                 230                 235                 240

Glu Asn Ile Tyr Val Thr Leu Glu Arg Lys Met Lys Cys Gly Ile Gly
                245                 250                 255

```
Lys Cys Gly His Cys Val Val Gly Thr Ser Thr Ser Leu Lys Tyr Ile
        260                 265                 270

Cys Lys Asp Gly Pro Val Phe Thr Tyr Phe Asp Ile Val Ser Thr Pro
        275                 280                 285

Gly Leu Leu Asp
        290

<210> SEQ ID NO 44
<211> LENGTH: 265
<212> TYPE: PRT
<213> ORGANISM: Pyrococcus horikoshii

<400> SEQUENCE: 44

Met Gly Glu Met Gly Lys Lys Ile Arg Ile Gly Phe Tyr Ala Leu
1               5                   10                  15

Thr Ser Cys Tyr Gly Cys Gln Leu Gln Leu Ala Met Met Asp Glu Leu
                20                  25                  30

Leu Leu Leu Leu Pro His Ile Glu Leu Val Cys Trp Tyr Met Val Asp
            35                  40                  45

Arg Asp Ser Ile Asp Asp Glu Pro Val Asp Ile Ala Phe Ile Glu Gly
        50                  55                  60

Ser Val Ser Thr Glu Glu Val Glu Leu Val Lys Lys Ile Arg Glu
65                  70                  75                  80

Asn Ser Lys Ile Val Val Ala Val Gly Ala Cys Ala Val Gln Gly Gly
                85                  90                  95

Val Gln Ser Trp Asp Lys Ser Leu Glu Glu Leu Trp Arg Thr Val Tyr
            100                 105                 110

Gly Asp Ala Lys Val Lys Phe Lys Pro Lys Lys Ala Glu Pro Val Ser
        115                 120                 125

Lys Tyr Ile Lys Val Asp Tyr Asn Ile Tyr Gly Cys Pro Pro Glu Lys
130                 135                 140

Arg Asp Phe Leu Tyr Ala Leu Gly Thr Phe Leu Ile Gly Ser Trp Pro
145                 150                 155                 160

Glu Asp Ile Asp Tyr Pro Val Cys Leu Glu Cys Arg Leu Asn Gly Tyr
                165                 170                 175

Pro Cys Val Leu Leu Glu Lys Gly Glu Pro Cys Leu Gly Pro Val Thr
            180                 185                 190

Arg Ala Gly Cys Asn Ala Arg Cys Pro Gly Phe Gly Ile Ala Cys Ile
        195                 200                 205

Gly Cys Arg Gly Ala Ile Gly Tyr Asp Val Ala Trp Phe Asp Ser Leu
    210                 215                 220

Ala Arg Val Phe Lys Glu Lys Gly Leu Thr Lys Glu Glu Ile Ile Glu
225                 230                 235                 240

Arg Met Lys Ile Phe Asn Gly His Asp Asp Arg Ile Glu Lys Met Val
                245                 250                 255

Glu Lys Ile Phe Gln Gly Val Lys Glu
            260                 265

<210> SEQ ID NO 45
<211> LENGTH: 429
<212> TYPE: PRT
<213> ORGANISM: Pyrococcus horikoshii

<400> SEQUENCE: 45

Met Lys Glu Ile Tyr Ile Pro Ile Thr Val Asp His Ile Ala Arg Ile
1               5                   10                  15
```

```
Glu Gly Lys Ala Gly Val Glu Ile Leu Val Gly Asp Gly Val Lys
         20                  25                  30
Glu Val Lys Leu Asn Ile Ile Glu Gly Pro Arg Phe Phe Glu Ala Ile
             35                  40                  45
Thr Leu Gly Lys Lys Leu Glu Glu Ala Leu Ala Ile Tyr Pro Arg Ile
 50                  55                  60
Cys Ser Phe Cys Ser Ala Ala His Lys Leu Thr Ala Leu Glu Ala Ala
 65                  70                  75                  80
Glu Lys Ala Ile Gly Phe Thr Pro Arg Glu Glu Ile Gln Ala Leu Arg
             85                  90                  95
Glu Ile Leu Tyr Ile Gly Asp Ile Ile Glu Ser His Ala Leu His Leu
                100                 105                 110
Tyr Leu Leu Val Leu Pro Asp Tyr Leu Gly Tyr Ser Ser Pro Leu Lys
             115                 120                 125
Met Val Asp Glu Tyr Lys Lys Glu Leu Glu Thr Ala Ile Lys Leu Lys
     130                 135                 140
Asn Leu Gly Ser Trp Ile Met Asp Val Leu Gly Ala Arg Ala Ile His
145                 150                 155                 160
Gln Glu Asn Ala Ile Leu Gly Gly Phe Gly Lys Leu Pro Ser Lys Glu
                165                 170                 175
Thr Leu Glu Lys Ile Lys Asp Glu Leu Lys Ser Ala Leu Pro Leu Ala
             180                 185                 190
Glu Tyr Thr Phe Glu Leu Phe Ser Lys Leu Glu Gln Tyr Lys Glu Val
         195                 200                 205
Glu Gly Glu Ile Thr His Leu Ala Val Lys Pro Arg Lys Asp Ala Tyr
     210                 215                 220
Gly Ile Tyr Gly Asp Arg Ile Lys Ala Ser Asp Gly Glu Glu Phe Pro
225                 230                 235                 240
Ser Glu Glu Tyr Lys Asn Tyr Ile Lys Glu Phe Val Val Glu His Ser
                245                 250                 255
Phe Ala Lys His Ser His Tyr Lys Gly Arg Pro Phe Met Val Gly Ala
             260                 265                 270
Ile Ser Arg Leu Val Asn Asn His Lys Leu Leu Tyr Gly Lys Ala Lys
         275                 280                 285
Glu Leu Tyr Glu Asn Asn Lys Asp Leu Leu Arg Pro Thr Asn Pro Phe
     290                 295                 300
Ala Asn Asn Leu Ala Gln Ala Leu Glu Ile Val Tyr Phe Met Glu Arg
305                 310                 315                 320
Ala Ile Asp Leu Ile Asp Glu Val Leu Ala Lys Trp Pro Ile Lys Pro
                325                 330                 335
Arg Asp Glu Val Lys Val Arg Asp Gly Phe Gly Val Ser Thr Thr Glu
             340                 345                 350
Ala Pro Arg Gly Ile Leu Val Tyr Ala Leu Lys Val Glu Asn Gly Arg
         355                 360                 365
Val Ser Tyr Ala Asp Ile Ile Thr Pro Thr Ala Phe Asn Leu Ala Met
     370                 375                 380
Met Glu Arg His Val Arg Met Met Ala Glu Glu His Tyr Lys Asp Asp
385                 390                 395                 400
Pro Glu Lys Leu Lys Leu Leu Ala Glu Met Val Val Arg Ala Tyr Asp
                405                 410                 415
Pro Cys Ile Ser Cys Ser Val His Val Val Lys Leu Gln
             420                 425
```

```
<210> SEQ ID NO 46
<211> LENGTH: 18
<212> TYPE: PRT
<213> ORGANISM: artificial
<220> FEATURE:
<223> OTHER INFORMATION: consensus L1 site
<220> FEATURE:
<221> NAME/KEY: MISC_FEATURE
<222> LOCATION: (2)..(2)
<223> OTHER INFORMATION: the amino acid at position 2 is Ile or Val
<220> FEATURE:
<221> NAME/KEY: MISC_FEATURE
<222> LOCATION: (4)..(4)
<223> OTHER INFORMATION: the amino acid at position 4 is Ala, Gly, or
      Ser
<220> FEATURE:
<221> NAME/KEY: MISC_FEATURE
<222> LOCATION: (5)..(5)
<223> OTHER INFORMATION: the amino acid at position 5 is Phe, Ile, or
      Leu
<220> FEATURE:
<221> NAME/KEY: MISC_FEATURE
<222> LOCATION: (7)..(9)
<223> OTHER INFORMATION: the amino acids at position 7-9 can be any
      amino acid
<220> FEATURE:
<221> NAME/KEY: MISC_FEATURE
<222> LOCATION: (10)..(10)
<223> OTHER INFORMATION: the amino acid at position 10 is His or Tyr
<220> FEATURE:
<221> NAME/KEY: MISC_FEATURE
<222> LOCATION: (11)..(12)
<223> OTHER INFORMATION: the amino acids at position 11-12 can be any
      amino acid
<220> FEATURE:
<221> NAME/KEY: MISC_FEATURE
<222> LOCATION: (13)..(13)
<223> OTHER INFORMATION: the amino acid at position 13 is Ala, Ser, or
      Thr
<220> FEATURE:
<221> NAME/KEY: MISC_FEATURE
<222> LOCATION: (14)..(14)
<223> OTHER INFORMATION: the amino acid at position 14 is Ala, Asn, or
      Ser
<220> FEATURE:
<221> NAME/KEY: MISC_FEATURE
<222> LOCATION: (15)..(16)
<223> OTHER INFORMATION: the amino acids at position 15-16 can be any
      amino acid
<220> FEATURE:
<221> NAME/KEY: MISC_FEATURE
<222> LOCATION: (17)..(17)
<223> OTHER INFORMATION: the amino acid at position 17 is Ala or Ser
<220> FEATURE:
<221> NAME/KEY: MISC_FEATURE
<222> LOCATION: (18)..(18)
<223> OTHER INFORMATION: the amino acid at position 18 is Ala, Ile, Leu,
      or Val

<400> SEQUENCE: 46

Arg Xaa Cys Xaa Xaa Cys Xaa Xaa Xaa Xaa Xaa Xaa Xaa Xaa Xaa Xaa
1               5                   10                  15

Xaa Xaa

<210> SEQ ID NO 47
<211> LENGTH: 18
<212> TYPE: PRT
<213> ORGANISM: artificial
<220> FEATURE:
<223> OTHER INFORMATION: L1 site

<400> SEQUENCE: 47

Arg Ile Cys Ser Phe Cys Ser Ala Ala His Lys Leu Thr Ala Leu Glu
1               5                   10                  15
```

Ala Ala

<210> SEQ ID NO 48
<211> LENGTH: 18
<212> TYPE: PRT
<213> ORGANISM: artificial
<220> FEATURE:
<223> OTHER INFORMATION: L1 site

<400> SEQUENCE: 48

Arg Val Cys Gly Ile Cys Ser Ala Ala His Lys Leu Thr Ala Leu Glu
1               5                   10                  15

Ala Ala

<210> SEQ ID NO 49
<211> LENGTH: 12
<212> TYPE: PRT
<213> ORGANISM: artificial
<220> FEATURE:
<223> OTHER INFORMATION: consensus L2 site
<220> FEATURE:
<221> NAME/KEY: MISC_FEATURE
<222> LOCATION: (2)..(2)
<223> OTHER INFORMATION: the amino acid at position 2 is Ala, Asn, or
      Ser
<220> FEATURE:
<221> NAME/KEY: MISC_FEATURE
<222> LOCATION: (3)..(3)
<223> OTHER INFORMATION: the amino acid at position 3 is Phe, His, or
      Tyr
<220> FEATURE:
<221> NAME/KEY: MISC_FEATURE
<222> LOCATION: (10)..(10)
<223> OTHER INFORMATION: the amino acid at position 10 is Ala or Ser
<220> FEATURE:
<221> NAME/KEY: MISC_FEATURE
<222> LOCATION: (11)..(11)
<223> OTHER INFORMATION: the amino acid at position 11 is Ala, Thr, or
      Val

<400> SEQUENCE: 49

Arg Xaa Xaa Asp Pro Cys Ile Ser Cys Xaa Xaa His
1               5                   10

<210> SEQ ID NO 50
<211> LENGTH: 81
<212> TYPE: DNA
<213> ORGANISM: Escherichia coli

<400> SEQUENCE: 50
ggtcatcacc atcatcacca cggctcgatc acaagtttgt acaaaaaagc aggctcagaa      60
aacctgtatt ttcagggagg a                                                81

<210> SEQ ID NO 51
<211> LENGTH: 28
<212> TYPE: PRT
<213> ORGANISM: artificial
<220> FEATURE:
<223> OTHER INFORMATION: fusion protein fragment

<400> SEQUENCE: 51

Met Gly His His His His His His Gly Ser Ile Thr Ser Leu Tyr Lys
1               5                   10                  15

Lys Ala Gly Ser Glu Asn Leu Tyr Phe Gln Gly Gly
                20                  25

```
<210> SEQ ID NO 52
<211> LENGTH: 10
<212> TYPE: DNA
<213> ORGANISM: artificial
<220> FEATURE:
<223> OTHER INFORMATION: CD-ABI intergenic sequence

<400> SEQUENCE: 52
gaggtggaaa                                                            10

<210> SEQ ID NO 53
<211> LENGTH: 72
<212> TYPE: DNA
<213> ORGANISM: artificial
<220> FEATURE:
<223> OTHER INFORMATION: hypD-hypA intergenic sequence

<400> SEQUENCE: 53
tttacaaata tggcgccctg atgtaggagg tggaaaatgc acgaatgggc gttggcagat     60
gcaatagtaa gg                                                         72

<210> SEQ ID NO 54
<211> LENGTH: 75
<212> TYPE: DNA
<213> ORGANISM: artificial
<220> FEATURE:
<223> OTHER INFORMATION: hypE-hypF intergenic sequence

<400> SEQUENCE: 54
gtgatcccgt tcctagagtt tgttaggagg tggaaaatga tctgggggag agaatgaaag     60
cttatagaat tcacg                                                      75

<210> SEQ ID NO 55
<211> LENGTH: 813
<212> TYPE: DNA
<213> ORGANISM: artificial
<220> FEATURE:
<223> OTHER INFORMATION: modified sequence of expression vector

<400> SEQUENCE: 55
ggatccccgt caccctggat gctgtacaat tgacgacgac aagggcccgg gcaaactagt     60
aatcagacgc ggtcgttcac ttgttcagca accagatcaa aagccattga ctcagcaagg    120
gttgaccgta taattcacgc gattacaccg cattgcggta tcaacgcgcc cttagctcag    180
ttggatagag caacgacctt ctaagtcgtg ggccgcaggt tcgaatcctg cagggcgcgc    240
cattacaatt caatcagtta cgccttcttt atatcctcca gccatggcct tgaaatggcg    300
ttagtcatga aatatagacc gccatcgagt acccccttgta cccttaactc ttcctgatac    360
gtaaataatg atttggtggc ccttgctgga cttgaaccag cgaccaagcg attatgagtc    420
gcctgctcta accactgagc taaagggcct tgagtgtgca ataacaatac ttataaacca    480
cgcaataaac atgatgatct agagaatccc gtcgtagcca ccatcttttt ttgcgggagt    540
ggcgaaattg gtagacgcac cagatttagg ttctggcgcc gctaggtgtg cgagttcaag    600
tctcgcctcc cgcaccattc accagaaagc gttgatcgga tgccctcgag tcgggcagcg    660
ttgggtcctg gccacgggtg cgcatgatcg tgctcctgtc gttgaggacc cggctaggct    720
ggcggggttg ccttactggt tagcagaatg aatcaccgat acgcgagcga acgtgaagcg    780
actgctgctg caaaacgtct gcgacctgag ctc                                 813

<210> SEQ ID NO 56
```

<211> LENGTH: 10484
<212> TYPE: DNA
<213> ORGANISM: Pyrococcus furiosus

<400> SEQUENCE: 56

| | | | | | |
|---|---|---|---|---|---|
| aggggttttt | aacctttggt | tttcaattt | cgggtttaaa | aaggcttttt | tatctccctc | 60 |
| accaacttta | gactgggaaa | caaaaatgtt | cactaacgaa | aatttgagga | gtattggtca | 120 |
| attatgctca | ttgggaggtg | gtttgtgtga | ggtatgttaa | gttacccaag | gaaaacactt | 180 |
| acgagttttt | ggaaagactt | aaagactggg | ggaagcttta | cgctccagta | aaaatttcgg | 240 |
| acaagttcta | tgacttcagg | gagattgatg | atgttagaaa | gatagaattc | cactacaaca | 300 |
| ggacaataat | gccacctaag | aagttcttct | tcaagccgag | ggaaaagctc | tttgagttcg | 360 |
| acatttcaaa | accagaatac | agggaggtaa | tagaggaagt | tgaaccattt | attatatttg | 420 |
| gagtccacgc | gtgtgacata | tatggcctaa | agatcctaga | cacggtatac | cttgatgagt | 480 |
| tccccgacaa | gtactacaag | gtgaggagag | agaaggggat | aatcattgga | ataagctgta | 540 |
| tgccagatga | atattgcttc | tgtaacttaa | gagaaacaga | cttcgctgat | gatggttttg | 600 |
| acttgttctt | ccatgaactg | cccgatggat | ggttggtaag | ggttggcact | ccaactgggc | 660 |
| acaggcttgt | tgacaagaac | ataaagctct | ttgaagaggg | aacggacaag | gatatctgtg | 720 |
| catttagaga | ttttgaaaag | aggagacagc | aagcattcaa | ataccacgaa | gactggggca | 780 |
| acttgaggta | tcttctcgag | ttggaaatgg | aacatccaat | gtgggatgag | gaggcagata | 840 |
| agtgcttggc | ttgtggaata | tgtaacacca | catgcccaac | gtgtagatgc | tatgaagttc | 900 |
| aggatattgt | aaacctagat | ggagttactg | gatacaggga | aagaagatgg | gattcttgtc | 960 |
| agttcagaag | tcatggctta | gttgctgggg | gccacaactt | caggcccaca | agaaggatc | 1020 |
| gctttaggaa | cagatacctc | tgtaagaacg | catataacga | aaagcttgga | ttaagctact | 1080 |
| gtgtcggttg | tggaaggtgt | actgcattct | gtccagccaa | tataagtttt | gtaggcaatc | 1140 |
| ttagaaggat | tttaggactt | gaggagaaca | aatgtccccc | aacggttagt | gaggagattc | 1200 |
| caaagagagg | atttgcatat | tcctctaaca | ttagaggtga | tggagtatga | tgttgccaaa | 1260 |
| agagattatg | atgccaaatg | ataatccgta | tgcccttcat | agagtcaaag | ttctaaaggt | 1320 |
| ttactccttg | acggaaacgg | aaaagctttt | cctctttaga | tttgaggatc | ccgagttggc | 1380 |
| agagaagtgg | acgttcaaac | ctggacagtt | tgtccagctg | acgatacctg | gagttggaga | 1440 |
| ggttcccata | agtatatgct | cttctccaat | gaggaaagga | ttctttgagc | tctgtataag | 1500 |
| aaaggcagga | agggtcacaa | ctgttgtcca | tagactaaag | cctggcgata | ctgttcttgt | 1560 |
| gagagggcct | tacggtaatg | gattcccagt | ggatgagtgg | gaaggaatgg | atctactatt | 1620 |
| aatagctgct | ggccttggaa | ctgcacctct | taggagcgtc | tttctctatg | caatggacaa | 1680 |
| caggtggaag | tatggaaaca | ttaccttcat | aaacaccgca | cgttatggga | aggatctcct | 1740 |
| cttctacaag | gagctggagg | caatgaaaga | cctagctgag | gctgaaaacg | tgaaaatcat | 1800 |
| ccagagcgtc | actagggatc | caaactggcc | gggcctaaag | ggtaggccac | agcagttcat | 1860 |
| cgttgaggcc | aacacaaatc | caaagaacac | tgcagttgca | atctgtgggc | ctcctagaat | 1920 |
| gtataagtca | gtgtttgagg | ccctcatcaa | ctacggttat | cgcccagaga | acatcttcgt | 1980 |
| gacattggag | agaagaatga | aatgtggaat | cgggaagtgc | ggccactgca | acgtcggaac | 2040 |
| gagcacgagc | tggaagtaca | tctgtaaaga | tggaccagtc | ttcacgtact | tcgacatagt | 2100 |
| ttcaaccccca | ggactgctgg | actgaggtga | ggaaaatggg | aaaagttagg | attggatttt | 2160 |
| acgcattaac | ctcgtgctac | ggctgtcaat | tgcagctagc | tatgatggac | gagttattac | 2220 |

```
aacttatccc aaatgctgaa atagtttgct ggttcatgat tgatagagat agcattgagg   2280
atgaaaaggt cgacatagct tttatagaag gaagcgtttc aactgaggaa gaagttgaac   2340
tcgtgaaaaa aattagggag aatgcaaaga tcgtcgttgc ggttggagct tgtgctgttc   2400
aaggaggagt tcagagctgg agtgaaaagc cattagaaga gctctggaag aaggtttatg   2460
gagacgcaaa agtcaagttc caaccgaaga aggctgaacc agtttcaaaa tacataaaag   2520
ttgactacaa catctacggt tgcccaccag agaagaagga cttcctctac gccctgggaa   2580
cattcttgat tggttcatgg ccagaggata tagattatcc agtttgtcta gaatgtaggc   2640
tcaatggaca tccatgtatc cttcttgaga aaggagaacc ctgtctaggt ccagtaacaa   2700
gggcaggatg taacgcgaga tgtccaggat ttggagttgc gtgtatagga tgcagagggg   2760
caataggta cgatgtagct tggttcgact ctctagctaa ggtgttcaag agaaggggga   2820
tgacaaaaga ggagataatt gagagaatga aaatgttcaa tggacatgat gagagggttg   2880
agaaaatggt tgaaaaaata ttctcaggtg gtgaacaatg aagaacctct atcttccaat   2940
caccattgat catatagcaa gagttgaggg gaagggtggt gtggagataa taattgggga   3000
tgatggagtc aaggaggtca agctaaacat aattgaaggg cccagattct ttgaggccat   3060
aactattggg aagaagcttg aggaagctct ggccatttac ccgagaatat gctcattctg   3120
ttcagccgcc cacaagttaa ccgcattaga ggctgcagaa aaggccgtcg gttttgtccc   3180
aagggaagag atacaggccc ttagagaagt actatacatc ggagacatga tagagagtca   3240
tgcccttcac ctatatcttc tagttcttcc cgactacagg ggctactcga gcccacttaa   3300
gatggtgaat gaatacaaga gggagataga gatagccctt aagctgaaga accttggcac   3360
ctggatgatg gacattctag ggtcaagagc catacaccaa gaaaatgcgg ttttgggcgg   3420
attcggaaag ctccctgaga agagtgtcct tgagaaaatg aaagccgagc ttagggaagc   3480
cctaccactt gccgagtata cttttgagtt atttgcaaag cttgagcagt acagcgaagt   3540
tgaagggcca ataacacact tggccgtgaa gccgagggga gatgcttatg gaatttatgg   3600
agattacata aaggcaagtg atggggagga gttcccaagt gaaaagtaca gagattatat   3660
aaaggagttc gtcgttgaac acagttttgc aaagcacagt cactcaaagg gcagacccct   3720
catggttggg gctatatcta gagttattaa caatgctgac ctcctatacg gcaaggccaa   3780
ggagctgtat gaggcaaaca aagacctatt aaagggaaca aatccgtttg caaataactt   3840
agcccaggcc ctcgaaatag tttacttttat agagagggca atagatctgc tcgacgaggc   3900
tctcgccaag tggccaatta agcccaggga tgaagttgag ataaaggacg ctttggtgt   3960
ctcaacgact gaggctccaa ggggaatctt agtctatgcc ctcaaagttg agaatggaag   4020
ggtttcttat gccgacataa taacacctac agcattcaac ttggcaatga tggaagaaca   4080
tgtaagaatg atggcagaaa agcactacaa tgacgatcca gaaaggttaa agatactggc   4140
tgagatggtt gttagggctt atgatccatg catatcttgc tcagtccacg tggttagact   4200
ttaatccttt ttatctattt ttgttgagta cttgtggaga ttctcattca catcacaata   4260
ggagagctct tctcttgagg agatgataac aatgcccttc tctttgagaa tttcgaggat   4320
agactttagg acttttatgtt ttgagtcctc atcaatggca caactggat cgtcaagaac   4380
ataaatctcg gcattcacta gcaaggtgga tgccaattga actcttctaa ttgttccctg   4440
ggaaagctct cccagcttct tctttaaatc caagacctcc acggattcaa gtgcatccat   4500
aatttcattt ttattaactt taactccata aagactggcc actgcttta aataatcctc   4560
```

```
aacacttatt ttcctgggca cgattatttc ttcaggaagg aaaaatattt tgcccttaac      4620
ttttgttata gggactccat tataaattat ttctcccttg aggggtttca aatatgttga      4680
tattgttttt aaaagtgtgg ttttttcctat cccatttgga ccgtggaagt tcacgacatt    4740 accttctct atggtcattg ttattctttc gagaactggt ttatcataac caacactaag      4800
atctctaatc tcaagtttca ttcccatccc tcccaaattc ctattattcc agaaatagat     4860
actaaaagga gggggattgc agcaatacca tttcctttgc taaccaatat tattcctata     4920
atgaagggag ctatgaatcc aagaatccag ccacacaact ttctaattga actaacttcc     4980
actgtcggtt cccacacaaa cattaatttc ttgaaatcta tagttacttt tacaggtgtc     5040
attaggggaa gatattgaag aacttcatga acatataccg ctccaactag tggcaacact     5100
acatttttca ctatagattt catatagcaa ttagtgaatt cccctgttat tttacctata    5160
agaaaactaa tccaaagtac tagagctaca agaaatccta catatatgct taccattttt    5220
atgaaattta aaaattgcct agacattct tatcaccctt tctagcttta tcctcacaaa     5280
atatgcaagt ggagagataa gaattaacaa gggaattacc cacataggaa taatttcct     5340 tataataaat ggagcaccca ggataattag atacagaaat aggaagctgt ttctttcaaa    5400
acttggcaat gttattgata atacaactct acttatcgct aacatgaaaa ataagatata    5460
tagtgtccct aaatactccc tttcaagaat tgccaaggaa taaaatgtca acggaacaat    5520
tagcgaaatc aagaagagta gaatttcctt tattagtctt cttaaatagt tctctggttt    5580
tagatagtgg atataggcta tataagaatc aacataacta tcaccaacca ggaataaagg    5640
ccaaatcata ggggcagtta tgcatatagt aactagcgta cttgcaatcc tctctataat    5700
atagaatttt tgcttatcta caatgatatg taatggtaac aaggctttaa atgctccaac    5760
tccacaccca aatttcactc cttgcattct caggtgctgg gccataagtg tgaaaactat    5820
agagagaata atagcgattc ccctaatttc aaaggaaagg gtagaaatat agatgtttct    5880
aactagataa actcttatca gcctatcttt tagaacagag gctaccaagt atgcaattac    5940
gaggatgata taacctatca gagtcatctt tctaccacta attgctagga gaccaagaat    6000
tgtggctatg cacttaatt taaatgaaac agacagtgga agtatagata aagcggcaaa    6060
tacaataata ttggagggca aaaaacctgg gtaaagatag gagcaactaa ggatggaggg    6120
gagatttata actactgaga caaatagcac aatgagatca gtgtcgggtc tatatttgag    6180
gatcactcca gttttcttag gatcaaagga atttgaaaag agaagtggaa ttgcacctaa    6240
caaggcaaaa actattatgt cttcgataat cttaccttt aagaagattg ttaatggtat     6300
aagagagatc atcccagcga gataattata gttttttata gataccaaaa tatggtatct    6360
taatatttcc actattctca ctttcattac ctcctaaatc ttctaaggat ttttattgag    6420
ctcacaaccc ccaaaagata acataggatt cttgttattg gagttaccct tactgagaca    6480
taatatggct catttattgc attaaataga atgccctgcc cgggtggtat tttatttgta    6540
gtcaaaatga agattgccaa caaataacta actaaaatag aaaatgaaag agctaagggt    6600
attgccgaaa ccaaggctag ggcaaaaaat agttttttag atcttaccac acgaaatcac    6660
ctcctatcgc agttggaagc gctggatctg taggattatc tggcatacat tcacagaggc    6720
atttgatctc aactcctgaa atagttgctt ttgtctgtgg cccacagtcg acattatac    6780 ctccacctgt actacacaag attgggcact ccctacaata gccatagcac atctttgtgt    6840
agtatgtcgc tgtagcagct attattacaa ataaaactat tacccacaat cctacaccat    6900 aatactttg ttttctttaa tacatatata atcaccattt aaattatgct actataaatt     6960
```

```
ttataaaatt ttcgagaata tcactataac agaagctatt aaatataat aattattcct    7020 aatttgatcg acgatactgt caggataact ggggtatcac ctcttgaagc cattcagtca    7080
catcaccagg cggtccacca aaccgagaat gaattctaac aaaattatac cagaatgaaa    7140
acagaaaaac aaacctgtga accctcctcc agtctctagc cctgaagtta ttccagaaac    7200
gctttgttct ctctttaaca gtcctaaacc agcgctcaac acagttcctc ggcccgaaag    7260
tcacatgcag ataatccagc ccgagagatt taaacgctga tttataccac ggcccttttgt   7320 caaccaggaa aattggctgt ccctcgcagg atttcaaaac aactagaatg aagtccctgg    7380
caatccacca gttcctaacg cttgtaatcc atactgctag gatttctttg ctctcaacgt    7440
cgattgcagc ccagagaaat ctcttctggc cgttgatctt tatcactgtc tcgtcaattg    7500
cgatgaagtt tctctgtttt ttgactgcga ggattttcgg ctggtaaact gctttcgcga    7560 attttttggac tgtttcccag actgttgtgt ggctgatttc gaggattgtt cctacctgtc   7620
tgtaacttag tccgtgcagg tacaggttta ttgccctggt tttctttttt gctgggattt    7680
tgttccggcg aaaggttttt aagactgaaa ccagtaagta gataatggtt tcagtcctca    7740
tttctctccc cttttctgaa gaggtatcag aaacttaaac ctaacgtccc actgcttatc    7800
ctgacagtgt cttgatcgac tttagaaaca ttttttattct tgtttatgtt cccttagact    7860
atgagcacca ggggagactt gatcagaatt ttaggtgaga tagaggaaaa gatgaacgaa    7920
ctgaaaatgg atggctttaa ccctgacata atccttttttg gcagagaggc ttataacttt   7980
ctttcaaatc tcttaaaaaa ggaaatggaa gaggaagggc cttttacgca tgtctctaat    8040
atcaagatag aaattcttga ggaattagga ggagacgcag ttgttataga ttcaaaagtc    8100
ctaggcctag ttcctggggc cgcaaagaga atcaaaatta ttaagtagcg ctttccaaag    8160
tacaggagat gctcacttcc tccttagcta ggattagacc aaaatataac ataaaggagt    8220
tgagtgttgc ccaggagggg actagcctcc ttgatattaa taaagggtct ctgcgaagag    8280
ttttgtcctg tatcatatta aagagttcgt taattcttgc atctgcaagt tgaaggccta    8340
accttgtccg agatttggct gtaatgactt taacagagta atgtttaacc aaaaaaagaa    8400
gactttaaaa ccttccactc acaataagta gacgagtcaa caacaatttg agggaaaaga    8460
catgggaaat gaaggtgtcc acccccacct gcggaaaagg ttttggagag agatgggtat    8520
aaatgcagaa tttgtgatca cagctatctc gatattcatt acaaggacgg gaatgtagag    8580
aacaagaatt tagaaaattt gatagttttg tgcaaacaat gtcattatcg acttcaccaa    8640
aaggaaagga tggaaagcat taaacaagct ttcgaggatt tcctcgatga actttctaaa    8700
aatcctattg aagttgttat agatttcagt ttcaaaaaaa ttgtagagag taatgaagaa    8760
aaaatccgaa gagagattat acagggattt actcgtcctt ttggtgttat atcaaggatc    8820
caagagaaag ttagggatgc aataatgaag gaaatcgagg aggaaataga aaaagagcaa    8880
gcaagtactc ctgaacatct ccgaaaggtt gttcttgaaa gaaataatta tagatgttca    8940
gtgtgcggat acggatattt agaggttcac catgtggatg gaaatattct aaataacacc    9000
ttggataatt tagtaaccct ctgtagaagg tgtcatcgta aagtccatta tcatccaagt    9060
tttcatacaa caccggagga tatggacaaa tgtattagaa gttttcatca tgagttttat    9120
agtacgatct atgaaataat gaagaacaaa aagggaaaca ttagaataag cattaaattc    9180
gatcaactag gtgttaaagg tgtaaaaatt agtagagctc aatttaaaag aattaatggg    9240
ctctttaatc atgaagtcat aaatgatggt attttttaagc agtgggaaag agaaattaag    9300
```

```
aattatttaa gccgacttga atgggaacag caaaaagaaa tatatagaaa tgtatacttc    9360
ttgctagaat gtattttgcc taaagattca tttgaagcgt tgttaacct tgcaaggaaa    9420 ggaaaatttg atagaagaac attaagggaa gcaaagaaag tactaaagaa ctcaattaaa    9480
taatttttgt aattttttccc tggaaataca gctcctattc tactattttt aaagtgctgt    9540
cttcttcttt tataaaccca tatttttgt tactctttag gaagttcttt attatttcac    9600
aaagctcagg gttgagagat cttttcagtt acacacttct tattattcct aaagtacgaa    9660
tagaacttag gacttccact ggagtggtat actccaagta tcttcttgtt tctcagcttt    9720
tcagctatgt cgggaaaaat cttcttgtat atttttttct ttttagccaa cttttttcata   9780 atttcgtagg actctcgccc caaacataaa attaagtccc ccgctatgaa atcaagtacg    9840
cgacctaaaa acttccctat gcagttttgt agggtttctg caggtagtgg gactctaaca    9900
ttttcactct cacagtatac taattctcca aacagaattg tacttcctcc ggtaaattaa    9960
aacagtcttt gctttctta agaattctag tgtgtttgca aagtatttat agtggaaagg    10020
atagttacgg tagttcttga taaattctga gacccatgtg tcatggattt ctttaaaagc    10080
tttgatggcg ttacttttgc tatattctga agtaaataat ccatgctttt tcaggatgtc    10140
tgtgtagtaa agtctttcaa atggtaagtg ggggcctgga tttattccaa aaataccaat    10200
ttttgctttt tctctggaag gctcgccttg aagtgtagaa aggattagaa cccttggaat    10260
aatgccctca tccttggaat tcttt atacc ttcacacttc tccttctctg agcataagat    10320
catctcactg cctaactcca agaatgcctc aggcatcatg gtaatgattt tacacagaga    10380
atttaataat aatttcggat ttctcaatgc ttcttaattg agaagctaca ttttgaaaat    10440
tgagaaaaat caaaggtacc agtgtgtctc agaaaagtga atat                    10484
```

```
<210> SEQ ID NO 57
<211> LENGTH: 10029
<212> TYPE: DNA
<213> ORGANISM: Pyrococcus furiosus

<400> SEQUENCE: 57
```

```
agtaataaaa ctacataaaa cttttacccct agttcccatc aggtcgttag aattattaag     60
tacttaaatt ttttgattgg ttggtggttg ttatgaactt tcagcaggaa atcctgatca    120
taaaatccga aatctatccg atagtcagca aacactaccc gaaaaacact cgcagggaag    180
taatcagcct ctacgacctg ataaccttcg caatactagc ccacctgcac ttcggaggag    240
tttacaaaca cgcttacgga gccctaatcg aggaaatgaa actgttcccc aaaatcaggt    300
acaacaaact aacagaacgc ttgaacaggc acgaaaaact tctgctccta gcgcaggaag    360
aattattcaa aaaacacgcc agagaatacg ttagaatact ggactcaaaa cccattcaga    420
ccaaggagtt ggccagaaaa aacaggaagg ataaggaggg ttcttcagaa atcatctctg    480
aaaagcccgc agttgggttt gttccctcta aaaaagtttt tactatgggt acaagctgac    540
ctgttactct gatgggaacc tgttggcttt gctgtccgtt gatccggcaa acaagcatga    600
tgtgagtgtt gtcagggaaa agttctgggt gattgttgag gagttttccg gctgttttct    660 gttttttggat aagggttacg ttagtagaga acttcaggag gaattcctga agtttggcgt    720
tgtttacacg ccggtgaagc gggagaatca ggttagtaat ctggaggaga agaagttta    780 caagtacttg tctgactttc gcagaaggat tgagactttg ttttcgaagt tttctgagtt    840
tcttctgagg ccgagcagga gtgttagttt gagggggtta gctgtcagga ttttaggggc    900
gattctggcc gtgaatctgg acagattata caacttcaca gatggtggga actagggtta    960
```

```
aaacttttg  atcgtcaatt  aatcataata  atggcaaaag  tttacttagt  ggattattat    1020
gccacttatg  atcttttcat  aggggttagt  atggaaaacc  atatcaagat  attgaaggac    1080
atgaagtggg  gggtaagaaa  tggttcgtgt  tacgctcgtt  aactatacaa  agaggcccct    1140
agaaacaata  acttgggctg  cccctataag  ctattggggg  gaatggagca  cggaatcatt    1200
tgaaaggata  agtgagaatg  atgtagaaaa  gcatctccct  cggatattgg  gttatggtca    1260
tgagagcatt  ttggagcatg  caacgtttac  tttctcaatc  gaaggttgta  gtagggtttg    1320
tactcatcaa  cttgtgaggc  atagaatagc  cagctacacc  cagcaaagcc  agcgttacat    1380
tgttcttgac  gaggagaacg  ttgaggaaac  gtttgtaatt  cctgaatcga  taaagaaaga    1440
tagagagctt  tatgaaaaat  ggaagaaggt  catggctgag  acaataagcc  tttacaagga    1500
gagcataaat  aggggagttc  accaggaaga  tgctcgattc  attcttcctc  aagctgtgaa    1560
aacgaagata  attgtgacga  tgaacttgag  agaattgaag  cacttctttg  gccttagact    1620
atgtgaaagg  gctcaatggg  agattaggga  agttgcatgg  aagatgttag  aggagatggc    1680
gaagagggat  gatataaggc  cgataataaa  gtgggctaaa  cttgggccta  ggtgcattca    1740
gtttggctat  tgtcccgaga  gagatctaat  gcctcctggg  tgcttaaaga  aaactagaaa    1800
aaagtgggaa  aaagttgcgg  aaagtaagag  ctaaattgtt  atattgagta  aaagctttct    1860
ttctttatt  gtctttatgg  caaaatccca  gaagttcagc  tattgaatta  gagaactgtt    1920
cgtcactgaa  agtaaacttc  tatgggattc  ttctgaatta  tatggtaagg  tttggaaaat    1980
ttggacataa  aagtcttaaa  gtttcctttt  tcaactctaa  actagggtga  gctaatggat    2040
actgaaaaac  ttatgaaagc  cggagaaata  gcaaaaaaag  taagagagaa  agctattaaa    2100
cttgctagac  ctgggatgtt  gttgttagaa  cttgcagagt  ctatagaaaa  gatgataatg    2160
gaacttgggg  gtaaacctgc  tttcccagta  aatttatcaa  ttaatgaaat  tgcagctcac    2220
tatactcctt  acaagggaga  tactactgtt  ctgaaagagg  gggattatct  aaagatcgac    2280
gtgggggttc  acatagatgg  atttatagca  gatactgcag  ttacagttag  agtagggatg    2340
gaagaagatg  agcttatgga  ggctgccaag  gaagcgttaa  acgccgcaat  ttctgtagct    2400
agggcgggag  tggagataaa  ggaactagga  aaggcaatag  aaaatgaaat  taggaagaga    2460
ggattcaaac  caatagttaa  tctaagtggg  cacaagatag  aaagatacaa  gcttcatgca    2520
gggattagca  ttccgaacat  ttatagaccg  catgataact  atgttttaaa  ggaaggagat    2580
gttttcgcaa  ttgagccttt  cgctactata  ggtgctggtc  aagtaattga  ggttccccca    2640
accttaatct  acatgtacgt  tagagatgtt  ccagttagag  tggcccaagc  taggttcctt    2700
ttggctaaga  taaaaaggga  atatggaacc  ctacccttg  cctataggtg  gcttcagaat    2760
gacatgccag  aaggacagct  taagttggcc  ctaaaaaccc  tcgaaaaggc  tggagctata    2820
tatggctatc  cagtgcttaa  agaaattaga  aatggcattg  tggcacaatt  tgagcacaca    2880
atcattgttg  aaaaggattc  tgtgatagtg  acgacagaat  gagttaaact  ttataagttc    2940
tcatgtatca  agaaattggg  agcgccgggg  tagcctagtc  agggaaggcg  cgggactcga    3000
gatcccgtgg  gcgttcgccc  gccggggttc  aaatccccgc  cccggcgcca  tttgttaagc    3060
acttggaggt  ttgataatat  ggcatttcta  aaggtagtgt  cattggaaga  agcaatttca    3120
ataattaata  gctttagact  tgaaatagga  tttgaggaag  ttactttaga  taaagctctg    3180
gggaggatag  ttgcagagga  tatttattcc  cccttggata  ttcctcccct  tgatagatcg    3240
accgttgatg  ggtatgctgt  tagggcggag  gatacttta  tggccagtga  agctaatcca    3300
```

```
gtggaactca aagtaattgg agaagttcat gccggagaac aaccttcagt aaagttaagc   3360
aagggagagg cggtctacat tacaacgggg tcaatgatgc cagagaacgc aaatgctgtg   3420
attccttttg aggatgttga gagagaagga gatattataa gaatttataa gcctgcatac   3480
ccaggtttag gagtcatgaa gaaaggaact gacataaaaa agggccaact cttaattaga   3540
agaggaacta agctaacgtt taaagaaact gccctgcttt ctgctgcggg atttttaaaa   3600
gtaaaggtct ttaaaaagcc taaagttgcg gtcataagta cggggaatga aattgttctc   3660
ccaggtgaag agcttaggcc tggccaaata tatgacatca atggtagagc aatagttgat   3720
gccgttaatg aattgggtgg agagggaata ttcgttggga ttgccaggga tgacagagaa   3780
agtctcaaaa aattaatact tcaagcctta gaagttggag atattatcgt tattagtggg   3840
ggggcaagtg ggggaataaa agacttaaca gcctcggtaa tagaggaact tggagaggtt   3900
aaagttcatg gaattgcaat tcagccaggt aaacccacaa taatagggt  tataaacggt   3960 aagcctgtct ttggcctacc tgggtatccg acaagttgcc taacaaactt caccctctta   4020
gttgctcccc tgcttttgag gctacttgga agggaaggaa aaattaagaa ggttaaggcg   4080
aaaattaagc ataaagtatt ttcggtaaag ggaagaagac aattcctccc agttaaactt   4140
gagggagatg tagcggttcc tatcttgaag ggaagcggag cagtcacaag ctttgtggag   4200
gcagatggtt ttgtggaaat tcccgagaat gtagaaagcc ttgatgaggg agaagaagta   4260
acggtaacgt tgttctcgtt ttaggagtg atagtatggt caaggttaag gttaagtact   4320
ttgctagatt taggcaactt gcaggagttg atgaagagga gattgagctt ccagagggag   4380
ctagagttag ggacttgata gaagaaataa agaaaagaca tgaaaaattt aaggaggagg   4440
tctttggaga aggatacgat gaggatgccg atgttaacat tgccgtaaat ggaaggtatg   4500
taagctggga tgaagagtta aaggatgggg atgttgttgg agtatttcct cccgtaagcg   4560
gaggttaaca tttacatact tttacataaa cttctcttct cctgggtcca tctaactcta   4620
caaagagaat gctctgccaa gttcctaaca taagttggcc atttactatt ggaatagtca   4680
cgcttgggcc aagtattata gctctgaggt gagagtgggc gttgttatct atagaatcgt   4740
gtctgtatcc tgcaccttt  ggaattaatt ttgagagaat attttctatg tcgttaagga   4800
gccttggctc gttctcattt actattattc ctgtggtggt atgcctagta tagacaacgg   4860
caattccatt atcgatgcca cttttttctaa cgatttcctg gacttttttcc gttatatcta   4920 ttatttcaac ttctttggaa gtccttatag tgatggtttc aatcatattt cttccctct    4980 agatacctt  ttatcatctc cctagcgttt tctatatgct tatttgcctc ttcttcatta   5040
atgtttttta acgtggccct aacagtaaca atgctctcaa aggcctccaa taacctttga   5100
tctgttgtct cttttagaat tcttttttagc attaagtatg cttcgtctat gctctccctct   5160 cttagggttt tcttagatag tccttcgagg attcgatcta gaatgaatat tctatcttgc   5220
aatagcttcc ttcttagtat taatcttctc attgactttc ccctctacca cttttactaa   5280
aagttcggaa gcaagttttg aagcaatacc tctatcttta atattcaaaa caacgtcaat   5340
agcatctcca acacgcccaa ttctaatgag ataatgggct aggaatccta aggcaactga   5400
cctgtgccgt tcgctattaa ttcttttttat tactctaact gcctgttgaa ggttgttgag   5460
ctctaaataa tactttgtta ttcctactag tatgtcttcg cttattccct ctttctcgag   5520
gaggacttga atcattggct ccatcttggg agaacccctc tctagaatcc taaatatgat   5580
atccttaacc attaggacca tatcagggg  aaggctttcc attaaaattt tcagcttatc   5640
taagtcttct ttagaaagta gagaagttag aatttcccta actattattc tttgcgtggt   5700
```

```
gggcggtatt gtctttaata cttcaatcga ttgttggata aatccgtgaa ttgcaaatat    5760
gtaggcaata tcttccctta tatcttctcc cactttttta gccagctcct cactctcttc    5820
tatcaaaatt tttactattt ctgagttttc ctcattattc ttcaaaaatt ctagaacctc    5880
atttaatgcc tgtgctatcc agagtttgct ccctatagag tttattaact caagaacaag    5940
cttgtattct cctagtgaaa gtagtggttt aattgacttg actattgcct cctctctata    6000
gggctcctca atagtttcga gaattaggag tactttcctt cttttatata tttgtttag    6060 ttttcccct tccaaatttt ctaaaacttt ttcgagtatt tcaagaagtt ttttgtttct    6120
aagcttcttg ttcttaatct ccacggcata aaataccgct tcgtcagtgt cttttaatga    6180
aagcaaataa tcgattgctt cggcttttac aatgtcctga atttcctctg aagaagttg    6240 tgccgatgat atggcctctc taatgctttt ctttgctgat ttaagccctg ctaaacttgt    6300
tgaatatcca atggcgagaa gagctcttac taaaatataa ggatcttcta tttttgataa    6360
ttcttcgaaa gcttttctga atgctttcc tgccctggga tcttttattt tagacaaata    6420
tactcctatt ctcccatatg ttaatacct aacgaatggg tctggtatcg agggtactaa    6480
ctctaatatt tcatctatta ccataatacc tcaccataag attatacatg gcaaaacgca    6540
cttactaagg taaatttatg gacatagata ttttaatctt ttcgttttg aagcaaatct    6600 ttttgtagga agatgatgaa ctaatggttt caaaatgttt aaataaaagc ttaaggtgta    6660
gtcaaaatgt tgtctcaaat ttaaagaaaa gaggcgaaac aaagaaaata gagggaagat    6720
actttacttc ttgagctttt cacacttctt tacccactcc tcaagaacgt ctctgagctt    6780
tggcttgcct atttcctcaa gctcatactt gactcttact gcaggcttgt tgaggttcat    6840
gaatcttctt aggtctactg gagttcccat aacgacaacg tctgcatctg ctctgttaat    6900
tgtttcctct agctctttga tctgcttctt gccgtatccc attgctggga gtatgttgct    6960
taggtgtggg tacttcttgt atgtttcaat tattgaccca acagcgtatg gccttggatc    7020
tactatctcc ttagctccga acttcttggc tgctatgtaa cctgcaccga agctcattcc    7080
accatgggtg agggtcggac catcctcaac tacgagaacg cgcttaccct tgattagctc    7140
tggcttgtcc acgaagattg gtgatgctgc ttcaatgact atagcatttg gatttatctt    7200
ttcaatgttc tctctaatct tctgtatgtt ctctggtggg gctgtgtcta ttttattgat    7260
tataataaca tcagcacttc tgaagtttgt ttcacctggg tggtgtgtca actcatgacc    7320
aggtctgtgt gggtcagtga caactatcca taagtcgggc tcgaagaatg ggaagtcgtt    7380
gttcccaccg tccagagga ttatgtcggc ctctttctct gcctccctca gtatcttctc    7440
gtagtcaact ccagcgtata ctaccattcc tctctctagg tatggctcat actcttctct    7500
ctcctcaatt gtacactcat atctgtcgag gtcctcaaag gtcgcaaagc gctgaacaac    7560
ttgctttctt agatcaccgt agggcattgg gtgtctgact gcaactacct tgaatcccat    7620
ctcttggagg atttgggcca ctttttcttga ggtctggctc tttccacatc ctgttctgac    7680
tgcagttacg gctacaacgg gcttgcttga ctttagcatt gtgctctttg gtccaagtag    7740
ccagaagtca gccccagcac tgtgggctct acttgctaag tgcatgacgt gttcgtgaga    7800
aacgtcagag tacgcgaaaa ccactatgtc aacatcatgc tctttgatta tcttttccaa    7860
atcatcttct ggtagaattg gaattccatt tggatacagt tcaccagcta gctctggggg    7920
atatattctc ccctctatat ctggaatttg ggtggcagtg aaggcaacaa cctcgtaatc    7980
tgggttatct ctgaaaaaga cgttgaagtt gtggaagtct ctacccgcag cacccagaat    8040
```

```
tacaacccctt ctcctttttt tctcggccat tttgatcacc tcagaatgtt ttatttcgag      8100
ataatactca atctagacat ttataacgat tttcatttaa attggaaata attttccgaa      8160
tgattttaag taaaagttgt gtaaagtcga aaatatttcg aataaatgtg tgtattatta      8220
aagggattaa gaaaagggaa aaggttgaaa acttcaagtt tcaaaaaccc ctaaaaagtc      8280
taaatcaaac cctctaatgg tgggagtaaa atgtgccttg caatcccagg gaaagtggtg      8340
gagattaaag gtaacgttgg aatagtggat tttggaggaa tacggagaga ggtaaggtta      8400
gatcttttga gtgatgttaa agttggcgat tacgttatag ttcacactgg ctttgctata      8460
gaaaagttag atgagaggag agctagaaaa attcttgaag cctgggaaga agttttctca      8520
gtaattgggg gtgagtaaat gcttgaaaaa tttggagaca aagctgtagc tcaaaagatt      8580
ttagaaaaaa ttaaagagga agctaaaggg atagaagagc tacgatttat gcacgtttgt      8640
gggactcatg aggacacagt aactaggagt ggaatcagat cacttcttcc agaaaatgta      8700
aaaatcatga gtggcccagg atgtcccgtc tgtataaccc ccgttgagga catagtgaag      8760
atgatggaaa ttatgaaagt tgcgagagag gagagggaag aaattattct cactactttt      8820
ggtgacatgt atagaattcc aactccaata ggaagctttg cagacttaaa gagtcagggt      8880
tacgatgtga ggatagttta ctctatatac gactcctata aaatagccaa ggaaaatcca      8940
gataagcttg tagtgcactt ttctcctggg tttgagacta ccgccgctcc aacagctgga      9000
atgcttgaga gcattgtgga agaggggcta gagaacttta gatttattc cgttcatagg      9060 ttaaccccctc ctgcagttga agctctccta aatgcgggga ctgttttttca cggtttaata      9120 gatcctggtc atgtctctac aataattggg gtgaaaggat gggcgtatct cacagaaaag      9180
tttggaattc ctcaagttgt ggctggcttt gagccagttg atgttttact cggaatactt      9240
attctcatta ggcttgtgaa gaggggcgaa gcgaaaataa tcaacgagta taatagagtt      9300
gtaaagtggg aaggaaatgt caaggcccaa gaactgattt ggaagtactt tgaagttaaa      9360
gatgcaaagt ggagggccct aggagtaatt ccaaggagcg gattggaact taagaaagag      9420
tggaaggagc tagaaattag aacttattac aatcccgagg ttccaaagct cccagatctt      9480
gaaaaaggat gtctctgtgg ggcagtcctt agaggattag ccttaccgac ccagtgccaa      9540
cactttggaa agacatgtac accaagacat ccggtaggtc cttgtatggt ttcgtacgaa      9600
ggaacttgtc acatatttta caaatatggc gccctgatgt agttttatt acgcaaaagt      9660 aatataccac tacagcataa accccaaata tggattatcg aaaaattctc gatattcatc      9720
atagttttgg ttgttttttc atcagttgct cttctgtcaa agccttatct tccaagagaa      9780
cagaaaagaa taacgtactc aggagaaaag ataatcttgc ctgccccaag aactgaagga      9840
gaaatgagtg ttgaagaagc tattgcaaaa agaaggagca ttaggacata caaaaatgag      9900
cctctaaaga tagaggagct tggtcaacta ttatgggctg cacaaggtat aactcatgaa      9960
tataagaggg cagccccaag tgcaggagca acatatcct ttgaaatctt cgttgtcgtt     10020
ggtaatgtc                                                             10029
```

<210> SEQ ID NO 58
<211> LENGTH: 12
<212> TYPE: PRT
<213> ORGANISM: artificial
<220> FEATURE:
<223> OTHER INFORMATION: Gateway attB1 site

<400> SEQUENCE: 58

Gly Ser Ile Thr Ser Leu Tyr Lys Lys Ala Gly Ser

```
<210> SEQ ID NO 59
<211> LENGTH: 7
<212> TYPE: PRT
<213> ORGANISM: artificial
<220> FEATURE:
<223> OTHER INFORMATION: TEV protease recognition site

<400> SEQUENCE: 59

Glu Asn Leu Tyr Phe Gln Gly
1               5
```